US012648995B2

(12) United States Patent
Yang et al.

(10) Patent No.: US 12,648,995 B2
(45) Date of Patent: Jun. 9, 2026

(54) FULLY HUMANIZED BISPECIFIC CHIMERIC ANTIGEN RECEPTOR TARGETING CD19 AND CD22 AND USE THEREOF

(71) Applicant: Nanjing IASO Biotherapeutics Co., Ltd., Nanjing (CN)

(72) Inventors: Yongkun Yang, Nanjing (CN); Guang Hu, Nanjing (CN); Taochao Tan, Nanjing (CN); Zhenyu Dai, Nanjing (CN); Panpan Niu, Nanjing (CN); Guangrong Meng, Nanjing (CN); Wei Cheng, Nanjing (CN); Xiangyin Jia, Nanjing (CN); Jialu Mo, Nanjing (CN); Wen Wang, Nanjing (CN); Bailu Xie, Nanjing (CN); Junfeng Yang, Nanjing (CN); Fei Zhou, Nanjing (CN)

(73) Assignee: NANJING IASO BIOTECHNOLOGY CO., LTD., Nanjing (CN)

( * ) Notice: Subject to any disclaimer, the term of this patent is extended or adjusted under 35 U.S.C. 154(b) by 707 days.

(21) Appl. No.: 18/002,714

(22) PCT Filed: Jun. 30, 2021

(86) PCT No.: PCT/CN2021/103698
§ 371 (c)(1),
(2) Date: Dec. 21, 2022

(87) PCT Pub. No.: WO2022/002154
PCT Pub. Date: Jan. 6, 2022

(65) Prior Publication Data
US 2023/0241212 A1 Aug. 3, 2023

(30) Foreign Application Priority Data

Jun. 30, 2020 (CN) .......................... 202010618929.6
Jul. 21, 2020 (CN) .......................... 202010707612.X

(51) Int. Cl.

| | |
|---|---|
| *A61K 40/31* | (2025.01) |
| *A61K 40/11* | (2025.01) |
| *A61K 40/41* | (2025.01) |
| *A61K 40/42* | (2025.01) |
| *A61P 35/02* | (2006.01) |
| *C07K 14/705* | (2006.01) |
| *C07K 16/28* | (2006.01) |
| *C12N 5/0783* | (2010.01) |

(52) U.S. Cl.
CPC .............. *A61K 40/31* (2025.01); *A61K 40/11* (2025.01); *A61K 40/41* (2025.01); *A61K 40/4211* (2025.01); *A61K 40/4212* (2025.01); *A61P 35/02* (2018.01); *C07K 14/7051* (2013.01); *C07K 14/70578* (2013.01); *C07K 16/2803* (2013.01); *C12N 5/0636* (2013.01); *C12N 5/0646* (2013.01); *A61K 2239/13* (2023.05); *A61K 2239/21* (2023.05); *A61K 2239/22* (2023.05); *A61K 2239/29* (2023.05); *A61K 2239/31* (2023.05); *A61K 2239/38* (2023.05); *A61K 2239/48* (2023.05); *C07K 2317/31* (2013.01); *C07K 2319/02* (2013.01); *C07K 2319/03* (2013.01)

(58) Field of Classification Search
CPC ........ A61K 40/31; A61K 40/11; A61K 40/41; A61K 40/4211; A61K 40/4212; A61K 2239/13; A61K 2239/21; A61K 2239/22; A61K 2239/29; A61K 2239/31; A61K 2239/38; A61K 2239/48; A61K 2239/28; A61K 35/17; A61K 2039/5156; A61K 2039/5158; A61P 35/02; A61P 35/00; C07K 14/7051; C07K 14/70578; C07K 16/2803; C07K 2317/31; C07K 2319/02; C07K 2319/03; C07K 14/71; C07K 2319/92; C07K 2317/622; C12N 5/0636; C12N 5/0646; C12N 2740/15041; C12N 2510/00
See application file for complete search history.

(56) References Cited

U.S. PATENT DOCUMENTS

| | | |
|---|---|---|
| 2022/0220200 A1 | 7/2022 | Tan et al. |
| 2023/0174654 A1 | 6/2023 | Hu et al. |

FOREIGN PATENT DOCUMENTS

| | | |
|---|---|---|
| CN | 109021114 A | 12/2018 |
| WO | 2020/233589 A1 | 11/2020 |
| WO | 2021/197483 A1 | 10/2021 |

OTHER PUBLICATIONS

African Journal of Biotechnology, 10(79):18294-18302, 2011 (Year: 2011).*
Annu. Rev. Biophys. Biophys. Chem., 16: 139-159, 1987 (Year: 1987).*
J. Immunol. Methods, 251(1-2): 137-149, 2001 (Year: 2001).*
(Continued)

*Primary Examiner* — Nelson B Moseley, II
*Assistant Examiner* — Josephine K Darpolor
(74) *Attorney, Agent, or Firm* — Christensen O'Connor Johnson Kindness PLLC

(57) ABSTRACT

Provided is a bispecific chimeric antigen receptor targeting CD19 and CD22, which comprises extracellular antigen binding domains of heavy-chain variable regions and light-chain variable regions of anti-CD19 and anti-CD22 antibodies. Further provided is a bispecific CAR-T cell targeting CD19 and CD22.

18 Claims, 16 Drawing Sheets
Specification includes a Sequence Listing.

(56)             References Cited

OTHER PUBLICATIONS

International Search Report mailed Sep. 28, 2021, issued in International Application No. PCT/CN2021/103698, filed Jun. 30, 2021, 12 pages.

Dai, H., et al., "Bispecific CAR-T Cells Targeting Both CD19 amd CD22 for Therapy of Adults With Relapsed or Refractory B Cell Acute Lymphoblastic Leukemia," Journal of Hematology and Oncology 13(1):30, Dec. 2020, 10 pages.

Jia, H., et al., "Haploidentical CD19/CD22 Bispecific CAR-T Cells Induced MRD-Negative Remission in a Patient With Relapsed and Refractory Adult B-ALL After Haploidentical Hematopoietic Stem Cell Transplantation," Journal of Hematology and Oncology 12(1):57, Jun. 2019, 9 pages.

Qin, H., et al., "Preclinical Development of Bivalent Chimeric Antigen Receptors Targeting Both CD19 and CD22," Molecular Therapy Oncolytics 6(11):127-137, Dec. 2018.

Extended European Search Report mailed Jul. 2, 2024, issued in related EP Application No. 21831797.2, filed Jun. 30, 2021, 12 pages.

Notice of Refusal mailed Mar. 18, 2025, issued in related JP Application No. 2022-579002, filed Jun. 30, 2021, 6 pages.

Office Action mailed Mar. 20, 2025, issued in related CA Application No. 3177234, filed Jun. 30, 2021, 4 pages.

Written Opinion mailed Sep. 28, 2021, issued in International Application No. PCT/CN2021/103698, filed Jun. 30, 2021, 9 pages.

* cited by examiner

| | | EGFR% | MFI (APC) | MFI (FITC) |
|---|---|---|---|---|
| PXL1419 | CD19 | 11.60% | 11.9 | 4.77 |
| | CD22 | 11.50% | 11.4 | 6.66 |
| PXL1435 | CD19 | 14.60% | 9.76 | 7.19 |
| | CD22 | 16.40% | 11.1 | 10.1 |
| PXL1436 | CD19 | 16.80% | 10.6 | 5.84 |
| | CD22 | 18.10% | 10.9 | 8.58 |
| PXL1437 | CD19 | 33.60% | 11.2 | 7.32 |
| | CD22 | 34.60% | 11.9 | 10 |

FIG. 13

| MFI ratio | Raji | CD19KO Raji | CD22KO Raji | K562 | buffer |
|---|---|---|---|---|---|
| PXL1419 | 11.15 | 10.86 | 10.32 | 1.84 | 1.88 |
| PXL1435 | 13.39 | 12.92 | 11.81 | 1.49 | 1.72 |
| PXL1436 | 15.76 | 14.04 | 13.54 | 1.32 | 1.43 |
| PXL1437 | 16.87 | 17.04 | 16.69 | 1.65 | 1.83 |
| LV60_CD22CAR | 17.08 | 16.13 | 6.59 | 1.96 | 1.75 |
| LV90_CD19CAR | 17.92 | 7.67 | 17.68 | 1.45 | 1.56 |
| LV60/LV90 mix | 17.98 | 17.88 | 6.75 | 1.83 | 1.65 |
| mock T | n/a | n/a | n/a | n/a | n/a |

| CD107a% | Raji | CD19KO Raji | CD22KO Raji | K562 | buffer |
|---|---|---|---|---|---|
| PXL1419 | 88.62% | 88.73% | 88.16% | 12.22% | 16.09% |
| PXL1435 | 93.44% | 93.73% | 93.63% | 12.85% | 12.94% |
| PXL1436 | 91.33% | 91.33% | 89.47% | 5.14% | 4.69% |
| PXL1437 | 91.14% | 90.66% | 93.57% | 8.05% | 4.71% |
| LV60_CD22CAR | 87.01% | 83.67% | 60.45% | 16.04% | 8.13% |
| LV90_CD19CAR | 90.46% | 86.75% | 90.27% | 6.51% | 7.40% |
| LV60/LV90 mix | 88.94% | 86.33% | 86.96% | 10.66% | 6.68% |
| mock T | 2.98% | 3.61% | 3.71% | 2.91% | 2.63% |

FIG. 14

| | raji | 19ko | 22ko |
|---|---|---|---|
| PXL1419 | 0.89 | 0.71 | 0.86 |
| PXL1435 | 0.87 | 0.88 | 0.88 |
| PXL1436 | 0.89 | 0.90 | 0.80 |
| PXL1437 | 0.87 | 0.86 | 0.68 |
| LV60(CD22CAR) | 0.68 | 0.71 | 0.11 |
| LV90(CD19-CAR) | 0.58 | 0.09 | 0.69 |
| LV60/90 | 0.54 | 0.56 | 0.31 |
| T | 0.00 | 0.13 | 0.16 |

FULLY HUMANIZED BISPECIFIC CHIMERIC ANTIGEN RECEPTOR TARGETING CD19 AND CD22 AND USE THEREOF

CROSS-REFERENCES TO RELATED APPLICATIONS

This application is a National Stage of International Application No. PCT/CN2021/103698, filed Jun. 30, 2021, which claims priority to Chinese Application No. 202010707612.X, filed Jul. 21, 2020, and to Chinese Application No. 202010618929.6, filed Jun. 30, 2020, the disclosures of which are incorporated herein by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is 1483-P7_USPNP Seq_List_20221215_ST25.txt. The text file is 176 KB; was created on Dec. 15, 2022, contains no new matter, and is being submitted electronically via Patent Center.

FIELD OF THE INVENTION

The present application relates to bispecific chimeric antigen receptors, in particular bispecific chimeric antigen receptors targeting CD19 and CD22.

BACKGROUND OF THE INVENTION

CD19 CAR-T therapy has achieved great clinical success. At present, two CAR-T drugs (Kymriah of Novartis and Yescarta of Gilead/Kite) have been approved for marketing in the world. For CD19 CAR-T, the complete response rate for treatment of B-ALL can reach 65-80%, and the complete response rate for treatment of adult lymphoma can also reach 50-60%. However, CD19 CAR-T therapy still faces the problem of relapse. About one third of patients with ALL will experience disease relapse due to CD19 antigen loss after CD19 CAR-T therapy. In addition, the immunogenicity of mouse-derived CD19 CAR-T leads to poor survival of CAR-T cells in the human body, which is another major reason for relapse after CAR-T treatment.

In addition, CD22 CAR-T has also shown good efficacy in clinical trials for the treatment of B-ALL, and a complete response rate can reach 73%. However, CD22 CAR-T therapy also faces the problem of relapse. Studies have shown that the down-regulation of CD22 antigen expression density is a possible cause of relapse after CD22 CAR-T therapy. Studies have also shown that CD22 is a key target after CD19-CAR relapse.

Therefore, how to overcome the escape and relapse of tumors through antigen loss or downregulation is an urgent problem to be solved for CAR-T therapy.

SUMMARY OF THE INVENTION

In an aspect, provided herein is a bispecific chimeric antigen receptor targeting CD19 and CD22, which comprises an extracellular antigen-binding domain comprising a heavy chain variable region and a light chain variable region of an anti-CD19 antibody and a heavy chain variable region and a light chain variable region of an anti-CD22 antibody, wherein the amino acid sequences of the heavy chain variable region and the light chain variable region of the anti-CD19 antibody are selected from any of the following combinations:

a heavy chain variable region sequence having at least 90% sequence identity with the sequence set forth in SEQ ID NO: 2 and a light chain variable region sequence having at least 90% sequence identity with the sequence set forth in SEQ ID NO: 4; and a heavy chain variable region sequence having at least 90% sequence identity with the sequence set forth in SEQ ID NO: 8 and a light chain variable region sequence having at least 90% sequence identity with the sequence set forth in SEQ ID NO: 6, and the amino acid sequences of the heavy chain variable region and the light chain variable region of the anti-CD22 antibody are selected from any of the following combinations:

a heavy chain variable region sequence having at least 90% sequence identity with the sequence set forth in SEQ ID NO: 10 and a light chain variable region sequence having at least 90% sequence identity with the sequence set forth in SEQ ID NO: 12; and a heavy chain variable region sequence having at least 90% sequence identity with the sequence set forth in SEQ ID NO: 14 and a light chain variable region sequence having at least 90% sequence identity with the sequence set forth in SEQ ID NO: 16.

In some embodiments, the amino acid sequences of the heavy chain variable region and the light chain variable region of the anti-CD19 antibody are selected from any of the following combinations:

the heavy chain variable region sequence set forth in SEQ ID NO: 2 and the light chain variable region sequence set forth in SEQ ID NO: 4; and the heavy chain variable region sequence set forth in SEQ ID NO: 8 and the light chain variable region sequence set forth in SEQ ID NO: 6, the amino acid sequences of the heavy chain variable region and the light chain variable region of the anti-CD22 antibody are selected from any of the following combinations:

the heavy chain variable region sequence set forth in SEQ ID NO: 10 and the light chain variable region sequence set forth in SEQ ID NO: 12; and the heavy chain variable region sequence set forth in SEQ ID NO: 14 and the light chain variable region sequence set forth in SEQ ID NO: 16.

In some embodiments, the heavy chain variable region of the anti-CD19 antibody has the sequence set forth in SEQ ID NO: 2, the light chain variable region of the anti-CD19 antibody has the sequence set forth in SEQ ID NO: 4, the heavy chain variable region of the anti-CD22 antibody has the sequence set forth in SEQ ID NO: 10, and the light chain variable region of the anti-CD22 antibody has the sequence set forth in SEQ ID NO: 12; or the heavy chain variable region of the anti-CD19 antibody has the sequence set forth in SEQ ID NO: 2, the light chain variable region of the anti-CD19 antibody has the sequence set forth in SEQ ID NO: 4, the heavy chain variable region of the anti-CD22 antibody has the sequence set forth in SEQ ID NO: 14, and the light chain variable region of the anti-CD22 antibody has the sequence set forth in SEQ ID NO: 16.

In some embodiments, the heavy chain variable region of the anti-CD19 antibody has the sequence set forth in SEQ ID NO: 8, the light chain variable region of the anti-CD19 antibody has the sequence set forth in SEQ ID NO: 6, the heavy chain variable region of the anti-CD22 antibody has the sequence set forth in SEQ ID NO: 10, and the light chain variable region of the anti-CD22 antibody has the light chain variable region sequence set forth in SEQ ID NO: 12.

In some embodiments, the heavy chain variable region and the light chain variable region of the anti-CD19 antibody and the heavy chain variable region and the light chain variable region of the anti-CD22 antibody are located in the extracellular antigen-binding domain, from the amino terminus to the carboxyl terminus, in the following order:

the light chain variable region of the anti-CD19 antibody, the heavy chain variable region of the anti-CD22 antibody, the light chain variable region of the anti-CD22 antibody, and the heavy chain variable region of the anti-CD19 antibody;

the heavy chain variable region of the anti-CD19 antibody, the light chain variable region of the anti-CD22 antibody, the heavy chain variable region of the anti-CD22 antibody, and the light chain variable region of the anti-CD19 antibody;

the light chain variable region of the anti-CD22 antibody, the heavy chain variable region of the anti-CD19 antibody, the light chain variable region of the anti-CD19 antibody, and the heavy chain variable region of the anti-CD22 antibody; or the heavy chain variable region of the anti-CD22 antibody, the light chain variable region of the anti-CD19 antibody, the heavy chain variable region of the anti-CD19 antibody, and the light chain variable region of the anti-CD22 antibody.

In some embodiments, the extracellular antigen binding domain, from the amino terminus to the carboxyl terminus, sequentially comprises:

the light chain variable region of the anti-CD19 antibody, a first linker, the heavy chain variable region of the anti-CD22 antibody, a second linker, the light chain variable region of the anti-CD22 antibody, a third linker, and the heavy chain variable region of the anti-CD19 antibody, the heavy chain variable region of the anti-CD19 antibody, a first linker, the light chain variable region of the anti-CD22 antibody, a second linker, the heavy chain variable region of the anti-CD22 antibody, a third linker, and the light chain variable region of the anti-CD19 antibody;

the light chain variable region of the anti-CD22 antibody, a first linker, the heavy chain variable region of the anti-CD19 antibody, a second linker, the light chain variable region of the anti-CD19 antibody, a third linker, and the heavy chain variable region of the anti-CD22 antibody; or the heavy chain variable region of the anti-CD22 antibody, a first linker, the light chain variable region of the anti-CD19 antibody, a second linker, the heavy chain variable region of the anti-CD19 antibody, a third linker, and the light chain variable region of the anti-CD22 antibody, wherein the first linker and the third linker have the amino acid sequence set forth in SEQ ID NO: 20, and the second linker has the amino acid sequence set forth in SEQ ID NO: 24.

In some embodiments, the bispecific chimeric antigen receptor, from the amino terminus to the carboxyl terminus, sequentially comprises a signal peptide sequence, the extracellular antigen-binding domain, a hinge region, a transmembrane domain, and an intracellular signaling domain, wherein the intracellular signaling domain, from the amino terminus to the carboxyl terminus, sequentially comprises a fragment from 4-1BB molecule and a fragment from CD3z molecule.

In some embodiments, the signal peptide sequence has the amino acid sequence set forth in SEQ ID NO: 36; the hinge region has the amino acid sequence set forth in SEQ ID NO: 26; the transmembrane domain has the amino acid sequence set forth in SEQ ID NO 28; the fragment from the 4-1BB molecule has the amino acid sequence set forth in SEQ ID NO: 30; and the fragment from the CD3z molecule has the amino acid sequence set forth in SEQ ID NO: 32.

In some embodiments, the bispecific chimeric antigen receptor comprises the amino acid sequence set forth in SEQ ID NO: 40, 42, 44, 46, 48, 50, 52, 54, 56, 58, 60, 62, 64, 66, 68 or 70.

In another aspect, provided herein is a nucleic acid molecule encoding the aforementioned bispecific chimeric antigen receptor.

In some embodiments, the nucleic acid molecule comprises the nucleotide sequence set forth in SEQ ID NO: 39, 41, 43, 45, 47, 49, 51, 53, 55, 57, 59, 61, 63, 65, 67 or 69.

In another aspect, provided herein is an expression vector comprising the aforementioned nucleic acid molecule.

In another aspect, provided herein is a host cell expressing the aforementioned bispecific chimeric antigen receptor or comprising the aforementioned expression vector.

In some embodiments, the host cell is an immune cell, preferably a T cell or an NK cell.

In another aspect, provided herein is use of the aforementioned bispecific chimeric antigen receptor, expression vector or host cell in the preparation of a drug for treating a cancer.

In some embodiments, the cancer is a B cell related cancer.

In some embodiments, the cancer is B-cell non-Hodgkin's lymphoma (B-NHL) or B-lineage acute lymphoblastic leukemia (B-ALL).

In some embodiments, the cancer expresses CD19 and/or CD22.

In another aspect, provided herein is a method for treating a cancer in a patient, which comprises administering the aforementioned bispecific chimeric antigen receptor, the aforementioned expression vector or the aforementioned host cell to the patient.

In some embodiments, the cancer is a B cell related cancer.

In some embodiments, the cancer is B-NHL or B-ALL.

In some embodiments, the cancer expresses CD19 and/or CD22.

In some embodiments, the host cells are administered to the patient at a dose of $0.5 \times 10^6$ host cells/kg patient body weight to $3 \times 10^6$ host cells/kg patient body weight.

In some embodiments, the patient is a patient with B-NHL, and the host cells are administered to the patient at a dose of $1 \times 10^6$ host cells/kg patient body weight to $3 \times 10^6$ host cells/kg patient body weight.

In some embodiments, the patient is a patient with B-ALL, and the host cells are administered to the patient at a dose of $0.5 \times 10^6$ host cells/kg patient body weight to $1 \times 10^6$ host cells/kg patient body weight. The bispecific CAR-T cells (CD19×22 CAR-Ts) that target both CD19 and CD22 provided herein can improve the efficacy of CAR-T and reduce the relapse rate.

DESCRIPTION OF DRAWINGS

FIG. 13 shows the mean fluorescence intensity (MFI) detected for the APC and FITC signaling pathways in FIG. 12, wherein the MFI of the APC channel reflects the expression of tEGFR molecules. The MFI of FITC channel reflects the binding of CD19 or CD22 antigen protein to the CAR molecules. Since the CAR molecule and tEGFR are linked through T2A, the expression of the tEGFR molecule is theoretically the same as that of the CAR molecule.

FIG. 14 shows the degranulation activity of bispecific CAR-Ts with different VH-VL sequential combinations. Degranulation signals produced by the CD8+/CAR+ cell population upon stimulation of different target cells were detected by flow cytometry with PE-Cy7 anti-CD107a antibody. Among others, the upper table shows the MFI of the PE-Cy7 signal of the CD8+/CAR+ cell population, which reflects the expression level of CD107a on the cell surface. The lower table shows the positive rate of CD107a in the CD8+/CAR+ cell population. Among them, LV60 and LV90 are the controls of CD22 and CD19 monospecific CAR-Ts, respectively, and LV60/LV90 is a mixed sample of the two monospecific CAR-Ts.

DETAILED DESCRIPTION OF THE INVENTION

Figures 1, 2:
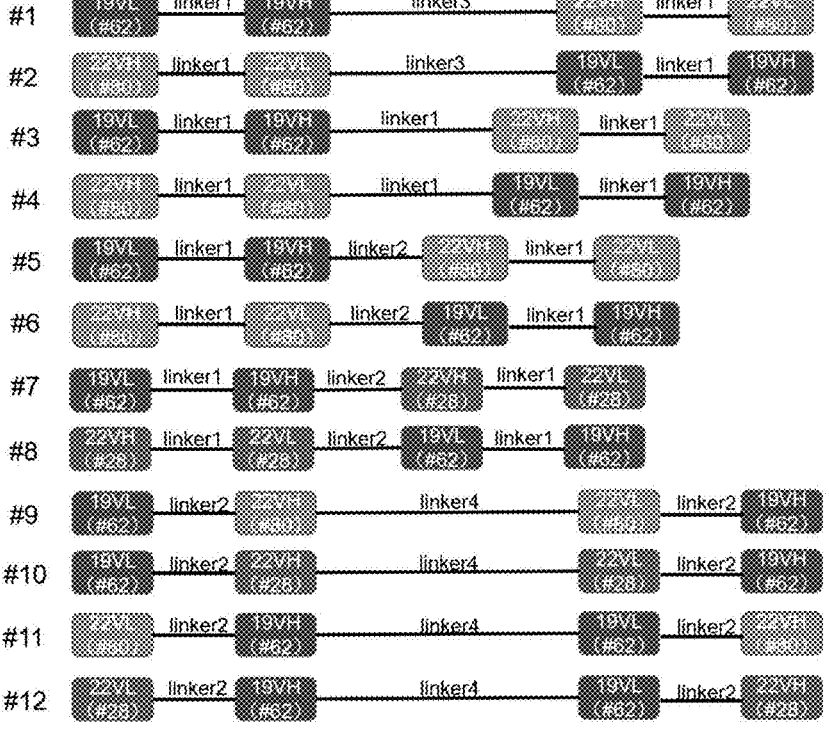
FIG. 1 is a schematic diagram of the structural design of the extracellular antigen recognition region (CD19×22 scFvs) of the CD19×22 bispecific CAR molecule.
FIG. 2 is a schematic diagram of the structure of the CD19×22 bispecific CAR molecule.

Unless otherwise defined, all technical and scientific terms used herein have the meaning as commonly understood by one of ordinary skill in the art.

"Antibody" refers to an immunoglobulin secreted by plasma cells (effector B cells) and used by the body's immune system to neutralize foreign substances (polypeptides, viruses, bacteria, etc.). The foreign substance is correspondingly called an antigen. The basic structure of a classical antibody molecule is a 4-mer consisting of 2 identical heavy chains and 2 identical light chains. According to the conservative differences in amino acid sequences, the heavy and light chains are divided into a variable region (V) at the amino terminus and a constant region (C) at the carboxyl terminus. The heavy chain variable region (VH) and the light chain variable region (VL) interact to form the antigen-binding site (Fv). In some cases, antibodies may also be used to refer to antibody fragments that have antigen-binding ability, such as scFv, Fab, and F(ab')2.

"Single chain fragment variable (scFv)" is composed of antibody heavy and light chain variable regions linked by a short peptide into a peptide chain. Through correct folding, the variable regions from the heavy chain and the light chain interact through non-covalent bonds to form the Fv segment, so the scFv can well retain its affinity to the antigen.

"Chimeric antigen receptor (CAR)", also known as chimeric T cell receptor, and chimeric immunoreceptor, is an engineered membrane protein receptor molecule that confers a desired specificity to immune effector cells, such as the ability to bind to specific tumor antigens. Chimeric antigen receptors generally consist of an extracellular antigen-binding domain, a transmembrane domain, and an intracellular signaling domain. In some cases, the antigen-binding domain is an scFv sequence responsible for recognizing and binding to a specific antigen. Intracellular signaling domains usually comprise immunoreceptor tyrosine activation motifs (ITAMs), such as the signaling domains derived from CD3z molecules, which are responsible for activating immune effector cells to produce killing effects. In addition, the chimeric antigen receptor may also comprise a signal peptide responsible for intracellular localization of the nascent protein at the amino terminus, and a hinge region between the antigen-binding domain and the transmembrane domain. In addition to signaling domains, intracellular signaling domains may also comprise costimulatory domains derived from, for example, 4-1BB or CD28 molecules.

"Bispecific chimeric antigen receptor" is intended to mean that the molecule comprises at least two different antigen-binding sites in the extracellular antigen-binding domain, which respectively recognize and bind to different antigen molecules on the target cell. As for the bispecific chimeric antigen receptor targeting CD19 and CD22 provided herein, it comprises a CD19 binding site (formed by the light and heavy chain variable regions of an anti-CD19 antibody) and a CD22 binding site (formed by the light and heavy chain variable regions of an anti-CD22 antibody).

When referring to a chimeric antigen receptor or an expression vector thereof, the term "host cell" used refers to a cell expressing the chimeric antigen receptor or comprising the expression vector, especially immune cells such as T cells or NK cells.

"CAR-T cells" refer to T cells expressing CAR molecules, which are usually obtained by transducing T cells with an expression vector encoding CARs. Commonly used expression vectors are viral vectors, such as lentiviral expression vectors. Chimeric antigen receptor-modified T cells (CAR-Ts) are not restricted by major histocompatibility complexes, and have specific targeted killing activity and the ability of persistent expansion. In addition to T cells, other lymphocytes such as NK cells can also be transduced with an expression vector encoding a CAR to obtain targeted killer cells expressing the CAR.

"CD19" is a B lymphocyte surface marker molecule that plays a role in regulating B cell activation and development. CD19 is not only expressed on normal B cells, but also expressed on many malignant B cell tumors, which constitutes the basis for the clinical treatment of B cell-related tumors by CAR-Ts targeting CD19.

"CD22" is a Siglec family lectin, including 7 IgG-like domains in the extramembrane portion, with a molecular weight of about 135 kD. Human CD22 and variants thereof are available in UniProt under accession number P20273. As a transmembrane glycoprotein, it is initially expressed on the surface of B cells at the pre-B cell stage, exists on mature B cells, and disappears on plasma cells.

The term "sequence identity" when referring to amino acid or nucleotide sequences refers to the degree of identity between two amino acid or nucleotide sequences (e.g., a query sequence and a reference sequence), usually expressed as a percentage. Typically, prior to calculating the percent identity between two amino acid or nucleotide sequences, the sequences are aligned and gaps (if any) are introduced. If at a certain alignment position, the amino acid residues or bases in the two sequences are the same, the two sequences are considered to be identical or matched at that position; and if the amino acid residues or bases in the two sequences are different, they are considered to be non-identical or mismatched at that position. In some algorithms, the number of matched positions is divided by the total number of positions in the alignment window to obtain sequence identity. In other algorithms, the number of gaps and/or the gap length are also taken into account. For the purposes of the present invention, the published alignment software BLAST (available at ncbi.nlm.nih.gov) can be employed to obtain optimal sequence alignments by using default settings and calculate the sequence identity between two amino acid or nucleotide sequences.

In some embodiments, the light chain variable region of the anti-CD19 antibody molecule provided herein comprises an amino acid sequence having at least 90% sequence identity (e.g., at least 95%, at least 98%, at least 99% or even 100% sequence identity) with the sequence set forth in SEQ ID NO: 4 or 6, and the heavy chain variable region comprises an amino acid sequence having at least 90% sequence identity (e.g., at least 95%, at least 98%, at least 99% or even 100% sequence identity) with the sequence set forth in SEQ ID NO: 2 or 8.

In some embodiments, the light chain variable region of the anti-CD22 antibody molecule provided by the invention comprises an amino acid sequence having at least 90% sequence identity (e.g., at least 95%, at least 98%, at least 99% or even 100% sequence identity) with the sequence set forth in SEQ ID NO: 12 or 16, and the heavy chain variable region comprises an amino acid sequence having at least 90% sequence identity (e.g., at least 95%, at least 98%, at least 99% or even 100% sequence identity) with the sequence set forth in SEQ ID NO: 10 or 14.

In some embodiments, the bispecific CAR molecule provided by the present invention comprises an amino acid sequence having at least 90% sequence identity (e.g., at least 95%, at least 98%, at least 99% or even 100% sequence identity) with the sequence set forth in SEQ ID NO: 40, 42, 44, 46, 48, 50, 52, 54, 56, 58, 60, 62, 64, 66 or 70.

Those skilled in the art can understand that, on the basis of the specific sequences provided herein, the corresponding variants of the bispecific chimeric antigen receptor provided herein can be obtained by substituting, deleting, adding a few amino acids, and verifying or screening the resultant product for its binding ability with the corresponding antigen or its biological activity, and these variants should also be included within the scope of the present invention.

After repeated screening, we obtained a bispecific chimeric antigen receptor molecule targeting both CD19 and CD22, which can specifically recognize and kill target cells expressing CD19 and/or CD22.

The present invention will be further described below through specific examples.

Example 1 Construction of Plasmid Vector for Bispecific CAR Molecules

Since the extracellular antigen recognition region of the bispecific CAR molecule comprises four domains, CD19

VH, CD19 VL, CD22 VH and CD22 VL, the folding and pairing of these domains will have a great impact on the function of the bispecific CAR molecule. Therefore, it is necessary to screen linkers between the domains, as well as sequential combinations of the domains. As shown in FIG. 1, we designed a total of 12 different extracellular recognition domain structures of CAR molecules for structural screening of extracellular recognition domains. In FIG. 1, 19VL represents the light chain variable region of the anti-CD19 antibody, 19VH represents the heavy chain variable region of the anti-19 antibody, 22VL represents the light chain variable region of the anti-CD22 antibody, and 22VH represents the heavy chain variable region of the anti-22 antibody, and the numbers after # in parentheses represent the IDs of the antibodies we screened out for CD19 or CD22 antigens, respectively. FIG. 1 is mainly used to illustrate screening various structural combinations of extracellular antigen recognition domains by us, of which the CD19 antibody and CD22 antibody and their combinations are some of the preferred antibodies screened out, and the antibody IDs in parentheses (62, 80, and 28) do not include all antibodies used in our screening studies. As shown in FIG. 2, these bispecific CAR molecules adopt the second-generation CAR structure and co-express a truncated EGFR membrane protein (tEGFR) via T2A. Nucleic acid sequences encoding these CAR molecules were synthesized and inserted into the pLKO expression vector.

Example 2 Detection of Expression and Antigen-Binding Ability of CAR Molecules by Flow Cytometry 1. Experiment Purpose and Principle When a plasmid encoding the CAR molecule is transfected into Jurkat cells by electrical transduction, the CAR molecule will be transiently expressed on the surface of Jurkat cells. Since the CAR molecule and tEGFR are co-expressed via the T2A peptide (FIG. 2), the expression level of the CAR molecule can be indirectly detected using the EGFR antibody by flow cytometry. Also, in flow cytometry, CD19 or CD22 protein staining can be carried out respectively to detect the binding ability of the bispecific CAR molecule to these two antigens.

2. Operation Steps i. Transiently transfect 4 μg of the plasmid encoding the CAR molecule into $2 \times 10^6$ Jurkat cells using a Celetrix electroporation kit. Culture the transfected cells at 37° C., 5% $CO_2$ for 24 h; and ii. Stain the Jurkat cells after electroporation with APCanti-EGFR antibody and CD19-FITC protein, or APCanti-EGFR antibody and CD22-FITC protein, respectively, and carry out flow cytometry analysis.

3. Screening Criteria

The CD19×22 CAR molecule can be expressed normally on Jurkat cells and can bind to CD19 and CD22 proteins, respectively.

Example 3 Detecting the Activity of CAR Molecules to Activate NFAT Transcription Factor by Reporter Gene Method 1. Experiment Purpose and Principle The activation of CAR-T cells is achieved by CD3z and costimulatory factors in the intracellular region of CAR molecules, wherein CD3z can activate the NFAT signaling pathway in the cells, which is a necessary condition for CAR-T cell activation. Therefore, CAR molecules with the function of activating the NFAT signaling pathway can be screened out by the NFAT reporter gene method.

Figure 3:
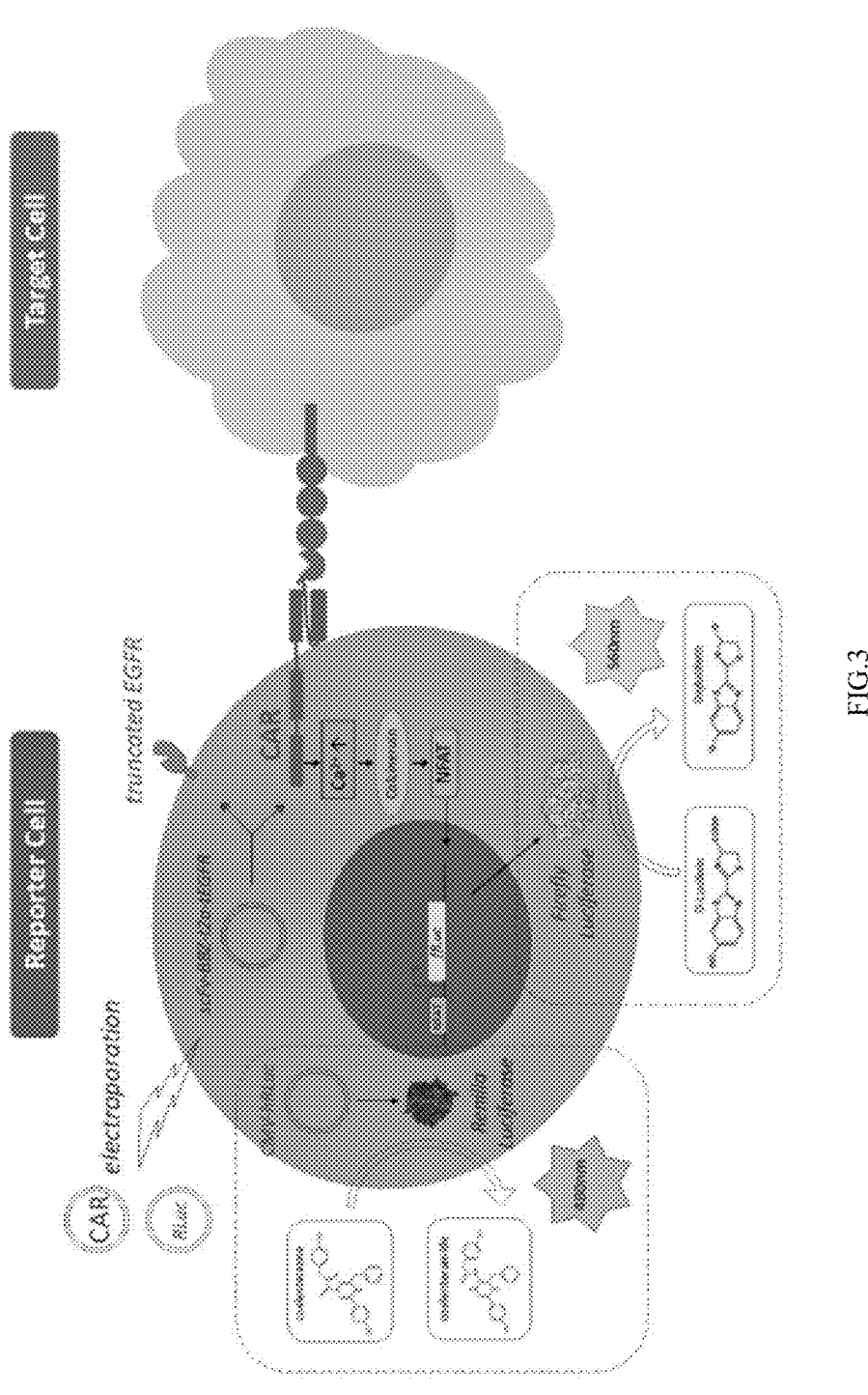
FIG. 3 is a schematic diagram of the working principle of the NFAT reporter gene method.

In the process of primary screening, Jurkat cells integrated with the NFAT-RE-ffLuc reporter gene (ffLuc, firefly luciferase) are used as reporter cells (as shown in FIG. 3, the cells are named JLuc307). CAR molecules are transiently expressed on the surface of reporter cells by plasmid electroporation. After a reporter cell expressing a CAR molecule and a target cell (expressing CD19 and/or CD22) are co-incubated, the target cell surface antigen can specifically activate the CAR molecule, thereby activating the expression of the reporter gene. Then, by detecting the activity of luciferase, the ability of the CAR molecule to activate the NFAT signaling pathway can be evaluated. In addition, since different CAR molecules have different electroporation efficiencies, the internal reference plasmid (CMV-hRLuc, Renilla luciferase) mixed with CAR molecules can be used to calibrate the electroporation efficiency.

2. Operation Steps i. Mix the CAR plasmid to be tested and the internal reference plasmid according to a fixed ratio, and transfect the reporter cells by the electroporation method;

ii. 48 h after transfection, take some cells and stain them with PE-anti human EGFR antibody for flow cytometry to evaluate the transient expression of CAR plasmid;

iii. 72 h after transfection, mix the reporter cells and target cells in a ratio of 1:1, and then place them separately in a U-bottom 96-well plate to incubate for 24 h; wherein $3 \times 10^4$ reporter cells are added to each well, and 3 duplicate wells are set for each target cell; and iv. After completion of incubation, perform centrifugation at 1000 g for 5 min at 4° C., remove the culture supernatant, add 100 μL of lysis buffer to each well to lyse the cells, and take 20 μL of the cell lysate for dual-luciferase activity detection.

3. Screening Criteria

The bispecific CAR molecules can be activated by CD19 or CD22 positive target cells, respectively, and generate fluorescent signals through NFAT-RE reporter genes. In the absence of stimulation by target cells or CD19-CD22-target cells, the fluorescent signal resulting from background (tonic effects) or non-specific activation is low.

Example 4 In Vitro Function Evaluation of Bispecific CAR-T Cells

The in vitro function evaluation of bispecific CAR-T cells was mainly conducted using two methods, CD107a degranulation assay and in vitro cytotoxicity assay.

1. CD107a Degranulation Assay 1.1 Experiment Purpose and Principle

CD107a is a marker for intracellular microvesicles, and CD107a on the cell membrane increases after granzyme-loaded microvesicles fuse with the cell membrane, and when its recovery is blocked by monesin (purchased from BioLegend), it can quantitatively reflect the strength of microvesicle release. Therefore, when CAR-T cells are stimulated by target cell surface antigens to undergo degranulation effect, the positive rate of CD107a on the surface of CAR-T cells can be detected by flow cytometry to determine the activation of CAR-T cells.

1.2 Operation Steps i. Centrifuge different target cells (such as Raji, CD19 KO Raji (CD19 knockout Raji cells), CD22 KO Raji (CD22 knockout Raji cells), and K562) separately at room temperature and 300 g for 5 min; discard the supernatant, and re-suspend the cells in T cell culture medium to $2\times10^5$ cells/mL;

ii. According to the CAR positive rate and E:T value (usually 0.3:1) of the CAR-T cells to be tested, re-suspend the CAR-T cells to an appropriate density, and add monensin and PE/Cy7 mouse anti-human CD107a antibody;

iii. In a U-bottom 96-well plate, add 100 μL/well CAR-T cells to be tested and 100 μL/well target cells, mix well, and then place the cells in an incubator (37° C., 5% $CO_2$) for incubation for 3 h;

iv. After completion of incubation, centrifuge at 4° C. and 600 g for 5 min, discard the supernatant, and wash the cells twice with 200 μL/well DPBS+1% HSA;

v. Re-suspend the cells with 20 μL/well DPBS+1% HSA, add APC mouse anti-human CD8 antibody and Alexa Fluor 488 anti-human EGFR antibody, mix the cells well and incubate them on ice in the dark for 20 min; and vi. After completion of incubation, wash the cells 3 times with 200 μL/well DPBS+1% HSA, and then re-suspend the cells with 200 μL/well DPBS+1% HSA for flow cytometry.

1.3 Screening Criteria

CD19×22 CAR can specifically recognize CD19+/CD22+ (Raji), CD19+/CD22-(CD22 KO Raji) and CD19-/CD22+ (CD19 KO Raji) cells, and effectively activate CAR-T cells (in the CD8+/CAR+ cell population, the proportion of CD107a positive cells is high).

CD19×22 CAR is not activated by CD19-/CD22- (K562) cells, and the CD107a positive ratio is low in the CD8+/CAR+ cell population.

2. In Vitro Cytotoxicity Assay 2.1 Experiment Purpose and Principle

In the evaluation of antigen-specific cytotoxicity of CAR-T cells, CD19+/CD22+ (NALM6-ffLuc), CD19+/CD22- (CD22 KO Raji-ffLuc), and CD19-/CD22+ (CD19 KO Raji-ffLuc) were used as target cells. These target cells are cell lines stably expressing firefly luciferase, which are obtained by lentiviral transduction. In addition, as mentioned below, K562, REH and JVM2 were used as target cells to carry out the cytotoxicity assay by detecting luciferase activity, and they were also made to stably express ffLuc by lentiviral transduction.

In the in vitro cytotoxicity assay, CAR-T cells and target cells are co-incubated with different effector-target ratios (E:T). When target cells are killed by CAR-T cells, luciferase is released and quickly inactivated (firefly luciferase has a half-life of about 0.5 h). If the target cells are not killed or inhibited by CAR-T cells, more luciferases will be produced as the target cells expand and continue to express luciferase. Therefore, the cytotoxicity of CAR-Ts to the target cells can be detected by the activity of luciferase.

2.2 Operation Steps i. Centrifuge the target cells at room temperature and 300 g for 5 min separately, discard the supernatant, and then re-suspended the cells in T cell complete medium to $2\times10^5$ cells/mL; and add 100 μL/well target cells to 96 well plates with transparent bottom separately;

ii. According to the CAR positive rate and E:T value (usually 2:1, 1:1, and 0.5:1) of the CAR-T cells to be tested, add 100 μL/well CAR-T cells to the 96-well plate, and after well mixing with the target cells, put them in an incubator (37° C., 5% $CO_2$) to incubate for 24 h;

iii. After completion of incubation, centrifuge the cells at room temperature and 800 g for 5 min, and collect 100

μL/well supernatant as a reserved sample for cytokine detection (stored at −80° C.); and iv. Use a luciferase detection kit to detect the luciferase activity of the remaining cells after sample reservation in each well.

2.2 Screening Criteria

CD19×22 CAR-T cells can effectively kill CD19+/CD22+ (NALM6-ffLuc), CD19+/CD22- (CD22 KO Raji-ffLuc) and CD19-/CD22+ (CD19 KO Raji-ffLuc) cells.

Results and Analysis

1. Detection of Expression and Antigen-Binding of Bispecific CAR Molecules

Figure 4:
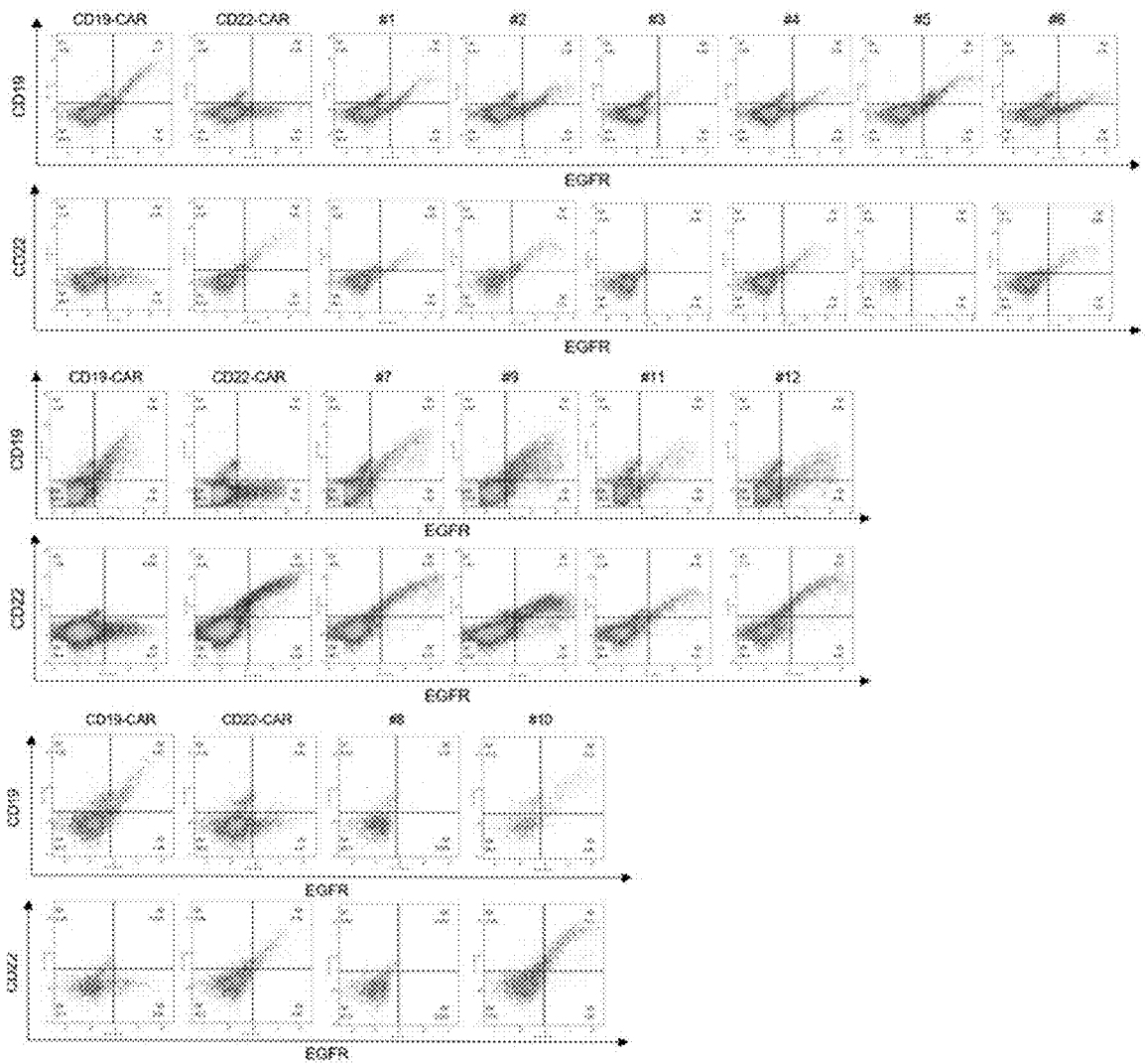
FIG. 4 shows the results of flow cytometry, showing the expression of CAR molecules on transiently transfected Jurkat cells, as well as the binding ability of CAR molecules to CD19 and CD22 proteins. Among them, CD19-CAR and CD22-CAR are monospecific CAR molecules as controls. The 12 CAR molecular structures constructed were divided into 3 batches for transient transfection and flow cytometry, and each batch contained CD19-CAR and CD22-CAR as controls.
Figure 5:
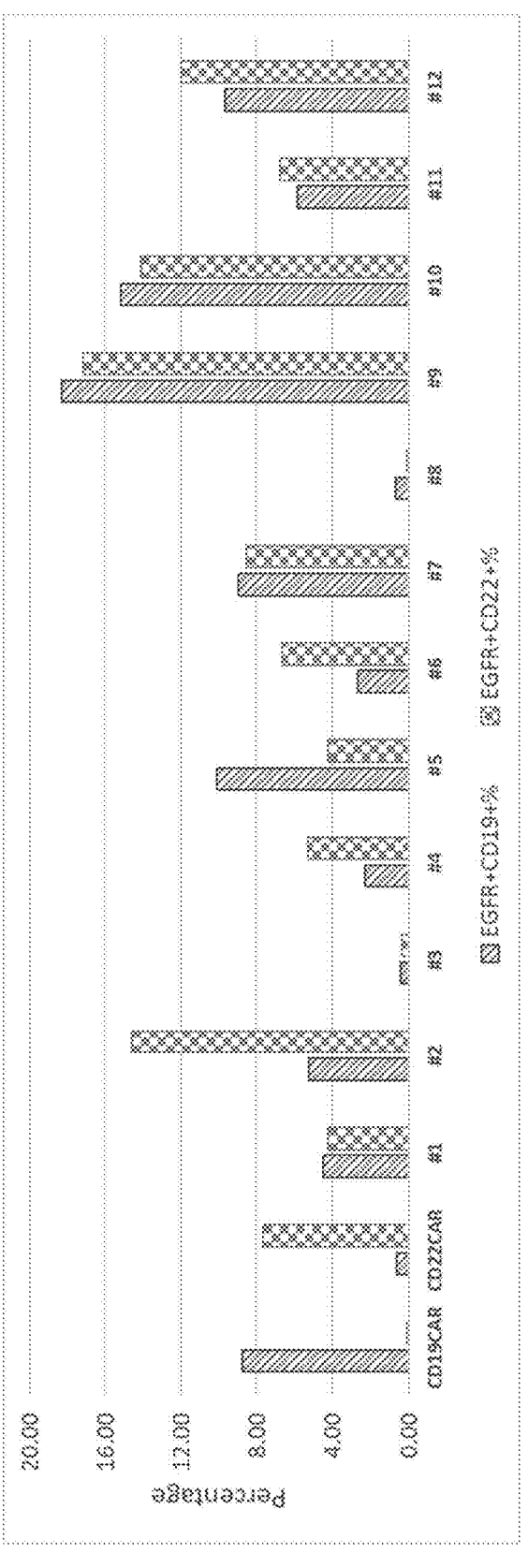
FIG. 5 shows the results of flow cytometry in FIG. 4 as a histogram of the proportion of double positive cells. The expression of CAR molecules and tEGFR molecules on the surface of transiently transfected Jurkat cells was stained with EGFR antibody and CD19-FITC protein, or EGFR antibody and CD22-FITC protein simultaneously, to obtain the proportion of double positive cells. The higher the proportion of double positive cells, the higher the expression level and protein binding ability of the CAR molecules.

The CAR plasmid vector described in Example 1 was transiently transfected into Jurkat cells according to the method described in Example 2. Transiently transfected cells were co-stained with APC anti-EGFR antibody and CD19-FITC or CD22-FITC respectively. The results of flow cytometry are shown in FIGS. 4 and 5. The flow cytometry results in FIG. 4 (percentages of EGFR$^+$/CD19$^+$ and EGFR$^+$/CD22$^+$ double positive cells) are shown in histogram of FIG. 5, and the percentages of CD19-CAR and CD22-CAR controls are the mean of the three measurements in FIG. 4. It can be seen from the figures that structures #9 and #10 each have strong binding ability to both CD19 and CD22 proteins.

2. NFAT Activation Function of Bispecific CAR Molecules

NFAT is an important transcription factor in T cells. The activation of T cells is accompanied by the activation of NFAT. The Jurkat-luciferase cell line is a cell line conditionally expressing Luciferase that is constructed on the basis of Jurkat by us. When the CAR expressed by Jurkat is activated, it transmits a signal downstream, and NFAT is activated to promote the expression of luciferase. Therefore, the activity of luciferase can be used to reflect the degree of activation of T cells. The target cells were co-incubated with Jurkat-luciferase cells electroporated with CAR, and the expression level of the reporter gene, that is, the activity of luciferase, can reflect the degree of activation of the CAR after binding to the target protein on the target cell.

Figure 6:
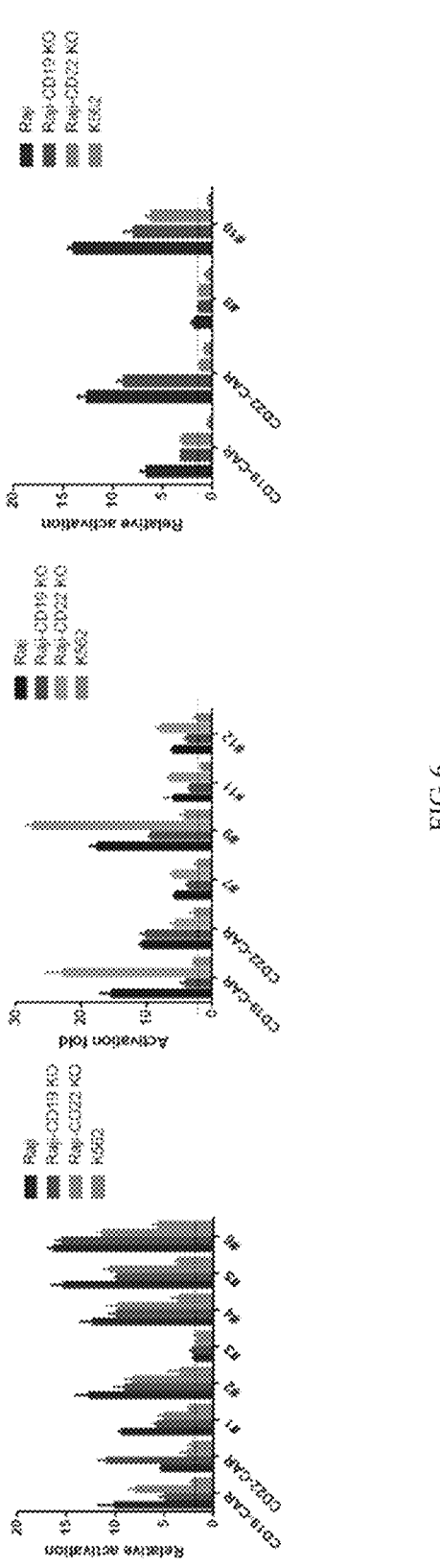
FIG. 6 shows the results of NFAT reporter gene detection for the bispecific CAR molecules. The reporter gene detection was conducted in three batches, and for each batch, the results of two monospecific CARs, CD19-CAR and CD22-CAR, were used as controls.

The CAR molecules of 12 structures constructed in Example 1 were activated by Raji (CD19+CD22+), CD19 KO Raji (CD19−CD22+), CD22 KO Raji (CD19+CD22−), K562 (CD19−CD22−) and the like target cells, respectively to generate the reporter gene signals, as shown in FIG. 6. Among them, the CAR molecules of structures #9 and #10 had a higher degree of NFAT activation. In addition, the structure #10 had better specificity to CD19 or CD22 antigen, and produced the lowest non-specific activation signal when co-incubated with K562 cells.

3. CD107a Degranulation Function of CD19×22 CAR-T Cells

Figure 7:
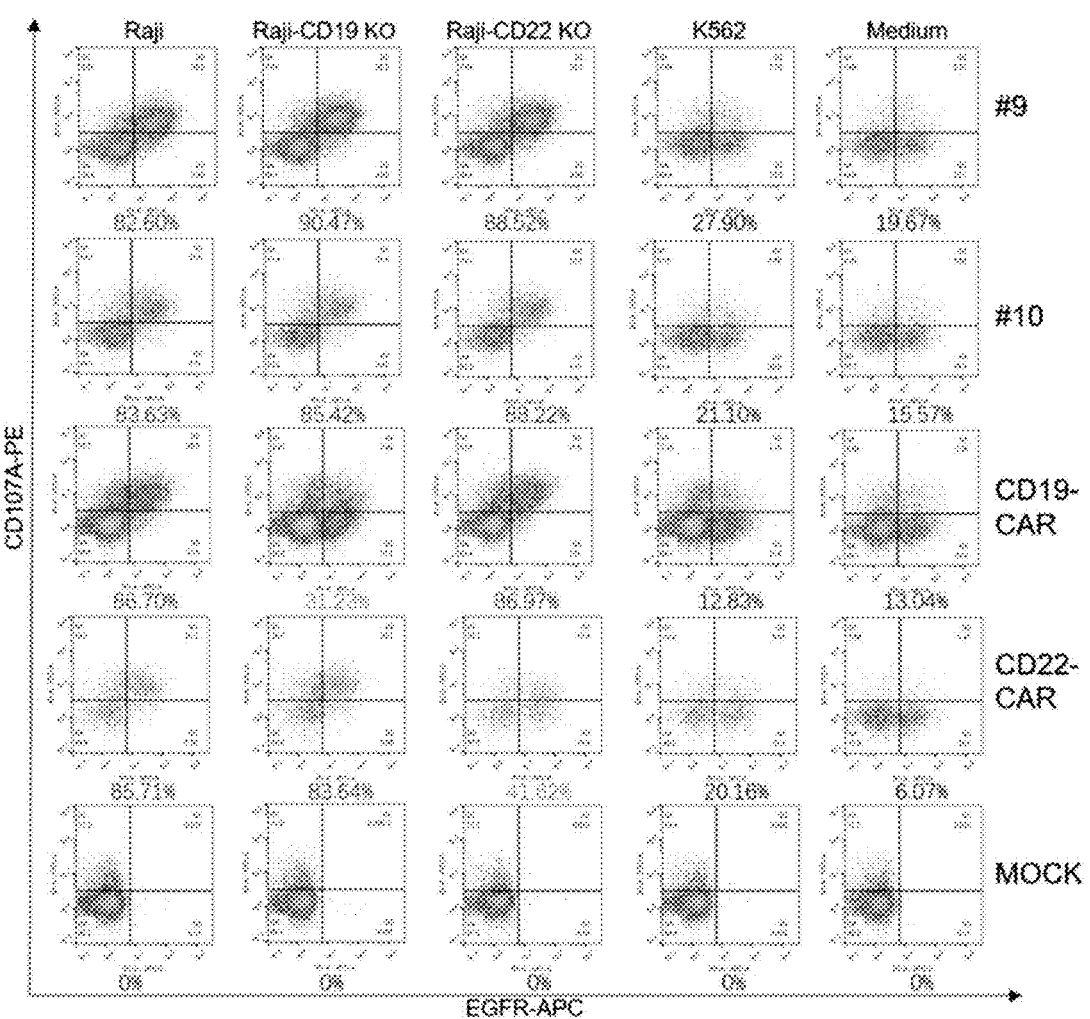
FIG. 7 shows the results of CD107a degranulation function test of the bispecific CAR-T cells. Among them, the scatter plot represents the CD8+ cell population, the abscissa represents the CAR molecule expression stained by APC anti-EGFR antibody, and the ordinate represents the PE anti-CD107a staining result.

Based on the above results, we selected CAR molecules of structures #9 and #10 to test the functions of CAR-T cells. CAR-T cells were prepared by lentiviral transduction. FIG. 7 shows the results of CD107a degranulation function assay of the CAR-T cells. The CAR molecules of structures #9 and #10 could each be activated by CD19 KO or CD22 KO target cells (Raji), and the resulting CD107a activation rate was comparable to that of monospecific CAR (CD19 CAR or CD22 CAR). This indicates that clones #9 and #10 can still activate CAR-T cells when CD19 or CD22 antigens escapes.

4. In Vitro Cytotoxicity Function of CD19×22 CAR-T Cells

Figure 8:
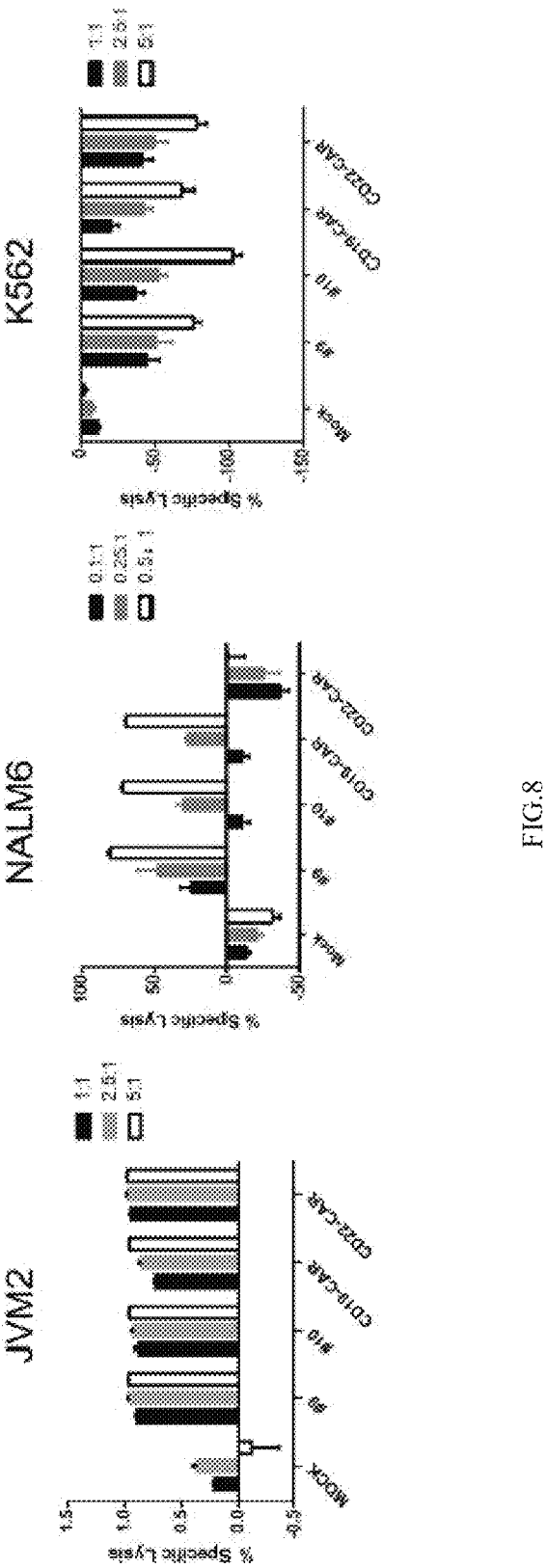
FIG. 8 shows the results of killing of various target cells by the bispecific CAR-Ts.

As shown in FIG. 8, the cytotoxicity ability of the bispecific CAR-T cells of structures #9 and #10 against CD19+CD22+ target cells (JVM2 and NALM6) was comparable to or better than that of the monospecific CAR-Ts (CD19 CAR and CD22 CAR). They did not kill CD19−/CD22− cells (K562), indicating good safety.

Figure 9:
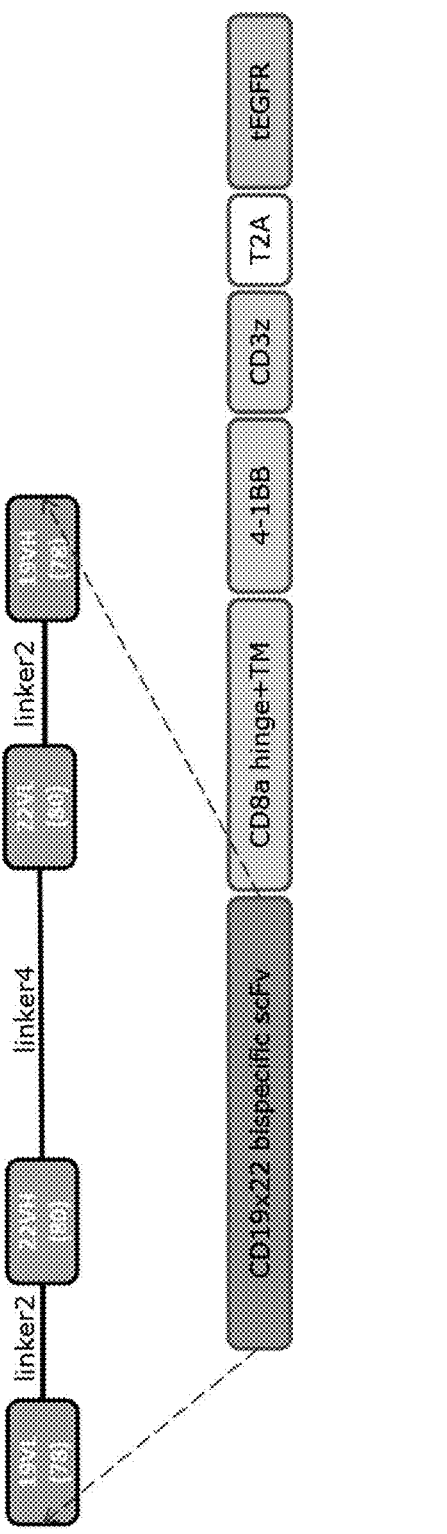
FIG. 9 is a schematic diagram of the molecular structure of the CD19×22 CAR comprising the antibody fragment No. 78.
Figure 10:
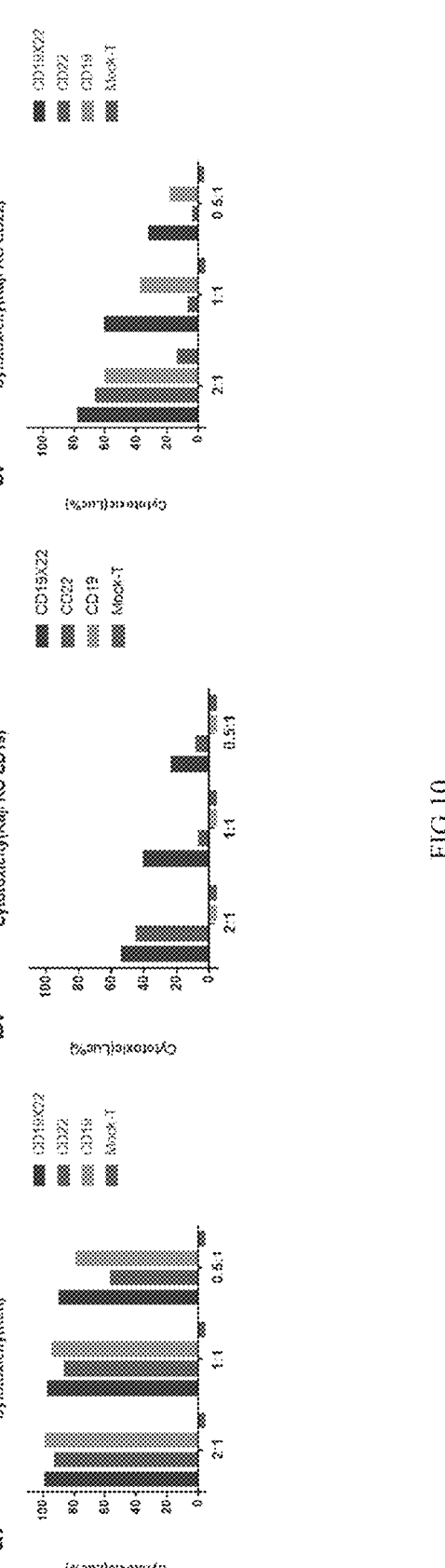
FIG. 10 shows the in vitro cytotoxicity results of CD19× 22 CAR-T cells comprising the antibody fragment No. 78. Among others, the target cells were REH (a), CD19-knockout Raji (b) and CD22-knockout Raji (c) cells, respectively.

Based on the above results, #9 and #10 have similar structures, and the CD19×22 CAR-Ts composed of such a structure has good in vitro function. It was speculated that the CAR molecular structures of #9 and #10 may have some generality. Therefore, we used the screened anti-CD19 antibody clone 78 instead of clone 62 to construct a new CAR molecule (as shown in FIG. 9), and evaluated its vitro cytotoxicity function according to the method described in Example 4. As shown in FIG. 10, clone 78 instead of clone 62 also had good in vitro cytotoxicity function.

Example 5 Structural Optimization of Bispecific CAR Molecule

Figure 11:
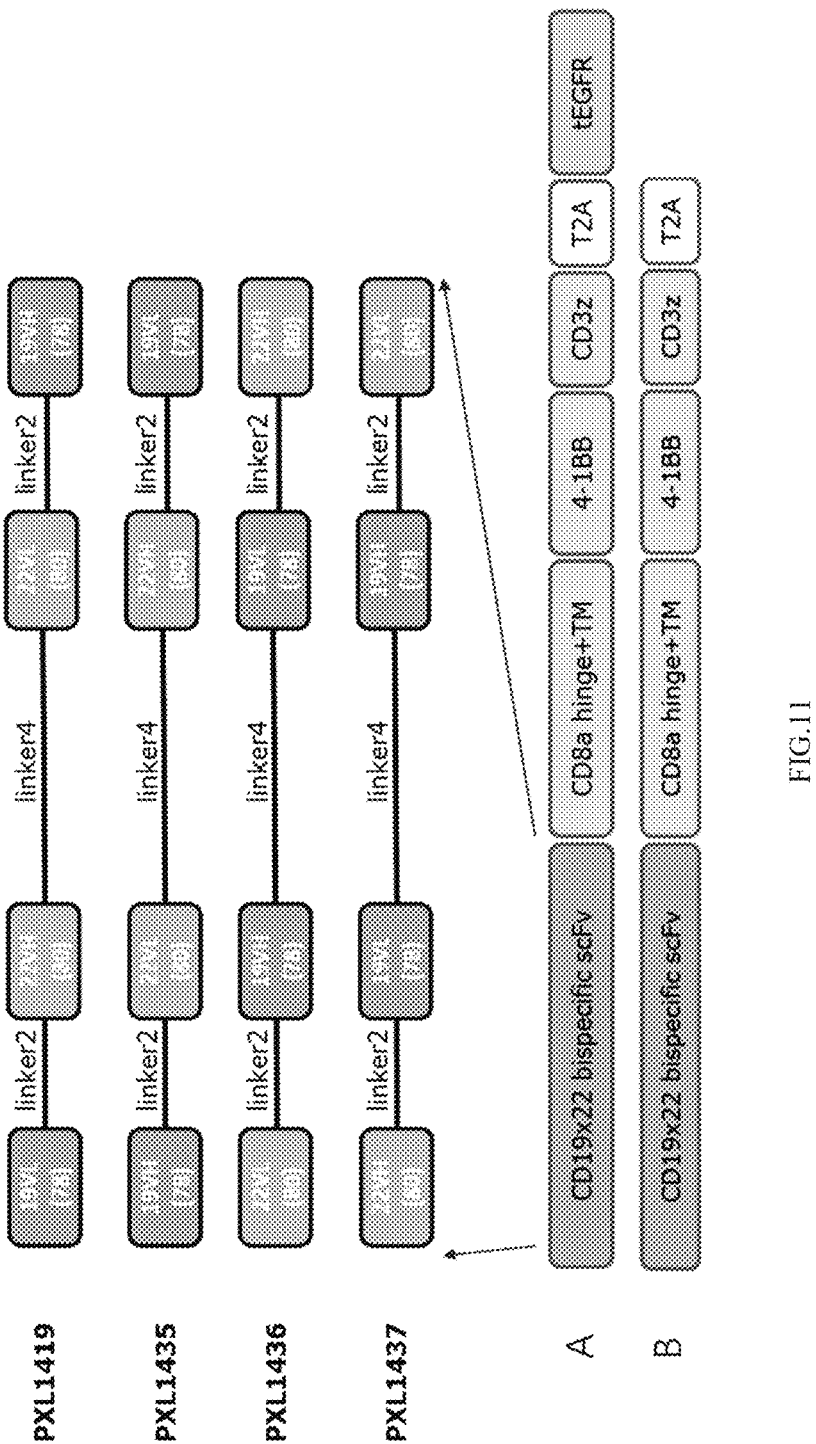
FIG. 11 is a schematic structural diagram of bispecific CAR molecules using different VH-VL sequential combinations.

Since the bispecific CAR molecule contains two pairs of VH-VL sequences, there may be steric hindrance and pairing interactions between them, so on the basis of the sequence structure of #9 or #10 obtained in the above Example, the order of the two VH-VL pairs were further changed (as shown in FIG. 11) to select the optimal CAR molecular structure.

Functional evaluation of these CAR molecules with different VH-VL sequential combinations was performed according to the method of Example 4. In addition, referring to Example 2, the ability of these CAR molecules to bind to CD19/CD22 antigens individually was evaluated.

Figure 12:
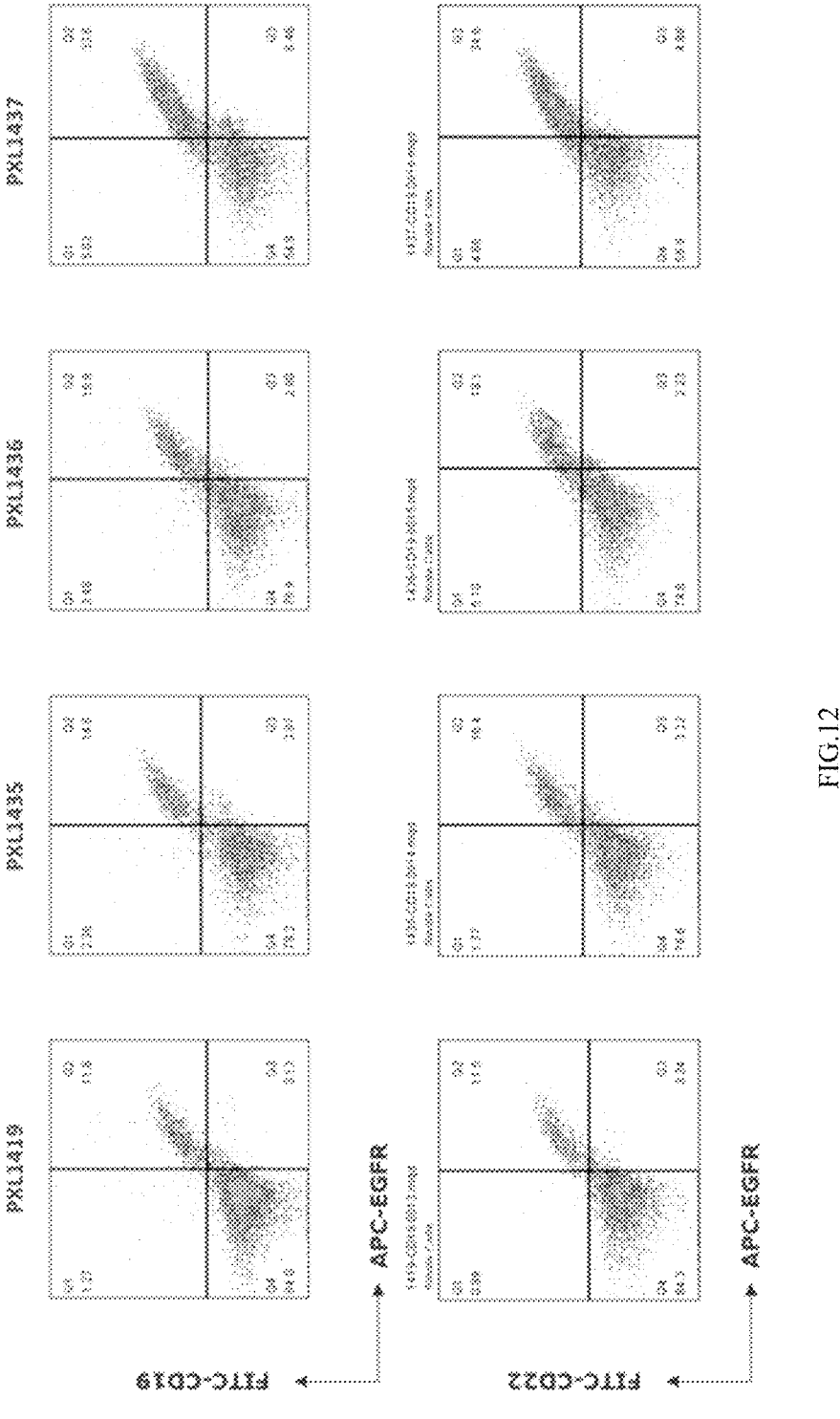
FIG. 12 is a flow cytometry scatter plot of the bispecific CAR molecules with different VH-VL sequential combinations expressed on the surface of CAR-T cells and double-stained with CD19-FITC or CD22-FITC protein and APC anti-EGFR antibody respectively.

Despite the use of the same clone antibodies (78 and 80) and the same linker sequences, there may still be functional differences between bispecific CAR molecules with different VH-VL orders. As shown in FIG. 12 and FIG. 13, bispecific CAR molecules with different VH-VL orders each had different binding abilities to CD19 and CD22 antigens. Among them, the binding ability of PXL1437 to both CD19 and CD22 proteins was relatively better.

FIG. 14 shows the data of degranulation function caused by CAR-T cells co-incubated with Raji (CD19+/CD22+), CD19KO raji (CD19−/CD22+), CD22KO raji (CD19+/CD22−), and K562 (CD19−/CD22−) cells, respectively. The results show that bispecific CAR molecules with different VH-VL orders could be normally activated by Raji, CD19KO raji, and CD22KO raji to produce degranulation effect, but the degranulation effect of PXL1437 was stronger (the mean fluorescence intensity MFI of CD107a was higher).

Figures 15, 16:
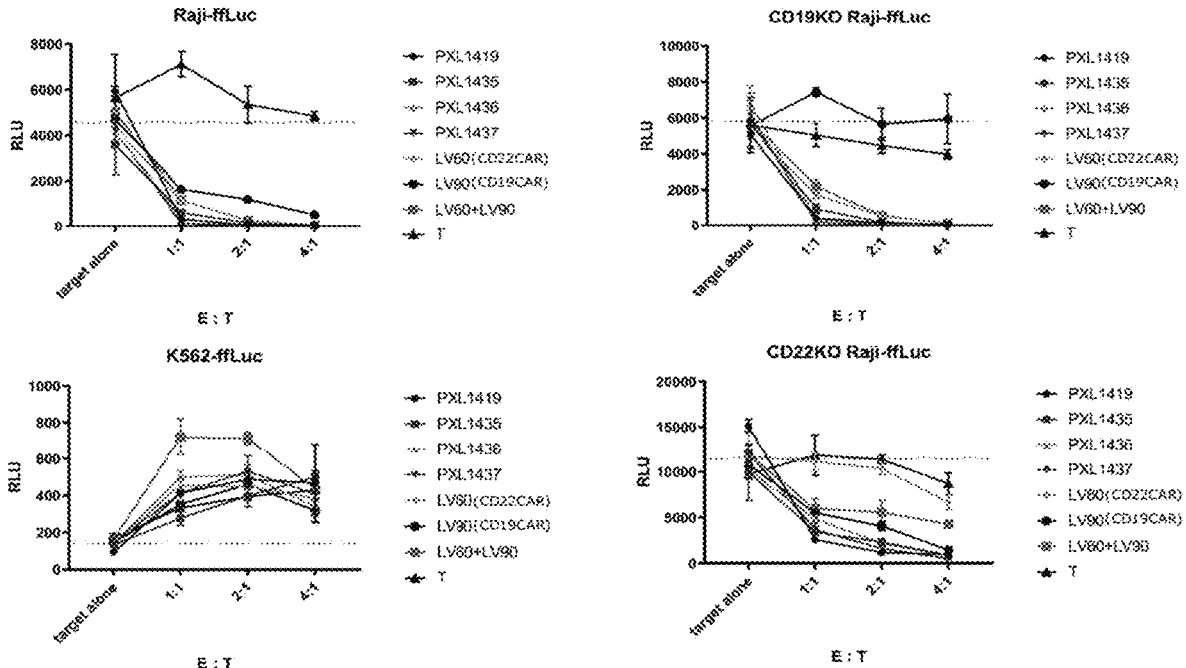
FIG. 15 shows the killing of different target cells by bispecific CAR-Ts with different VH-VL sequential combinations. The axis of ordinate shows the fluorescence intensity (RLU) detected for luciferase-labeled target cells after co-incubation with CAR-Ts for 24 h. The lower the fluorescence intensity, the more the target cells killed.
FIG. 16 shows the ranked average scores of killing ability of bispecific CAR-Ts with different VH-VL sequential combinations. Calculation of the average score: the killing experiment was repeated for several times (as shown in FIG. 15), ranking was conducted for the samples of each experiment to obtain scores between 0 and 1 (1 represents the highest killing, and 0 represents the lowest killing), and the average of these scores is the average score in the table.

As shown in FIG. 15, bispecific CAR-T cells with different VH-VL orders could normally kill the three target cells: Raji, CD19KO raji, and CD22KO raji. However, since the in vitro cytotoxicity assay was affected by various experimental conditions, no significant difference could be observed in a single experiment. Therefore, after repeating the in vitro cytotoxicity assay for many times, the cytotoxicity of each CAR molecule in each experiment was ranked and scored. The results are shown in FIG. 16. Among them, PXL1437 had higher cytotoxicity effect on the three target cells.

Based on the above experiments, it can be seen that the selection of specific antibodies, the composition of different extracellular antigen-binding domains, and the connection order of antibody VH-VL can all affect the antigen-binding ability, degranulation function, and in vitro cytotoxicity function of bispecific CAR molecules.

Compared to monospecific CAR molecules, bispecific CAR molecules add a light chain variable region and a heavy chain variable region (which together form a new antigen-binding site) within their extracellular antigen-binding domain. These newly added polypeptide fragments often adversely affect the binding of the original antigen-binding fragment to its antigen. Or, the original antigen-binding fragment has an adverse effect on the binding of the newly added antigen-binding fragment to its antigen. While not wishing to be bound by any particular theory, it is believed that this effect may be caused by changes in the folded morphology of the antigen-binding fragments, steric hindrance, interactions between different antigen-binding fragments, and the like. After repeated screening, we found that the combination of clone 62 and clone 78 (anti-CD19 antibody) with clone 80 and clone 28 (anti-CD22 antibody) can provide bispecific CAR molecules with high binding affinity to both CD19 and CD22 and having obvious cytotoxicity function to the corresponding target cells.

According to the present invention, fully humanized CD19 and CD22 antibodies are adopted to construct bispecific CAR-Ts targeting both CD19 and CD22 (CD19×22 CAR-Ts), which can improve the curative effect of CAR-T and reduce the relapse rate. Compared with co-transfection of CD19-CAR and CD22-CAR in T cells, the bispecific CAR-T (CD19×22 CAR-T) can stably target both CD19 and CD22, prevent antigen escape, avoid relapse, and also provide better homogeneity, making the product easy to control. Compared with sequential CD19-CAR and CD22-CAR, the treatment duration is shorter, the efficacy is better, and the cost is lower.

The bispecific chimeric antigen receptors provided herein, especially lymphocytes (such as CAR-T cells) modified to express the bispecific chimeric antigen receptors, can be used for the treatment of some lymphomas and leukemias. These CAR-T cells can be formulated into pharmaceutical compositions together with a pharmaceutically acceptable carrier for administration.

Example 6 Study on the Ability of CD19×22 CAR-T Cells to Expand In Vitro

Unless otherwise stated, this Example and the following Examples were performed using CD19×22 CAR-T expressing the PXL1437 structure (see FIG. 11). Specifically, both the structures A and B of PXL1437 in FIG. 11 can realize the cell therapy product of CD19×22 CAR-Ts, and the specific structure of B in FIG. 11 was adopted in this Example.

The number of CD19×22 CAR-T cells at different time points was counted by double fluorescence cytometry to analyze their expansion characteristics. Three batches of products (HD201110-01, HD201110-02 and HD201114-01) were obtained with the same preparation method and the experiment was performed for three times, and the results are shown in Table 1.

TABLE 1

| | | | | | | | | Expansion Fold 1 | Expansion Fold 2 | |
| Batch No. | Day 2/ Day 1 | Day 3/ Day 2 | Day 6/ Day 3 | Day 8/ Day 6 | Day 10/ Day 8 | Day 12/ Day 10 | Day 14/ Day 12 | (Day 12/ Day 1) | (Day 14/ Day 1) | Doubling Time |
|---|---|---|---|---|---|---|---|---|---|---|
| HD201110-01 | 1.35 | 1.23 | 15.40 | 2.67 | 3.63 | 2.14 | 1.44 | 531.66 | 766.82 | 1.36 |
| HD201110-02 | 1.38 | 1.05 | 9.40 | 4.94 | 2.76 | 2.35 | 1.50 | 436.66 | 654.99 | 1.39 |
| HD201114-01 | 0.87 | 1.11 | 11.93 | 4.23 | 3.17 | 1.87 | N/A | 290.49 | N/A | 1.34 |
| Mean | N/A | N/A | N/A | N/A | N/A | N/A | N/A | 419.61 | 710.90 | 1.36 |
| SD | N/A | N/A | N/A | N/A | N/A | N/A | N/A | 121.49 | 79.08 | 0.02 |

According to the analysis of the test results in the above table, CD19×22 CAR-T has a stable expansion ability in vitro, with the expansion fold being 419.61±121.49 on D12, and 710.90±79.08 on D14, and the doubling time being 1.36±0.02 day. Therefore, CD19×22 CAR-T has stable and good expansion ability.

Example 7 Study on Cytokine Release of CD19×22 CAR-T In Vitro

The expression levels of Interleukin-2 (IL-2), Interleukin-4 (IL-4), Interleukin-6 (IL-6), Interleukin-10 (IL-10), Tumor Necrosis Factor (TNF), Interferon-γ (IFN-γ), and Interleukin-17A (IL-17A) secreted by CD19×22 CAR-T after co-incubation with the target cells were studied, to understand the killing of tumor cells by the injection.

Figure 17:
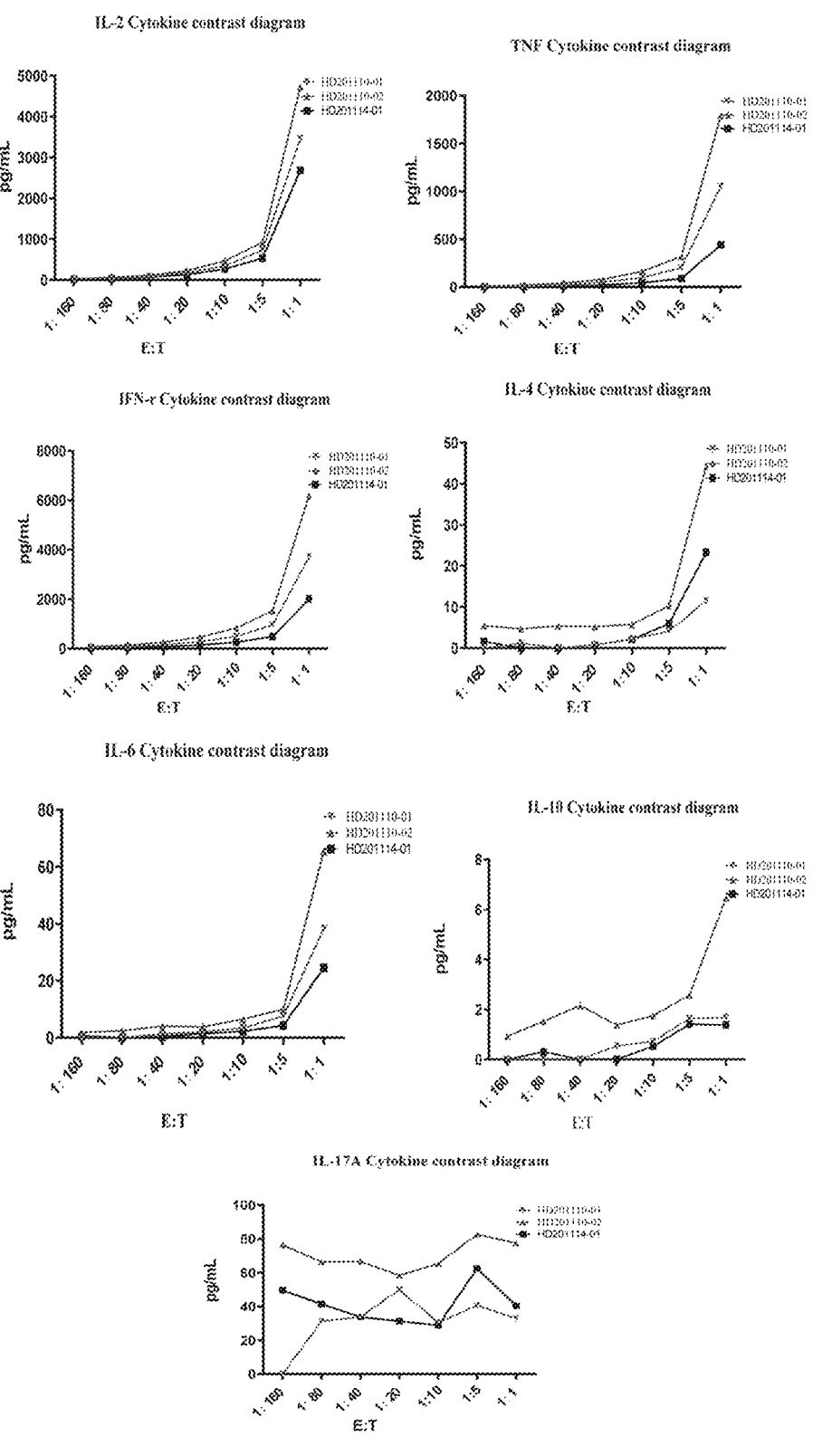
FIG. 17 is a diagram showing cytokine secretion of 3 batches of CD19×22 CAR-Ts with different effector-to-target ratios, the ordinate represents cytokine secretion, and the abscissa represents effector-to-target ratio.

The secretion levels of cytokines in the cell supernatant were detected by CBA (Cytometric Bead Array). After incubating CD19×22 CAR-T with positive cells, the single $CD3^+CAR^+$ release of Th1-type cytokines (IL-2, TNF, IFN-γ) was significant (>1.7 fg), while the single $^+CAR^+$ release of Th2-type cytokines (IL-4, IL-6, IL-10) and Th17-type cytokines (IL-17A) was very low (<0.3 fg). According to the analysis of the results in FIG. 17, it can be seen that CD19×22 CAR-T has stable, specific and good cytokine secretion function. IL-4/IL-6/IL-2/TNF-α/IFN-γ increased significantly.

Example 8 In Vivo Efficacy Study 8.1 Study on Efficacy of CD19×22 CAR-T in Tumor-Bearing Immunodeficient Mice Using tumor-bearing mice with B-lineage acute lymphoblastic leukemia (Nalm6) as the experimental system, the inhibitory effect of CD19×22 CAR-T on tumor cell proliferation in mice was evaluated.

Experimental Method:

1) Screening and grouping: 1 day after intravenous inoculation of $0.5×10^6$ Nalm6 cells in each of 80 female NCG mice, 57 animals were screened out and divided into 7 groups according to their body weight: cell protection solution group, Mock-T control group ($10×10^6$ cells/animal), CD19 CAR-T group ($0.2×10^6$ CAR-T cells/animal), CD22 CAR-T group ($0.2×10^6$ CAR-T cells/animal), and experimental group low- ($0.2×10^6$ CAR-T cells/animal), medium- ($1.0×10^6$ CAR-T cells/animal), and high- ($3.0×10^6$ CAR-T cells/animal) dose groups, wherein the CD19 CAR-T group and the CD22 CAR-T group had 3 and 4 animals, respectively, and they were no longer reported as valid data groups due to so few animals, and there were 10 animals in each of the remaining groups.

2) Mode of administration: All animals were given a single injection into the tail vein, and the day of the first dose was taken as D1.

3) Detection index: General clinical observation was performed twice a day, and the survival rate of each group was counted to D30. The animals were weighed once before grouping, and weighed on D3, D7, D10, D14, D17, D21, D24, and D28 after dosing. On D7, D14, D21, and D28, all animals were photographed for chemiluminescence signal by a Bruker small animal imager. On D3, D7, and D28, except for all animals on D28, half of the animals in each group were subjected to blood collection at each time point to detect lymphocyte subsets. On D2, D3, D5, D7, and D28, except for all animals on D28, half of the animals in each group were subjected to blood collection at each time point to detect the levels of cytokines IL-2, IL-4, IL-6, IL-10, TNF-α and IFN-γ.

Figure 18:
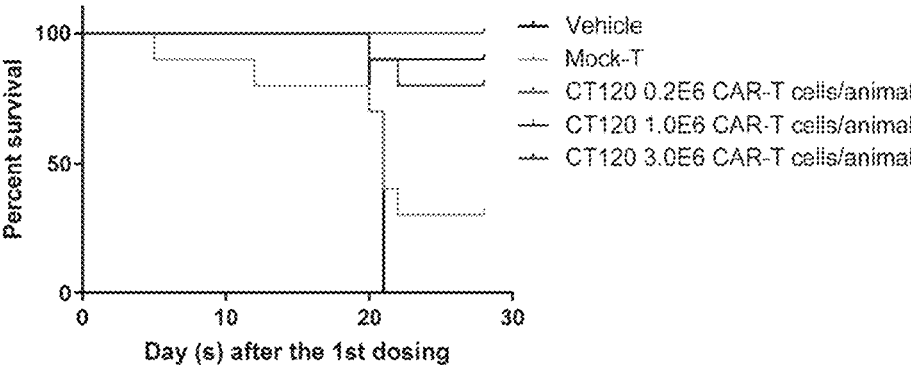
FIG. 18 shows the curve of survival rate of each group of animals during the experiment. Vehicle=cell protection solution group, Mock-T=Mock-T control group, CD19×22 CAR-T=test product group.

Results:

1) During the general clinical observation experiment, the animals in the cell protection solution group began to die from D20, and by D21, 10/10 animals in the cell protection solution group died, where the clinical manifestations of these animals before death included listlessness, arched back, stiffness, etc., which were presumably related to the proliferation of tumor cells. By D28, 10/10, 7/10, 0/10, 1/10, and 2/10 animals died in the cell protection solution group, Mock-T control group, and experimental group low-, medium- and high-dose groups, respectively. Compared with the cell protection solution group, animals in the low-dose, medium-dose and high-dose experimental groups had significantly improved survival rate (P<0.001). See FIG. 18 for the results of the survival rate curve of each group of animal during the experiment. During the experiment, the animals in the Mock-T control group, except animal No. Y20-6465 who died when taking blood on D5, began to die from D12, and by D28, 7/10 animals died, and their clinical manifestations before death included listlessness, arched back and stiffness, etc. It was speculated that the death of this group of animals was related to the proliferation of tumor cells. During the experiment, 1/10 and 2/10 of the animals in the medium- and high-dose experimental groups died by D28, respectively. Among others, the animal No. Y20-6509 in the medium-dose experimental group and the animal No. Y20-6520 in the high-dose the experimental group were found dead on D20, and their clinical manifestations before death were normal. The animal No. Y20-6519 in the high-dose experimental group was found dead on D28. Its clinical manifestations before death were arched back and rough coat. During the experiment, no tumor signal was detected in this animal, and its body weight began to drop from D21, 20.7 g, and dropped to 17.9 g on D24.

Figure 19:
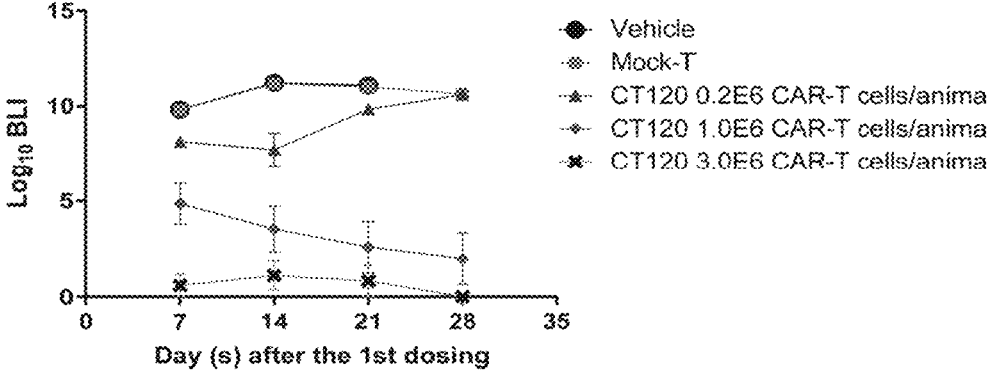
FIG. 19 is a graph showing changes in average biolumi-nescence intensity for each group of animals during the experiment. The ordinate represents the luminous intensity for the survived animals, and the abscissa represents the date. Vehicle=cell protection solution group, Mock-T=Mock-T control group, CD19×22 CAR-T=test product group.

2) Tumor cell proliferation (tumor cell bioluminescence intensity): During the experiment, the average bioluminescence intensity for the animals in the cell protection solution group showed an upward trend, and the average bioluminescence intensity on D7 and D14 were $6.96 \times 10^9$ and $1.74 \times 10^{11}$ P/S, respectively. During the experiment, the average bioluminescence intensities on D7, D14, D21, and D28 in the Mock-T control group were $6.99 \times 10^9$, $1.66 \times 10^{11}$, $1.55 \times 10^{11}$, and $6.36 \times 10^{10}$ P/S, respectively. During the experiment, the average bioluminescence intensities on D7, D14, D21, and D28 in the low-dose experimental group were $2.12 \times 10^8$, $5.59 \times 10^8$, $9.42 \times 10^9$, and $6.88 \times 10^{10}$ P/S, respectively. Compared with the cell protection solution group, the average bioluminescence intensities on D7 and D14 decreased by about 32 times and 310 times respectively, with statistical difference (P<0.001). Compared with the Mock-T control group, the average bioluminescence intensities on D7 and D14 decreased by about 32 times and 296 times respectively, with statistical difference (P<0.001). During the experiment, the average bioluminescence intensities on D7, D14, D21, and D28 in the medium-dose experimental group were $1.04 \times 10^7$, $5.51 \times 10^7$, $1.49 \times 10^9$, and $2.21 \times 10^{10}$ P/S, respectively. Compared with the cell protection solution group, the average bioluminescence intensities on D7 and D14 decreased by about 668 times and 3157 times respectively, with statistical difference (P<0.001). Compared with the Mock-T control group, the average bioluminescence intensities on D7, D14, D21, and D28 decreased by about 672 times, 3012 times, 104 times, and 28 times respectively, with statistical difference (P<0.001). During the experiment, no tumor signal was detected in the high-dose experimental group on D28, tumor signals were detected in 1/10, 2/10, and 1/9 animals on D7, D14, and D21, respectively, and the average bioluminescence intensities thereof were $9.51 \times 10^4$, $8.83 \times 10^4$, and $3.43 \times 10^6$, respectively. Compared with both the cell protection solution group and the Mock-T control group, there was statistical difference (P<0.001). FIG. 19 shows the changes in average bioluminescence intensity in each group of animals during the experiment in detail.

3) Lymphocyte subsets: During the experiment, CD45$^+$ cells were basically not detected in the peripheral blood of the animals in the cell protection solution group. In the Mock-T control group, continuous expansion was found, and by D28, the proportion of CD45$^+$CD3$^+$ cells was 12.8±9.7%. In the low-, medium- and high-dose experimental groups, continuous expansion of T cells was found in a dose-dependent manner, and by D28, the proportions of CD45$^+$CD3$^+$ cells in the peripheral blood of the animals in the low-, medium- and high-dose experimental groups were 0.2±0.5%, 23.5±30.3%, and 73.8±6.7%, respectively.

4) Cytokines: Elevated level of IFN-γ is generally considered to be the main marker of T cell activation. The cell protection solution group during the experiment. By D28, the levels of IFN-γ in the Mock-T control group and the low-, medium- and high-dose experimental groups rose to the highest levels, which were 165.26±175.17, 27.37±39.95, 48.07±75.85, and 377.53±271.88 pg/mL, respectively, with a dose-dependent manner in the experimental groups.

Under the experimental conditions, the levels of IL-2, IL-4, IL-6, IL-10 and TNF-α did not change significantly.

5) Body weight: by D17, the body weights of the animals in the cell protection solution group, Mock-T control group, and low-, medium- and high-dose experimental groups were 20.2±1.2, 20.6±1.3, 20.1±1.6, 20.2±1.0, and 19.7±0.8 g, respectively, and no abnormality was found in the body weight of animals in each group. During the period from D17 to D28, the body weight of the animals in the Mock-T control group began to decrease from D21, to D28, the body weight of the animals decreased to 18.6±3.6 g, and no abnormality was found in the body weight of the animals in the other groups.

Therefore, under the present experimental conditions, the human B-lineage acute lymphoblastic leukemia cell line Nalm6 could proliferate in NCG mice after intravenous inoculation. A single intravenous administration of CD19× 22 CAR-T at doses of 0.2, 1.0, and $3.0 \times 10^6$CAR-T cells per animal could, in a dose-dependent manner, eliminate tumor cells and prolong the survival of animals.

8.2. Tissue Distribution Test

This test investigated the distribution of CD19×22 CAR-T in NCG tumor-bearing mice after a single tail vein injection in the NCG tumor-bearing mice in the experimental group, to provide a reference for subsequent studies.

Study Method:

A total of 70 (60+10 surrogate animals) NCG mice, half male and half female, were used in the experiment. Human acute lymphocytes Nalm6 ($5 \times 10^5$ cells/animal) was transplanted intravenously to establish a tumor-bearing mouse model, and each animal was administered with $2 \times 10^6$ CAR-T cells by a single injection via the tail vein. The animals were euthanized at 168 h (7 d), 336 h (14 d), 672 h (28 d), 1008 h (42 d), 1344 h (56 d), and 1704 h (71 d) after dosing individually, 5 animals/sex at each time point, and whole blood (EDTA-K$_2$ anticoagulation), brain, spinal cord (cervical), femoral bone marrow, skeletal muscle, ovary/testis, abdominal organs (stomach, small intestine, liver, kidney, spleen), thoracic organs (heart, lungs) and other tissues were collected. 120 h (5 d), 240 h (10 d), 408 h (17 d), 504 h (21 d), 840 h (35 d), 1176 h (49 d), and 1272 h (53 d) after dosing, orbital blood samples were collected, 5 animals/sex for all time points, except for 3 animals/sex at three time points including 408 h (17 d), 504 h (21 d), and 840 h (35 d), to carry out flow cytometry on the CAR-T cells (CD3$^+$, CD22 antibody$^+$) and tumor cells (CD19$^+$).

Study results and conclusion: This report described the relevant data before 28 days; the number of DNA copies of CD19×22 CAR-Ts in each tissue and whole blood was detected by q-PCR, and the lower limit of quantification of the method was 100 copies/μg DNA; the q-PCR results showed that after a single tail vein injection of CD19×22 CAR-T into the NCG tumor-bearing mice, the CAR-T DNA content in the total tissue DNAs increased over time, the drug CAR-T cells were distributed throughout the body, the CAR-T cells were distributed in macroscopic tissues with abundant blood flow 7 days after dosing, and CAR-T DNAs could be detected in all tissues 28 days after dosing.

Figure 20:
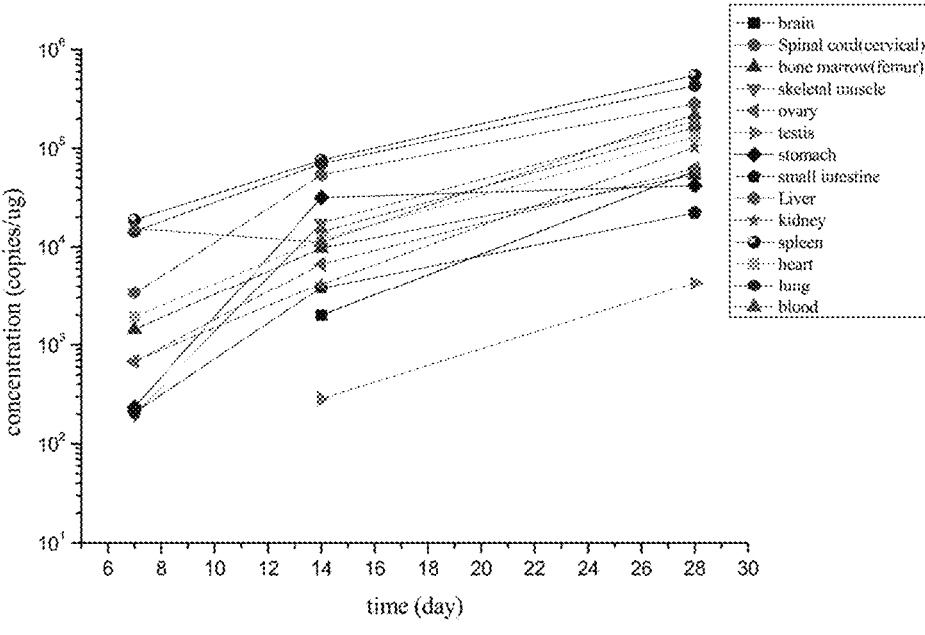
FIG. 20 shows the tissue distribution of CD19×22 CAR-Ts in experimental animals.

Flow cytometry was used to detect CAR-T cells (CD3+, CD22 antibody$^+$) and tumor cells (CD19$^+$), and the results showed that by D28 after dosing, there were few tumor cells (CD19$^+$) in the peripheral blood, almost undetectable; and the proportion of CAR-T cells (CD3$^+$, CD22 antibody$^+$) increased over time. See FIG. 20 for details.

Example 9 Exploratory Clinical Study

An exploratory clinical study on CD19×22 CAR-T cell therapy products was conducted to investigate the safety and primary efficacy of CAR-T cells modified by this sequence in treatment of B-cell non-Hodgkin's lymphoma (B-NHL) and B-lineage acute lymphoblastic leukemia (B-ALL), and also explore their pharmacokinetic (PK) profile in the human body. The study followed GCP principles in terms of investigators and research institutions, trial protocols, ethical review and informed consent processes, subject enrollment screening, adverse event reporting and processing, and summary and statistical analysis of trial data. Effective CAR-T cells were CD3$^+$ CAR$^+$ cells, and their infusion dose unit was CD3$^+$ CAR$^+$ cells/kg. The study adopted the dose escalation design principle. According to the CAR-T cell therapeutic dose, subjects with B-cell non-Hodgkin lymphoma (B-NHL) were divided into 3 dose groups: $1.0 \times 10^6$ CD3$^+$ CAR$^+$ cells/kg, $2.0 \times 10^6$ CD3$^+$ CAR$^+$ cells/kg and $3.0 \times 10^6$ CD3$^+$ CAR$^+$ cells/kg; and B-ALL subjects were divided into 2 dose groups: $0.5 \times 10^6$ CD3$^+$ CAR$^+$ cells/kg and $1.0 \times 10^6$ CD3$^+$ CAR$^+$ cells/kg.

Figure 21:
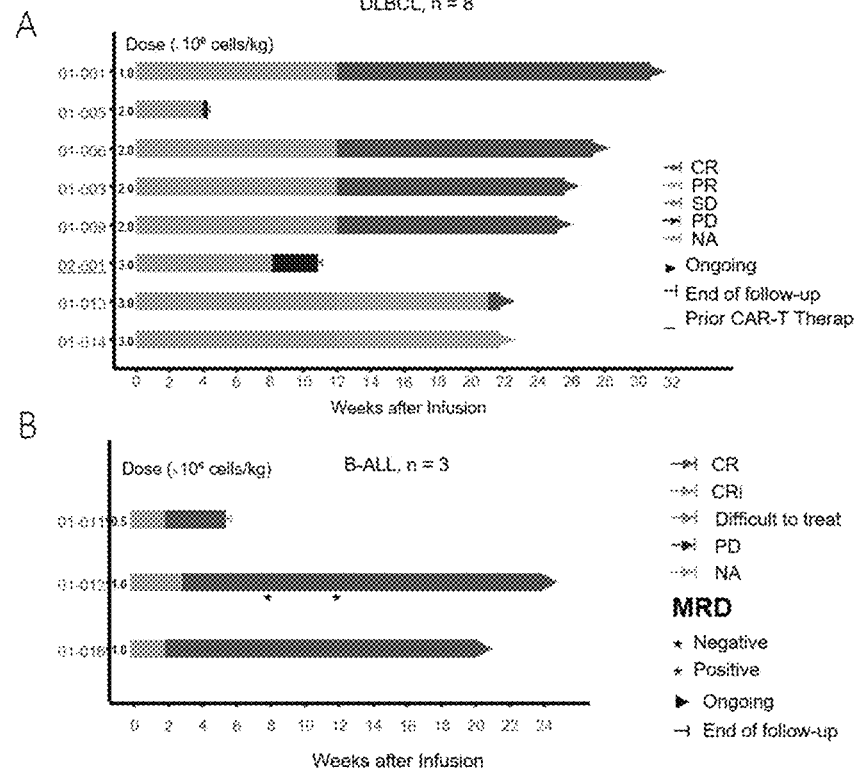
FIG. 21A shows the efficacy results of different doses of CAR-T cells in B-NHL subjects at different time points after CAR-T cell infusion.
FIG. 21B shows the efficacy results of different doses of CAR-T cells in B-ALL subjects at different time points after CAR-T cell infusion.

As of June 2021, 11 subjects (No. 01-001, 01-003, 01-005, 01-006, 01-009, 02-001, 01-013, 01-014, 01-011, 01-012 and 01-016 respectively), including 8 subjects with B-cell non-Hodgkin lymphoma (B-NHL) and 3 subjects with B-ALL, received CAR-T cell infusion. The 8-month overall response rate (ORR) of these 11 subjects after CAR-T cell infusion was 81.8% (9/11); and the complete response (CR) of the subjects was 72.7% (8/11). The results are shown in FIG. 21.

Example 10 In Vivo Pharmacokinetic Analysis of Subjects

R 3.6.2 software PKNCA package was used to further analyze the CAR in the peripheral blood of the 11 subjects who received CAR-T cell infusion described in Example 9, and the PK-related parameters were calculated. The results are shown in Table 2. In Table 2, the drug peak concentration ($C_{max}$) represents the highest blood concentration reached by the DNA copies, the time to peak ($T_{max}$) represents the time it takes for the DNA copies to reach $C_{max}$, and $AUC_{0-28}$ represents the area under the concentration-time curve from D0 to D28. $AUC_{0-last}$ represents the area under the concentration-time curve from day 0 to the last observation time point.

TABLE 2

Pharmacokinetic analysis results of CAR-T cells

| | | B-NHL | | | B-ALL | |
|---|---|---|---|---|---|---|
| PK Parameter | | $1.0 \times 10^6$ CD3$^+$ CAR$^+$ cells/kg (n = 1) | $2.0 \times 10^6$ CD3$^+$ CAR$^+$ cells/kg (n = 4) | $3.0 \times 10^6$ CD3$^+$ CAR$^+$ cells/kg (n = 3) | $0.5 \times 10^6$ CD3$^+$ CAR$^+$ cells/kg (n = 1) | $1.0 \times 10^6$ CD3$^+$ CAR$^+$ cells/kg (n = 2) |
| $T_{max}$ | Median | 21.0 | 12.5 | 14.0 | 21.0 | 12.5 |
| (days) | Min, Max | 21.0, 21.0 | 11.0, 24.0 | 14.0, 21.0 | 21.0, 21.0 | 11.0, 14.0 |
| $C_{max}$ | Median | 70200.0 | 44423.5 | 59875.0 | 152137.0 | 73474.5 |
| (copy number/ | Min, Max | 70200.0, 70200.0 | 21966.0, 52875.0 | 21996.0, 97200.0 | 152137.0, 152137.0 | 45749.0, 101200.0 |
| µg DNA) | Geometric mean | 70200.0 | 43697.5 | 50398.6 | 152137.0 | 68042.6 |
| $AUC_{0-28}$ | Median | 900064.0 | 314116.9 | 545294.0 | 1977077.6 | 827054.8 |
| (days × copy | Min, Max | 900064.0, 900064.0 | 183618.5, 631350.5 | 228538.5, 905254.0 | 1977077.6, 1977077.6 | 443364.3, 1210745.3 |
| number/µg DNA) | Geometric mean | 900064.0 | 327032.8 | 483022.7 | 1977077.6 | 732667.2 |
| $AUC_{0-last}$ | Median | 1240261.7 | 675212.7 | 1335959.6 | 1977077.6 | 1682277.1 |
| (days × copy | Min, Max | 1240261.7, 1240261.7 | 418723.0, 1260345.5 | 228297.5, 2573617.4 | 1977077.6, 1977077.6 | 581969.4, 2782584.8 |
| number/µg DNA) | Geometric mean | 1240261.7 | 674457.9 | 922457.1 | 1977077.6 | 1272548.4 |

The results showed that after the B-NHL subjects received cell infusion of $1.0 \times 10^6$ CD3$^+$ CAR$^+$ cells/kg, $2.0 \times 10^6$ CD3$^+$ CAR$^+$ cells/kg and $3.0 \times 10^6$ CD3$^+$ CAR$^+$ cells/kg dose group, the median time to peak for DNA copy number was 21 days, 12.5 days, and 14 days, respectively, the median peak values were 70200.0 copies/μg DNA, 35087.0 copies/μg DNA, and 59875.0 copies/μg DNA, respectively, and the geometric means of the peak values were 70200 copies/μg DNA, 34586.2 copies/μg DNA and 50398.6 copies/μg DNA, respectively. After the B-ALL subjects received cell infusion of $0.5 \times 10^6$ CD$^+$ CAR$^+$ cells/kg and $1.0 \times 10^6$ CD3$^+$ CAR$^+$ cells/kg dose group, the median peak time for DNA copy number was 21.0 days and 12.5 days, the median peak values were 152137.0 copies/μg DNA and 73474.5 copies/μg DNA, and the geometric means of the peak values were 152137.0 copies/μg DNA and 68042.6 copies/μg DNA.

Some of the amino acid and nucleic acid sequences appearing herein and in the accompanying drawings are listed below:

```
CD19-62 VH nucleic acid sequence (SEQ ID NO: 1):
ATGGCCGAAGTGCAGCTGGTGCAGTCTGGGGCAGAGGTGAAAAAGCCCGGGGAG

TCTCTGAAGATCTCCTGTAAGGGGTCTGGATACAGCTTTACCAACTCCTGGATCGGAT

GGGTGCGCCAGATGCCCGGGAAAGGCCTGGAGTGGATGGGACTCATTTACCCTGATG

ACTCTGATACCAGATACAGCCCATCCTTCCAAGGCCAGGTCACCATCTCAGCCGACAG

CGCCATCAACACCGCCTACCTGCAGTGGAGCAGCCTGAAGGCCTCGGACACCGCCAT

GTATTACTGTGCGCGCCAGTCTACCTACATCTACGGTGGTTACTACGATACCTGGGGTC

AAGGTACTCTGGTGACCGTCTCCTCA

CD19-62 VH protein sequence (SEQ ID NO: 2)
MAEVQLVQSGAEVKKPGESLKISCKGSGYSFTNSWIGWVRQMPGKGLEWMGLIYPD

DSDTRYSPSFQGQVTISADSAINTAYLQWSSLKASDTAMYYCARQSTYIYGGYYDTWGQ

GTLVTVSS

CD19-62 VL nucleic acid sequence (SEQ ID NO: 3)
CAGTCTGTCGTGACGCAGCCGCCCTCAGTGTCTGGGGCCCCAGGGCAGAGGGTC

ACCATCTCCTGCACTGGGAGCAGCTCCAACATCGGGGCAGGTTATGATGTACACTGGT

ACCAGCAACTTCCAGGAACAGCCCCCAAACTCCTCATCTATGAGAACACCAATCGGC

CCTCAGGGGTCCCTGACCGATTCTCTGGCTCCAAGTCTGGCACCTCAGCCTCCCTGGC

CATCACTGGGCTCCAGGCTGAGGATGAGGCTGATTATTACTGCCAGTCCTATGACAGC

AGCCTGAGTGGTTGGAGGGTGTTCGGCGGAGGGACCAAGCTGACCGTCCTAGGT

CD19-62 VL protein sequence (SEQ ID NO: 4)
QSVVTQPPSVSGAPGQRVTISCTGSSSNIGAGYDVHWYQQLPGTAPKLLIYENTNRPS

GVPDRFSGSKSGTSASLAITGLQAEDEADYYCQSYDSSLSGWRVFGGGTKLTVLG

CD19-78 VL nucleic acid sequence (SEQ ID NO: 5)
CAGGCTGTGCTGACTCAGCCACCCTCGGTGTCTGAAGCCCCCAGGCAGAGGGTC

ACCATCTCCTGTTCTGGAAGCAGCTCCAACATCGGAAATAATGCTGTAAGCTGGTACC

AGCAGCTCCCAGGAAAGGCTCCCAAACTCCTCATCTATTATGATGATCTGCTCCCCTC

AGGGGTCTCTGACCGATTCTCTGGCTCCAAGTCTGGCACCTCAGCCTCCCTGGCCATC

AGTGGGCTCCAGTCTGAGGATGAGGCTGATTATTACTGTGCAGCATGGGATGACAGCC

TGAATGGTTGGGTGTTCGGCGGAGGGACCAAGGTCACCGTCCTAGGT

CD19-78 VL protein sequence (SEQ ID NO: 6)
QAVLTQPPSVSEAPRQRVTISCSGSSSNIGNNAVSWYQQLPGKAPKLLIYYDDLLPSGV

SDRFSGSKSGTSASLAISGLQSEDEADYYCAAWDDSLNGWVFGGGTKVTVLG

CD19-78 VH nucleic acid sequence (SEQ ID NO: 7)
GAGGTGCAGCTGGTGCAGTCTGGAGCAGAGGTGAAAAAGCCCGGGGAGTCTCTG

AAGATCTCCTGTAAGGGGTTCTGGATACAGCTTTACCAGCTACTGGATCGGCTGGGTGC

GCCAGATGCCCGGGAAAGGCCTGGAGTGGATGGGGATCATCTATCCTGGTGACTCTG

ATACCAGATACAGCCCGTCCTTCCAAGGCCAGGTCACCATCTCAGCCGACAAGTCCAT

CAGCACCGCCTACCTGCAGTGGAGCAGCCTGAAGGCCTCGGACACCGCCATGTATTA
```

-continued

CTGTGCGCGCCTGTCTTACTCTTGGTCTTCTTGGTACTGGGATTTCTGGGGTCAAGGTA

CTCTGGTGACCGTCTCCTCA

CD19-78 VH protein sequence (SEQ ID NO: 8)
EVQLVQSGAEVKKPGESLKISCKGSGYSFTSYWIGWVRQMPGKGLEWMGIIYPGDS

DTRYSPSFQGQVTISADKSISTAYLQWSSLKASDTAMYYCARLSYSWSSWYWDFWGQG

TLVTVSS

CD22-80 VH nucleic acid sequence (SEQ ID NO: 9)
CAGGTGCAGCTGCAGGAGTCGGGCCCAGGACTGGTGAAGCCTTCGGGGACCCTG

TCCCTCACCTGCGCTGTCTCTGGTGGCTCCATCAGCAGTAGTAACTGGTGGAGTTGGG

TCCGCCAGCCCCCAGGGAAGGGGCTGGAGTGGATTGGGGAAATCTATCATAGTGGGA

GCACCAACTACAACCCGTCCCTCAAGAGTCGAGTCACCATATCAGTAGACAAGTCCA

AGAACCAGTTCTCCCTGAAGCTGAGCTCTGTGACCGCCGCGGACACGGCGGTGTACT

ACTGCGCCAGACTTCCTGGATACGAGTCAGCTTTCGACATATGGGGTCAGGGTACAAT

GGTCACCGTCAGCTCA

CD22-80 VH protein sequence (SEQ ID NO: 10)
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARLPGYESAFDIWGQGTMVTV

SS

CD22-80 VL nucleic acid sequence (SEQ ID NO: 11)
GAAATTGTGTTGACGCAGTCTCCAGGCACCCTGTCTTTGTCTCCAGGGGAAAGAG

CCACCCTCTCCTGCAGGGCCAGTCAGAGTGTTAGCAGCAGCTACTTAGCCTGGTACC

AGCAGAAACCTGGCCAGGCTCCCAGGCTCCTCATCTATGGTGCATCCAGCAGGGCCA

CTGGCATCCCAGACAGGTTCAGTGGCAGTGGGTCTGGGACAGACTTCACTCTCACCA

TCAGCAGACTGGAGCCTGAAGATTTTGCAGTGTATTACTGTCAGCAGGCCGGACTCTT

CCCTTACACTTTTGGCGGAGGGACCAAGGTTGAGATCAAA

CD22-80 VL protein sequence (SEQ ID NO: 12)
EIVLTQSPGTLSLSPGERATLSCRASQSVSSSYLAWYQQKPGQAPRLLIYGASSRATGIP

DRFSGSGSGTDFTLTISRLEPEDFAVYYCQQAGLFPYTFGGGTKVEIK

CD22-28 VH nucleic acid sequence (SEQ ID NO: 13)
CAGGTGCAGCTGCAGGAGTCGGGCCCAGGACTGGTGAAGCCTTCGGAGACCCTG

TCCCTCACCTGCACTGTCTCTGGTGGCTCCATCAGTAGTTACTACTGGAGCTGGATCC

GGCAGCCCGCCGGGAAGGGACTGGAGTGGATTGGGCGTATCTATACCAGTGGGAGCA

CCAACTACAACCCCTCCCTCAAGAGTCGAGTCACCATGTCAGTAGACACGTCCAAGA

ACCAGTTCTCCCTGAAGCTGAGCTCTGTGACCGCCGCGGACACGGCGGTGTACTACT

GCGCCAGAGACTTGTACAGAGATGGAATGGACGTATGGGGCCAGGGAACAACTGTCA

CCGTCAGCTCA

CD22-28 VH protein sequence (SEQ ID NO: 14)
QVQLQESGPGLVKPSETLSLTCTVSGGSISSYYWSWIRQPAGKGLEWIGRIYTSGSTN

YNPSLKSRVTMSVDTSKNQFSLKLSSVTAADTAVYYCARDLYRDGMDVWGQGTTVTVS

S

CD22-28 VL nucleic acid sequence (SEQ ID NO: 15)
GACATCCAGATGACCCAGTCTCCTTCCACCCTGTCTGCATCTGTAGGAGACAGAGT

CACCATCACTTGCCGGGCCAGTCAGAGTATTAGTAGCTGGTTGGCCTGGTATCAGCAG

-continued

AAACCAGGGAAAGCCCCTAAGCTCCTGATCTCCGATGCCTCCAGTTTGGAAAGTGGG

GTCCCATCAAGGTTCAGCGGCAGTGGATCTGGGACAGAATTCACTCTCACCATCAGC

AGCCTGCAGCCTGATGATTTTGCAACTTATTACTGCCAGCAGGCCAATACCTACTCTCC

TACTTTTGGCGGAGGGACCAAGGTTGAGATCAAA

CD22-28 VL protein sequence (SEQ ID NO: 16)
DIQMTQSPSTLSASVGDRVTITCRASQSISSWLAWYQQKPGKAPKLLISDASSLESGVP

SRFSGSGSGTEFTLTISSLQPDDFATYYCQQANTYSPTFGGGTKVEIK

Linker 1 nucleic acid sequence (SEQ ID NO: 17)
GGTGGTGGTGGTAGCGGCGGCGGCGGCTCTGGTGGTGGTGGATCC Linker 1 protein sequence (SEQ ID NO: 18)
GGGGSGGGGSGGGGS Linker 2 nucleic acid sequence (SEQ ID NO: 19)
GGCGGAGGTGGGTCC Linker 2 protein sequence (SEQ ID NO: 20)
GGGGS Linker 3 nucleic acid sequence (SEQ ID NO: 21)
GGCGGAGGTGGGTCCGGTGGCGGGGGAAGCGGAGGCGGAGGGAGCGGAGGAGG

GGGATCTGGAGGCGGTGGGTCT

Linker 3 protein sequence (SEQ ID NO: 22)
GGGGSGGGGSGGGGSGGGGSGGGGS

Linker 4 nucleic acid sequence (SEQ ID NO: 23)
GGCAGCACCAGCGGCTCCGGCAAGCCTGGCTCTGGCGAGGGCAGCACAAAGGGA Linker 4 protein sequence (SEQ ID NO: 24)
GSTSGSGKPGSGEGSTKG CD8a hinge nucleic acid sequence (SEQ ID NO: 25)
ACTACTACCCCTGCACCTAGGCCTCCCACCCCAGCCCCAACAATCGCCAGCCAGC

CTCTGTCTCTGCGGCCCGAAGCCTGTAGACCTGCTGCCGGCGGAGCCGTGCACACCA

GAGGCCTGGACTTCGCCTGCGAC

CD8a hinge protein sequence (SEQ ID NO: 26)
TTTPAPRPPTPAPTIASQPLSLRPEACRPAAGGAVHTRGLDFACD CD8a TM nucleic acid sequence (SEQ ID NO: 27)
ATCTACATCTGGGCCCCTCTGGCCGGCACCTGTGGCGTGCTGCTGCTGAGCCTGGT

GATCACCCTGTACTGC

CD8a TM protein sequence (SEQ ID NO: 28)
IYIWAPLAGTCGVLLLSLVITLYC 4-1BB intracellular domain (IC) nucleic acid sequence
(SEQ ID NO: 29)
AAACGGGGCAGAAAGAAACTCCTGTATATATTCAAACAACCATTTATGAGACCAGT

ACAAACTACTCAAGAGGAAGATGGCTGTAGCTGCCGATTTCCAGAAGAAGAAGAAG

GAGGATGTGAACTG 4-1BB intracellular domain (IC) sequence (SEQ ID NO: 30)
KRGRKKLLYIFKQPFMRPVQTTQEEDGCSCRFPEEEEGGCEL CD3z intracellular signaling domain nucleic acid sequence
(SEQ ID NO: 31)
AGAGTGAAGTTCAGCAGATCCGCCGACGCCCCTGCCTACCAGCAGGGACAGAAC

CAGCTGTACAACGAGCTGAACCTGGGCAGACGGGAAGAGTACGACGTGCTGGACAA

GCGGAGAGGCCGGGACCCCGAGATGGGCGGAAAGCCCAGACGGAAGAACCCCCAG

-continued

GAAGGCCTGTATAACGAACTGCAGAAAGACAAGATGGCCGAGGCCTACAGCGAGATC

GGCATGAAGGGCGAGCGGAGGCGCGGCAAGGGCCACGATGGCCTGTACCAGGGCCT

GAGCACCGCCACCAAGGACACCTACGACGCCCTGCACATGCAGGCCCTGCCCCCCAG

A

CD3z intracellular signaling domain sequence (SEQ ID NO: 32)
RVKFSRSADAPAYQQGQNQLYNELNLGRREEYDVLDKRRGRDPEMGGKPRRKNPQE

GLYNELQKDKMAEAYSEIGMKGERRRGKGHDGLYQGLSTATKDTYDALHMQALPPR

T2A nucleic acid sequence (SEQ ID NO: 33)
GAGGGAAGGGGCAGCTTATTAACATGTGGCGATGTGGAAGAGAACCCCGGTCCC T2A protein sequence (SEQ ID NO: 34)
EGRGSLLTCGDVEENPGP CSF2RA signal nucleic acid sequence (SEQ ID NO: 35)
ATGCTGCTGCTCGTGACCTCTTTACTGTTATGTGAGCTGCCCCACCCCGCTTTTTTA

CTGATCCCT

CSF2RA signal protein sequence (SEQ ID NO: 36)
MLLLVTSLLLCELPHPAFLLIP tEGFR nucleic acid sequence (SEQ ID NO: 37)
CGTAAGGTGTGTAACGGAATCGGCATTGGCGAGTTCAAGGACTCTTTAAGCATCA

ACGCCACAAACATCAAGCACTTCAAGAATTGTACCTCCATCAGCGGCGATTTACACAT

TCTCCCCGTGGCTTTTCGTGGCGATTCCTTCACCCACACCCCCCCTCTGGACCCCCAA

GAGCTGGACATTTTAAAAACCGTGAAGGAGATCACCGGCTTTCTGCTGATCCAAGCTT

GGCCCGAGAATCGTACCGACCTCCACGCCTTCGAGAATTTAGAGATTATTCGTGGAAG

GACCAAGCAGCACGGCCAGTTCTCTTTAGCCGTCGTGTCTTTAAACATTACCAGCCTC

GGTTTAAGGTCTTTAAAGGAGATTAGCGACGGCGACGTGATCATCTCCGGCAACAAG

AACCTCTGCTACGCCAACACCATCAACTGGAAGAAGCTGTTCGGAACCAGCGGCCAA

AAGACCAAGATCATCAGCAATCGTGGAGAGAACTCTTGTAAGGCCACTGGTCAAGTT

TGCCACGCCCTCTGTAGCCCCGAAGGATGTTGGGGCCCCGAGCCTAGGGACTGTGTT

AGCTGCAGAAACGTGAGCAGAGGCAGAGAGTGTGTGGACAAATGCAATTTACTGGA

AGGAGAGCCTAGGGAGTTCGTGGAGAACAGCGAATGTATCCAGTGCCACCCCGAGTG

TTTACCTCAAGCCATGAACATCACTTGTACCGGAAGGGGCCCCGATAACTGCATCCAA

TGCGCCCACTACATCGACGGACCCCACTGCGTGAAAACTTGTCCCGCCGGAGTGATG

GGAGAGAATAACACTTTAGTGTGGAAGTACGCCGACGCTGGCCACGTCTGCCATCTG

TGCCACCCCAACTGTACCTACGGCTGCACTGGTCCCGGTTTAGAGGGATGTCCTACCA

ACGGCCCCAAGATCCCCTCCATCGCCACCGGAATGGTGGGCGCTCTGTTATTACTGCT

GGTGGTGGCTCTGGGCATCGGTTTATTCATG tEGFR protein sequence (SEQ ID NO: 38)
RKVCNGIGIGEFKDSLSINATNIKHFKNCTSISGDLHILPVAFRGDSFTHTPPLDPQELDI

LKTVKEITGFLLIQAWPENRTDLHAFENLEIIRGRTKQHGQFSLAVVSLNITSLGLRSLKEIS

DGDVIISGNKNLCYANTINWKKLFGTSGQKTKIISNRGENSCKATGQVCHALCSPEGCWG

PEPRDCVSCRNVSRGRECVDKCNLLEGEPREFVENSECIQCHPECLPQAMNITCTGRGPD

NCIQCAHYIDGPHCVKTCPAGVMGENNTLVWKYADAGHVCHLCHPNCTYGCTGPGLEG

CPTNGPKIPSIATGMVGALLLLLVVALGIGLFM

-continued

1# CAR nucleic acid sequence (SEQ ID NO: 39)
ATGGCCCTGCCTGTGACAGCTCTGCTCCTCCCTCTGGCCCTGCTGCTCCATGCCGC

CAGACCCCAGTCTGTCGTGACGCAGCCGCCCTCAGTGTCTGGGGCCCCAGGGCAGAG

GGTCACCATCTCCTGCACTGGGAGCAGCTCCAACATCGGGGCAGGTTATGATGTACAC

TGGTACCAGCAACTTCCAGGAACAGCCCCCAAACTCCTCATCTATGAGAACACCAATC

GGCCCTCAGGGGTCCCTGACCGATTCTCTGGCTCCAAGTCTGGCACCTCAGCCTCCCT

GGCCATCACTGGGCTCCAGGCTGAGGATGAGGCTGATTATTACTGCCAGTCCTATGAC

AGCAGCCTGAGTGGTTGGAGGGTGTTCGGCGGAGGGACCAAGCTGACCGTCCTAGG

TGGTGGTGGTGGTAGCGGCGGCGGCGGCTCTGGTGGTGGTGGATCCATGGCCGAAGT

GCAGCTGGTGCAGTCTGGGGCAGAGGTGAAAAAGCCCGGGGAGTCTCTGAAGATCT

CCTGTAAGGGGTCTGGATACAGCTTTACCAACTCCTGGATCGGATGGGTGCGCCAGAT

GCCCGGGAAAGGCCTGGAGTGGATGGGACTCATTTACCCTGATGACTCTGATACCAG

ATACAGCCCATCCTTCCAAGGCCAGGTCACCATCTCAGCCGACAGCGCCATCAACACC

GCCTACCTGCAGTGGAGCAGCCTGAAGGCCTCGGACACCGCCATGTATTACTGTGCG

CGCCAGTCTACCTACATCTACGGTGGTTACTACGATACCTGGGGTCAAGGTACTCTGG

TGACCGTCTCCTCAGGCGGAGGTGGGTCCGGTGGCGGGGGAAGCGGAGGCGGAGGG

AGCGGAGGAGGGGGATCTGGAGGCGGTGGGTCTCAGGTGCAGCTGCAGGAGTCGGG

CCCAGGACTGGTGAAGCCTTCGGGGACCCTGTCCCTCACCTGCGCTGTCTCTGGTGG

CTCCATCAGCAGTAGTAACTGGTGGAGTTGGGTCCGCCAGCCCCCAGGGAAGGGGCT

GGAGTGGATTGGGGAAATCTATCATAGTGGGAGCACCAACTACAACCCGTCCCTCAA

GAGTCGAGTCACCATATCAGTAGACAAGTCCAAGAACCAGTTCTCCCTGAAGCTGAG

CTCTGTGACCGCCGCGGACACGGCGGTGTACTACTGCGCCAGACTTCCTGGATACGA

GTCAGCTTTCGACATATGGGGTCAGGGTACAATGGTCACCGTCAGCTCAGGTGGCGG

GGGCAGCGGCGGAGGCGGATCCGGAGGCGGAGGGAGTGAAATTGTGTTGACGCAGT

CTCCAGGCACCCTGTCTTTGTCTCCAGGGGAAAGAGCCACCCTCTCCTGCAGGGCCA

GTCAGAGTGTTAGCAGCAGCTACTTAGCCTGGTACCAGCAGAAACCTGGCCAGGCTC

CCAGGCTCCTCATCTATGGTGCATCCAGCAGGGCCACTGGCATCCCAGACAGGTTCAG

TGGCAGTGGGTCTGGGACAGACTTCACTCTCACCATCAGCAGACTGGAGCCTGAAGA

TTTTGCAGTGTATTACTGTCAGCAGGCCGGACTCTTCCCTTACACTTTTGGCGGAGGG

ACCAAGGTTGAGATCAAATTCGTGCCCGTGTTCCTGCCCGCCAAACCTACTACTACCC

CTGCACCTAGGCCTCCCACCCCAGCCCCAACAATCGCCAGCCAGCCTCTGTCTCTGCG

GCCCGAAGCCTGTAGACCTGCTGCCGGCGGAGCCGTGCACACCAGAGGCCTGGACTT

CGCCTGCGACATCTACATCTGGGCCCCTCTGGCCGGCACCTGTGGCGTGCTGCTGCTG

AGCCTGGTGATCACCCTGTACTGCAACCACCGGAACAAACGGGGCAGAAAGAAACT

CCTGTATATATTCAAACAACCATTTATGAGACCAGTACAAACTACTCAAGAGGAAGAT

GGCTGTAGCTGCCGATTTCCAGAAGAAGAAGAAGGAGGATGTGAACTGAGAGTGAA

GTTCAGCAGATCCGCCGACGCCCCTGCCTACCAGCAGGGACAGAACCAGCTGTACAA

CGAGCTGAACCTGGGCAGACGGGAAGAGTACGACGTGCTGGACAAGCGGAGAGGCC

GGGACCCCGAGATGGGCGGAAAGCCCAGACGGAAGAACCCCCAGGAAGGCCTGTAT

AACGAACTGCAGAAAGACAAGATGGCCGAGGCCTACAGCGAGATCGGCATGAAGGG

-continued

CGAGCGGAGGCGCGGCAAGGGCCACGATGGCCTGTACCAGGGCCTGAGCACCGCCA

CCAAGGACACCTACGACGCCCTGCACATGCAGGCCCTGCCCCCCAGA

1# CAR protein sequence (SEQ ID NO: 40)
MALPVTALLLPLALLLHAARPQSVVTQPPSVSGAPGQRVTISCTGSSSNIGAGYDVH

WYQQLPGTAPKLLIYENTNRPSGVPDRFSGSKSGTSASLAITGLQAEDEADYYCQSYDSS

LSGWRVFGGGTKLTVLGGGGGSGGGGSGGGGSMAEVQLVQSGAEVKKPGESLKISCKG

SGYSFTNSWIGWVRQMPGKGLEWMGLIYPDDSDTRYSPSFQGQVTISADSAINTAYLQW

SSLKASDTAMYYCARQSTYIYGGYYDTWGQGTLVTVSSGGGGSGGGGSGGGGSGGGG

SGGGGSQVQLQESGPGLVKPSGTLSLTCAVSGGSISSSNWWSWVRQPPGKGLEWIGEIYH

SGSTNYNPSLKSRVTISVDKSKNQFSLKLSSVTAADTAVYYCARLPGYESAFDIWGQGTM

VTVSSGGGGSGGGGSGGGGSEIVLTQSPGTLSLSPGERATLSCRASQSVSSSYLAWYQQK

PGQAPRLLIYGASSRATGIPDRFSGSGSGTDFTLTISRLEPEDFAVYYCQQAGLFPYTFGGG

TKVEIKFVPVFLPAKPTTTPAPRPPTPAPTIASQPLSLRPEACRPAAGGAVHTRGLDFACDI

YIWAPLAGTCGVLLLSLVITLYCNHRNKRGRKKLLYIFKQPFMRPVQTTQEEDGCSCRFP

EEEEGGCELRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKDTYDALHM

QALPPR*

2# CAR nucleic acid sequence (SEQ ID NO: 41)
ATGGCCCTGCCTGTGACAGCTCTGCTCCTCCCTCTGGCCCTGCTGCTCCATGCCGC

CAGACCCCAGGTGCAGCTGCAGGAGTCGGGCCCAGGACTGGTGAAGCCTTCGGGGA

CCCTGTCCCTCACCTGCGCTGTCTCTGGTGGCTCCATCAGCAGTAGTAACTGGTGGAG

TTGGGTCCGCCAGCCCCCAGGGAAGGGGCTGGAGTGGATTGGGGAAATCTATCATAG

TGGGAGCACCAACTACAACCCGTCCCTCAAGAGTCGAGTCACCATATCAGTAGACAA

GTCCAAGAACCAGTTCTCCCTGAAGCTGAGCTCTGTGACCGCCGCGGACACGGCGGT

GTACTACTGCGCCAGACTTCCTGGATACGAGTCAGCTTTCGACATATGGGGTCAGGGT

ACAATGGTCACCGTCAGCTCAGGTGGCGGGGGCAGCGGCGGAGGCGGATCCGGAGG

CGGAGGGGAGTGAAATTGTGTTGACGCAGTCTCCAGGCACCCTGTCTTTGTCTCCAGG

GGAAAGAGCCACCCTCTCCTGCAGGGCCAGTCAGAGTGTTAGCAGCAGCTACTTAGC

CTGGTACCAGCAGAAACCTGGCCAGGCTCCCAGGCTCCTCATCTATGGTGCATCCAGC

AGGGCCACTGGCATCCCAGACAGGTTCAGTGGCAGTGGGTCTGGGACAGACTTCACT

CTCACCATCAGCAGACTGGAGCCTGAAGATTTTGCAGTGTATTACTGTCAGCAGGCCG

GACTCTTCCCTTACACTTTTGGCGGAGGGACCAAGGTTGAGATCAAAGGCGGAGGTG

GGTCCGGTGGCGGGGGAAGCGGAGGCGGAGGGAGCGGAGGAGGGGGATCTGGAGG

CGGTGGGTCTCAGTCTGTCGTGACGCAGCCGCCCTCAGTGTCTGGGGCCCCAGGGCA

GAGGGTCACCATCTCCTGCACTGGGAGCAGCTCCAACATCGGGGCAGGTTATGATGTA

CACTGGTACCAGCAACTTCCAGGAACAGCCCCCAAACTCCTCATCTATGAGAACACC

AATCGGCCCTCAGGGGTCCCTGACCGATTCTCTGGCTCCAAGTCTGGCACCTCAGCCT

CCCTGGCCATCACTGGGCTCCAGGCTGAGGATGAGGCTGATTATTACTGCCAGTCCTA

TGACAGCAGCCTGAGTGGTTGGAGGGTGTTCGGCGGAGGGACCAAGCTGACCGTCC

TAGGTGGTGGTGGTGGTAGCGGCGGCGGCGGCTCTGGTGGTGGTGGATCCATGGCCG

AAGTGCAGCTGGTGCAGTCTGGGGCAGAGGTGAAAAAGCCCGGGGAGTCTCTGAAG

ATCTCCTGTAAGGGGTCTGGATACAGCTTTACCAACTCCTGGATCGGATGGGTGCGCC

AGATGCCCGGGAAAGGCCTGGAGTGGATGGGACTCATTTACCCTGATGACTCTGATAC

CAGATACAGCCCATCCTTCCAAGGCCAGGTCACCATCTCAGCCGACAGCGCCATCAA

CACCGCCTACCTGCAGTGGAGCAGCCTGAAGGCCTCGGACACCGCCATGTATTACTGT

GCGCGCCAGTCTACCTACATCTACGGTGGTTACTACGATACCTGGGGTCAAGGTACTC

TGGTGACCGTCTCCTCATTCGTGCCCGTGTTCCTGCCCGCCAAACCTACTACTACCCCT

GCACCTAGGCCTCCCACCCCAGCCCCAACAATCGCCAGCCAGCCTCTGTCTCTGCGG

CCCGAAGCCTGTAGACCTGCTGCCGGCGGAGCCGTGCACACCAGAGGCCTGGACTTC

GCCTGCGACATCTACATCTGGGCCCCTCTGGCCGGCACCTGTGGCGTGCTGCTGCTGA

GCCTGGTGATCACCCTGTACTGCAACCACCGGAACAAACGGGGCAGAAAGAAACTC

CTGTATATATTCAAACAACCATTTATGAGACCAGTACAAACTACTCAAGAGGAAGATG

GCTGTAGCTGCCGATTTCCAGAAGAAGAAGAAGGAGGATGTGAACTGAGAGTGAAG

TTCAGCAGATCCGCCGACGCCCCTGCCTACCAGCAGGGACAGAACCAGCTGTACAAC

GAGCTGAACCTGGGCAGACGGGAAGAGTACGACGTGCTGGACAAGCGGAGAGGCC

GGGACCCCGAGATGGGCGGAAAGCCCAGACGGAAGAACCCCCAGGAAGGCCTGTAT

AACGAACTGCAGAAAGACAAGATGGCCGAGGCCTACAGCGAGATCGGCATGAAGGG

CGAGCGGAGGCGCGGCAAGGGCCACGATGGCCTGTACCAGGGCCTGAGCACCGCCA

CCAAGGACACCTACGACGCCCTGCACATGCAGGCCCTGCCCCCCAGA

2# CAR protein sequence (SEQ ID NO: 42)
MALPVTALLLPLALLLHAARPQVQLQESGPGLVKPSGTLSLTCAVSGGSISSSNWWS

WVRQPPGKGLEWIGEIYHSGSTNYNPSLKSRVTISVDKSKNQFSLKLSSVTAADTAVYYC

ARLPGYESAFDIWGQGTMVTVSSGGGGSGGGGSGGGGSEIVLTQSPGTLSLSPGERATLS

CRASQSVSSSYLAWYQQKPGQAPRLLIYGASSRATGIPDRFSGSGSGTDFTLTISRLEPEDF

AVYYCQQAGLFPYTFGGGTKVEIKGGGGSGGGGSGGGGSGGGGSGGGGSQSVVTQPPS

VSGAPGQRVTISCTGSSSNIGAGYDVHWYQQLPGTAPKLLIYENTNRPSGVPDRFSGSKS

GTSASLAITGLQAEDEADYYCQSYDSSLSGWRVFGGGTKLTVLGGGGSGGGGSGGGG

SMAEVQLVQSGAEVKKPGESLKISCKGSGYSFTNSWIGWVRQMPGKGLEWMGLIYPDD

SDTRYSPSFQGQVTISADSAINTAYLQWSSLKASDTAMYYCARQSTYIYGGYYDTWGQG

TLVTVSSFVPVFLPAKPTTTPAPRPPTPAPTIASQPLSLRPEACRPAAGGAVHTRGLDFACDI

YIWAPLAGTCGVLLLSLVITLYCNHRNKRGRKKLLYIFKQPFMRPVQTTQEEDGCSCRFP

EEEEGGCELRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKDTYDALHM

QALPPR*

3# CAR nucleic acid sequence (SEQ ID NO: 43)
ATGGCCCTGCCTGTGACAGCTCTGCTCCTCCCTCTGGCCCTGCTGCTCCATGCCGC

CAGACCCCAGTCTGTCGTGACGCAGCCGCCCTCAGTGTCTGGGGCCCCAGGGCAGAG

GGTCACCATCTCCTGCACTGGGAGCAGCTCCAACATCGGGGCAGGTTATGATGTACAC

TGGTACCAGCAACTTCCAGGAACAGCCCCCAAACTCCTCATCTATGAGAACACCAATC

GGCCCTCAGGGGTCCCTGACCGATTCTCTGGCTCCAAGTCTGGCACCTCAGCCTCCCT

GGCCATCACTGGGCTCCAGGCTGAGGATGAGGCTGATTATTACTGCCAGTCCTATGAC

AGCAGCCTGAGTGGTTGGAGGGTGTTCGGCGGAGGGACCAAGCTGACCGTCCTAGG

TGGTGGTGGTGGTAGCGGCGGCGGCGGCTCTGGTGGTGGTGGATCCATGGCCGAAGT

GCAGCTGGTGCAGTCTGGGGCAGAGGTGAAAAAGCCCGGGGAGTCTCTGAAGATCT

CCTGTAAGGGGTCTGGATACAGCTTTACCAACTCCTGGATCGGATGGGTGCGCCAGAT

GCCCGGGAAAGGCCTGGAGTGGATGGGACTCATTTACCCTGATGACTCTGATACCAG

ATACAGCCCATCCTTCCAAGGCCAGGTCACCATCTCAGCCGACAGCGCCATCAACACC

GCCTACCTGCAGTGGAGCAGCCTGAAGGCCTCGGACACCGCCATGTATTACTGTGCG

CGCCAGTCTACCTACATCTACGGTGGTTACTACGATACCTGGGGTCAAGGTACTCTGG

TGACCGTCTCCTCAGGCGGAGGTGGGTCCGGTGGCGGGGGAAGCGGAGGCGGAGGG

AGCCAGGTGCAGCTGCAGGAGTCGGGCCCAGGACTGGTGAAGCCTTCGGGGACCCT

GTCCCTCACCTGCGCTGTCTCTGGTGGCTCCATCAGCAGTAGTAACTGGTGGAGTTGG

GTCCGCCAGCCCCCAGGGAAGGGGCTGGAGTGGATTGGGGAAATCTATCATAGTGGG

AGCACCAACTACAACCCGTCCCTCAAGAGTCGAGTCACCATATCAGTAGACAAGTCC

AAGAACCAGTTCTCCCTGAAGCTGAGCTCTGTGACCGCCGCGGACACGGCGGTGTAC

TACTGCGCCAGACTTCCTGGATACGAGTCAGCTTTCGACATATGGGGTCAGGGTACAA

TGGTCACCGTCAGCTCAGGTGGCGGGGGCAGCGGCGGAGGCGGATCCGGAGGCGGA

GGGAGTGAAATTGTGTTGACGCAGTCTCCAGGCACCCTGTCTTTGTCTCCAGGGGAA

AGAGCCACCCTCTCCTGCAGGGCCAGTCAGAGTGTTAGCAGCAGCTACTTAGCCTGG

TACCAGCAGAAACCTGGCCAGGCTCCCAGGCTCCTCATCTATGGTGCATCCAGCAGG

GCCACTGGCATCCCAGACAGGTTCAGTGGCAGTGGGTCTGGGACAGACTTCACTCTC

ACCATCAGCAGACTGGAGCCTGAAGATTTTGCAGTGTATTACTGTCAGCAGGCCGGA

CTCTTCCCTTACACTTTTGGCGGAGGGACCAAGGTTGAGATCAAATTCGTGCCCGTGT

TCCTGCCCGCCAAACCTACTACTACCCCTGCACCTAGGCCTCCCACCCCAGCCCCAAC

AATCGCCAGCCAGCCTCTGTCTCTGCGGCCCGAAGCCTGTAGACCTGCTGCCGGCGG

AGCCGTGCACACCAGAGGCCTGGACTTCGCCTGCGACATCTACATCTGGGCCCCTCT

GGCCGGCACCTGTGGCGTGCTGCTGCTGAGCCTGGTGATCACCCTGTACTGCAACCA

CCGGAACAAACGGGGCAGAAAGAAACTCCTGTATATATTCAAACAACCATTTATGAGA

CCAGTACAAACTACTCAAGAGGAAGATGGCTGTAGCTGCCGATTTCCAGAAGAAGAA

GAAGGAGGATGTGAACTGAGAGTGAAGTTCAGCAGATCCGCCGACGCCCCTGCCTAC

CAGCAGGGACAGAACCAGCTGTACAACGAGCTGAACCTGGGCAGACGGGAAGAGTA

CGACGTGCTGGACAAGCGGAGAGGCCGGGACCCCGAGATGGGCGGAAAGCCCAGAC

GGAAGAACCCCCAGGAAGGCCTGTATAACGAACTGCAGAAAGACAAGATGGCCGAG

GCCTACAGCGAGATCGGCATGAAGGGCGAGCGGAGGCGCGGCAAGGGCCACGATGG

CCTGTACCAGGGCCTGAGCACCGCCACCAAGGACACCTACGACGCCCTGCACATGCA

GGCCCTGCCCCCCAGA

3# CAR protein sequence (SEQ ID NO: 44)
MALPVTALLLPLALLLHAARPQSVVTQPPSVSGAPGQRVTISCTGSSSNIGAGYDVH

WYQQLPGTAPKLLIYENTNRPSGVPDRFSGSKSGTSASLAITGLQAEDEADYYCQSYDSS

LSGWRVFGGGTKLTVLGGGGSGGGGSGGGGSMAEVQLVQSGAEVKKPGESLKISCKG

SGYSFTNSWIGWVRQMPGKGLEWMGLIYPDDSDTRYSPSFQGQVTISADSAINTAYLQW

-continued

```
SSLKASDTAMYYCARQSTYIYGGYYDTWGQGTLVTVSSGGGGSGGGGSGGGGSQVQL

QESGPGLVKPSGTLSLTCAVSGGSISSSNWWSWVRQPPGKGLEWIGEIYHSGSTNYNPSL

KSRVTISVDKSKNQFSLKLSSVTAADTAVYYCARLPGYESAFDIWGQGTMVTVSSGGGG

SGGGGSGGGGSEIVLTQSPGTLSLSPGERATLSCRASQSVSSSYLAWYQQKPGQAPRLLIY

GASSRATGIPDRFSGSGSGTDFTLTISRLEPEDFAVYYCQQAGLFPYTFGGGTKVEIKFVPV

FLPAKPTTTPAPRPPTPAPTIASQPLSLRPEACRPAAGGAVHTRGLDFACDIYIWAPLAGTC

GVLLLSLVITLYCNHRNKRGRKKLLYIFKQPFMRPVQTTQEEDGCSCRFPEEEEGGCELR

VKFSRSADAPAYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQALPPR*
```

4# CAR nucleic acid sequence (SEQ ID NO: 45)
```
ATGGCCCTGCCTGTGACAGCTCTGCTCCTCCCTCTGGCCCTGCTGCTCCATGCCGC

CAGACCCCAGGTGCAGCTGCAGGAGTCGGGCCCAGGACTGGTGAAGCCTTCGGGGA

CCCTGTCCCTCACCTGCGCTGTCTCTGGTGGCTCCATCAGCAGTAGTAACTGGTGGAG

TTGGGTCCGCCAGCCCCCAGGGAAGGGGCTGGAGTGGATTGGGGAAATCTATCATAG

TGGGAGCACCAACTACAACCCGTCCCTCAAGAGTCGAGTCACCATATCAGTAGACAA

GTCCAAGAACCAGTTCTCCCTGAAGCTGAGCTCTGTGACCGCCGCGGACACGGCGGT

GTACTACTGCGCCAGACTTCCTGGATACGAGTCAGCTTTCGACATATGGGGTCAGGGT

ACAATGGTCACCGTCAGCTCAGGTGGCGGGGGCAGCGGCGGAGGCGGATCCGGAGG

CGGAGGGAGTGAAATTGTGTTGACGCAGTCTCCAGGCACCCTGTCTTTGTCTCCAGG

GGAAAGAGCCACCCTCTCCTGCAGGGCCAGTCAGAGTGTTAGCAGCAGCTACTTAGC

CTGGTACCAGCAGAAACCTGGCCAGGCTCCCAGGCTCCTCATCTATGGTGCATCCAGC

AGGGCCACTGGCATCCCAGACAGGTTCAGTGGCAGTGGGTCTGGGACAGACTTCACT

CTCACCATCAGCAGACTGGAGCCTGAAGATTTTGCAGTGTATTACTGTCAGCAGGCCG

GACTCTTCCCTTACACTTTTGGCGGAGGGACCAAGGTTGAGATCAAAGGCGGAGGTG

GGTCCGGTGGCGGGGGAAGCGGAGGCGGAGGGAGCCAGTCTGTCGTGACGCAGCCG

CCCTCAGTGTCTGGGGCCCCAGGGCAGAGGGTCACCATCTCCTGCACTGGGAGCAGC

TCCAACATCGGGGCAGGTTATGATGTACACTGGTACCAGCAACTTCCAGGAACAGCC

CCCAAACTCCTCATCTATGAGAACACCAATCGGCCCTCAGGGGTCCCTGACCGATTCT

CTGGCTCCAAGTCTGGCACCTCAGCCTCCCTGGCCATCACTGGGCTCCAGGCTGAGG

ATGAGGCTGATTATTACTGCCAGTCCTATGACAGCAGCCTGAGTGGTTGGAGGGTGTT

CGGCGGAGGGACCAAGCTGACCGTCCTAGGTGGTGGTGGTGGTAGCGGCGGCGGCG

GCTCTGGTGGTGGTGGATCCATGGCCGAAGTGCAGCTGGTGCAGTCTGGGGCAGAGG

TGAAAAAGCCCGGGGAGTCTCTGAAGATCTCCTGTAAGGGGTCTGGATACAGCTTTA

CCAACTCCTGGATCGGATGGGTGCGCCAGATGCCCGGGAAAGGCCTGGAGTGGATGG

GACTCATTTACCCTGATGACTCTGATACCAGATACAGCCCATCCTTCCAAGGCCAGGT

CACCATCTCAGCCGACAGCGCCATCAACACCGCCTACCTGCAGTGGAGCAGCCTGAA

GGCCTCGGACACCGCCATGTATTACTGTGCGCGCCAGTCTACCTACATCTACGGTGGT

TACTACGATACCTGGGGTCAAGGTACTCTGGTGACCGTCTCCTCATTCGTGCCCGTGTT

CCTGCCCGCCAAACCTACTACTACCCCTGCACCTAGGCCTCCCACCCCAGCCCCAACA

ATCGCCAGCCAGCCTCTGTCTCTGCGGCCCGAAGCCTGTAGACCTGCTGCCGGCGGA
```

-continued

GCCGTGCACACCAGAGGCCTGGACTTCGCCTGCGACATCTACATCTGGGCCCCTCTG

GCCGGCACCTGTGGCGTGCTGCTGCTGAGCCTGGTGATCACCCTGTACTGCAACCAC

CGGAACAAACGGGGCAGAAAGAAACTCCTGTATATATTCAAACAACCATTTATGAGAC

CAGTACAAACTACTCAAGAGGAAGATGGCTGTAGCTGCCGATTTCCAGAAGAAGAAG

AAGGAGGATGTGAACTGAGAGTGAAGTTCAGCAGATCCGCCGACGCCCCTGCCTACC

AGCAGGGACAGAACCAGCTGTACAACGAGCTGAACCTGGGCAGACGGGAAGAGTAC

GACGTGCTGGACAAGCGGAGAGGCCGGGACCCCGAGATGGGCGGAAAGCCCAGAC

GGAAGAACCCCCAGGAAGGCCTGTATAACGAACTGCAGAAAGACAAGATGGCCGAG

GCCTACAGCGAGATCGGCATGAAGGGCGAGCGGAGGCGCGGCAAGGGCCACGATGG

CCTGTACCAGGGCCTGAGCACCGCCACCAAGGACACCTACGACGCCCTGCACATGCA

GGCCCTGCCCCCCAGA

4# CAR protein sequence (SEQ ID NO: 46)
MALPVTALLLPLALLLHAARPQVQLQESGPGLVKPSGTLSLTCAVSGGSISSSNWWS

WVRQPPGKGLEWIGEIYHSGSTNYNPSLKSRVTISVDKSKNQFSLKLSSVTAADTAVYYC

ARLPGYESAFDIWGQGTMVTVSSGGGGSGGGGSGGGGSEIVLTQSPGTLSLSPGERATLS

CRASQSVSSSYLAWYQQKPGQAPRLLIYGASSRATGIPDRFSGSGSGTDFTLTISRLEPEDF

AVYYCQQAGLFPYTFGGGTKVEIKGGGGSGGGGSGGGGSQSVVTQPPSVSGAPGQRVTI

SCTGSSSNIGAGYDVHWYQQLPGTAPKLLIYENTNRPSGVPDRFSGSKSGTSASLAITGL

QAEDEADYYCQSYDSSLSGWRVFGGGTKLTVLGGGGSGGGGSGGGGSMAEVQLVQS

GAEVKKPGESLKISCKGSGYSFTNSWIGWVRQMPGKGLEWMGLIYPDDSDTRYSPSFQG

QVTISADSAINTAYLQWSSLKASDTAMYYCARQSTYIYGGYYDTWGQGTLVTVSSFVPV

FLPAKPTTTPAPRPPTPAPTIASQPLSLRPEACRPAAGGAVHTRGLDFACDIYIWAPLAGTC

GVLLLSLVITLYCNHRNKRGRKKLLYIFKQPFMRPVQTTQEEDGCSCRFPEEEEGGCELR

VKFSRSADAPAYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQALPPR*

5# CAR nucleic acid sequence (SEQ ID NO: 47)
ATGGCCCTGCCTGTGACAGCTCTGCTCCTCCCTCTGGCCCTGCTGCTCCATGCCGC

CAGACCCCAGTCTGTCGTGACGCAGCCGCCCTCAGTGTCTGGGGCCCCAGGGCAGAG

GGTCACCATCTCCTGCACTGGGAGCAGCTCCAACATCGGGGCAGGTTATGATGTACAC

TGGTACCAGCAACTTCCAGGAACAGCCCCCAAACTCCTCATCTATGAGAACACCAATC

GGCCCTCAGGGGTCCCTGACCGATTCTCTGGCTCCAAGTCTGGCACCTCAGCCTCCCT

GGCCATCACTGGGCTCCAGGCTGAGGATGAGGCTGATTATTACTGCCAGTCCTATGAC

AGCAGCCTGAGTGGTTGGAGGGTGTTCGGCGGAGGGACCAAGCTGACCGTCCTAGG

TGGTGGTGGTGGTAGCGGCGGCGGCGGCTCTGGTGGTGGTGGATCCATGGCCGAAGT

GCAGCTGGTGCAGTCTGGGGCAGAGGTGAAAAAGCCCGGGGAGTCTCTGAAGATCT

CCTGTAAGGGGTCTGGATACAGCTTTACCAACTCCTGGATCGGATGGGTGCGCCAGAT

GCCCGGGAAAGGCCTGGAGTGGATGGGACTCATTTACCCTGATGACTCTGATACCAG

ATACAGCCCATCCTTCCAAGGCCAGGTCACCATCTCAGCCGACAGCGCCATCAACACC

GCCTACCTGCAGTGGAGCAGCCTGAAGGCCTCGGACACCGCCATGTATTACTGTGCG

CGCCAGTCTACCTACATCTACGGTGGTTACTACGATACCTGGGGTCAAGGTACTCTGG

-continued

```
TGACCGTCTCCTCAGGCGGAGGTGGGTCCCAGGTGCAGCTGCAGGAGTCGGGCCCA

GGACTGGTGAAGCCTTCGGGGACCCTGTCCCTCACCTGCGCTGTCTCTGGTGGCTCC

ATCAGCAGTAGTAACTGGTGGAGTTGGGTCCGCCAGCCCCCAGGGAAGGGGCTGGA

GTGGATTGGGGAAATCTATCATAGTGGGAGCACCAACTACAACCCGTCCCTCAAGAGT

CGAGTCACCATATCAGTAGACAAGTCCAAGAACCAGTTCTCCCTGAAGCTGAGCTCT

GTGACCGCCGCGGACACGGCGGTGTACTACTGCGCCAGACTTCCTGGATACGAGTCA

GCTTTCGACATATGGGGTCAGGGTACAATGGTCACCGTCAGCTCAGGTGGCGGGGGC

AGCGGCGGAGGCGGATCCGGAGGCGGAGGGAGTGAAATTGTGTTGACGCAGTCTCC

AGGCACCCTGTCTTTGTCTCCAGGGGAAAGAGCCACCCTCTCCTGCAGGGCCAGTCA

GAGTGTTAGCAGCAGCTACTTAGCCTGGTACCAGCAGAAACCTGGCCAGGCTCCCAG

GCTCCTCATCTATGGTGCATCCAGCAGGGCCACTGGCATCCCAGACAGGTTCAGTGGC

AGTGGGTCTGGGACAGACTTCACTCTCACCATCAGCAGACTGGAGCCTGAAGATTTT

GCAGTGTATTACTGTCAGCAGGCCGGACTCTTCCCTTACACTTTTGGCGGAGGGACCA

AGGTTGAGATCAAATTCGTGCCCGTGTTCCTGCCCGCCAAACCTACTACTACCCCTGC

ACCTAGGCCTCCCACCCCAGCCCCAACAATCGCCAGCCAGCCTCTGTCTCTGCGGCC

CGAAGCCTGTAGACCTGCTGCCGGCGGAGCCGTGCACACCAGAGGCCTGGACTTCGC

CTGCGACATCTACATCTGGGCCCCTCTGGCCGGCACCGTGTGGCGTGCTGCTGAGC

CTGGTGATCACCCTGTACTGCAACCACCGGAACAAACGGGGCAGAAAGAAACTCCT

GTATATATTCAAACAACCATTTATGAGACCAGTACAAACTACTCAAGAGGAAGATGGC

TGTAGCTGCCGATTTCCAGAAGAAGAAGAAGGAGGATGTGAACTGAGAGTGAAGTT

CAGCAGATCCGCCGACGCCCCTGCCTACCAGCAGGGACAGAACCAGCTGTACAACGA

GCTGAACCTGGGCAGACGGGAAGAGTACGACGTGCTGGACAAGCGGAGAGGCCGG

GACCCCGAGATGGGCGGAAAGCCCAGACGGAAGAACCCCCAGGAAGGCCTGTATAA

CGAACTGCAGAAAGACAAGATGGCCGAGGCCTACAGCGAGATCGGCATGAAGGGCG

AGCGGAGGCGCGGCAAGGGCCACGATGGCCTGTACCAGGGCCTGAGCACCGCCACC

AAGGACACCTACGACGCCCTGCACATGCAGGCCCTGCCCCCCAGA
```

5# CAR protein sequence (SEQ ID NO: 48)
```
MALPVTALLLPLALLLHAARPQSVVTQPPSVSGAPGQRVTISCTGSSSNIGAGYDVH

WYQQLPGTAPKLLIYENTNRPSGVPDRFSGSKSGTSASLAITGLQAEDEADYYCQSYDSS

LSGWRVFGGGTKLTVLGGGGSGGGGSGGGGSMAEVQLVQSGAEVKKPGESLKISCK

GSGYSFTNSWIGWVRQMPGKGLEWMGLIYPDDSDTRYSPSFQGQVTISADSAINTAYLQ

WSSLKASDTAMYYCARQSTYIYGGYYDTWGQGTLVTVSSGGGGSQVQLQESGPGLVK

PSGTLSLTCAVSGGSISSSNWWSWVRQPPGKGLEWIGEIYHSGSTNYNPSLKSRVTISVD

KSKNQFSLKLSSVTAADTAVYYCARLPGYESAFDIWGQGTMVTVSSGGGGSGGGGSGG

GGSEIVLTQSPGTLSLSPGERATLSCRASQSVSSSYLAWYQQKPGQAPRLLIYGASSRATG

IPDRFSGSGSGTDFTLTISRLEPEDFAVYYCQQAGLFPYTFGGGTKVEIKFVPVFLPAKPTT

TPAPRPPTPAPTIASQPLSLRPEACRPAAGGAVHTRGLDFACDIYIWAPLAGTCGVLLLSL

VITLYCNHRNKRGRKKLLYIFKQPFMRPVQTTQEEDGCSCRFPEEEEGGCELRVKFSRSA

DAPAYQQGQNQLYNELNLGRREEYDVLDKRRGRDPEMGGKPRRKNPQEGLYNELQKD

KMAEAYSEIGMKGERRRGKGHDGLYQGLSTATKDTYDALHMQALPPR*
```

6# CAR nucleic acid sequence (SEQ ID NO: 49)
ATGGCCCTGCCTGTGACAGCTCTGCTCCTCCCTCTGGCCCTGCTGCTCCATGCCGC

CAGACCCCAGGTGCAGCTGCAGGAGTCGGGCCCAGGACTGGTGAAGCCTTCGGGGA

CCCTGTCCCTCACCTGCGCTGTCTCTGGTGGCTCCATCAGCAGTAGTAACTGGTGGA

GTTGGGTCCGCCAGCCCCCAGGGAAGGGGCTGGAGTGGATTGGGGAAATCTATCAT

AGTGGGAGCACCAACTACAACCCGTCCCTCAAGAGTCGAGTCACCATATCAGTAGA

CAAGTCCAAGAACCAGTTCTCCCTGAAGCTGAGCTCTGTGACCGCCGCGGACACGGC

GGTGTACTACTGCGCCAGACTTCCTGGATACGAGTCAGCTTTCGACATATGGGGTCA

GGGTACAATGGTCACCGTCAGCTCAGGTGGCGGGGGCAGCGGCGGAGGCGGATCCG

GAGGCGGAGGGAGTGAAATTGTGTTGACGCAGTCTCCAGGCACCCTGTCTTTGTCTC

CAGGGGAAAGAGCCACCCTCTCCTGCAGGGCCAGTCAGAGTGTTAGCAGCAGCTAC

TTAGCCTGGTACCAGCAGAAACCTGGCCAGGCTCCCAGGCTCCTCATCTATGGTGCA

TCCAGCAGGGCCACTGGCATCCCAGACAGGTTCAGTGGCAGTGGGTCTGGGACAGA

CTTCACTCTCACCATCAGCAGACTGGAGCCTGAAGATTTTGCAGTGTATTACTGTCA

GCAGGCCGGACTCTTCCCTTACACTTTTGGCGGAGGGACCAAGGTTGAGATCAAAGG

CGGAGGTGGGTCCCAGTCTGTCGTGACGCAGCCGCCCTCAGTGTCTGGGGCCCCAGG

GCAGAGGGTCACCATCTCCTGCACTGGGAGCAGCTCCAACATCGGGGCAGGTTATG

ATGTACACTGGTACCAGCAACTTCCAGGAACAGCCCCCAAACTCCTCATCTATGAGA

ACACCAATCGGCCCTCAGGGGTCCCTGACCGATTCTCTGGCTCCAAGTCTGGCACCT

CAGCCTCCCTGGCCATCACTGGGCTCCAGGCTGAGGATGAGGCTGATTATTACTGCC

AGTCCTATGACAGCAGCCTGAGTGGTTGGAGGGTGTTCGGCGGAGGGACCAAGCTG

ACCGTCCTAGGTGGTGGTGGTGGTAGCGGCGGCGGCGGCTCTGGTGGTGGTGGATCC

ATGGCCGAAGTGCAGCTGGTGCAGTCTGGGGCAGAGGTGAAAAAGCCCGGGGAGTC

TCTGAAGATCTCCTGTAAGGGGTCTGGATACAGCTTTACCAACTCCTGGATCGGATG

GGTGCGCCAGATGCCCGGGAAAGGCCTGGAGTGGATGGGACTCATTTACCCTGATG

ACTCTGATACCAGATACAGCCCATCCTTCCAAGGCCAGGTCACCATCTCAGCCGACA

GCGCCATCAACACCGCCTACCTGCAGTGGAGCAGCCTGAAGGCCTCGGACACCGCC

ATGTATTACTGTGCGCGCCAGTCTACCTACATCTACGGTGGTTACTACGATACCTGG

GGTCAAGGTACTCTGGTGACCGTCTCCTCATTCGTGCCCGTGTTCCTGCCCGCCAAAC

CTACTACTACCCCTGCACCTAGGCCTCCCACCCCAGCCCCAACAATCGCCAGCCAGC

CTCTGTCTCTGCGGCCCGAAGCCTGTAGACCTGCTGCCGGCGGAGCCGTGCACACCA

GAGGCCTGGACTTCGCCTGCGACATCTACATCTGGGCCCCTCTGGCCGGCACCTGTG

GCGTGCTGCTGCTGAGCCTGGTGATCACCCTGTACTGCAACCACCGGAACAAACGGG

GCAGAAAGAAACTCCTGTATATATTCAAACAACCATTTATGAGACCAGTACAAACTA

CTCAAGAGGAAGATGGCTGTAGCTGCCGATTTCCAGAAGAAGAAGAAGGAGGATGT

GAACTGAGAGTGAAGTTCAGCAGATCCGCCGACGCCCCTGCCTACCAGCAGGGACA

GAACCAGCTGTACAACGAGCTGAACCTGGGCAGACGGGAAGAGTACGACGTGCTGG

ACAAGCGGAGAGGCCGGGACCCCGAGATGGGCGGAAAGCCCAGACGGAAGAACCC

CCAGGAAGGCCTGTATAACGAACTGCAGAAAGACAAGATGGCCGAGGCCTACAGCG

AGATCGGCATGAAGGGCGAGCGGAGGCGCGGCAAGGGCCACGATGGCCTGTACCAG

-continued

GGCCTGAGCACCGCCACCAAGGACACCTACGACGCCCTGCACATGCAGGCCCTGCC

CCCCAGA

6# CAR protein sequence (SEQ ID NO: 50)
MALPVTALLLPLALLLHAARPQVQLQESGPGLVKPSGTLSLTCAVSGGSISSSNWWS

WVRQPPGKGLEWIGEIYHSGSTNYNPSLKSRVTISVDKSKNQFSLKLSSVTAADTAVYY

CARLPGYESAFDIWGQGTMVTVSSGGGGSGGGGSGGGGSEIVLTQSPGTLSLSPGERAT

LSCRASQSVSSSYLAWYQQKPGQAPRLLIYGASSRATGIPDRFSGSGSGTDFTLTISRLEP

EDFAVYYCQQAGLFPYTFGGGTKVEIKGGGGSQSVVTQPPSVSGAPGQRVTISCTGSSSN

IGAGYDVHWYQQLPGTAPKLLIYENTNRPSGVPDRFSGSKSGTSASLAITGLQAEDEADY

YCQSYDSSLSGWRVFGGGTKLTVLGGGGSGGGGSGGGGSMAEVQLVQSGAEVKKPG

ESLKISCKGSGYSFTNSWIGWVRQMPGKGLEWMGLIYPDDSDTRYSPSFQGQVTISADS

AINTAYLQWSSLKASDTAMYYCARQSTYIYGGYYDTWGQGTLVTVSSFVPVFLPAKPT

TTPAPRPPTPAPTIASQPLSLRPEACRPAAGGAVHTRGLDFACDIYIWAPLAGTCGVLLLS

LVITLYCNHRNKRGRKKLLYIFKQPFMRPVQTTQEEDGCSCRFPEEEEGGCELRVKFSRS

ADAPAYQQGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPR*

7# CAR nucleic acid sequence (SEQ ID NO: 51)
ATGGCCCTGCCTGTGACAGCTCTGCTCCTCCCTCTGGCCCTGCTGCTCCATGCCGC

CAGACCCCAGTCTGTCGTGACGCAGCCGCCCTCAGTGTCTGGGGCCCCAGGGCAGAG

GGTCACCATCTCCTGCACTGGGAGCAGCTCCAACATCGGGGCAGGTTATGATGTACA

CTGGTACCAGCAACTTCCAGGAACAGCCCCCAAACTCCTCATCTATGAGAACACCAA

TCGGCCCTCAGGGGTCCCTGACCGATTCTCTGGCTCCAAGTCTGGCACCTCAGCCTCC

CTGGCCATCACTGGGCTCCAGGCTGAGGATGAGGCTGATTATTACTGCCAGTCCTAT

GACAGCAGCCTGAGTGGTTGGAGGGTGTTCGGCGGAGGGACCAAGCTGACCGTCCT

AGGTGGTGGTGGTGGTAGCGGCGGCGGCGGCTCTGGTGGTGGTGGATCCATGGCCG

AAGTGCAGCTGGTGCAGTCTGGGGCAGAGGTGAAAAAGCCCGGGGAGTCTCTGAAG

ATCTCCTGTAAGGGGTCTGGATACAGCTTTACCAACTCCTGGATCGGATGGGTGCGC

CAGATGCCCGGGAAAGGCCTGGAGTGGATGGGACTCATTTACCCTGATGACTCTGAT

ACCAGATACAGCCCATCCTTCCAAGGCCAGGTCACCATCTCAGCCGACAGCGCCATC

AACACCGCCTACCTGCAGTGGAGCAGCCTGAAGGCCTCGGACACCGCCATGTATTAC

TGTGCGCGCCAGTCTACCTACATCTACGGTGGTTACTACGATACCTGGGGTCAAGGT

ACTCTGGTGACCGTCTCCTCAGGCGGAGGTGGGTCCCAGGTGCAGCTGCAGGAGTCG

GGCCCAGGACTGGTGAAGCCTTCGGAGACCCTGTCCCTCACCTGCACTGTCTCTGGT

GGCTCCATCAGTAGTTACTACTGGAGCTGGATCCGGCAGCCCGCCGGGAAGGGACT

GGAGTGGATTGGGCGTATCTATACCAGTGGGAGCACCAACTACAACCCCTCCCTCAA

GAGTCGAGTCACCATGTCAGTAGACACGTCCAAGAACCAGTTCTCCCTGAAGCTGAG

CTCTGTGACCGCCGCGGACACGGCGGTGTACTACTGCGCCAGAGACTTGTACAGAGA

TGGAATGGACGTATGGGGCCAGGGAACAACTGTCACCGTCAGCTCAGGTGGCGGGG

GCAGCGGCGGAGGCGGATCCGGAGGCGGAGGGAGTGACATCCAGATGACCCAGTCT

CCTTCCACCCTGTCTGCATCTGTAGGAGACAGAGTCACCATCACTTGCCGGGCCAGT

CAGAGTATTAGTAGCTGGTTGGCCTGGTATCAGCAGAAACCAGGGAAAGCCCCTAA

-continued

GCTCCTGATCTCCGATGCCTCCAGTTTGGAAAGTGGGGTCCCATCAAGGTTCAGCGG

CAGTGGATCTGGGACAGAATTCACTCTCACCATCAGCAGCCTGCAGCCTGATGATTT

TGCAACTTATTACTGCCAGCAGGCCAATACCTACTCTCCTACTTTTGGCGGAGGGAC

CAAGGTTGAGATCAAATTCGTGCCCGTGTTCCTGCCCGCCAAACCTACTACTACCCC

TGCACCTAGGCCTCCCACCCCAGCCCCAACAATCGCCAGCCAGCCTCTGTCTCTGCG

GCCCGAAGCCTGTAGACCTGCTGCCGGCGGAGCCGTGCACACCAGAGGCCTGGACT

TCGCCTGCGACATCTACATCTGGGCCCCTCTGGCCGGCACCTGTGGCGTGCTGCTGCT

GAGCCTGGTGATCACCCTGTACTGCAACCACCGGAACAAACGGGGCAGAAAGAAAC

TCCTGTATATATTCAAACAACCATTTATGAGACCAGTACAAACTACTCAAGAGGAAG

ATGGCTGTAGCTGCCGATTTCCAGAAGAAGAAGAAGGAGGATGTGAACTGAGAGTG

AAGTTCAGCAGATCCGCCGACGCCCCTGCCTACCAGCAGGGACAGAACCAGCTGTA

CAACGAGCTGAACCTGGGCAGACGGGAAGAGTACGACGTGCTGGACAAGCGGAGA

GGCCGGGACCCCGAGATGGGCGGAAAGCCCAGACGGAAGAACCCCCAGGAAGGCC

TGTATAACGAACTGCAGAAAGACAAGATGGCCGAGGCCTACAGCGAGATCGGCATG

AAGGGCGAGCGGAGGCGCGGCAAGGGCCACGATGGCCTGTACCAGGGCCTGAGCAC

CGCCACCAAGGACACCTACGACGCCCTGCACATGCAGGCCCTGCCCCCCAGA

7# CAR protein sequence (SEQ ID NO: 52)
MALPVTALLLPLALLLHAARPQSVVTQPPSVSGAPGQRVTISCTGSSSNIGAGYDVH

WYQQLPGTAPKLLIYENTNRPSGVPDRFSGSKSGTSASLAITGLQAEDEADYYCQSYDSS

LSGWRVFGGGTKLTVLGGGGGSGGGGSGGGGSMAEVQLVQSGAEVKKPGESLKISCK

GSGYSFTNSWIGWVRQMPGKGLEWMGLIYPDDSDTRYSPSFQGQVTISADSAINTAYLQ

WSSLKASDTAMYYCARQSTYIYGGYYDTWGQGTLVTVSSGGGGSQVQLQESGPGLVK

PSETLSLTCTVSGGSISSYYWSWIRQPAGKGLEWIGRIYTSGSTNYNPSLKSRVTMSVDTS

KNQFSLKLSSVTAADTAVYYCARDLYRDGMDVWGQGTTVTVSSGGGGSGGGGSGGG

GSDIQMTQSPSTLSASVGDRVTITCRASQSISSWLAWYQQKPGKAPKLLISDASSLESGVP

SRFSGSGSGTEFTLTISSLQPDDFATYYCQQANTYSPTFGGGTKVEIKFVPVFLPAKPTTTP

APRPPTPAPTIASQPLSLRPEACRPAAGGAVHTRGLDFACDIYIWAPLAGTCGVLLLSLVI

TLYCNHRNKRGRKKLLYIFKQPFMRPVQTTQEEDGCSCRFPEEEEGGCELRVKFSRSAD

APAYQQGQNQLYNELNLGRREEYDVLDKRRGRDPEMGGKPRRKNPQEGLYNELQKDK

MAEAYSEIGMKGERRRGKGHDGLYQGLSTATKDTYDALHMQALPPR*

8# CAR nucleic acid sequence (SEQ ID NO: 53)
ATGGCCCTGCCTGTGACAGCTCTGCTCCTCCCTCTGGCCCTGCTGCTCCATGCCGC

CAGACCCCAGGTGCAGCTGCAGGAGTCGGGCCCAGGACTGGTGAAGCCTTCGGAGA

CCCTGTCCCTCACCTGCACTGTCTCTGGTGGCTCCATCAGTAGTTACTACTGGAGCTG

GATCCGGCAGCCCGCCGGGAAGGGACTGGAGTGGATTGGGCGTATCTATACCAGTG

GGAGCACCAACTACAACCCCTCCCTCAAGAGTCGAGTCACCATGTCAGTAGACACGT

CCAAGAACCAGTTCTCCCTGAAGCTGAGCTCTGTGACCGCCGCGGACACGGCGGTGT

ACTACTGCGCCAGAGACTTGTACAGAGATGGAATGGACGTATGGGGCCAGGGAACA

ACTGTCACCGTCAGCTCAGGTGGCGGGGGCAGCGGCGGAGGCGGATCCGGAGGCGG

AGGGAGTGACATCCAGATGACCCAGTCTCCTTCCACCCTGTCTGCATCTGTAGGAGA

-continued

CAGAGTCACCATCACTTGCCGGGCCAGTCAGAGTATTAGTAGCTGGTTGGCCTGGTA

TCAGCAGAAACCAGGGAAAGCCCCTAAGCTCCTGATCTCCGATGCCTCCAGTTTGGA

AAGTGGGGTCCCATCAAGGTTCAGCGGCAGTGGATCTGGGACAGAATTCACTCTCAC

CATCAGCAGCCTGCAGCCTGATGATTTTGCAACTTATTACTGCCAGCAGGCCAATAC

CTACTCTCCTACTTTTGGCGGAGGGACCAAGGTTGAGATCAAAGGCGGAGGTGGGTC

CCAGTCTGTCGTGACGCAGCCGCCCTCAGTGTCTGGGGCCCCAGGGCAGAGGGTCAC

CATCTCCTGCACTGGGAGCAGCTCCAACATCGGGGCAGGTTATGATGTACACTGGTA

CCAGCAACTTCCAGGAACAGCCCCCAAACTCCTCATCTATGAGAACACCAATCGGCC

CTCAGGGGTCCCTGACCGATTCTCTGGCTCCAAGTCTGGCACCTCAGCCTCCCTGGCC

ATCACTGGGCTCCAGGCTGAGGATGAGGCTGATTATTACTGCCAGTCCTATGACAGC

AGCCTGAGTGGTTGGAGGGTGTTCGGCGGAGGGACCAAGCTGACCGTCCTAGGTGG

TGGTGGTGGTAGCGGCGGCGGCGGCTCTGGTGGTGGTGGATCCATGGCCGAAGTGC

AGCTGGTGCAGTCTGGGGCAGAGGTGAAAAAGCCCGGGGAGTCTCTGAAGATCTCC

TGTAAGGGGTCTGGATACAGCTTTACCAACTCCTGGATCGGATGGGTGCGCCAGATG

CCCGGGAAAGGCCTGGAGTGGATGGGACTCATTTACCCTGATGACTCTGATACCAGA

TACAGCCCATCCTTCCAAGGCCAGGTCACCATCTCAGCCGACAGCGCCATCAACACC

GCCTACCTGCAGTGGAGCAGCCTGAAGGCCTCGGACACCGCCATGTATTACTGTGCG

CGCCAGTCTACCTACATCTACGGTGGTTACTACGATACCTGGGGTCAAGGTACTCTG

GTGACCGTCTCCTCATTCGTGCCCGTGTTCCTGCCCGCCAAACCTACTACTACCCCTG

CACCTAGGCCTCCCACCCCAGCCCCAACAATCGCCAGCCAGCCTCTGTCTCTGCGGC

CCGAAGCCTGTAGACCTGCTGCCGGCGGAGCCGTGCACACCAGAGGCCTGGACTTC

GCCTGCGACATCTACATCTGGGCCCCTCTGGCCGGCACCTGTGGCGTGCTGCTGCTG

AGCCTGGTGATCACCCTGTACTGCAACCACCGGAACAAACGGGGCAGAAAGAAACT

CCTGTATATATTCAAACAACCATTTATGAGACCAGTACAAACTACTCAAGAGGAAGA

TGGCTGTAGCTGCCGATTTCCAGAAGAAGAAGAAGGAGGATGTGAACTGAGAGTGA

AGTTCAGCAGATCCGCCGACGCCCCTGCCTACCAGCAGGGACAGAACCAGCTGTAC

AACGAGCTGAACCTGGGCAGACGGGAAGAGTACGACGTGCTGGACAAGCGGAGAG

GCCGGGACCCCGAGATGGGCGGAAAGCCCAGACGGAAGAACCCCCAGGAAGGCCT

GTATAACGAACTGCAGAAAGACAAGATGGCCGAGGCCTACAGCGAGATCGGCATGA

AGGGCGAGCGGAGGCGCGGCAAGGGCCACGATGGCCTGTACCAGGGCCTGAGCACC

GCCACCAAGGACACCTACGACGCCCTGCACATGCAGGCCCTGCCCCCCAGA

8# CAR protein sequence (SEQ ID NO: 54)
MALPVTALLLPLALLLHAARPQVQLQESGPGLVKPSETLSLTCTVSGGSISSYYWSWI

RQPAGKGLEWIGRIYTSGSTNYNPSLKSRVTMSVDTSKNQFSLKLSSVTAADTAVYYCA

RDLYRDGMDVWGQGTTVTVSSGGGGSGGGGSGGGGSDIQMTQSPSTLSASVGDRVTIT

CRASQSISSWLAWYQQKPGKAPKLLISDASSLESGVPSRFSGSGSGTEFrLTISSLQPDDF

ATYYCQQANTYSPTFGGGTKVEIKGGGGSQSVVTQPPSVSGAPGQRVTISCTGSSSNIGA

GYDVHWYQQLPGTAPKLLIYENTNRPSGVPDRFSGSKSGTSASLAITGLQAEDEADYYC

QSYDSSLSGWRVFGGGTKLTVLGGGGSGGGGSGGGGSMAEVQLVQSGAEVKKPGES

LKISCKGSGYSFTNSWIGWVRQMPGKGLEWMGLIYPDDSDTRYSPSFQGQVTISADSAIN

-continued

TAYLQWSSLKASDTAMYYCARQSTYIYGGYYDTWGQGTLVTVSSFVPVFLPAKPTTTP

APRPPTPAPTIASQPLSLRPEACRPAAGGAVHTRGLDFACDIYIWAPLAGTCGVLLLSLVI

TLYCNHRNKRGRKKLLYIFKQPFMRPVQTTQEEDGCSCRFPEEEEGGCELRVKFSRSAD

APAYQQGQNQLYNELNLGRREEYDVLDKRRGRDPEMGGKPRRKNPQEGLYNELQKDK

MAEAYSEIGMKGERRRGKGHDGLYQGLSTATKDTYDALHMQALPPR*

9# CAR nucleic acid sequence (SEQ ID NO: 55)
ATGGCCCTGCCTGTGACAGCTCTGCTCCTCCCTCTGGCCCTGCTGCTCCATGCCGC

CAGACCCCAGTCTGTCGTGACGCAGCCGCCCTCAGTGTCTGGGGCCCCAGGGCAGAG

GGTCACCATCTCCTGCACTGGGAGCAGCTCCAACATCGGGGCAGGTTATGATGTACA

CTGGTACCAGCAACTTCCAGGAACAGCCCCCAAACTCCTCATCTATGAGAACACCAA

TCGGCCCTCAGGGGTCCCTGACCGATTCTCTGGCTCCAAGTCTGGCACCTCAGCCTCC

CTGGCCATCACTGGGCTCCAGGCTGAGGATGAGGCTGATTATTACTGCCAGTCCTAT

GACAGCAGCCTGAGTGGTTGGAGGGTGTTCGGCGGAGGGACCAAGCTGACCGTCCT

AGGTGGTGGTGGTGGTAGCCAGGTGCAGCTGCAGGAGTCGGGCCCAGGACTGGTGA

AGCCTTCGGGGACCCTGTCCCTCACCTGCGCTGTCTCTGGTGGCTCCATCAGCAGTA

GTAACTGGTGGAGTTGGGTCCGCCAGCCCCCAGGGAAGGGGCTGGAGTGGATTGGG

GAAATCTATCATAGTGGGAGCACCAACTACAACCCGTCCCTCAAGAGTCGAGTCACC

ATATCAGTAGACAAGTCCAAGAACCAGTTCTCCCTGAAGCTGAGCTCTGTGACCGCC

GCGGACACGGCGGTGTACTACTGCGCCAGACTTCCTGGATACGAGTCAGCTTTCGAC

ATATGGGGTCAGGGTACAATGGTCACCGTCAGCTCAGGCAGCACCAGCGGCTCCGG

CAAGCCTGGCTCTGGCGAGGGCAGCACAAAGGGAGAAATTGTGTTGACGCAGTCTC

CAGGCACCCTGTCTTTGTCTCCAGGGGAAAGAGCCACCCTCTCCTGCAGGGCCAGTC

AGAGTGTTAGCAGCAGCTACTTAGCCTGGTACCAGCAGAAACCTGGCCAGGCTCCCA

GGCTCCTCATCTATGGTGCATCCAGCAGGGCCACTGGCATCCCAGACAGGTTCAGTG

GCAGTGGGTCTGGGACAGACTTCACTCTCACCATCAGCAGACTGGAGCCTGAAGATT

TTGCAGTGTATTACTGTCAGCAGGCCGGACTCTTCCCTTACACTTTTGGCGGAGGGA

CCAAGGTTGAGATCAAAGGTGGCGGGGGCAGCATGGCCGAAGTGCAGCTGGTGCAG

TCTGGGGCAGAGGTGAAAAAGCCCGGGGAGTCTCTGAAGATCTCCTGTAAGGGGTC

TGGATACAGCTTTACCAACTCCTGGATCGGATGGGTGCGCCAGATGCCCGGGAAAG

GCCTGGAGTGGATGGGACTCATTTACCCTGATGACTCTGATACCAGATACAGCCCAT

CCTTCCAAGGCCAGGTCACCATCTCAGCCGACAGCGCCATCAACACCGCCTACCTGC

AGTGGAGCAGCCTGAAGGCCTCGGACACCGCCATGTATTACTGTGCGCGCCAGTCTA

CCTACATCTACGGTGGTTACTACGATACCTGGGGTCAAGGTACTCTGGTGACCGTCT

CCTCATTCGTGCCCGTGTTCCTGCCCGCCAAACCTACTACTACCCCTGCACCTAGGCC

TCCCACCCCAGCCCCAACAATCGCCAGCCAGCCTCTGTCTCTGCGGCCCGAAGCCTG

TAGACCTGCTGCCGGCGGAGCCGTGCACACCAGAGGCCTGGACTTCGCCTGCGACAT

CTACATCTGGGCCCCTCTGGCCGGCACCTGTGGCGTGCTGCTGCTGAGCCTGGTGAT

CACCCTGTACTGCAACCACCGGAACAAACGGGGCAGAAAGAAACTCCTGTATATAT

TCAAACAACCATTTATGAGACCAGTACAAACTACTCAAGAGGAAGATGGCTGTAGC

TGCCGATTTCCAGAAGAAGAAGAAGGAGGATGTGAACTGAGAGTGAAGTTCAGCAG

-continued

ATCCGCCGACGCCCCTGCCTACCAGCAGGGACAGAACCAGCTGTACAACGAGCTGA

ACCTGGGCAGACGGGAAGAGTACGACGTGCTGGACAAGCGGAGAGGCCGGGACCC

CGAGATGGGCGGAAAGCCCAGACGGAAGAACCCCCAGGAAGGCCTGTATAACGAA

CTGCAGAAAGACAAGATGGCCGAGGCCTACAGCGAGATCGGCATGAAGGGCGAGC

GGAGGCGCGGCAAGGGCCACGATGGCCTGTACCAGGGCCTGAGCACCGCCACCAAG

GACACCTACGACGCCCTGCACATGCAGGCCCTGCCCCCCAGA

9# CAR protein sequence (SEQ ID NO: 56)
MALPVTALLLPLALLLHAARPQSVVTQPPSVSGAPGQRVTISCTGSSSNIGAGYDVH

WYQQLPGTAPKLLIYENTNRPSGVPDRFSGSKSGTSASLAITGLQAEDEADYYCQSYDSS

LSGWRVFGGGTKLTVLGGGGGSQVQLQESGPGLVKPSGTLSLTCAVSGGSISSSNWWS

WVRQPPGKGLEWIGEIYHSGSTNYNPSLKSRVTISVDKSKNQFSLKLSSVTAADTAVYY

CARLPGYESAFDIWGQGTMVTVSSGSTSGSGKPGSGEGSTKGEIVLTQSPGTLSLSPGER

ATLSCRASQSVSSSYLAWYQQKPGQAPRLLIYGASSRATGIPDRFSGSGSGTDFTLTISRL

EPEDFAVYYCQQAGLFPYTFGGGTKVEIKGGGGSMAEVQLVQSGAEVKKPGESLKISCK

GSGYSFTNSWIGWVRQMPGKGLEWMGLIYPDDSDTRYSPSFQGQVTISADSAINTAYLQ

WSSLKASDTAMYYCARQSTYIYGGYYDTWGQGTLVTVSSFVPVFLPAKPTTTPAPRPPT

PAPTIASQPLSLRPEACRPAAGGAVHTRGLDFACDIYIWAPLAGTCGVLLLSLVITLYCNH

RNKRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEAYS

EIGMKGERRRGKGHDGLYQGLSTATKDTYDALHMQALPPR*

10# CAR nucleic acid sequence (SEQ ID NO: 57)
ATGGCCCTGCCTGTGACAGCTCTGCTCCTCCCTCTGGCCCTGCTGCTCCATGCCGC

CAGACCCCAGTCTGTCGTGACGCAGCCGCCCTCAGTGTCTGGGGCCCCAGGGCAGAG

GGTCACCATCTCCTGCACTGGGAGCAGCTCCAACATCGGGGCAGGTTATGATGTACA

CTGGTACCAGCAACTTCCAGGAACAGCCCCCAAACTCCTCATCTATGAGAACACCAA

TCGGCCCTCAGGGGTCCCTGACCGATTCTCTGGCTCCAAGTCTGGCACCTCAGCCTCC

CTGGCCATCACTGGGCTCCAGGCTGAGGATGAGGCTGATTATTACTGCCAGTCCTAT

GACAGCAGCCTGAGTGGTTGGAGGGTGTTCGGCGGAGGGACCAAGCTGACCGTCCT

AGGTGGTGGTGGTGGTAGCCAGGTGCAGCTGCAGGAGTCGGGCCCAGGACTGGTGA

AGCCTTCGGAGACCCTGTCCCTCACCTGCACTGTCTCTGGTGGCTCCATCAGTAGTTA

CTACTGGAGCTGGATCCGGCAGCCCGCCGGGAAGGGACTGGAGTGGATTGGGCGTA

TCTATACCAGTGGGAGCACCAACTACAACCCCTCCCTCAAGAGTCGAGTCACCATGT

CAGTAGACACGTCCAAGAACCAGTTCTCCCTGAAGCTGAGCTCTGTGACCGCCGCGG

ACACGGCGGTGTACTACTGCGCCAGAGACTTGTACAGAGATGGAATGGACGTATGG

GGCCAGGGAACAACTGTCACCGTCAGCTCAGGCAGCACCAGCGGCTCCGGCAAGCC

TGGCTCTGGCGAGGGCAGCACAAAGGGAGACATCCAGATGACCCAGTCTCCTTCCA

CCCTGTCTGCATCTGTAGGAGACAGAGTCACCATCACTTGCCGGGCCAGTCAGAGTA

TTAGTAGCTGGTTGGCCTGGTATCAGCAGAAACCAGGGAAAGCCCCTAAGCTCCTGA

TCTCCGATGCCTCCAGTTTGGAAAGTGGGGTCCCATCAAGGTTCAGCGGCAGTGGAT

CTGGGACAGAATTCACTCTCACCATCAGCAGCCTGCAGCCTGATGATTTTGCAACTT

ATTACTGCCAGCAGGCCAATACCTACTCTCCTACTTTTGGCGGAGGGACCAAGGTTG

AGATCAAAGGTGGCGGGGGCAGCATGGCCGAAGTGCAGCTGGTGCAGTCTGGGGCA

GAGGTGAAAAAGCCCGGGGAGTCTCTGAAGATCTCCTGTAAGGGGTCTGGATACAG

CTTTACCAACTCCTGGATCGGATGGGTGCGCCAGATGCCCGGGAAAGGCCTGGAGTG

GATGGGACTCATTTACCCTGATGACTCTGATACCAGATACAGCCCATCCTTCCAAGG

CCAGGTCACCATCTCAGCCGACAGCGCCATCAACACCGCCTACCTGCAGTGGAGCAG

CCTGAAGGCCTCGGACACCGCCATGTATTACTGTGCGCGCCAGTCTACCTACATCTA

CGGTGGTTACTACGATACCTGGGGTCAAGGTACTCTGGTGACCGTCTCCTCATTCGT

GCCCGTGTTCCTGCCCGCCAAACCTACTACTACCCCTGCACCTAGGCCTCCCACCCCA

GCCCCAACAATCGCCAGCCAGCCTCTGTCTCTGCGGCCCGAAGCCTGTAGACCTGCT

GCCGGCGGAGCCGTGCACACCAGAGGCCTGGACTTCGCCTGCGACATCTACATCTGG

GCCCCTCTGGCCGGCACCTGTGGCGTGCTGCTGCTGAGCCTGGTGATCACCCTGTAC

TGCAACCACCGGAACAAACGGGGCAGAAAGAAACTCCTGTATATATTCAAACAACC

ATTTATGAGACCAGTACAAACTACTCAAGAGGAAGATGGCTGTAGCTGCCGATTTCC

AGAAGAAGAAGAAGGAGGATGTGAACTGAGAGTGAAGTTCAGCAGATCCGCCGAC

GCCCCTGCCTACCAGCAGGGACAGAACCAGCTGTACAACGAGCTGAACCTGGGCAG

ACGGGAAGAGTACGACGTGCTGGACAAGCGGAGAGGCCGGGACCCCGAGATGGGC

GGAAAGCCCAGACGGAAGAACCCCCAGGAAGGCCTGTATAACGAACTGCAGAAAG

ACAAGATGGCCGAGGCCTACAGCGAGATCGGCATGAAGGGCGAGCGGAGGCGCGG

CAAGGGCCACGATGGCCTGTACCAGGGCCTGAGCACCGCCACCAAGGACACCTACG

ACGCCCTGCACATGCAGGCCCTGCCCCCCAGA

10# CAR protein sequence (SEQ ID NO: 58)
MALPVTALLLPLALLLHAARPQSVVTQPPSVSGAPGQRVTISCTGSSSNIGAGYDVH

WYQQLPGTAPKLLIYENTNRPSGVPDRFSGSKSGTSASLAITGLQAEDEADYYCQSYDSS

LSGWRVFGGGTKLTVLGGGGGSQVQLQESGPGLVKPSETLSLTCTVSGGSISSYYWSWI

RQPAGKGLEWIGRIYTSGSTNYNPSLKSRVTMSVDTSKNQFSLKLSSVTAADTAVYYCA

RDLYRDGMDVWGQGTTVTVSSGSTSGSGKPGSGEGSTKGDIQMTQSPSTLSASVGDRV

TITCRASQSISSWLAWYQQKPGKAPKLLISDASSLESGVPSRFSGSGSGTEFTLTISSLQPD

DFATYYCQQANTYSPTFGGGTKVEIKGGGGSMAEVQLVQSGAEVKKPGESLKISCKGSG

YSFTNSWIGWVRQMPGKGLEWMGLIYPDDSDTRYSPSFQGQVTISADSAINTAYLQWSS

LKASDTAMYYCARQSTYIYGGYYDTWGQGTLVTVSSFVPVFLPAKPTTTPAPRPPTPAP

TIASQPLSLRPEACRPAAGGAVHTRGLDFACDIYIWAPLAGTCGVLLLSLVITLYCNHRN

KRGRKKLLYIFKQPFMRPVQTTQEEDGCSCRFPEEEEGGCELRVKFSRSADAPAYQQGQ

NQLYNELNLGRREEYDVLDKRRGRDPEMGGKPRRKNPQEGLYNELQKDKMAEAYSEI

GMKGERRRGKGHDGLYQGLSTATKDTYDALHMQALPPR*

11# CAR nucleic acid sequence (SEQ ID NO: 59)
ATGGCCCTGCCTGTGACAGCTCTGCTCCTCCCTCTGGCCCTGCTGCTCCATGCCGC

CAGACCCGAAATTGTGTTGACGCAGTCTCCAGGCACCCTGTCTTTGTCTCCAGGGGA

AAGAGCCACCCTCTCCTGCAGGGCCAGTCAGAGTGTTAGCAGCAGCTACTTAGCCTG

GTACCAGCAGAAACCTGGCCAGGCTCCCAGGCTCCTCATCTATGGTGCATCCAGCAG

GGCCACTGGCATCCCAGACAGGTTCAGTGGCAGTGGGTCTGGGACAGACTTCACTCT

CACCATCAGCAGACTGGAGCCTGAAGATTTTGCAGTGTATTACTGTCAGCAGGCCGG

ACTCTTCCCTTACACTTTTGGCGGAGGGACCAAGGTTGAGATCAAAGGTGGCGGGGG

CAGCATGGCCGAAGTGCAGCTGGTGCAGTCTGGGGCAGAGGTGAAAAAGCCCGGGG

AGTCTCTGAAGATCTCCTGTAAGGGGTCTGGATACAGCTTTACCAACTCCTGGATCG

GATGGGTGCGCCAGATGCCCGGGAAAGGCCTGGAGTGGATGGGACTCATTTACCCT

GATGACTCTGATACCAGATACAGCCCATCCTTCCAAGGCCAGGTCACCATCTCAGCC

GACAGCGCCATCAACACCGCCTACCTGCAGTGGAGCAGCCTGAAGGCCTCGGACAC

CGCCATGTATTACTGTGCGCGCCAGTCTACCTACATCTACGGTGGTTACTACGATACC

TGGGGTCAAGGTACTCTGGTGACCGTCTCCTCAGGCAGCACCAGCGGCTCCGGCAAG

CCTGGCTCTGGCGAGGGCAGCACAAAGGGACAGTCTGTCGTGACGCAGCCGCCCTC

AGTGTCTGGGGCCCCAGGGCAGAGGGTCACCATCTCCTGCACTGGGAGCAGCTCCA

ACATCGGGGCAGGTTATGATGTACACTGGTACCAGCAACTTCCAGGAACAGCCCCCA

AACTCCTCATCTATGAGAACACCAATCGGCCCTCAGGGGTCCCTGACCGATTCTCTG

GCTCCAAGTCTGGCACCTCAGCCTCCCTGGCCATCACTGGGCTCCAGGCTGAGGATG

AGGCTGATTATTACTGCCAGTCCTATGACAGCAGCCTGAGTGGTTGGAGGGTGTTCG

GCGGAGGGACCAAGCTGACCGTCCTAGGTGGTGGTGGTGGTAGCCAGGTGCAGCTG

CAGGAGTCGGGCCCAGGACTGGTGAAGCCTTCGGGGACCCTGTCCCTCACCTGCGCT

GTCTCTGGTGGCTCCATCAGCAGTAGTAACTGGTGGAGTTGGGTCCGCCAGCCCCCA

GGGAAGGGGCTGGAGTGGATTGGGGAAATCTATCATAGTGGGAGCACCAACTACAA

CCCGTCCCTCAAGAGTCGAGTCACCATATCAGTAGACAAGTCCAAGAACCAGTTCTC

CCTGAAGCTGAGCTCTGTGACCGCCGCGGACACGGCGGTGTACTACTGCGCCAGACT

TCCTGGATACGAGTCAGCTTTCGACATATGGGGTCAGGGTACAATGGTCACCGTCAG

CTCATTCGTGCCCGTGTTCCTGCCCGCCAAACCTACTACTACCCCTGCACCTAGGCCT

CCCACCCCAGCCCCAACAATCGCCAGCCAGCCTCTGTCTCTGCGGCCCGAAGCCTGT

AGACCTGCTGCCGGCGGAGCCGTGCACACCAGAGGCCTGGACTTCGCCTGCGACATC

TACATCTGGGCCCCTCTGGCCGGCACCTGTGGCGTGCTGCTGCTGAGCCTGGTGATC

ACCCTGTACTGCAACCACCGGAACAAACGGGGCAGAAAGAAACTCCTGTATATATT

CAAACAACCATTTATGAGACCAGTACAAACTACTCAAGAGGAAGATGGCTGTAGCT

GCCGATTTCCAGAAGAAGAAGAAGGAGGATGTGAACTGAGAGTGAAGTTCAGCAGA

TCCGCCGACGCCCCTGCCTACCAGCAGGGACAGAACCAGCTGTACAACGAGCTGAA

CCTGGGCAGACGGGAAGAGTACGACGTGCTGGACAAGCGGAGAGGCCGGGACCCC

GAGATGGGCGGAAAGCCCAGACGGAAGAACCCCCAGGAAGGCCTGTATAACGAACT

GCAGAAAGACAAGATGGCCGAGGCCTACAGCGAGATCGGCATGAAGGGCGAGCGG

AGGCGCGGCAAGGGCCACGATGGCCTGTACCAGGGCCTGAGCACCGCCACCAAGGA

CACCTACGACGCCCTGCACATGCAGGCCCTGCCCCCCAGA

11# CAR protein sequence (SEQ ID NO: 60)
MALPVTALLLPLALLLHAARPEIVLTQSPGTLSLSPGERATLSCRASQSVSSSYLAWY

QQKPGQAPRLLIYGASSRATGIPDRFSGSGSGTDFTLTISRLEPEDFAVYYCQQAGLFPYT

FGGGTKVEIKGGGGSMAEVQLVQSGAEVKKPGESLKISCKGSGYSFTNSWIGWVRQMP

GKGLEWMGLIYPDDSDTRYSPSFQGQVTISADSAINTAYLQWSSLKASDTAMYYCARQS

-continued

TYIYGGYYDTWGQGTLVTVSSGSTSGSGKPGSGEGSTKGQSVVTQPPSVSGAPGQRVTIS

CTGSSSNIGAGYDVHWYQQLPGTAPKLLIYENTNRPSGVPDRFSGSKSGTSASLAITGLQ

AEDEADYYCQSYDSSLSGWRVFGGGTKLTVLGGGGGSQVQLQESGPGLVKPSGTLSLT

CAVSGGSISSSNWWSWVRQPPGKGLEWIGEIYHSGSTNYNPSLKSRVTISVDKSKNQFSL

KLSSVTAADTAVYYCARLPGYESAFDIWGQGTMVTVSSFVPVFLPAKPTTTPAPRPPTPA

PTIASQPLSLRPEACRPAAGGAVHTRGLDFACDIYIWAPLAGTCGVLLLSLVITLYCNHR

NKRGRKKLLYIFKQPFMRPVQTTQEEDGCSCRFPEEEEGGCELRVKFSRSADAPAYQQG

QNQLYNELNLGRREEYDVLDKRRGRDPEMGGKPRRKNPQEGLYNELQKDKMAEAYSE

IGMKGERRRGKGHDGLYQGLSTATKDTYDALHMQALPPR*

12# CAR nucleic acid sequence (SEQ ID NO: 61)
ATGGCCCTGCCTGTGACAGCTCTGCTCCTCCCTCTGGCCCTGCTGCTCCATGCCGC

CAGACCCGACATCCAGATGACCCAGTCTCCTTCCACCCTGTCTGCATCTGTAGGAGA

CAGAGTCACCATCACTTGCCGGGCCAGTCAGAGTATTAGTAGCTGGTTGGCCTGGTA

TCAGCAGAAACCAGGGAAAGCCCCTAAGCTCCTGATCTCCGATGCCTCCAGTTTGGA

AAGTGGGGTCCCATCAAGGTTCAGCGGCAGTGGATCTGGGACAGAATTCACTCTCAC

CATCAGCAGCCTGCAGCCTGATGATTTTGCAACTTATTACTGCCAGCAGGCCAATAC

CTACTCTCCTACTTTTGGCGGAGGGACCAAGGTTGAGATCAAAGGTGGCGGGGGCA

GCATGGCCGAAGTGCAGCTGGTGCAGTCTGGGGCAGAGGTGAAAAAGCCCGGGGAG

TCTCTGAAGATCTCCTGTAAGGGGTCTGGATACAGCTTTACCAACTCCTGGATCGGA

TGGGTGCGCCAGATGCCCGGGAAAGGCCTGGAGTGGATGGGACTCATTTACCCTGAT

GACTCTGATACCAGATACAGCCCATCCTTCCAAGGCCAGGTCACCATCTCAGCCGAC

AGCGCCATCAACACCGCCTACCTGCAGTGGAGCAGCCTGAAGGCCTCGGACACCGC

CATGTATTACTGTGCGCGCCAGTCTACCTACATCTACGGTGGTTACTACGATACCTGG

GGTCAAGGTACTCTGGTGACCGTCTCCTCAGGCAGCACCAGCGGCTCCGGCAAGCCT

GGCTCTGGCGAGGGCAGCACAAAGGGACAGTCTGTCGTGACGCAGCCGCCCTCAGT

GTCTGGGGCCCCAGGGCAGAGGGTCACCATCTCCTGCACTGGGAGCAGCTCCAACAT

CGGGGCAGGTTATGATGTACACTGGTACCAGCAACTTCCAGGAACAGCCCCCAAACT

CCTCATCTATGAGAACACCAATCGGCCCTCAGGGGTCCCTGACCGATTCTCTGGCTC

CAAGTCTGGCACCTCAGCCTCCCTGGCCATCACTGGGCTCCAGGCTGAGGATGAGGC

TGATTATTACTGCCAGTCCTATGACAGCAGCCTGAGTGGTTGGAGGGTGTTCGGCGG

AGGGACCAAGCTGACCGTCCTAGGTGGTGGTGGTGGTAGCCAGGTGCAGCTGCAGG

AGTCGGGCCCAGGACTGGTGAAGCCTTCGGAGACCCTGTCCCTCACCTGCACTGTCT

CTGGTGGCTCCATCAGTAGTTACTACTGGAGCTGGATCCGGCAGCCCGCCGGGAAGG

GACTGGAGTGGATTGGGCGTATCTATACCAGTGGGAGCACCAACTACAACCCCTCCC

TCAAGAGTCGAGTCACCATGTCAGTAGACACGTCCAAGAACCAGTTCTCCCTGAAGC

TGAGCTCTGTGACCGCCGCGGACACGGCGGTGTACTACTGCGCCAGAGACTTGTACA

GAGATGGAATGGACGTATGGGGCCAGGGAACAACTGTCACCGTCAGCTCATTCGTG

CCCGTGTTCCTGCCCGCCAAACCTACTACTACCCCTGCACCTAGGCCTCCCACCCCAG

CCCCAACAATCGCCAGCCAGCCTCTGTCTCTGCGGCCCCGAAGCCTGTAGACCTGCTG

CCGGCGGAGCCGTGCACACCAGAGGCCTGGACTTCGCCTGCGACATCTACATCTGGG

```
CCCCTCTGGCCGGCACCTGTGGCGTGCTGCTGCTGAGCCTGGTGATCACCCTGTACT

GCAACCACCGGAACAAACGGGGCAGAAAGAAACTCCTGTATATATTCAAACAACCA

TTTATGAGACCAGTACAAACTACTCAAGAGGAAGATGGCTGTAGCTGCCGATTTCCA

GAAGAAGAAGAGGAGGATGTGAACTGAGAGTGAAGTTCAGCAGATCCGCCGACG

CCCCTGCCTACCAGCAGGGACAGAACCAGCTGTACAACGAGCTGAACCTGGGCAGA

CGGGAAGAGTACGACGTGCTGGACAAGCGGAGAGGCCGGGACCCCGAGATGGGCG

GAAAGCCCAGACGGAAGAACCCCCAGGAAGGCCTGTATAACGAACTGCAGAAAGA

CAAGATGGCCGAGGCCTACAGCGAGATCGGCATGAAGGGCGAGCGGAGGCGCGGC

AAGGGCCACGATGGCCTGTACCAGGGCCTGAGCACCGCCACCAAGGACACCTACGA

CGCCCTGCACATGCAGGCCCTGCCCCCCAGA
```

12# CAR protein sequence (SEQ ID NO: 62)
```
MALPVTALLLPLALLLHAARPDIQMTQSPSTLSASVGDRVTITCRASQSISSWLAWYQ

QKPGKAPKLLISDASSLESGVPSRFSGSGSGTEFTLTISSLQPDDFATYYCQQANTYSPTFG

GGTKVEIKGGGGSMAEVQLVQSGAEVKKPGESLKISCKGSGYSFTNSWIGWVRQMPGK

GLEWMGLIYPDDSDTRYSPSFQGQVTISADSAINTAYLQWSSLKASDTAMYYCARQSTY

IYGGYYDTWGQGTLVTVSSGSTSGSGKPGSGEGSTKGQSVVTQPPSVSGAPGQRVTISCT

GSSSNIGAGYDVHWYQQLPGTAPKLLIYENTNRPSGVPDRFSGSKSGTSASLAITGLQAE

DEADYYCQSYDSSLSGWRVFGGGTKLTVLGGGGGSQVQLQESGPGLVKPSETLSLTCT

VSGGSISSYYWSWIRQPAGKGLEWIGRIYTSGSTNYNPSLKSRVTMSVDTSKNQFSLKLS

SVTAADTAVYYCARDLYRDGMDVWGQGTTVTVSSFVPVFLPAKPTTTPAPRPPTPAPTI

ASQPLSLRPEACRPAAGGAVHTRGLDFACDIYIWAPLAGTCGVLLLSLVITLYCNHRNKR

GRKKLLYIFKQPFMRPVQTTQEEDGCSCRFPEEEEGGCELRVKFSRSADAPAYQQGQNQ

LYNELNLGRREEYDVLDKRRGRDPEMGGKPRRKNPQEGLYNELQKDKMAEAYSEIGM

KGERRRGKGHDGLYQGLSTATKDTYDALHMQALPPR*
```

PXL1419 CAR nucleic acid sequence (SEQ ID NO: 63)
```
ATGGCACTTCCTGTGACAGCCTTGCTCTTGCCCTTAGCACTGCTGCTTCATGCGGC

GAGACCTCAAGCAGTACTGACGCAGCCGCCCTCAGTGTCAGAGGCGCCAAGGCAAA

GAGTAACCATAAGTTGTTCTGGATCTTCCAGCAATATTGGTAACAACGCAGTGAGCT

GGTATCAGCAGCTACCGGGAAAGGCTCCCAAGCTATTGATATATTATGACGATCTTC

TTCCTTCAGGAGTGTCAGACAGGTTCTCGGGTTCTAAATCAGGCACATCAGCATCAC

TTGCCATCAGCGGCCTGCAGAGCGAAGATGAAGCAGATTATTATTGTGCCGCGTGGG

ATGATTCACTTAACGGATGGGTGTTCGGCGGAGGCACGAAGGTGACAGTACTTGGTG

GAGGGGGAGGGAGCCAGGTTCAACTTCAAGAATCCGGCCCAGGTTTGGTAAAGCCT

TCAGGTACCTTATCGCTGACTTGTGCAGTGTCAGGAGGATCAATCTCCAGTAGTAAT

TGGTGGTCATGGGTCCGACAGCCTCCAGGGAAAGGACTAGAGTGGATTGGCGAGAT

TTACCACTCTGGGAGTACCAACTACAACCCTTCACTTAAATCACGAGTCACAATTAG

TGTTGATAAATCAAAGAATCAATTCAGCCTCAAGCTATCATCAGTGACAGCAGCAGA

TACAGCGGTCTATTATTGTGCTAGACTTCCAGGCTACGAATCAGCATTTGATATCTGG

GGACAAGGAACCATGGTAACTGTTAGTAGCGGTAGTACCTCCGGATCAGGAAAGCC

GGGCTCTGGAGAAGGATCTACAAAGGGCGAGATCGTCCTCACTCAGTCTCCAGGCA

CCCTGTCTTTGTCACCTGGAGAACGGGCAACACTTTCATGCAGAGCATCACAAAGCG
```

-continued

TTAGTAGTAGCTATCTTGCCTGGTATCAGCAAAAACCGGGCCAGGCACCTAGACTGC

TCATTTATGGAGCTTCCTCAAGAGCAACAGGAATCCCTGACCGGTTCAGCGGGTCCG

GCTCTGGTACTGATTTCACCTTAACAATCTCAAGACTTGAACCTGAAGATTTCGCAGT

GTATTATTGTCAGCAGGCAGGACTCTTCCCGTATACATTCGGCGGAGGCACAAAAGT

GGAAATTAAAGGAGGAGGTGGCTCCGAGGTCCAACTTGTGCAATCAGGAGCAGAAG

TGAAGAAGCCAGGCGAATCACTTAAGATTTCCTGCAAAGGATCAGGATACTCATTTA

CATCATACTGGATCGGATGGGTCCGGCAGATGCCCGGCAAAGGATTGGAGTGGATG

GGCATCATCTACCCTGGAGATTCAGATACAAGATACTCACCTTCCTTCCAAGGCCAG

GTCACCATATCGGCTGACAAATCAATCTCAACAGCATACCTTCAATGGTCATCACTT

AAAGCATCAGATACAGCAATGTACTACTGCGCAAGGCTTAGCTATTCATGGTCATCA

TGGTACTGGGATTTCTGGGGGCAAGGCACGCTGGTTACAGTCTCATCCTTTGTACCT

GTGTTTCTTCCTGCAAAGCCGACCACAACTCCCGCACCTAGACCTCCAACTCCGGCA

CCAACCATTGCATCACAACCTCTAAGTCTGAGGCCCGAGGCATGCAGACCTGCAGCA

GGAGGAGCAGTGCACACAAGAGGACTTGATTTCGCGTGTGATATCTACATCTGGGCA

CCCCTGGCCGGAACATGTGGAGTGCTTCTTCTTTCACTTGTGATCACACTTTACTGCA

ACCACAGAAACAAGCGCGGTAGAAAGAAGCTACTGTACATCTTTAAACAACCTTTC

ATGCGTCCTGTGCAAACAACACAAGAAGAAGATGGATGCTCATGCAGATTTCCTGA

AGAAGAAGAAGGAGGATGCGAACTTAGAGTGAAATTCAGCCGATCAGCAGATGCAC

CTGCATACCAACAAGGACAGAATCAGCTCTATAATGAGCTGAATTTGGGAAGAAGA

GAAGAATACGATGTGCTTGATAAGCGCAGAGGTCGAGACCCAGAAATGGGAGGAAA

GCCGAGGAGGAAGAATCCGCAAGAAGGACTATATAATGAGCTCCAGAAGGATAAG

ATGGCTGAAGCATACTCAGAAATCGGAATGAAAGGAGAAAGAAGAAGAGGAAAGG

GCCATGATGGACTTTACCAAGGACTTTCAACAGCAACAAAGGACACTTACGATGCAC

TTCACATGCAAGCACTTCCTCCTAGA

PXL1419 CAR protein sequence (SEQ ID NO: 64)
MALPVTALLLPLALLLHAARPQAVLTQPPSVSEAPRQRVTISCSGSSSNIGNNAVSWY

QQLPGKAPKLLIYYDDLLPSGVSDRFSGSKSGTSASLAISGLQSEDEADYYCAAWDDSLN

GWVFGGGTKVTVLGGGGGSQVQLQESGPGLVKPSGTLSLTCAVSGGSISSSNWWSWVR

QPPGKGLEWIGEIYHSGSTNYNPSLKSRVTISVDKSKNQFSLKLSSVTAADTAVYYCARL

PGYESAFDIWGQGTMVTVSSGSTSGSGKPGSGEGSTKGEIVLTQSPGTLSLSPGERATLSC

RASQSVSSSYLAWYQQKPGQAPRLLIYGASSRATGIPDRFSGSGSGTDFTLTISRLEPEDF

AVYYCQQAGLFPYTFGGGTKVEIKGGGGSEVQLVQSGAEVKKPGESLKISCKGSGYSFT

SYWIGWVRQMPGKGLEWMGIIYPGDSDTRYSPSFQGQVTISADKSISTAYLQWSSLKAS

DTAMYYCARLSYSWSSWYWDFWGQGTLVTVSSFVPVFLPAKPTTTPAPRPPTPAPTIAS

QPLSLRPEACRPAAGGAVHTRGLDFACDIYIWAPLAGTCGVLLLSLVITLYCNHRNKRG

RKKLLYIFKQPFMRPVQTTQEEDGCSCRFPEEEEGGCELRVKFSRSADAPAYQQGQNQL

YNELNLGRREEYDVLDKRRGRDPEMGGKPRRKNPQEGLYNELQKDKMAEAYSEIGMK

GERRRGKGHDGLYQGLSTATKDTYDALHMQALPPR

-continued

PXL1435 CAR nucleic acid sequence (SEQ ID NO: 65)
ATGGCACTTCCTGTGACAGCCTTGCTCTTGCCCTTAGCACTGCTGCTTCATGCGGC

GAGACCTGAGGTCCAACTTGTGCAATCAGGAGCAGAAGTGAAGAAGCCAGGCGAAT

CACTTAAGATTTCCTGCAAAGGATCAGGATACTCATTTACATCATACTGGATCGGAT

GGGTCCGGCAGATGCCCGGCAAAGGATTGGAGTGGATGGGCATCATCTACCCTGGA

GATTCAGATACAAGATACTCACCTTCCTTCCAAGGCCAGGTCACCATATCGGCTGAC

AAATCAATCTCAACAGCATACCTTCAATGGTCATCACTTAAAGCATCAGATACAGCA

ATGTACTACTGCGCAAGGCTTAGCTATTCATGGTCATCATGGTACTGGGATTTCTGG

GGGCAAGGCACGCTGGTTACAGTCTCATCCGGAGGGGGAGGGAGCGAGATCGTCCT

CACTCAGTCTCCAGGCACCCTGTCTTTGTCACCTGGAGAACGGGCAACACTTTCATG

CAGAGCATCACAAAGCGTTAGTAGTAGCTATCTTGCCTGGTATCAGCAAAAACCGGG

CCAGGCACCTAGACTGCTCATTTATGGAGCTTCCTCAAGAGCAACAGGAATCCCTGA

CCGGTTCAGCGGGTCCGGCTCTGGTACTGATTTCACCTTAACAATCTCAAGACTTGA

ACCTGAAGATTTCGCAGTGTATTATTGTCAGCAGGCAGGACTCTTCCCGTATACATTC

GGCGGAGGCACAAAAGTGGAAATTAAAGGTAGTACCTCCGGATCAGGAAAGCCGGG

CTCTGGAGAAGGATCTACAAAGGGCCAGGTTCAACTTCAAGAATCCGGCCCAGGTTT

GGTAAAGCCTTCAGGTACCTTATCGCTGACTTGTGCAGTGTCAGGAGGATCAATCTC

CAGTAGTAATTGGTGGTCATGGGTCCGACAGCCTCCAGGGAAAGGACTAGAGTGGA

TTGGCGAGATTTACCACTCTGGGAGTACCAACTACAACCCTTCACTTAAATCACGAG

TCACAATTAGTGTTGATAAATCAAAGAATCAATTCAGCCTCAAGCTATCATCAGTGA

CAGCAGCAGATACAGCGGTCTATTATTGTGCTAGACTTCCAGGCTACGAATCAGCAT

TTGATATCTGGGGACAAGGAACCATGGTAACTGTTAGTAGCGGAGGAGGTGGCTCC

CAAGCAGTACTGACGCAGCCGCCCTCAGTGTCAGAGGCGCCAAGGCAAAGAGTAAC

CATAAGTTGTTCTGGATCTTCCAGCAATATTGGTAACAACGCAGTGAGCTGGTATCA

GCAGCTACCGGGAAAGGCTCCCAAGCTATTGATATATTATGACGATCTTCTTCCTTC

AGGAGTGTCAGACAGGTTCTCGGGTTCTAAATCAGGCACATCAGCATCACTTGCCAT

CAGCGGCCTGCAGAGCGAAGATGAAGCAGATTATTATTGTGCCGCGTGGGATGATTC

ACTTAACGGATGGGTGTTCGGCGGAGGCACGAAGGTGACAGTACTTGGTTTTGTACC

TGTGTTTCTTCCTGCAAAGCCGACCACAACTCCCGCACCTAGACCTCCAACTCCGGC

ACCAACCATTGCATCACAACCTCTAAGTCTGAGGCCCGAGGCATGCAGACCTGCAGC

AGGAGGAGCAGTGCACACAAGAGGACTTGATTTCGCGTGTGATATCTACATCTGGGC

ACCCCTGGCCGGAACATGTGGAGTGCTTCTTCTTTCACTTGTGATCACACTTTACTGC

AACCACAGAAACAAGCGCGGTAGAAAGAAGCTACTGTACATCTTTAAACAACCTTT

CATGCGTCCTGTGCAAACAACACAAGAAGAAGATGGATGCTCATGCGAGATTTCCTGA

AGAAGAAGAAGGAGGATGCGAACTTAGAGTGAAATTCAGCCGATCAGCAGATGCAC

CTGCATACCAACAAGGACAGAATCAGCTCTATAATGAGCTGAATTTGGGAAGAAGA

GAAGAATACGATGTGCTTGATAAGCGCAGAGGTCGAGACCCAGAAATGGGAGGAAA

GCCGAGGAGGAAGAATCCGCAAGAAGGACTATATAATGAGCTCCAGAAGGATAAG

ATGGCTGAAGCATACTCAGAAATCGGAATGAAAGGAGAAAGAAGAAGAGGAAAGG

GCCATGATGGACTTTACCAAGGACTTTCAACAGCAACAAAGGACACTTACGATGCAC

TTCACATGCAAGCACTTCCTCCTAGA

PXL1435 CAR protein sequence (SEQ ID NO: 66)
MALPVTALLLPLALLLHAARPEVQLVQSGAEVKKPGESLKISCKGSGYSFTSYWIGW

VRQMPGKGLEWMGIIYPGDSDTRYSPSFQGQVTISADKSISTAYLQWSSLKASDTAMYY

CARLSYSWSSWYWDFWGQGTLVTVSSGGGGSEIVLTQSPGTLSLSPGERATLSCRASQS

VSSSYLAWYQQKPGQAPRLLIYGASSRATGIPDRFSGSGSGTDFTLTISRLEPEDFAVYYC

QQAGLFPYTFGGGTKVEIKGSTSGSGKPGSGEGSTKGQVQLQESGPGLVKPSGTLSLTCA

VSGGSISSSNWWSWVRQPPGKGLEWIGEIYHSGSTNYNPSLKSRVTISVDKSKNQFSLKL

SSVTAADTAVYYCARLPGYESAFDIWGQGTMVTVSSGGGGSQAVLTQPPSVSEAPRQR

VTISCSGSSSNIGNNAVSWYQQLPGKAPKLLIYYDDLLPSGVSDRFSGSKSGTSASLAISG

LQSEDEADYYCAAWDDSLNGWVFGGGTKVTVLGFVPVFLPAKPTTTPAPRPPTPAPTIA

SQPLSLRPEACRPAAGGAVHTRGLDFACDIYIWAPLAGTCGVLLLSLVITLYCNHRNKRG

RKKLLYIFKQPFMRPVQTTQEEDGCSCRFPEEEEGGCELRVKFSRSADAPAYQQGQNQL

YNELNLGRREEYDVLDKRRGRDPEMGGKPRRKNPQEGLYNELQKDKMAEAYSEIGMK

GERRRGKGHDGLYQGLSTATKDTYDALHMQALPPR

PXL1436 CAR nucleic acid sequence (SEQ ID NO: 67)
ATGGCACTTCCTGTGACAGCCTTGCTCTTGCCCTTAGCACTGCTGCTTCATGCGGC

GAGACCTGAGATCGTCCTCACTCAGTCTCCAGGCACCCTGTCTTTGTCACCTGGAGA

ACGGGCAACACTTTCATGCAGAGCATCACAAAGCGTTAGTAGTAGCTATCTTGCCTG

GTATCAGCAAAAACCGGGCCAGGCACCTAGACTGCTCATTTATGGAGCTTCCTCAAG

AGCAACAGGAATCCCTGACCGGTTCAGCGGGTCCGGCTCTGGTACTGATTTCACCTT

AACAATCTCAAGACTTGAACCTGAAGATTTCGCAGTGTATTATTGTCAGCAGGCAGG

ACTCTTCCCGTATACATTCGGCGGAGGCACAAAAGTGGAAATTAAAGGAGGGGGAG

GGAGCGAGGTCCAACTTGTGCAATCAGGAGCAGAAGTGAAGAAGCCAGGCGAATCA

CTTAAGATTTCCTGCAAAGGATCAGGATACTCATTTACATCATACTGGATCGGATGG

GTCCGGCAGATGCCCGGCAAAGGATTGGAGTGGATGGGCATCATCTACCCTGGAGA

TTCAGATACAAGATACTCACCTTCCTTCCAAGGCCAGGTCACCATATCGGCTGACAA

ATCAATCTCAACAGCATACCTTCAATGGTCATCACTTAAAGCATCAGATACAGCAAT

GTACTACTGCGCAAGGCTTAGCTATTCATGGTCATCATGGTACTGGGATTTCTGGGG

GCAAGGCACGCTGGTTACAGTCTCATCCGGTAGTACCTCCGGATCAGGAAAGCCGG

GCTCTGGAGAAGGATCTACAAAGGGCCAAGCAGTACTGACGCAGCCGCCCTCAGTG

TCAGAGGCGCCAAGGCAAAGAGTAACCATAAGTTGTTCTGGATCTTCCAGCAATATT

GGTAACAACGCAGTGAGCTGGTATCAGCAGCTACCGGGAAAGGCTCCCAAGCTATT

GATATATTATGACGATCTTCTTCCTTCAGGAGTGTCAGACAGGTTCTCGGGTTCTAAA

TCAGGCACATCAGCATCACTTGCCATCAGCGGCCTGCAGAGCGAAGATGAAGCAGA

TTATTATTGTGCCGCGTGGGATGATTCACTTAACGGATGGGTGTTCGGCGGAGGCAC

GAAGGTGACAGTACTTGGTGGAGGAGGTGGCTCCCAGGTTCAACTTCAAGAATCCG

GCCCAGGTTTGGTAAAGCCTTCAGGTACCTTATCGCTGACTTGTGCAGTGTCAGGAG

-continued

GATCAATCTCCAGTAGTAATTGGTGGTCATGGGTCCGACAGCCTCCAGGGAAAGGAC

TAGAGTGGATTGGCGAGATTTACCACTCTGGGAGTACCAACTACAACCCTTCACTTA

AATCACGAGTCACAATTAGTGTTGATAAATCAAAGAATCAATTCAGCCTCAAGCTAT

CATCAGTGACAGCAGCAGATACAGCGGTCTATTATTGTGCTAGACTTCCAGGCTACG

AATCAGCATTTGATATCTGGGGACAAGGAACCATGGTAACTGTTAGTAGCTTTGTAC

CTGTGTTTCTTCCTGCAAAGCCGACCACAACTCCCGCACCTAGACCTCCAACTCCGG

CACCAACCATTGCATCACAACCTCTAAGTCTGAGGCCCGAGGCATGCAGACCTGCAG

CAGGAGGAGCAGTGCACACAAGAGGACTTGATTTCGCGTGTGATATCTACATCTGGG

CACCCCTGGCCGGAACATGTGGAGTGCTTCTTCTTTCACTTGTGATCACACTTTACTG

CAACCACAGAAACAAGCGCGGTAGAAAGAAGCTACTGTACATCTTTAAACAACCTT

TCATGCGTCCTGTGCAAACAACACAAGAAGAAGATGGATGCTCATGCAGATTTCCTG

AAGAAGAAGAAGGAGGATGCGAACTTAGAGTGAAATTCAGCCGATCAGCAGATGCA

CCTGCATACCAACAAGGACAGAATCAGCTCTATAATGAGCTGAATTTGGGAAGAAG

AGAAGAATACGATGTGCTTGATAAGCGCAGAGGTCGAGACCCAGAAATGGGAGGAA

AGCCGAGGAGGAAGAATCCGCAAGAAGGACTATATAATGAGCTCCAGAAGGATAA

GATGGCTGAAGCATACTCAGAAATCGGAATGAAAGGAGAAAGAAGAAGAGGAAAG

GGCCATGATGGACTTTACCAAGGACTTTCAACAGCAACAAAGGACACTTACGATGC

ACTTCACATGCAAGCACTTCCTCCTAGA

PXL1436 CAR protein sequence (SEQ ID NO: 68)
MALPVTALLLPLALLLHAARPEIVLTQSPGTLSLSPGERATLSCRASQSVSSSYLAWY

QQKPGQAPRLLIYGASSRATGIPDRFSGSGSGTDFTLTISRLEPEDFAVYYCQQAGLFPYT

FGGGTKVEIKGGGGSEVQLVQSGAEVKKPGESLKISCKGSGYSFTSYWIGWVRQMPGK

GLEWMGIIYPGDSDTRYSPSFQGQVTISADKSISTAYLQWSSLKASDTAMYYCARLSYS

WSSWYWDFWGQGTLVTVSSGSTSGSGKPGSGEGSTKGQAVLTQPPSVSEAPRQRVTISC

SGSSSNIGNNAVSWYQQLPGKAPKLLIYYDDLLPSGVSDRFSGSKSGTSASLAISGLQSED

EADYYCAAWDDSLNGWVFGGGTKVTVLGGGGGSQVQLQESGPGLVKPSGTLSLTCAV

SGGSISSSNWWSWVRQPPGKGLEWIGEIYHSGSTNYNPSLKSRVTISVDKSKNQFSLKLS

SVTAADTAVYYCARLPGYESAFDIWGQGTMVTVSSFVPVFLPAKPTTTPAPRPPTPAPTI

ASQPLSLRPEACRPAAGGAVHTRGLDFACDIYIWAPLAGTCGVLLLSLVITLYCNHRNKR

GRKKLLYIFKQPFMRPVQTTQEEDGCSCRFPEEEEGGCELRVKFSRSADAPAYQQGQNQ

LYNELNLGRREEYDVLDKRRGRDPEMGGKPRRKNPQEGLYNELQKDKMAEAYSEIGM

KGERRRGKGHDGLYQGLSTATKDTYDALHMQALPPR

PXL1437 CAR nucleic acid sequence (SEQ ID NO: 69)
ATGGCACTTCCTGTGACAGCCTTGCTCTTGCCCTTAGCACTGCTGCTTCATGCGGC

GAGACCTCAGGTTCAACTTCAAGAATCCGGCCCAGGTTTGGTAAAGCCTTCAGGTAC

CTTATCGCTGACTTGTGCAGTGTCAGGAGGATCAATCTCCAGTAGTAATTGGTGGTC

ATGGGTCCGACAGCCTCCAGGGAAAGGACTAGAGTGGATTGGCGAGATTTACCACT

CTGGGAGTACCAACTACAACCCTTCACTTAAATCACGAGTCACAATTAGTGTTGATA

AATCAAAGAATCAATTCAGCCTCAAGCTATCATCAGTGACAGCAGCAGATACAGCG

GTCTATTATTGTGCTAGACTTCCAGGCTACGAATCAGCATTTGATATCTGGGGACAA

GGAACCATGGTAACTGTTAGTAGCGGAGGGGGAGGGAGCCAAGCAGTACTGACGCA

```
GCCGCCCTCAGTGTCAGAGGCGCCAAGGCAAAGAGTAACCATAAGTTGTTCTGGATC

TTCCAGCAATATTGGTAACAACGCAGTGAGCTGGTATCAGCAGCTACCGGGAAAGG

CTCCCAAGCTATTGATATATTATGACGATCTTCTTCCTTCAGGAGTGTCAGACAGGTT

CTCGGGTTCTAAATCAGGCACATCAGCATCACTTGCCATCAGCGGCCTGCAGAGCGA

AGATGAAGCAGATTATTATTGTGCCGCGTGGGATGATTCACTTAACGGATGGGTGTT

CGGCGGAGGCACGAAGGTGACAGTACTTGGTGGTAGTACCTCCGGATCAGGAAAGC

CGGGCTCTGGAGAAGGATCTACAAAGGGCGAGGTCCAACTTGTGCAATCAGGAGCA

GAAGTGAAGAAGCCAGGCGAATCACTTAAGATTTCCTGCAAAGGATCAGGATACTC

ATTTACATCATACTGGATCGGATGGGTCCGGCAGATGCCCGGCAAAGGATTGGAGTG

GATGGGCATCATCTACCCTGGAGATTCAGATACAAGATACTCACCTTCCTTCCAAGG

CCAGGTCACCATATCGGCTGACAAATCAATCTCAACAGCATACCTTCAATGGTCATC

ACTTAAAGCATCAGATACAGCAATGTACTACTGCGCAAGGCTTAGCTATTCATGGTC

ATCATGGTACTGGGATTTCTGGGGGCAAGGCACGCTGGTTACAGTCTCATCCGGAGG

AGGTGGCTCCGAGATCGTCCTCACTCAGTCTCCAGGCACCCTGTCTTTGTCACCTGGA

GAACGGGCAACACTTTCATGCAGAGCATCACAAAGCGTTAGTAGTAGCTATCTTGCC

TGGTATCAGCAAAAACCGGGCCAGGCACCTAGACTGCTCATTTATGGAGCTTCCTCA

AGAGCAACAGGAATCCCTGACCGGTTCAGCGGGTCCGGCTCTGGTACTGATTTCACC

TTAACAATCTCAAGACTTGAACCTGAAGATTTCGCAGTGTATTATTGTCAGCAGGCA

GGACTCTTCCCGTATACATTCGGCGGAGGCACAAAAGTGGAAATTAAATTTGTACCT

GTGTTTCTTCCTGCAAAGCCGACCACAACTCCCGCACCTAGACCTCCAACTCCGGCA

CCAACCATTGCATCACAACCTCTAAGTCTGAGGCCCGAGGCATGCAGACCTGCAGCA

GGAGGAGCAGTGCACACAAGAGGACTTGATTTCGCGTGTGATATCTACATCTGGGCA

CCCCTGGCCGGAACATGTGGAGTGCTTCTTCTTTCACTTGTGATCACACTTTACTGCA

ACCACAGAAACAAGCGCGGTAGAAAGAAGCTACTGTACATCTTTAAACAACCTTTC

ATGCGTCCTGTGCAAACAACACAAGAAGAAGATGGATGCTCATGCAGATTTCCTGA

AGAAGAAGAAGGAGGATGCGAACTTAGAGTGAAATTCAGCCGATCAGCAGATGCAC

CTGCATACCAACAAGGACAGAATCAGCTCTATAATGAGCTGAATTTGGGAAGAAGA

GAAGAATACGATGTGCTTGATAAGCGCAGAGGTCGAGACCCAGAAATGGGAGGAAA

GCCGAGGAGGAAGAATCCGCAAGAAGGACTATATAATGAGCTCCAGAAGGATAAG

ATGGCTGAAGCATACTCAGAAATCGGAATGAAAGGAGAAAGAAGAAGAGGAAAGG

GCCATGATGGACTTTACCAAGGACTTTCAACAGCAACAAAGGACACTTACGATGCAC

TTCACATGCAAGCACTTCCTCCTAGA
```

PXL1437 CAR protein sequence (SEQ ID NO: 70)
```
MALPVTALLLPLALLLHAARPQVQLQESGPGLVKPSGTLSLTCAVSGGSISSSNWWS

WVRQPPGKGLEWIGEIYHSGSTNYNPSLKSRVTISVDKSKNQFSLKLSSVTAADTAVYY

CARLPGYESAFDIWGQGTMVTVSSGGGGSQAVLTQPPSVSEAPRQRVTISCSGSSSNIGN

NAVSWYQQLPGKAPKLLIYYDDLLPSGVSDRFSGSKSGTSASLAISGLQSEDEADYYCA

AWDDSLNGWVFGGGTKVTVLGGSTSGSGKPGSGEGSTKGEVQLVQSGAEVKKPGESL

KISCKGSGYSFTSYWIGWVRQMPGKGLEWMGIIYPGDSDTRYSPSFQGQVTISADKSIST

AYLQWSSLKASDTAMYYCARLSYSWSSWYWDFWGQGTLVTVSSGGGGSEIVLTQSPG
```

TLSLSPGERATLSCRASQSVSSSYLAWYQQKPGQAPRLLIYGASSRATGIPDRFSGSGSGT

DFTLTISRLEPEDFAVYYCQQAGLFPYTFGGGTKVEIKFVPVFLPAKPTTTPAPRPPTPAPT

IASQPLSLRPEACRPAAGGAVHTRGLDFACDIYIWAPLAGTCGVLLLSLVITLYCNHRNK

RGRKKLLYIFKQPFMRPVQTTQEEDGCSCRFPEEEEGGCELRVKFSRSADAPAYQQGQN

QLYNELNLGRREEYDVLDKRRGRDPEMGGKPRRKNPQEGLYNELQKDKMAEAYSEIG

MKGERRRGKGHDGLYQGLSTATKDTYDALHMQALPPR

The invention claimed is:

1. A bispecific chimeric antigen receptor targeting CD19 and CD22, comprising an extracellular antigen-binding domain, the extracellular antigen-binding domain comprises a heavy chain variable region and a light chain variable region of an anti-CD19 antibody and a heavy chain variable region and a light chain variable region of an anti-CD22 antibody, wherein the amino acid sequences of the heavy chain variable region and the light chain variable region of the anti-CD19 antibody are selected from any of the following combinations:

the heavy chain variable region sequence comprising SEQ ID NO: 2 and the light chain variable region sequence comprising SEQ ID NO: 4; and the heavy chain variable region sequence comprising SEQ ID NO: 8 and the light chain variable region sequence comprising SEQ ID NO: 6, and the amino acid sequences of the heavy chain variable region and the light chain variable region of the anti-CD22 antibody are selected from any of the following combinations:

the heavy chain variable region sequence comprising SEQ ID NO: 10 and the light chain variable region sequence comprising SEQ ID NO: 12; and the heavy chain variable region sequence comprising SEQ ID NO: 14 and the light chain variable region sequence comprising SEQ ID NO: 16.

2. The bispecific chimeric antigen receptor of claim 1, wherein the heavy chain variable region of the anti-CD19 antibody comprises SEQ ID NO: 2, the light chain variable region of the anti-CD19 antibody comprises SEQ ID NO: 4, the heavy chain variable region of the anti-CD22 antibody comprises SEQ ID NO: 10, and the light chain variable region of the anti-CD22 antibody comprises SEQ ID NO: 12;

or, the heavy chain variable region of the anti-CD19 antibody comprises SEQ ID NO: 2, the light chain variable region of the anti-CD19 antibody comprises SEQ ID NO: 4, the heavy chain variable region of the anti-CD22 antibody comprises SEQ ID NO: 14, and the light chain variable region of the anti-CD22 antibody comprises SEQ ID NO: 16;

or, the heavy chain variable region of the anti-CD19 antibody comprises SEQ ID NO: 8, the light chain variable region of the anti-CD19 antibody comprises SEQ ID NO: 6, the heavy chain variable region of the anti-CD22 antibody comprises SEQ ID NO: 10, and the light chain variable region of the anti-CD22 antibody comprises SEQ ID NO: 12.

3. The bispecific chimeric antigen receptor of claim 1, wherein the heavy chain variable region and the light chain variable regions of the anti-CD19 antibody and the heavy chain variable region and the light chain variable regions of the anti-CD22 antibody are located in the extracellular antigen-binding domain, from the amino terminus to the carboxyl terminus, in the following order:

the light chain variable region of the anti-CD19 antibody, the heavy chain variable region of the anti-CD22 antibody, the light chain variable region of the anti-CD22 antibody, and the heavy chain variable region of the anti-CD19 antibody;

the heavy chain variable region of the anti-CD19 antibody, the light chain variable region of the anti-CD22 antibody, the heavy chain variable region of the anti-CD22 antibody, and the light chain variable region of the anti-CD19 antibody;

the light chain variable region of the anti-CD22 antibody, the heavy chain variable region of the anti-CD19 antibody, the light chain variable region of the anti-CD19 antibody, and the heavy chain variable region of the anti-CD22 antibody; or the heavy chain variable region of the anti-CD22 antibody, the light chain variable region of the anti-CD19 antibody, the heavy chain variable region of the anti-CD19 antibody, and the light chain variable region of the anti-CD22 antibody.

4. The bispecific chimeric antigen receptor of claim 1, wherein the extracellular antigen-binding domain, from the amino terminus to the carboxyl terminus, sequentially comprises:

the light chain variable region of the anti-CD19 antibody, a first linker, the heavy chain variable region of the anti-CD22 antibody, a second linker, the light chain variable region of the anti-CD22 antibody, a third linker, and the heavy chain variable region of the anti-CD19 antibody, the heavy chain variable region of the anti-CD19 antibody, a first linker, the light chain variable region of the anti-CD22 antibody, a second linker, the heavy chain variable region of the anti-CD22 antibody, a third linker, and the light chain variable region of the anti-CD19 antibody;

the light chain variable region of the anti-CD22 antibody, a first linker, the heavy chain variable region of the anti-CD19 antibody, a second linker, the light chain variable region of the anti-CD19 antibody, a third linker, and the heavy chain variable region of the anti-CD22 antibody; or the heavy chain variable region of the anti-CD22 antibody, a first linker, the light chain variable region of the anti-CD19 antibody, a second linker, the heavy chain variable region of the anti-CD19 antibody, a third linker, and the light chain variable region of the anti-CD22 antibody, wherein the first linker and the third linker have the amino acid sequence set forth in SEQ ID NO: 20, and the second linker has the amino acid sequence set forth in SEQ ID NO: 24.

5. The bispecific chimeric antigen receptor of claim 1, wherein the bispecific chimeric antigen receptor, from the amino terminus to the carboxyl terminus, sequentially comprises a signal peptide sequence, the extracellular antigen-binding domain, a hinge region, a transmembrane domain, and an intracellular signaling domain, wherein the intracellular signaling domain, from the amino terminus to the carboxyl terminus, comprises a fragment from 4-1BB molecule and a fragment from CD3z molecule.

6. The bispecific chimeric antigen receptor of claim 1, wherein the signal peptide sequence comprises SEQ ID NO: 36;

the hinge region comprises SEQ ID NO: 26;

the transmembrane domain comprises SEQ ID NO: 28;

the fragment from 4-1BB molecules comprises SEQ ID NO: 30; and the fragment from CD3z molecules comprises SEQ ID NO: 32.

7. The bispecific chimeric antigen receptor of claim 1, comprising the amino acid sequence set forth in SEQ ID NO: 40, 42, 44, 46, 48, 50, 52, 54, 56, 58, 60, 62, 64, 66, 68 or 70.

8. A nucleic acid molecule encoding the bispecific chimeric antigen receptor of claim 1.

9. The nucleic acid molecule of claim 8, comprising the nucleotide sequence set forth in SEQ ID NO: 39, 41, 43, 45, 47, 49, 51, 53, 55, 57, 59, 61, 63, 65, 67 or 69.

10. An expression vector comprising the nucleic acid molecule of claim 8.

11. A host cell expressing the bispecific chimeric antigen receptor of claim 1.

12. The host cell of claim 11, wherein the host cell is a T cell or an NK cell.

13. A method for treating a CD-19-expressing or CD22-expressing cancer in a patient, comprising administering the host cell of claim 11 to the patient.

14. The method of claim 13, wherein the cancer is a B cell related cancer.

15. The method of claim 13, wherein the cancer is B-cell non-Hodgkin's lymphoma (B-NHL) or B-lineage acute lymphoblastic leukemia (B-ALL).

16. The method of claim 13, wherein the host cells are administered to the patient at a dose of $0.5 \times 10^6$ host cells/kg patient body weight to $3 \times 10^6$ host cells/kg patient body weight.

17. The method of claim 13, wherein the patient is a patient with B-NHL, and the host cells are administered to the patient at a dose of $1 \times 10^6$ host cells/kg patient body weight to $3 \times 10^6$ host cells/kg patient body weight.

18. The method of claim 13, wherein the patient is a patient with B-ALL, and the host cells are administered to the patient at a dose of $0.5 \times 10^6$ host cells/kg patient body weight to $1 \times 10^6$ host cells/kg patient body weight.

* * * * *

SEQUENCE LISTING

<160> NUMBER OF SEQ ID NOS: 70

<210> SEQ ID NO 1
<211> LENGTH: 369
<212> TYPE: DNA
<213> ORGANISM: Artificial Sequence
<220> FEATURE:
<223> OTHER INFORMATION: CD19-62 VH nucleic acid sequence

<400> SEQUENCE: 1
atggccgaag tgcagctggt gcagtctggg gcagaggtga aaaagcccgg ggagtctctg     60
aagatctcct gtaaggggtc tggatacagc tttaccaact cctggatcgg atgggtgcgc    120
cagatgcccg ggaaaggcct ggagtggatg ggactcattt accctgatga ctctgatacc    180
agatacagcc atccttcca aggccaggtc accatctcag ccgacagcgc catcaacacc    240
gcctacctgc agtggagcag cctgaaggcc tcggacaccg ccatgtatta ctgtgcgcgc    300
cagtctacct acatctacgg tggttactac gatacctggg gtcaaggtac tctggtgacc    360
gtctcctca    369

<210> SEQ ID NO 2
<211> LENGTH: 123
<212> TYPE: PRT
<213> ORGANISM: Artificial Sequence
<220> FEATURE:
<223> OTHER INFORMATION: CD19-62 VH protein sequence

<400> SEQUENCE: 2

Met Ala Glu Val Gln Leu Val Gln Ser Gly Ala Glu Val Lys Lys Pro
1            5                 10                15

Gly Glu Ser Leu Lys Ile Ser Cys Lys Gly Ser Gly Tyr Ser Phe Thr
          20               25              30

Asn Ser Trp Ile Gly Trp Val Arg Gln Met Pro Gly Lys Gly Leu Glu
       35               40                45

Trp Met Gly Leu Ile Tyr Pro Asp Asp Ser Asp Thr Arg Tyr Ser Pro
    50               55                60

Ser Phe Gln Gly Gln Val Thr Ile Ser Ala Asp Ser Ala Ile Asn Thr
65              70              75                80

Ala Tyr Leu Gln Trp Ser Ser Leu Lys Ala Ser Asp Thr Ala Met Tyr
               85              90               95

Tyr Cys Ala Arg Gln Ser Thr Tyr Ile Tyr Gly Gly Tyr Tyr Asp Thr
          100             105            110

Trp Gly Gln Gly Thr Leu Val Thr Val Ser Ser
        115             120

-continued

<210> SEQ ID NO 3
<211> LENGTH: 339
<212> TYPE: DNA
<213> ORGANISM: Artificial Sequence
<220> FEATURE:
<223> OTHER INFORMATION: CD19-62 VL nucleic acid sequence

<400> SEQUENCE: 3
cagtctgtcg tgacgcagcc gccctcagtg tctggggccc cagggcagag ggtcaccatc      60
tcctgcactg ggagcagctc caacatcggg gcaggttatg atgtacactg gtaccagcaa     120
cttccaggaa cagcccccaa actcctcatc tatgagaaca ccaatcggcc ctcaggggtc     180
cctgaccgat tctctggctc caagtctggc acctcagcct ccctggccat cactgggctc     240
caggctgagg atgaggctga ttattactgc cagtcctatg acagcagcct gagtggttgg     300
agggtgttcg gcggagggac caagctgacc gtcctaggt                            339

<210> SEQ ID NO 4
<211> LENGTH: 113
<212> TYPE: PRT
<213> ORGANISM: Artificial Sequence
<220> FEATURE:
<223> OTHER INFORMATION: CD19-62 VL protein sequence

<400> SEQUENCE: 4

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Glu Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Arg Val Phe Gly Gly Gly Thr Lys Leu Thr Val Leu
            100                 105                 110

Gly

<210> SEQ ID NO 5
<211> LENGTH: 333
<212> TYPE: DNA
<213> ORGANISM: Artificial Sequence
<220> FEATURE:
<223> OTHER INFORMATION: CD19-78 VL nucleic acid sequence

<400> SEQUENCE: 5
caggctgtgc tgactcagcc accctcggtg tctgaagccc ccaggcagag ggtcaccatc      60
tcctgttctg gaagcagctc caacatcgga aataatgctg taagctggta ccagcagctc     120
ccaggaaagg ctcccaaact cctcatctat tatgatgatc tgctcccctc aggggtctct     180
gaccgattct ctggctccaa gtctggcacc tcagcctccc tggccatcag tgggctccag     240
tctgaggatg aggctgatta ttactgtgca gcatgggatg acagcctgaa tggttgggtg     300
ttcggcggag ggaccaaggt caccgtccta ggt                                  333

<210> SEQ ID NO 6
<211> LENGTH: 111

-continued

<212> TYPE: PRT
<213> ORGANISM: Artificial Sequence
<220> FEATURE:
<223> OTHER INFORMATION: CD19-78 VL protein sequence

<400> SEQUENCE: 6

```
Gln Ala Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Ser Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Val Thr Val Leu Gly
            100                 105                 110
```

<210> SEQ ID NO 7
<211> LENGTH: 363
<212> TYPE: DNA
<213> ORGANISM: Artificial Sequence
<220> FEATURE:
<223> OTHER INFORMATION: CD19-78 VH nucleic acid sequence

<400> SEQUENCE: 7

```
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct ccaaggcca ggtcaccatc tcagccgaca gtccatcag caccgcctac       240 ctgcagtgga gcagcctgaa ggcctcggac accgccatgt attactgtgc gcgcctgtct     300
tactcttggt cttcttggta ctgggatttc tggggtcaag gtactctggt gaccgtctcc     360
tca                                                                    363
```

<210> SEQ ID NO 8
<211> LENGTH: 121
<212> TYPE: PRT
<213> ORGANISM: Artificial Sequence
<220> FEATURE:
<223> OTHER INFORMATION: CD19-78 VH protein sequence

<400> SEQUENCE: 8

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

Ala Arg Leu Ser Tyr Ser Trp Ser Ser Trp Tyr Trp Asp Phe Trp Gly
            100                 105                 110

Gln Gly Thr Leu Val Thr Val Ser Ser
        115                 120

<210> SEQ ID NO 9
<211> LENGTH: 357
<212> TYPE: DNA
<213> ORGANISM: Artificial Sequence
<220> FEATURE:
<223> OTHER INFORMATION: CD22-80 VH nucleic acid sequence

<400> SEQUENCE: 9
caggtgcagc tgcaggagtc gggcccagga ctggtgaagc cttcggggac cctgtccctc      60
acctgcgctg tctctggtgg ctccatcagc agtagtaact ggtggagttg ggtccgccag     120
cccccaggga aggggctgga gtggattggg gaaatctatc atagtgggag caccaactac     180
aacccgtccc tcaagagtcg agtcaccata tcagtagaca gtccaagaa ccagttctcc      240 ctgaagctga gctctgtgac cgccgcggac acggcggtgt actactgcgc cagacttcct     300
ggatacgagt cagctttcga catatggggt cagggtacaa tggtcaccgt cagctca       357

<210> SEQ ID NO 10
<211> LENGTH: 119
<212> TYPE: PRT
<213> ORGANISM: Artificial Sequence
<220> FEATURE:
<223> OTHER INFORMATION: CD22-80 VH protein sequence

<400> SEQUENCE: 10

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Pro Gly Tyr Glu Ser Ala Phe Asp Ile Trp Gly Gln Gly
            100                 105                 110

Thr Met Val Thr Val Ser Ser
        115

<210> SEQ ID NO 11
<211> LENGTH: 324
<212> TYPE: DNA
<213> ORGANISM: Artificial Sequence
<220> FEATURE:
<223> OTHER INFORMATION: CD22-80 VL nucleic acid sequence

<400> SEQUENCE: 11
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180

-continued

```
gacaggttca gtggcagtgg gtctgggaca gacttcactc tcaccatcag cagactggag      240
cctgaagatt ttgcagtgta ttactgtcag caggccggac tcttccctta cacttttggc      300
ggagggacca aggttgagat caaa                                             324
```

```
<210> SEQ ID NO 12
<211> LENGTH: 108
<212> TYPE: PRT
<213> ORGANISM: Artificial Sequence
<220> FEATURE:
<223> OTHER INFORMATION: CD22-80 VL protein sequence

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Leu Phe Pro
                85                  90                  95

Tyr Thr Phe Gly Gly Gly Thr Lys Val Glu Ile Lys
            100                 105
```

```
<210> SEQ ID NO 13
<211> LENGTH: 351
<212> TYPE: DNA
<213> ORGANISM: Artificial Sequence
<220> FEATURE:
<223> OTHER INFORMATION: CD22-28 VH nucleic acid sequence

<400> SEQUENCE: 13
caggtgcagc tgcaggagtc gggcccagga ctggtgaagc cttcggagac cctgtccctc      60
acctgcactg tctctggtgg ctccatcagt agttactact ggagctggat ccggcagccc      120
gccgggaagg gactggagtg gattgggcgt atctatacca gtgggagcac caactacaac      180
ccctccctca gagtcgagt caccatgtca gtagacacgt ccaagaacca gttctccctg      240
aagctgagct ctgtgaccgc cgcggacacg gcggtgtact actgcgccag agacttgtac      300
agagatggaa tggacgtatg gggccaggga caaactgtca ccgtcagctc a              351
```

```
<210> SEQ ID NO 14
<211> LENGTH: 117
<212> TYPE: PRT
<213> ORGANISM: Artificial Sequence
<220> FEATURE:
<223> OTHER INFORMATION: CD22-28 VH protein sequence

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
```

```
             50                    55                    60

Ser Arg Val Thr Met Ser Val Asp Thr Ser Lys Asn Gln Phe Ser Leu
65                    70                    75                    80

Lys Leu Ser Ser Val Thr Ala Ala Asp Thr Ala Val Tyr Tyr Cys Ala
                      85                    90                    95

Arg Asp Leu Tyr Arg Asp Gly Met Asp Val Trp Gly Gln Gly Thr Thr
             100                    105                    110

Val Thr Val Ser Ser
         115
```

```
<210> SEQ ID NO 15
<211> LENGTH: 321
<212> TYPE: DNA
<213> ORGANISM: Artificial Sequence
<220> FEATURE:
<223> OTHER INFORMATION: CD22-28 VL nucleic acid sequence

<400> SEQUENCE: 15
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctccgat gcctccagtt tggaaagtgg ggtcccatca     180
aggttcagcg gcagtggatc tgggacagaa ttcactctca ccatcagcag cctgcagcct     240
gatgattttg caacttatta ctgccagcag gccaatacct actctcctac ttttggcgga     300
gggaccaagg ttgagatcaa a                                               321
```

```
<210> SEQ ID NO 16
<211> LENGTH: 107
<212> TYPE: PRT
<213> ORGANISM: Artificial Sequence
<220> FEATURE:
<223> OTHER INFORMATION: CD22-28 VL protein sequence

<400> SEQUENCE: 16

Asp Ile Gln Met Thr Gln Ser Pro Ser Thr Leu Ser Ala Ser Val Gly
1                    5                    10                    15

Asp Arg Val Thr Ile Thr Cys Arg Ala Ser Gln Ser Ile Ser Ser Trp
                      20                    25                    30

Leu Ala Trp Tyr Gln Gln Lys Pro Gly Lys Ala Pro Lys Leu Leu Ile
             35                    40                    45

Ser Asp Ala Ser Ser Leu Glu Ser Gly Val Pro Ser Arg Phe Ser Gly
         50                    55                    60

Ser Gly Ser Gly Thr Glu Phe Thr Leu Thr Ile Ser Ser Leu Gln Pro
65                    70                    75                    80

Asp Asp Phe Ala Thr Tyr Tyr Cys Gln Gln Ala Asn Thr Tyr Ser Pro
                      85                    90                    95

Thr Phe Gly Gly Gly Thr Lys Val Glu Ile Lys
             100                    105
```

```
<210> SEQ ID NO 17
<211> LENGTH: 45
<212> TYPE: DNA
<213> ORGANISM: Artificial Sequence
<220> FEATURE:
<223> OTHER INFORMATION: Linker1 nucleic acid sequence

<400> SEQUENCE: 17
ggtggtggtg gtagcggcgg cggcggctct ggtggtggtg gatcc                      45
```

-continued

```
<210> SEQ ID NO 18
<211> LENGTH: 15
<212> TYPE: PRT
<213> ORGANISM: Artificial Sequence
<220> FEATURE:
<223> OTHER INFORMATION: Linker1 protein sequence

<400> SEQUENCE: 18

Gly Gly Gly Gly Ser Gly Gly Gly Ser Gly Gly Gly Gly Ser
1               5                   10                  15

<210> SEQ ID NO 19
<211> LENGTH: 15
<212> TYPE: DNA
<213> ORGANISM: Artificial Sequence
<220> FEATURE:
<223> OTHER INFORMATION: Linker2 nucleic acid sequence

<400> SEQUENCE: 19
ggcggaggtg ggtcc                                                    15

<210> SEQ ID NO 20
<211> LENGTH: 5
<212> TYPE: PRT
<213> ORGANISM: Artificial Sequence
<220> FEATURE:
<223> OTHER INFORMATION: Linker2 protein sequence

<400> SEQUENCE: 20

Gly Gly Gly Gly Ser
1               5

<210> SEQ ID NO 21
<211> LENGTH: 75
<212> TYPE: DNA
<213> ORGANISM: Artificial Sequence
<220> FEATURE:
<223> OTHER INFORMATION: Linker3 nucleic acid sequence

<400> SEQUENCE: 21
ggcggaggtg ggtccggtgg cgggggaagc ggaggcggag ggagcggagg aggggggatct    60 ggaggcggtg ggtct                                                    75

<210> SEQ ID NO 22
<211> LENGTH: 25
<212> TYPE: PRT
<213> ORGANISM: Artificial Sequence
<220> FEATURE:
<223> OTHER INFORMATION: Linker3 protein sequence

<400> SEQUENCE: 22

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 23
<211> LENGTH: 54
<212> TYPE: DNA
<213> ORGANISM: Artificial Sequence
<220> FEATURE:
<223> OTHER INFORMATION: Linker4 nucleic acid sequence

<400> SEQUENCE: 23
ggcagcacca gcggctccgg caagcctggc tctggcgagg gcagcacaaa ggga           54
```

```
<210> SEQ ID NO 24
<211> LENGTH: 18
<212> TYPE: PRT
<213> ORGANISM: Artificial Sequence
<220> FEATURE:
<223> OTHER INFORMATION: Linker4 protein sequence

<400> SEQUENCE: 24

Gly Ser Thr Ser Gly Ser Gly Lys Pro Gly Ser Gly Glu Gly Ser Thr
1               5                   10                  15

Lys Gly

<210> SEQ ID NO 25
<211> LENGTH: 135
<212> TYPE: DNA
<213> ORGANISM: Artificial Sequence
<220> FEATURE:
<223> OTHER INFORMATION: CD8a hinge nucleic acid sequence

<400> SEQUENCE: 25
actactaccc ctgcacctag gcctcccacc ccagccccaa caatcgccag ccagcctctg       60
tctctgcggc ccgaagcctg tagacctgct gccggcggag ccgtgcacac cagaggcctg      120
gacttcgcct gcgac                                                       135

<210> SEQ ID NO 26
<211> LENGTH: 45
<212> TYPE: PRT
<213> ORGANISM: Artificial Sequence
<220> FEATURE:
<223> OTHER INFORMATION: CD8a hinge protein sequence

<400> SEQUENCE: 26

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 27
<211> LENGTH: 72
<212> TYPE: DNA
<213> ORGANISM: Artificial Sequence
<220> FEATURE:
<223> OTHER INFORMATION: CD8a TM nucleic acid sequence

<400> SEQUENCE: 27
atctacatct gggcccctct ggccggcacc tgtggcgtgc tgctgctgag cctggtgatc       60
accctgtact gc                                                           72

<210> SEQ ID NO 28
<211> LENGTH: 24
<212> TYPE: PRT
<213> ORGANISM: Artificial Sequence
<220> FEATURE:
<223> OTHER INFORMATION: CD8a TM protein sequence

<400> SEQUENCE: 28

Ile Tyr Ile Trp Ala Pro Leu Ala Gly Thr Cys Gly Val Leu Leu Leu
1               5                   10                  15

Ser Leu Val Ile Thr Leu Tyr Cys
```

-continued

```
                20
```

```
<210> SEQ ID NO 29
<211> LENGTH: 126
<212> TYPE: DNA
<213> ORGANISM: Artificial Sequence
<220> FEATURE:
<223> OTHER INFORMATION: 4-1BB intracellular domain (IC) nucleic acid
      sequence

<400> SEQUENCE: 29
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                              126

<210> SEQ ID NO 30
<211> LENGTH: 42
<212> TYPE: PRT
<213> ORGANISM: Artificial Sequence
<220> FEATURE:
<223> OTHER INFORMATION: 4-1BB intracellular domain (IC) sequence

<400> SEQUENCE: 30

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 31
<211> LENGTH: 336
<212> TYPE: DNA
<213> ORGANISM: Artificial Sequence
<220> FEATURE:
<223> OTHER INFORMATION: CD3z intracellular signaling domain nucleic
      acid sequence

<400> SEQUENCE: 31
agagtgaagt tcagcagatc cgccgacgcc cctgcctacc agcagggaca gaaccagctg      60
tacaacgagc tgaacctggg cagacgggaa gagtacgacg tgctggacaa gcggagaggc     120
cgggaccccg agatgggcgg aaagcccaga cggaagaacc cccaggaagg cctgtataac     180
gaactgcaga agacaagat ggccgaggcc tacagcgaga tcggcatgaa gggcgagcgg     240
aggcgcggca agggccacga tggcctgtac cagggcctga gcaccgccac caaggacacc     300
tacgacgccc tgcacatgca ggccctgccc cccaga                              336

<210> SEQ ID NO 32
<211> LENGTH: 112
<212> TYPE: PRT
<213> ORGANISM: Artificial Sequence
<220> FEATURE:
<223> OTHER INFORMATION: CD3z intracellular signaling domain sequence

<400> SEQUENCE: 32

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45
```

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 33
<211> LENGTH: 54
<212> TYPE: DNA
<213> ORGANISM: Artificial Sequence
<220> FEATURE:
<223> OTHER INFORMATION: T2A nucleic acid sequence

<400> SEQUENCE: 33
gagggaaggg gcagcttatt aacatgtggc gatgtggaag agaaccccgg tccc          54

<210> SEQ ID NO 34
<211> LENGTH: 18
<212> TYPE: PRT
<213> ORGANISM: Artificial Sequence
<220> FEATURE:
<223> OTHER INFORMATION: T2A protein sequence

<400> SEQUENCE: 34

Glu Gly Arg Gly Ser Leu Leu Thr Cys Gly Asp Val Glu Glu Asn Pro
1               5                   10                  15

Gly Pro

<210> SEQ ID NO 35
<211> LENGTH: 66
<212> TYPE: DNA
<213> ORGANISM: Artificial Sequence
<220> FEATURE:
<223> OTHER INFORMATION: CSF2RA signal nucleic acid sequence

<400> SEQUENCE: 35
atgctgctgc tcgtgacctc tttactgtta tgtgagctgc cccacccccgc ttttttactg          60 atccct                                                          66

<210> SEQ ID NO 36
<211> LENGTH: 22
<212> TYPE: PRT
<213> ORGANISM: Artificial Sequence
<220> FEATURE:
<223> OTHER INFORMATION: CSF2RA signal protein sequence

<400> SEQUENCE: 36

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 37
<211> LENGTH: 1005
<212> TYPE: DNA
<213> ORGANISM: Artificial Sequence
<220> FEATURE:
<223> OTHER INFORMATION: tEGFR nucleic acid sequence

<400> SEQUENCE: 37

-continued

```
cgtaaggtgt gtaacggaat cggcattggc gagttcaagg actctttaag catcaacgcc        60
acaaacatca agcacttcaa gaattgtacc tccatcagcg gcgatttaca cattctcccc       120
gtggcttttc gtggcgattc cttcacccac accccccctc tggaccccca agagctggac       180 atttttaaaaa ccgtgaagga gatcaccggc tttctgctga tccaagcttg gcccgagaat       240
cgtaccgacc tccacgcctt cgagaattta gagattattc gtggaaggac caagcagcac       300
ggccagttct ctttagccgt cgtgtcttta aacattacca gcctcggttt aaggtcttta       360
aaggagatta gcgacggcga cgtgatcatc tccggcaaca agaacctctg ctacgccaac       420
accatcaact ggaagaagct gttcggaacc agcggccaaa agaccaagat catcagcaat       480
cgtggagaga actcttgtaa ggccactggt caagtttgcc acgccctctg tagccccgaa       540
ggatgttggg gccccgagcc tagggactgt gttagctgca gaaacgtgag cagaggcaga       600
gagtgtgtgg acaaatgcaa tttactggaa ggagagccta gggagttcgt ggagaacagc       660
gaatgtatcc agtgccaccc cgagtgttta cctcaagcca tgaacatcac ttgtaccgga       720
aggggccccg ataactgcat ccaatgcgcc cactacatcg acggacccca ctgcgtgaaa       780
acttgtcccg ccggagtgat gggagagaat aacactttag tgtggaagta cgccgacgct       840
ggccacgtct gccatctgtg ccaccccaac tgtacctacg gctgcactgg tcccggttta       900
gagggatgtc ctaccaacgg ccccaagatc ccctccatcg ccaccggaat ggtgggcgct       960
ctgttattac tgctggtggt ggctctgggc atcggtttat tcatg                      1005
```

```
<210> SEQ ID NO 38
<211> LENGTH: 335
<212> TYPE: PRT
<213> ORGANISM: Artificial Sequence
<220> FEATURE:
<223> OTHER INFORMATION: tEGFR protein sequence

<400> SEQUENCE: 38

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
```

```
               180              185                190
Cys Arg Asn Val Ser Arg Gly Arg Glu Cys Val Asp Lys Cys Asn Leu
           195             200             205
Leu Glu Gly Glu Pro Arg Glu Phe Val Glu Asn Ser Glu Cys Ile Gln
           210             215             220
Cys His Pro Glu Cys Leu Pro Gln Ala Met Asn Ile Thr Cys Thr Gly
225             230             235             240
Arg Gly Pro Asp Asn Cys Ile Gln Cys Ala His Tyr Ile Asp Gly Pro
               245             250             255
His Cys Val Lys Thr Cys Pro Ala Gly Val Met Gly Glu Asn Asn Thr
           260             265             270
Leu Val Trp Lys Tyr Ala Asp Ala Gly His Val Cys His Leu Cys His
           275             280             285
Pro Asn Cys Thr Tyr Gly Cys Thr Gly Pro Gly Leu Glu Gly Cys Pro
           290             295             300
Thr Asn Gly Pro Lys Ile Pro Ser Ile Ala Thr Gly Met Val Gly Ala
305             310             315             320
Leu Leu Leu Leu Leu Val Val Ala Leu Gly Ile Gly Leu Phe Met
               325             330             335
```

<210> SEQ ID NO 39
<211> LENGTH: 2328
<212> TYPE: DNA
<213> ORGANISM: Artificial Sequence
<220> FEATURE:
<223> OTHER INFORMATION: 1# car nucleic acid sequence

<400> SEQUENCE: 39

```
atggccctgc ctgtgacagc tctgctcctc cctctggccc tgctgctcca tgccgccaga     60
ccccagtctg tcgtgacgca gccgccctca gtgtctgggg ccccagggca gagggtcacc    120
atctcctgca ctgggagcag ctccaacatc ggggcaggtt atgatgtaca ctggtaccag    180
caacttccag gaacagcccc caaactcctc atctatgaga acaccaatcg gccctcaggg    240
gtccctgacc gattctctgg ctccaagtct ggcacctcag cctccctggc catcactggg    300
ctccaggctg aggatgaggc tgattattac tgccagtcct atgacagcag cctgagtggt    360
tggagggtgt tcggcggagg gaccaagctg accgtcctag gtggtggtgg tggtagcggc    420
ggcggcggct ctggtggtgg tggatccatg gccgaagtgc agctggtgca gtctggggca    480
gaggtgaaaa agcccgggga gtctctgaag atctcctgta aggggtctgg atacagcttt    540
accaactcct ggatcggatg ggtgcgccag atgcccggga aaggcctgga gtggatggga    600
ctcatttacc ctgatgactc tgataccaga tacagcccat ccttccaagg ccaggtcacc    660
atctcagccg acagcgccat caacaccgcc tacctgcagt ggagcagcct gaaggcctcg    720
gacaccgcca tgtattactg tgcgcgccag tctacctaca tctacggtgg ttactacgat    780
acctggggtc aaggtactct ggtgaccgtc tcctcaggcg gaggtgggtc cggtggcggg    840
ggaagcggag gcggagggag cggaggaggg ggatctggag gcggtgggtc tcaggtgcag    900
ctgcaggagt cgggcccagg actggtgaag ccttcgggga ccctgtccct cacctgcgct    960
gtctctggtg gctccatcag cagtagtaac tggtggagtt gggtccgcca gcccccaggg   1020
aaggggctgg agtggattgg ggaaatctat catagtggga gcaccaacta caacccgtcc   1080
ctcaagagtc gagtcaccat atcagtagac aagtccaaga accagttctc cctgaagctg   1140
agctctgtga ccgccgcgga cacggcggtg tactactgcg ccagacttcc tggatacgag   1200
```

-continued

```
tcagctttcg acatatgggg tcagggtaca atggtcaccg tcagctcagg tggcgggggc    1260
agcggcggag gcggatccgg aggcggaggg agtgaaattg tgttgacgca gtctccaggc    1320
accctgtctt tgtctccagg ggaaagagcc accctctcct gcagggccag tcagagtgtt    1380
agcagcagct acttagcctg gtaccagcag aaacctggcc aggctcccag gctcctcatc    1440
tatggtgcat ccagcagggc cactggcatc ccagacaggt tcagtggcag tgggtctggg    1500
acagacttca ctctcaccat cagcagactg gagcctgaag attttgcagt gtattactgt    1560
cagcaggccg gactcttccc ttacactttt ggcggaggga ccaaggttga gatcaaattc    1620
gtgcccgtgt tcctgcccgc caaacctact actacccctg cacctaggcc tcccacccca    1680
gccccaacaa tcgccagcca gcctctgtct ctgcggcccg aagcctgtag acctgctgcc    1740
ggcggagccg tgcacaccag aggcctggac ttcgcctgcg acatctacat ctgggcccct    1800
ctggccggca cctgtggcgt gctgctgctg agcctggtga tcaccctgta ctgcaaccac    1860
cggaacaaac ggggcagaaa gaaactcctg tatatattca acaaccatt tatgagacca    1920 gtacaaacta ctcaagagga agatggctgt agctgccgat ttccagaaga agaagaagga    1980
ggatgtgaac tgagagtgaa gttcagcaga tccgccgacg cccctgccta ccagcaggga    2040
cagaaccagc tgtacaacga gctgaacctg ggcagacggg aagagtacga cgtgctggac    2100
aagcggagag gccgggaccc cgagatgggc ggaaagccca gacggaagaa cccccaggaa    2160
ggcctgtata cgaactgca gaaagacaag atggccgagg cctacagcga gatcggcatg    2220
aagggcgagc ggaggcgcgg caagggccac gatggcctgt accagggcct gagcaccgcc    2280
accaaggaca cctacgacgc cctgcacatg caggccctgc cccccaga              2328
```

```
<210> SEQ ID NO 40
<211> LENGTH: 776
<212> TYPE: PRT
<213> ORGANISM: Artificial Sequence
<220> FEATURE:
<223> OTHER INFORMATION: 1# CAR protein sequence

<400> SEQUENCE: 40

Met Ala Leu Pro Val Thr Ala Leu Leu Leu Pro Leu Ala Leu Leu Leu
1               5                   10                  15

His Ala Ala Arg Pro Gln Ser Val Val Thr Gln Pro Pro Ser Val Ser
            20                  25                  30

Gly Ala Pro Gly Gln Arg Val Thr Ile Ser Cys Thr Gly Ser Ser Ser
        35                  40                  45

Asn Ile Gly Ala Gly Tyr Asp Val His Trp Tyr Gln Gln Leu Pro Gly
    50                  55                  60

Thr Ala Pro Lys Leu Leu Ile Tyr Glu Asn Thr Asn Arg Pro Ser Gly
65                  70                  75                  80

Val Pro Asp Arg Phe Ser Gly Ser Lys Ser Gly Thr Ser Ala Ser Leu
                85                  90                  95

Ala Ile Thr Gly Leu Gln Ala Glu Asp Glu Ala Asp Tyr Tyr Cys Gln
            100                 105                 110

Ser Tyr Asp Ser Ser Leu Ser Gly Trp Arg Val Phe Gly Gly Gly Thr
        115                 120                 125

Lys Leu Thr Val Leu Gly Gly Gly Gly Ser Gly Gly Gly Gly Ser
    130                 135                 140

Gly Gly Gly Gly Ser Met Ala Glu Val Gln Leu Val Gln Ser Gly Ala
145                 150                 155                 160

Glu Val Lys Lys Pro Gly Glu Ser Leu Lys Ile Ser Cys Lys Gly Ser
```

-continued

```
              165               170               175
Gly Tyr Ser Phe Thr Asn Ser Trp Ile Gly Trp Val Arg Gln Met Pro
          180               185               190

Gly Lys Gly Leu Glu Trp Met Gly Leu Ile Tyr Pro Asp Asp Ser Asp
          195               200               205

Thr Arg Tyr Ser Pro Ser Phe Gln Gly Gln Val Thr Ile Ser Ala Asp
          210               215               220

Ser Ala Ile Asn Thr Ala Tyr Leu Gln Trp Ser Ser Leu Lys Ala Ser
225               230               235               240

Asp Thr Ala Met Tyr Tyr Cys Ala Arg Gln Ser Thr Tyr Ile Tyr Gly
              245               250               255

Gly Tyr Tyr Asp Thr Trp Gly Gln Gly Thr Leu Val Thr Val Ser Ser
              260               265               270

Gly Gly Gly Gly Ser Gly Gly Gly Ser Gly Gly Gly Gly Ser Gly
          275               280               285

Gly Gly Gly Ser Gly Gly Gly Ser Gln Val Gln Leu Gln Glu Ser
          290               295               300

Gly Pro Gly Leu Val Lys Pro Ser Gly Thr Leu Ser Leu Thr Cys Ala
305               310               315               320

Val Ser Gly Gly Ser Ile Ser Ser Ser Asn Trp Trp Ser Trp Val Arg
              325               330               335

Gln Pro Pro Gly Lys Gly Leu Glu Trp Ile Gly Glu Ile Tyr His Ser
              340               345               350

Gly Ser Thr Asn Tyr Asn Pro Ser Leu Lys Ser Arg Val Thr Ile Ser
              355               360               365

Val Asp Lys Ser Lys Asn Gln Phe Ser Leu Lys Leu Ser Ser Val Thr
          370               375               380

Ala Ala Asp Thr Ala Val Tyr Tyr Cys Ala Arg Leu Pro Gly Tyr Glu
385               390               395               400

Ser Ala Phe Asp Ile Trp Gly Gln Gly Thr Met Val Thr Val Ser Ser
              405               410               415

Gly Gly Gly Gly Ser Gly Gly Gly Gly Ser Gly Gly Gly Gly Ser Glu
          420               425               430

Ile Val Leu Thr Gln Ser Pro Gly Thr Leu Ser Leu Ser Pro Gly Glu
          435               440               445

Arg Ala Thr Leu Ser Cys Arg Ala Ser Gln Ser Val Ser Ser Ser Tyr
          450               455               460

Leu Ala Trp Tyr Gln Gln Lys Pro Gly Gln Ala Pro Arg Leu Leu Ile
465               470               475               480

Tyr Gly Ala Ser Ser Arg Ala Thr Gly Ile Pro Asp Arg Phe Ser Gly
              485               490               495

Ser Gly Ser Gly Thr Asp Phe Thr Leu Thr Ile Ser Arg Leu Glu Pro
              500               505               510

Glu Asp Phe Ala Val Tyr Tyr Cys Gln Gln Ala Gly Leu Phe Pro Tyr
              515               520               525

Thr Phe Gly Gly Gly Thr Lys Val Glu Ile Lys Phe Val Pro Val Phe
          530               535               540

Leu Pro Ala Lys Pro Thr Thr Thr Pro Ala Pro Arg Pro Pro Thr Pro
545               550               555               560

Ala Pro Thr Ile Ala Ser Gln Pro Leu Ser Leu Arg Pro Glu Ala Cys
              565               570               575

Arg Pro Ala Ala Gly Gly Ala Val His Thr Arg Gly Leu Asp Phe Ala
          580               585               590
```

```
Cys Asp Ile Tyr Ile Trp Ala Pro Leu Ala Gly Thr Cys Gly Val Leu
        595                 600                 605

Leu Leu Ser Leu Val Ile Thr Leu Tyr Cys Asn His Arg Asn Lys Arg
        610                 615                 620

Gly Arg Lys Lys Leu Leu Tyr Ile Phe Lys Gln Pro Phe Met Arg Pro
625                 630                 635                 640

Val Gln Thr Thr Gln Glu Glu Asp Gly Cys Ser Cys Arg Phe Pro Glu
                645                 650                 655

Glu Glu Glu Gly Gly Cys Glu Leu Arg Val Lys Phe Ser Arg Ser Ala
                660                 665                 670

Asp Ala Pro Ala Tyr Gln Gln Gly Gln Asn Gln Leu Tyr Asn Glu Leu
        675                 680                 685

Asn Leu Gly Arg Arg Glu Glu Tyr Asp Val Leu Asp Lys Arg Arg Gly
        690                 695                 700

Arg Asp Pro Glu Met Gly Gly Lys Pro Arg Arg Lys Asn Pro Gln Glu
705                 710                 715                 720

Gly Leu Tyr Asn Glu Leu Gln Lys Asp Lys Met Ala Glu Ala Tyr Ser
                725                 730                 735

Glu Ile Gly Met Lys Gly Glu Arg Arg Arg Gly Lys Gly His Asp Gly
                740                 745                 750

Leu Tyr Gln Gly Leu Ser Thr Ala Thr Lys Asp Thr Tyr Asp Ala Leu
        755                 760                 765

His Met Gln Ala Leu Pro Pro Arg
        770                 775
```

```
<210> SEQ ID NO 41
<211> LENGTH: 2328
<212> TYPE: DNA
<213> ORGANISM: Artificial Sequence
<220> FEATURE:
<223> OTHER INFORMATION: 2# CAR nucleic acid sequence

<400> SEQUENCE: 41
atggccctgc ctgtgacagc tctgctcctc cctctggccc tgctgctcca tgccgccaga      60
ccccaggtgc agctgcagga gtcgggccca ggactggtga gccttcgggg accctgtcc      120 ctcacctgcg ctgtctctgg tggctccatc agcagtagta actggtggag ttgggtccgc      180
cagcccccag ggaaggggct ggagtggatt ggggaaatct atcatagtgg gagcaccaac      240
tacaacccgt ccctcaagag tcgagtcacc atatcagtag acaagtccaa gaaccagttc      300
tccctgaagc tgagctctgt gaccgccgcg gacacggcgg tgtactactg cgccagactt      360
cctggatacg agtcagcttt cgacatatgg ggtcagggta caatggtcac cgtcagctca      420
ggtggcgggg gcagcggcgg aggcggatcc ggaggcggag ggagtgaaat tgtgttgacg      480
cagtctccag gcaccctgtc tttgtctcca ggggaaagag ccaccctctc ctgcagggcc      540
agtcagagtg ttagcagcag ctacttagcc tggtaccagc agaaacctgg ccaggctccc      600
aggctcctca tctatggtgc atccagcagg gccactggca tcccagacag gttcagtggc      660
agtgggtctg ggacagactt cactctcacc atcagcagac tggagcctga agattttgca      720
gtgtattact gtcagcaggc cggactcttc ccttacactt ttggcggagg gaccaaggtt      780
gagatcaaag gcggaggtgg gtccggtggc gggggaagcg gaggcggagg gagcggagga      840
gggggatctg gaggcggtgg gtctcagtct gtcgtgacgc agccgccctc agtgtctggg      900
gccccagggc agagggtcac catctcctgc actgggagca gctccaacat cggggcaggt      960
```

-continued

```
tatgatgtac actggtacca gcaacttcca ggaacagccc ccaaactcct catctatgag      1020
aacaccaatc ggccctcagg ggtccctgac cgattctctg gctccaagtc tggcacctca      1080
gcctccctgg ccatcactgg gctccaggct gaggatgagg ctgattatta ctgccagtcc      1140
tatgacagca gcctgagtgg ttggagggtg ttcggcggag ggaccaagct gaccgtccta      1200
ggtggtggtg gtggtagcgg cggcggcggc tctggtggtg gtggatccat ggccgaagtg      1260
cagctggtgc agtctggggc agaggtgaaa aagcccgggg agtctctgaa gatctcctgt      1320
aaggggtctg gatacagctt taccaactcc tggatcggat gggtgcgcca gatgcccggg      1380
aaaggcctgg agtggatggg actcatttac cctgatgact ctgataccag atacagccca      1440
tccttccaag gccaggtcac catctcagcc gacagcgcca tcaacaccgc ctacctgcag      1500
tggagcagcc tgaaggcctc ggacaccgcc atgtattact gtgcgcgcca gtctacctac      1560
atctacggtg gttactacga tacctggggt caaggtactc tggtgaccgt ctcctcattc      1620
gtgcccgtgt tcctgcccgc caaacctact actaccctg cacctaggcc tcccacccca      1680
gccccaacaa tcgccagcca gcctctgtct ctgcggccg aagcctgtag acctgctgcc      1740
ggcggagccg tgcacaccag aggcctggac ttcgcctgcg acatctacat ctgggcccct      1800
ctggccggca cctgtggcgt gctgctgctg agcctggtga tcaccctgta ctgcaaccac      1860
cggaacaaac ggggcagaaa gaaactcctg tatatattca acaaccatt tatgagacca      1920 gtacaaacta ctcaagagga agatggctgt agctgccgat ttccagaaga agaagaagga      1980
ggatgtgaac tgagagtgaa gttcagcaga tccgccgacg cccctgccta ccagcaggga      2040
cagaaccagc tgtacaacga gctgaacctg gcagacgggg aagagtacga cgtgctggac      2100
aagcggagag ccgggaccc cgagatgggc ggaaagccca acggaagaa ccccaggaa      2160 ggcctgtata cgaactgca gaaagacaag atggccgagg cctacagcga gatcggcatg      2220
aagggcgagc ggaggcgcgg caagggccac gatggcctgt accagggcct gagcaccgcc      2280
accaaggaca cctacgacgc cctgcacatg caggccctgc cccccaga                  2328
```

<210> SEQ ID NO 42
<211> LENGTH: 776
<212> TYPE: PRT
<213> ORGANISM: Artificial Sequence
<220> FEATURE:
<223> OTHER INFORMATION: 2# CAR protein sequence

<400> SEQUENCE: 42

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Gly Thr Leu Ser Leu Thr Cys Ala Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Thr Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Leu Pro Gly Tyr Glu Ser Ala Phe Asp
        115                 120                 125
```

-continued

```
Ile Trp Gly Gln Gly Thr Met Val Thr Val Ser Ser Gly Gly Gly
    130                 135                 140

Ser Gly Gly Gly Gly Ser Gly Gly Gly Gly Ser Glu Ile Val Leu Thr
145                 150                 155                 160

Gln Ser Pro Gly Thr Leu Ser Leu Ser Pro Gly Glu Arg Ala Thr Leu
                165                 170                 175

Ser Cys Arg Ala Ser Gln Ser Val Ser Ser Ser Tyr Leu Ala Trp Tyr
            180                 185                 190

Gln Gln Lys Pro Gly Gln Ala Pro Arg Leu Leu Ile Tyr Gly Ala Ser
        195                 200                 205

Ser Arg Ala Thr Gly Ile Pro Asp Arg Phe Ser Gly Ser Gly Ser Gly
    210                 215                 220

Thr Asp Phe Thr Leu Thr Ile Ser Arg Leu Glu Pro Glu Asp Phe Ala
225                 230                 235                 240

Val Tyr Tyr Cys Gln Gln Ala Gly Leu Phe Pro Tyr Thr Phe Gly Gly
                245                 250                 255

Gly Thr Lys Val Glu Ile Lys Gly Gly Gly Gly Ser Gly Gly Gly Gly
            260                 265                 270

Ser Gly Gly Gly Gly Ser Gly Gly Gly Gly Ser Gly Gly Gly Gly Ser
            275                 280                 285

Gln Ser Val Val Thr Gln Pro Pro Ser Val Ser Gly Ala Pro Gly Gln
    290                 295                 300

Arg Val Thr Ile Ser Cys Thr Gly Ser Ser Ser Asn Ile Gly Ala Gly
305                 310                 315                 320

Tyr Asp Val His Trp Tyr Gln Gln Leu Pro Gly Thr Ala Pro Lys Leu
                325                 330                 335

Leu Ile Tyr Glu Asn Thr Asn Arg Pro Ser Gly Val Pro Asp Arg Phe
            340                 345                 350

Ser Gly Ser Lys Ser Gly Thr Ser Ala Ser Leu Ala Ile Thr Gly Leu
            355                 360                 365

Gln Ala Glu Asp Glu Ala Asp Tyr Tyr Cys Gln Ser Tyr Asp Ser Ser
    370                 375                 380

Leu Ser Gly Trp Arg Val Phe Gly Gly Gly Thr Lys Leu Thr Val Leu
385                 390                 395                 400

Gly Gly Gly Gly Gly Ser Gly Gly Gly Gly Ser Gly Gly Gly Gly Ser
                405                 410                 415

Met Ala Glu Val Gln Leu Val Gln Ser Gly Ala Glu Val Lys Lys Pro
            420                 425                 430

Gly Glu Ser Leu Lys Ile Ser Cys Lys Gly Ser Gly Tyr Ser Phe Thr
        435                 440                 445

Asn Ser Trp Ile Gly Trp Val Arg Gln Met Pro Gly Lys Gly Leu Glu
    450                 455                 460

Trp Met Gly Leu Ile Tyr Pro Asp Asp Ser Asp Thr Arg Tyr Ser Pro
465                 470                 475                 480

Ser Phe Gln Gly Gln Val Thr Ile Ser Ala Asp Ser Ala Ile Asn Thr
                485                 490                 495

Ala Tyr Leu Gln Trp Ser Ser Leu Lys Ala Ser Asp Thr Ala Met Tyr
            500                 505                 510

Tyr Cys Ala Arg Gln Ser Thr Tyr Ile Tyr Gly Gly Tyr Tyr Asp Thr
            515                 520                 525

Trp Gly Gln Gly Thr Leu Val Thr Val Ser Ser Phe Val Pro Val Phe
    530                 535                 540
```

```
Leu Pro Ala Lys Pro Thr Thr Thr Pro Ala Pro Arg Pro Pro Thr Pro
545                 550                 555                 560

Ala Pro Thr Ile Ala Ser Gln Pro Leu Ser Leu Arg Pro Glu Ala Cys
                565                 570                 575

Arg Pro Ala Ala Gly Gly Ala Val His Thr Arg Gly Leu Asp Phe Ala
                580                 585                 590

Cys Asp Ile Tyr Ile Trp Ala Pro Leu Ala Gly Thr Cys Gly Val Leu
            595                 600                 605

Leu Leu Ser Leu Val Ile Thr Leu Tyr Cys Asn His Arg Asn Lys Arg
        610                 615                 620

Gly Arg Lys Lys Leu Leu Tyr Ile Phe Lys Gln Pro Phe Met Arg Pro
625                 630                 635                 640

Val Gln Thr Thr Gln Glu Glu Asp Gly Cys Ser Cys Arg Phe Pro Glu
                645                 650                 655

Glu Glu Glu Gly Gly Cys Glu Leu Arg Val Lys Phe Ser Arg Ser Ala
                660                 665                 670

Asp Ala Pro Ala Tyr Gln Gln Gly Gln Asn Gln Leu Tyr Asn Glu Leu
            675                 680                 685

Asn Leu Gly Arg Arg Glu Glu Tyr Asp Val Leu Asp Lys Arg Arg Gly
        690                 695                 700

Arg Asp Pro Glu Met Gly Gly Lys Pro Arg Arg Lys Asn Pro Gln Glu
705                 710                 715                 720

Gly Leu Tyr Asn Glu Leu Gln Lys Asp Lys Met Ala Glu Ala Tyr Ser
                725                 730                 735

Glu Ile Gly Met Lys Gly Glu Arg Arg Arg Gly Lys Gly His Asp Gly
            740                 745                 750

Leu Tyr Gln Gly Leu Ser Thr Ala Thr Lys Asp Thr Tyr Asp Ala Leu
        755                 760                 765

His Met Gln Ala Leu Pro Pro Arg
    770                 775
```

<210> SEQ ID NO 43
<211> LENGTH: 2298
<212> TYPE: DNA
<213> ORGANISM: Artificial Sequence
<220> FEATURE:
<223> OTHER INFORMATION: 3# CAR nucleic acid sequence

<400> SEQUENCE: 43

```
atggccctgc ctgtgacagc tctgctcctc cctctggccc tgctgctcca tgccgccaga      60
ccccagtctg tcgtgacgca gccgccctca gtgtctgggg ccccagggca gagggtcacc     120
atctcctgca ctgggagcag ctccaacatc ggggcaggtt atgatgtaca ctggtaccag     180
caacttccag gaacagcccc caaactcctc atctatgaga acaccaatcg gccctcaggg     240
gtccctgacc gattctctgg ctccaagtct ggcacctcag cctccctggc catcactggg     300
ctccaggctg aggatgaggc tgattattac tgccagtcct atgacagcag cctgagtggt     360
tggagggtgt tcggcggagg gaccaagctg accgtcctag gtggtggtgg tggtagcggc     420
ggcggcggct ctggtggtgg tggatccatg gccgaagtgc agctggtgca gtctggggca     480
gaggtgaaaa agcccgggga gtctctgaag atcctgtgta aggggtctgg atacagcttt     540
accaactcct ggatcggatg ggtgcgccag atgcccggga aaggcctgga gtggatggga     600
ctcatttacc ctgatgactc tgataccaga tacagcccat ccttccaagg ccaggtcacc     660
atctcagccg acagcgccat caacaccgcc tacctgcagt ggagcagcct gaaggcctcg     720
```

-continued

```
gacaccgcca tgtattactg tgcgcgccag tctacctaca tctacggtgg ttactacgat        780
acctggggtc aaggtactct ggtgaccgtc tcctcaggcg gaggtgggtc cggtggcggg        840
ggaagcggag gcggagggag ccaggtgcag ctgcaggagt cgggcccagg actggtgaag        900
ccttcgggga ccctgtccct cacctgcgct gtctctggtg ctccatcag cagtagtaac        960 tggtggagtt gggtccgcca gccccagggg aaggggctgg agtggattgg ggaaatctat       1020
catagtggga gcaccaacta caacccgtcc ctcaagagtc gagtcaccat atcagtagac       1080
aagtccaaga accagttctc cctgaagctg agctctgtga ccgccgcgga cacggcggtg       1140
tactactgcg ccagacttcc tggatacgag tcagctttcg acatatgggg tcagggtaca       1200
atggtcaccg tcagctcagg tggcgggggc agcggcggag gcggatccgg aggcggaggg       1260
agtgaaattg tgttgacgca gtctccaggc accctgtctt tgtctccagg ggaaagagcc       1320
accctctcct gcagggccag tcagagtgtt agcagcagct acttagcctg gtaccagcag       1380
aaacctggcc aggctcccag gctcctcatc tatggtgcat ccagcagggc cactggcatc       1440
ccagacaggt tcagtggcag tgggtctggg acagacttca ctctcaccat cagcagactg       1500
gagcctgaag attttgcagt gtattactgt cagcaggccg gactcttccc ttacactttt       1560
ggcggaggga ccaaggttga gatcaaattc gtgcccgtgt tcctgcccgc caaacctact       1620 actaccctg cacctaggcc tcccacccca gccccaacaa tcgccagcca gcctctgtct       1680
ctgcggcccg aagcctgtag acctgctgcc ggcggagccg tgcacaccag aggcctggac       1740
ttcgcctgcg acatctacat ctgggcccct ctggccggca cctgtggcgt gctgctgctg       1800
agcctggtga tcaccctgta ctgcaaccac cggaacaaac ggggcagaaa gaaactcctg       1860
tatatattca acaaccatt tatgagacca gtacaaacta ctcaagagga agatggctgt       1920
agctgccgat ttccagaaga agaagaagga ggatgtgaac tgagagtgaa gttcagcaga       1980
tccgccgacg cccctgccta ccagcaggga cagaaccagc tgtacaacga gctgaacctg       2040 ggcagacgg aagagtacga cgtgctggac aagcggagag ccgggaccc cgagatgggc       2100 ggaaagccca gacggaagaa cccccaggaa ggcctgtata cgaactgca gaaagacaag       2160 atggccgagg cctacagcga gatcggcatg aagggcgagc ggaggcgcgg caaggggccac       2220 gatggcctgt accagggcct gagcaccgcc accaaggaca cctacgacgc cctgcacatg       2280
caggccctgc cccccaga                                                      2298
```

<210> SEQ ID NO 44
<211> LENGTH: 766
<212> TYPE: PRT
<213> ORGANISM: Artificial Sequence
<220> FEATURE:
<223> OTHER INFORMATION: 3# CAR protein sequence

<400> SEQUENCE: 44

```
Met Ala Leu Pro Val Thr Ala Leu Leu Leu Pro Leu Ala Leu Leu Leu
1               5                   10                  15

His Ala Ala Arg Pro Gln Ser Val Val Thr Gln Pro Pro Ser Val Ser
            20                  25                  30

Gly Ala Pro Gly Gln Arg Val Thr Ile Ser Cys Thr Gly Ser Ser Ser
        35                  40                  45

Asn Ile Gly Ala Gly Tyr Asp Val His Trp Tyr Gln Gln Leu Pro Gly
    50                  55                  60

Thr Ala Pro Lys Leu Leu Ile Tyr Glu Asn Thr Asn Arg Pro Ser Gly
65                  70                  75                  80
```

```
Val Pro Asp Arg Phe Ser Gly Ser Lys Ser Gly Thr Ser Ala Ser Leu
                85                  90                  95

Ala Ile Thr Gly Leu Gln Ala Glu Asp Glu Ala Asp Tyr Tyr Cys Gln
            100                 105                 110

Ser Tyr Asp Ser Ser Leu Ser Gly Trp Arg Val Phe Gly Gly Gly Thr
            115                 120                 125

Lys Leu Thr Val Leu Gly Gly Gly Gly Ser Gly Gly Gly Gly Ser
    130                 135                 140

Gly Gly Gly Gly Ser Met Ala Glu Val Gln Leu Val Gln Ser Gly Ala
145                 150                 155                 160

Glu Val Lys Lys Pro Gly Glu Ser Leu Lys Ile Ser Cys Lys Gly Ser
                165                 170                 175

Gly Tyr Ser Phe Thr Asn Ser Trp Ile Gly Trp Val Arg Gln Met Pro
            180                 185                 190

Gly Lys Gly Leu Glu Trp Met Gly Leu Ile Tyr Pro Asp Asp Ser Asp
            195                 200                 205

Thr Arg Tyr Ser Pro Ser Phe Gln Gly Gln Val Thr Ile Ser Ala Asp
    210                 215                 220

Ser Ala Ile Asn Thr Ala Tyr Leu Gln Trp Ser Ser Leu Lys Ala Ser
225                 230                 235                 240

Asp Thr Ala Met Tyr Tyr Cys Ala Arg Gln Ser Thr Tyr Ile Tyr Gly
                245                 250                 255

Gly Tyr Tyr Asp Thr Trp Gly Gln Gly Thr Leu Val Thr Val Ser Ser
            260                 265                 270

Gly Gly Gly Gly Ser Gly Gly Gly Gly Ser Gly Gly Gly Gly Ser Gln
            275                 280                 285

Val Gln Leu Gln Glu Ser Gly Pro Gly Leu Val Lys Pro Ser Gly Thr
    290                 295                 300

Leu Ser Leu Thr Cys Ala Val Ser Gly Gly Ser Ile Ser Ser Ser Asn
305                 310                 315                 320

Trp Trp Ser Trp Val Arg Gln Pro Pro Gly Lys Gly Leu Glu Trp Ile
                325                 330                 335

Gly Glu Ile Tyr His Ser Gly Ser Thr Asn Tyr Asn Pro Ser Leu Lys
            340                 345                 350

Ser Arg Val Thr Ile Ser Val Asp Lys Ser Lys Asn Gln Phe Ser Leu
            355                 360                 365

Lys Leu Ser Ser Val Thr Ala Ala Asp Thr Ala Val Tyr Tyr Cys Ala
    370                 375                 380

Arg Leu Pro Gly Tyr Glu Ser Ala Phe Asp Ile Trp Gly Gln Gly Thr
385                 390                 395                 400

Met Val Thr Val Ser Ser Gly Gly Gly Gly Ser Gly Gly Gly Gly Ser
                405                 410                 415

Gly Gly Gly Gly Ser Glu Ile Val Leu Thr Gln Ser Pro Gly Thr Leu
            420                 425                 430

Ser Leu Ser Pro Gly Glu Arg Ala Thr Leu Ser Cys Arg Ala Ser Gln
            435                 440                 445

Ser Val Ser Ser Ser Tyr Leu Ala Trp Tyr Gln Gln Lys Pro Gly Gln
    450                 455                 460

Ala Pro Arg Leu Leu Ile Tyr Gly Ala Ser Ser Arg Ala Thr Gly Ile
465                 470                 475                 480

Pro Asp Arg Phe Ser Gly Ser Gly Ser Gly Thr Asp Phe Thr Leu Thr
                485                 490                 495

Ile Ser Arg Leu Glu Pro Glu Asp Phe Ala Val Tyr Tyr Cys Gln Gln
```

-continued

```
            500              505              510
Ala Gly Leu Phe Pro Tyr Thr Phe Gly Gly Gly Thr Lys Val Glu Ile
        515              520              525

Lys Phe Val Pro Val Phe Leu Pro Ala Lys Pro Thr Thr Thr Pro Ala
        530              535              540

Pro Arg Pro Pro Thr Pro Ala Pro Thr Ile Ala Ser Gln Pro Leu Ser
545              550              555              560

Leu Arg Pro Glu Ala Cys Arg Pro Ala Ala Gly Gly Ala Val His Thr
                565              570              575

Arg Gly Leu Asp Phe Ala Cys Asp Ile Tyr Ile Trp Ala Pro Leu Ala
                580              585              590

Gly Thr Cys Gly Val Leu Leu Leu Ser Leu Val Ile Thr Leu Tyr Cys
                595              600              605

Asn His Arg Asn Lys Arg Gly Arg Lys Lys Leu Leu Tyr Ile Phe Lys
        610              615              620

Gln Pro Phe Met Arg Pro Val Gln Thr Thr Gln Glu Glu Asp Gly Cys
625              630              635              640

Ser Cys Arg Phe Pro Glu Glu Glu Glu Gly Gly Cys Glu Leu Arg Val
                645              650              655

Lys Phe Ser Arg Ser Ala Asp Ala Pro Ala Tyr Gln Gln Gly Gln Asn
                660              665              670

Gln Leu Tyr Asn Glu Leu Asn Leu Gly Arg Arg Glu Glu Tyr Asp Val
        675              680              685

Leu Asp Lys Arg Arg Gly Arg Asp Pro Glu Met Gly Gly Lys Pro Arg
        690              695              700

Arg Lys Asn Pro Gln Glu Gly Leu Tyr Asn Glu Leu Gln Lys Asp Lys
705              710              715              720

Met Ala Glu Ala Tyr Ser Glu Ile Gly Met Lys Gly Glu Arg Arg Arg
                725              730              735

Gly Lys Gly His Asp Gly Leu Tyr Gln Gly Leu Ser Thr Ala Thr Lys
                740              745              750

Asp Thr Tyr Asp Ala Leu His Met Gln Ala Leu Pro Pro Arg
        755              760              765
```

```
<210> SEQ ID NO 45
<211> LENGTH: 2298
<212> TYPE: DNA
<213> ORGANISM: Artificial Sequence
<220> FEATURE:
<223> OTHER INFORMATION: 4# CAR nucleic acid sequence

<400> SEQUENCE: 45
atggccctgc ctgtgacagc tctgctcctc cctctggccc tgctgctcca tgccgccaga      60
ccccaggtgc agctgcagga gtcgggccca ggactggtga agccttcggg gaccctgtcc     120
ctcacctgcg ctgtctctgg tggctccatc agcagtagta actggtggag ttgggtccgc     180
cagcccccag ggaaggggct ggagtggatt ggggaaatct atcatagtgg gagcaccaac     240
tacaacccgt ccctcaagag tcgagtcacc atatcagtag acaagtccaa gaaccagttc     300
tccctgaagc tgagctctgt gaccgccgcg gacacggcgg tgtactactg cgccagactt     360
cctggatacg agtcagcttt cgacatatgg ggtcagggta caatggtcac cgtcagctca     420
ggtggcgggg gcagcggcgg aggcggatcc ggaggcggag ggagtgaaat tgtgttgacg     480
cagtctccag gcaccctgtc tttgtctcca ggggaaagag ccaccctctc ctgcagggcc     540
agtcagagtg ttagcagcag ctacttagcc tggtaccagc agaaacctgg ccaggctccc     600
```

-continued

```
aggctcctca tctatggtgc atccagcagg gccactggca tcccagacag gttcagtggc    660
agtgggtctg ggacagactt cactctcacc atcagcagac tggagcctga agattttgca    720
gtgtattact gtcagcaggc cggactcttc ccttacactt ttggcggagg gaccaaggtt    780
gagatcaaag gcggaggtgg gtccggtggc gggggaagcg gaggcggagg gagccagtct    840
gtcgtgacgc agccgccctc agtgtctggg gccccagggc agagggtcac catctcctgc    900
actgggagca gctccaacat cggggcaggt tatgatgtac actggtacca gcaacttcca    960
ggaacagccc ccaaactcct catctatgag aacaccaatc ggccctcagg ggtccctgac    1020
cgattctctg gctccaagtc tggcacctca gcctccctgg ccatcactgg gctccaggct    1080
gaggatgagg ctgattatta ctgccagtcc tatgacagca gcctgagtgg ttggagggtg    1140
ttcggcggag ggaccaagct gaccgtccta ggtggtggtg gtggtagcgg cggcggcggc    1200
tctggtggtg gtggatccat ggccgaagtg cagctggtgc agtctggggc agaggtgaaa    1260
aagcccgggg agtctctgaa gatctcctgt aaggggtctg gatacagctt taccaactcc    1320
tggatcggat gggtgcgcca gatgcccggg aaaggcctgg agtggatggg actcatttac    1380
cctgatgact ctgataccag atacagccca tccttccaag gccaggtcac catctcagcc    1440
gacagcgcca tcaacaccgc ctacctgcag tggagcagcc tgaaggcctc ggacaccgcc    1500
atgtattact gtgcgcgcca gtctacctac atctacggtg gttactacga tacctggggt    1560
caaggtactc tggtgaccgt ctcctcattc gtgcccgtgt tcctgcccgc caaacctact    1620 actaccctg cacctaggcc tcccacccca gccccaacaa tcgccagcca gcctctgtct    1680
ctgcggcccg aagcctgtag acctgctgcc ggcggagccg tgcacaccag aggcctggac    1740
ttcgcctgcg acatctacat ctgggcccct ctggccggca cctgtggcgt gctgctgctg    1800
agcctggtga tcaccctgta ctgcaaccac cggaacaaac ggggcagaaa gaaactcctg    1860
tatatattca acaaccatt tatgagacca gtacaaacta ctcaagagga agatggctgt    1920
agctgccgat ttccagaaga agaagaagga ggatgtgaac tgagagtgaa gttcagcaga    1980
tccgccgacg cccctgccta ccagcaggga cagaaccagc tgtacaacga gctgaacctg    2040
ggcagacggg aagagtacga cgtgctggac aagcggagag ccgggacccc cgagatgggc    2100
ggaaagccca gacggaagaa cccccaggaa ggcctgtata cgaactgcag aaagacaag    2160 atggccgagg cctacagcga gatcggcatg aagggcgagc ggaggcgcgg caagggccac    2220
gatggcctgt accagggcct gagcaccgcc accaaggaca cctacgacgc cctgcacatg    2280
caggccctgc ccccaga                                                    2298
```

```
<210> SEQ ID NO 46
<211> LENGTH: 766
<212> TYPE: PRT
<213> ORGANISM: Artificial Sequence
<220> FEATURE:
<223> OTHER INFORMATION: 4# CAR protein sequence

<400> SEQUENCE: 46

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Gly Thr Leu Ser Leu Thr Cys Ala Val Ser Gly Gly
        35                  40                  45

Ser Ile Ser Ser Ser Asn Trp Trp Ser Trp Val Arg Gln Pro Pro Gly
```

-continued

```
              50                    55                    60

Lys Gly Leu Glu Trp Ile Gly Glu Ile Tyr His Ser Gly Ser Thr Asn
65                    70                    75                    80

Tyr Asn Pro Ser Leu Lys Ser Arg Val Thr Ile Ser Val Asp Lys Ser
                  85                    90                    95

Lys Asn Gln Phe Ser Leu Lys Leu Ser Ser Val Thr Ala Ala Asp Thr
                 100                   105                   110

Ala Val Tyr Tyr Cys Ala Arg Leu Pro Gly Tyr Glu Ser Ala Phe Asp
             115                   120                   125

Ile Trp Gly Gln Gly Thr Met Val Thr Val Ser Ser Gly Gly Gly
             130                   135                   140

Ser Gly Gly Gly Gly Ser Gly Gly Gly Ser Glu Ile Val Leu Thr
145                   150                   155                   160

Gln Ser Pro Gly Thr Leu Ser Leu Ser Pro Gly Glu Arg Ala Thr Leu
                 165                   170                   175

Ser Cys Arg Ala Ser Gln Ser Val Ser Ser Ser Tyr Leu Ala Trp Tyr
             180                   185                   190

Gln Gln Lys Pro Gly Gln Ala Pro Arg Leu Leu Ile Tyr Gly Ala Ser
             195                   200                   205

Ser Arg Ala Thr Gly Ile Pro Asp Arg Phe Ser Gly Ser Gly Ser Gly
         210                   215                   220

Thr Asp Phe Thr Leu Thr Ile Ser Arg Leu Glu Pro Glu Asp Phe Ala
225                   230                   235                   240

Val Tyr Tyr Cys Gln Gln Ala Gly Leu Phe Pro Tyr Thr Phe Gly Gly
                 245                   250                   255

Gly Thr Lys Val Glu Ile Lys Gly Gly Gly Gly Ser Gly Gly Gly Gly
                 260                   265                   270

Ser Gly Gly Gly Gly Ser Gln Ser Val Val Thr Gln Pro Pro Ser Val
             275                   280                   285

Ser Gly Ala Pro Gly Gln Arg Val Thr Ile Ser Cys Thr Gly Ser Ser
         290                   295                   300

Ser Asn Ile Gly Ala Gly Tyr Asp Val His Trp Tyr Gln Gln Leu Pro
305                   310                   315                   320

Gly Thr Ala Pro Lys Leu Leu Ile Tyr Glu Asn Thr Asn Arg Pro Ser
                 325                   330                   335

Gly Val Pro Asp Arg Phe Ser Gly Ser Lys Ser Gly Thr Ser Ala Ser
                 340                   345                   350

Leu Ala Ile Thr Gly Leu Gln Ala Glu Asp Glu Ala Asp Tyr Tyr Cys
             355                   360                   365

Gln Ser Tyr Asp Ser Ser Leu Ser Gly Trp Arg Val Phe Gly Gly Gly
         370                   375                   380

Thr Lys Leu Thr Val Leu Gly Gly Gly Gly Ser Gly Gly Gly Gly
385                   390                   395                   400

Ser Gly Gly Gly Gly Ser Met Ala Glu Val Gln Leu Val Gln Ser Gly
                 405                   410                   415

Ala Glu Val Lys Lys Pro Gly Glu Ser Leu Lys Ile Ser Cys Lys Gly
             420                   425                   430

Ser Gly Tyr Ser Phe Thr Asn Ser Trp Ile Gly Trp Val Arg Gln Met
             435                   440                   445

Pro Gly Lys Gly Leu Glu Trp Met Gly Leu Ile Tyr Pro Asp Asp Ser
         450                   455                   460

Asp Thr Arg Tyr Ser Pro Ser Phe Gln Gly Gln Val Thr Ile Ser Ala
465                   470                   475                   480
```

```
Asp Ser Ala Ile Asn Thr Ala Tyr Leu Gln Trp Ser Ser Leu Lys Ala
            485                 490                 495

Ser Asp Thr Ala Met Tyr Tyr Cys Ala Arg Gln Ser Thr Tyr Ile Tyr
            500                 505                 510

Gly Gly Tyr Tyr Asp Thr Trp Gly Gln Gly Thr Leu Val Thr Val Ser
            515                 520                 525

Ser Phe Val Pro Val Phe Leu Pro Ala Lys Pro Thr Thr Thr Pro Ala
            530                 535                 540

Pro Arg Pro Pro Thr Pro Ala Pro Thr Ile Ala Ser Gln Pro Leu Ser
545                 550                 555                 560

Leu Arg Pro Glu Ala Cys Arg Pro Ala Ala Gly Gly Ala Val His Thr
            565                 570                 575

Arg Gly Leu Asp Phe Ala Cys Asp Ile Tyr Ile Trp Ala Pro Leu Ala
            580                 585                 590

Gly Thr Cys Gly Val Leu Leu Leu Ser Leu Val Ile Thr Leu Tyr Cys
            595                 600                 605

Asn His Arg Asn Lys Arg Gly Arg Lys Lys Leu Leu Tyr Ile Phe Lys
            610                 615                 620

Gln Pro Phe Met Arg Pro Val Gln Thr Thr Gln Glu Glu Asp Gly Cys
625                 630                 635                 640

Ser Cys Arg Phe Pro Glu Glu Glu Glu Gly Gly Cys Glu Leu Arg Val
            645                 650                 655

Lys Phe Ser Arg Ser Ala Asp Ala Pro Ala Tyr Gln Gln Gly Gln Asn
            660                 665                 670

Gln Leu Tyr Asn Glu Leu Asn Leu Gly Arg Arg Glu Glu Tyr Asp Val
            675                 680                 685

Leu Asp Lys Arg Arg Gly Arg Asp Pro Glu Met Gly Gly Lys Pro Arg
            690                 695                 700

Arg Lys Asn Pro Gln Glu Gly Leu Tyr Asn Glu Leu Gln Lys Asp Lys
705                 710                 715                 720

Met Ala Glu Ala Tyr Ser Glu Ile Gly Met Lys Gly Glu Arg Arg Arg
            725                 730                 735

Gly Lys Gly His Asp Gly Leu Tyr Gln Gly Leu Ser Thr Ala Thr Lys
            740                 745                 750

Asp Thr Tyr Asp Ala Leu His Met Gln Ala Leu Pro Pro Arg
            755                 760                 765
```

<210> SEQ ID NO 47
<211> LENGTH: 2268
<212> TYPE: DNA
<213> ORGANISM: Artificial Sequence
<220> FEATURE:
<223> OTHER INFORMATION: 5# CAR nucleic acid sequence

<400> SEQUENCE: 47

```
atggccctgc ctgtgacagc tctgctcctc cctctggccc tgctgctcca tgccgccaga      60
ccccagtctg tcgtgacgca gccgccctca gtgtctgggg ccccagggca gagggtcacc     120
atctcctgca ctgggagcag ctccaacatc ggggcaggtt atgatgtaca ctggtaccag     180
caacttccag gaacagcccc caaactcctc atctatgaga caccaatcg gccctcaggg     240 gtccctgacc gattctctgg ctccaagtct ggcacctcag cctcctggc catcactggg     300 ctccaggctg aggatgaggc tgattattac tgccagtcct atgacagcag cctgagtggt     360
tggagggtgt tcggcggagg gaccaagctg accgtcctag gtggtggtgg tggtagcggc     420
```

```
ggcggcggct ctggtggtgg tggatccatg gccgaagtgc agctggtgca gtctggggca    480
gaggtgaaaa agcccgggga gtctctgaag atctcctgta aggggtctgg atacagcttt    540
accaactcct ggatcggatg ggtgcgccag atgcccggga aaggcctgga gtggatggga    600
ctcatttacc ctgatgactc tgataccaga tacagcccat ccttccaagg ccaggtcacc    660
atctcagccg acagcgccat caacaccgcc tacctgcagt ggagcagcct gaaggcctcg    720
gacaccgcca tgtattactg tgcgcgccag tctacctaca tctacggtgg ttactacgat    780
acctggggtc aaggtactct ggtgaccgtc tcctcaggcg gaggtgggtc ccaggtgcag    840
ctgcaggagt cgggcccagg actggtgaag ccttcgggga ccctgtccct cacctgcgct    900
gtctctggtg gctccatcag cagtagtaac tggtggagtt gggtccgcca gcccccaggg    960
aaggggctgg agtggattgg ggaaatctat catagtggga gcaccaacta caacccgtcc    1020
ctcaagagtc gagtcaccat atcagtagac aagtccaaga accagttctc cctgaagctg    1080
agctctgtga ccgccgcgga cacggcggtg tactactgcg ccagacttcc tggatacgag    1140
tcagctttcg acatatgggg tcagggtaca atggtcaccg tcagctcagg tggcgggggc    1200
agcggcggag gcggatccgg aggcggaggg agtgaaattg tgttgacgca gtctccaggc    1260
accctgtctt tgtctccagg ggaaagagcc accctctcct gcagggccag tcagagtgtt    1320
agcagcagct acttagcctg gtaccagcag aaacctggcc aggctcccag gctcctcatc    1380
tatggtgcat ccagcagggc cactggcatc ccagacaggt tcagtggcag tgggtctggg    1440
acagacttca ctctcaccat cagcagactg gagcctgaag attttgcagt gtattactgt    1500
cagcaggccg gactcttccc ttacactttt ggcggaggga ccaaggttga gatcaaattc    1560
gtgcccgtgt tcctgcccgc caaacctact actcccctg cacctaggcc tcccacccca    1620
gccccaacaa tcgccagcca gcctctgtct ctgcggcccg aagcctgtag acctgctgcc    1680
ggcggagccg tgcacaccag aggcctggac ttcgcctgcg acatctacat ctgggcccct    1740
ctggccggca cctgtggcgt gctgctgctg agcctggtga tcaccctgta ctgcaaccac    1800
cggaacaaac ggggcagaaa gaaactcctg tatatattca acaaccatt tatgagacca    1860 gtacaaacta ctcaagagga agatggctgt agctgccgat ttccagaaga agaagaagga    1920
ggatgtgaac tgagagtgaa gttcagcaga tccgccgacg cccctgccta ccagcaggga    1980
cagaaccagc tgtacaacga gctgaacctg ggcagacggg aagagtacga cgtgctggac    2040
aagcggagag ccgggacccc cgagatgggc ggaaagccca cacggaagaa ccccaggaa    2100 ggcctgtata cgaactgca gaaagacaag atggccgagg cctacagcga gatcggcatg    2160
aagggcgagc ggaggcgcgg caagggccac gatggcctgt accagggcct gagcaccgcc    2220
accaaggaca cctacgacgc cctgcacatg caggccctgc cccccaga    2268
```

<210> SEQ ID NO 48
<211> LENGTH: 756
<212> TYPE: PRT
<213> ORGANISM: Artificial Sequence
<220> FEATURE:
<223> OTHER INFORMATION: 5# CAR protein sequence

<400> SEQUENCE: 48

```
Met Ala Leu Pro Val Thr Ala Leu Leu Leu Pro Leu Ala Leu Leu Leu
1               5                   10                  15

His Ala Ala Arg Pro Gln Ser Val Val Thr Gln Pro Pro Ser Val Ser
            20                  25                  30

Gly Ala Pro Gly Gln Arg Val Thr Ile Ser Cys Thr Gly Ser Ser Ser
```

```
              35                    40                    45

Asn Ile Gly Ala Gly Tyr Asp Val His Trp Tyr Gln Gln Leu Pro Gly
    50                    55                    60

Thr Ala Pro Lys Leu Leu Ile Tyr Glu Asn Thr Asn Arg Pro Ser Gly
65                    70                    75                    80

Val Pro Asp Arg Phe Ser Gly Ser Lys Ser Gly Thr Ser Ala Ser Leu
                85                    90                    95

Ala Ile Thr Gly Leu Gln Ala Glu Asp Glu Ala Asp Tyr Tyr Cys Gln
            100                   105                   110

Ser Tyr Asp Ser Ser Leu Ser Gly Trp Arg Val Phe Gly Gly Gly Thr
            115                   120                   125

Lys Leu Thr Val Leu Gly Gly Gly Gly Ser Gly Gly Gly Gly Ser
    130                   135                   140

Gly Gly Gly Gly Ser Met Ala Glu Val Gln Leu Val Gln Ser Gly Ala
145                   150                   155                   160

Glu Val Lys Lys Pro Gly Glu Ser Leu Lys Ile Ser Cys Lys Gly Ser
                165                   170                   175

Gly Tyr Ser Phe Thr Asn Ser Trp Ile Gly Trp Val Arg Gln Met Pro
            180                   185                   190

Gly Lys Gly Leu Glu Trp Met Gly Leu Ile Tyr Pro Asp Asp Ser Asp
            195                   200                   205

Thr Arg Tyr Ser Pro Ser Phe Gln Gly Gln Val Thr Ile Ser Ala Asp
    210                   215                   220

Ser Ala Ile Asn Thr Ala Tyr Leu Gln Trp Ser Ser Leu Lys Ala Ser
225                   230                   235                   240

Asp Thr Ala Met Tyr Tyr Cys Ala Arg Gln Ser Thr Tyr Ile Tyr Gly
                245                   250                   255

Gly Tyr Tyr Asp Thr Trp Gly Gln Gly Thr Leu Val Thr Val Ser Ser
            260                   265                   270

Gly Gly Gly Gly Ser Gln Val Gln Leu Gln Glu Ser Gly Pro Gly Leu
            275                   280                   285

Val Lys Pro Ser Gly Thr Leu Ser Leu Thr Cys Ala Val Ser Gly Gly
    290                   295                   300

Ser Ile Ser Ser Ser Asn Trp Trp Ser Trp Val Arg Gln Pro Pro Gly
305                   310                   315                   320

Lys Gly Leu Glu Trp Ile Gly Glu Ile Tyr His Ser Gly Ser Thr Asn
                325                   330                   335

Tyr Asn Pro Ser Leu Lys Ser Arg Val Thr Ile Ser Val Asp Lys Ser
            340                   345                   350

Lys Asn Gln Phe Ser Leu Lys Leu Ser Ser Val Thr Ala Ala Asp Thr
            355                   360                   365

Ala Val Tyr Tyr Cys Ala Arg Leu Pro Gly Tyr Glu Ser Ala Phe Asp
    370                   375                   380

Ile Trp Gly Gln Gly Thr Met Val Thr Val Ser Ser Gly Gly Gly Gly
385                   390                   395                   400

Ser Gly Gly Gly Gly Ser Gly Gly Gly Gly Ser Glu Ile Val Leu Thr
                405                   410                   415

Gln Ser Pro Gly Thr Leu Ser Leu Ser Pro Gly Glu Arg Ala Thr Leu
            420                   425                   430

Ser Cys Arg Ala Ser Gln Ser Val Ser Ser Ser Tyr Leu Ala Trp Tyr
            435                   440                   445

Gln Gln Lys Pro Gly Gln Ala Pro Arg Leu Leu Ile Tyr Gly Ala Ser
    450                   455                   460
```

```
Ser Arg Ala Thr Gly Ile Pro Asp Arg Phe Ser Gly Ser Gly Ser Gly
465                 470                 475                 480

Thr Asp Phe Thr Leu Thr Ile Ser Arg Leu Glu Pro Glu Asp Phe Ala
                    485                 490                 495

Val Tyr Tyr Cys Gln Gln Ala Gly Leu Phe Pro Tyr Thr Phe Gly Gly
            500                 505                 510

Gly Thr Lys Val Glu Ile Lys Phe Val Pro Val Phe Leu Pro Ala Lys
            515                 520                 525

Pro Thr Thr Thr Pro Ala Pro Arg Pro Pro Thr Pro Ala Pro Thr Ile
    530                 535                 540

Ala Ser Gln Pro Leu Ser Leu Arg Pro Glu Ala Cys Arg Pro Ala Ala
545                 550                 555                 560

Gly Gly Ala Val His Thr Arg Gly Leu Asp Phe Ala Cys Asp Ile Tyr
            565                 570                 575

Ile Trp Ala Pro Leu Ala Gly Thr Cys Gly Val Leu Leu Leu Ser Leu
            580                 585                 590

Val Ile Thr Leu Tyr Cys Asn His Arg Asn Lys Arg Gly Arg Lys Lys
            595                 600                 605

Leu Leu Tyr Ile Phe Lys Gln Pro Phe Met Arg Pro Val Gln Thr Thr
            610                 615                 620

Gln Glu Glu Asp Gly Cys Ser Cys Arg Phe Pro Glu Glu Glu Glu Gly
625                 630                 635                 640

Gly Cys Glu Leu Arg Val Lys Phe Ser Arg Ser Ala Asp Ala Pro Ala
            645                 650                 655

Tyr Gln Gln Gly Gln Asn Gln Leu Tyr Asn Glu Leu Asn Leu Gly Arg
            660                 665                 670

Arg Glu Glu Tyr Asp Val Leu Asp Lys Arg Arg Gly Arg Asp Pro Glu
            675                 680                 685

Met Gly Gly Lys Pro Arg Arg Lys Asn Pro Gln Glu Gly Leu Tyr Asn
    690                 695                 700

Glu Leu Gln Lys Asp Lys Met Ala Glu Ala Tyr Ser Glu Ile Gly Met
705                 710                 715                 720

Lys Gly Glu Arg Arg Arg Gly Lys Gly His Asp Gly Leu Tyr Gln Gly
            725                 730                 735

Leu Ser Thr Ala Thr Lys Asp Thr Tyr Asp Ala Leu His Met Gln Ala
            740                 745                 750

Leu Pro Pro Arg
    755
```

```
<210> SEQ ID NO 49
<211> LENGTH: 2268
<212> TYPE: DNA
<213> ORGANISM: Artificial Sequence
<220> FEATURE:
<223> OTHER INFORMATION: 6# CAR nucleic acid sequence

<400> SEQUENCE: 49
atggccctgc ctgtgacagc tctgctcctc cctctggccc tgctgctcca tgccgccaga      60
ccccaggtgc agctgcagga gtcgggccca ggactggtga agccttcggg gaccctgtcc     120
ctcacctgcg ctgtctctgg tggctccatc agcagtagta actggtggag ttgggtccgc     180
cagcccccag ggaaggggct ggagtggatt ggggaaatct atcatagtgg gagcaccaac     240
tacaacccgt ccctcaagag tcgagtcacc atatcagtag acaagtccaa gaaccagttc     300
tccctgaagc tgagctctgt gaccgccgcg gacacggcgg tgtactactg cgccagactt     360
```

```
cctggatacg agtcagcttt cgacatatgg ggtcagggta caatggtcac cgtcagctca      420
ggtggcgggg gcagcggcgg aggcggatcc ggaggcggag ggagtgaaat tgtgttgacg      480
cagtctccag gcaccctgtc tttgtctcca ggggaaagag ccaccctctc ctgcagggcc      540
agtcagagtg ttagcagcag ctacttagcc tggtaccagc agaaacctgg ccaggctccc      600
aggctcctca tctatggtgc atccagcagg gccactggca tcccagacag gttcagtggc      660
agtgggtctg ggacagactt cactctcacc atcagcagac tggagcctga agattttgca      720
gtgtattact gtcagcaggc cggactcttc ccttacactt ttggcggagg gaccaaggtt      780
gagatcaaag gcgaggtgg gtcccagtct gtcgtgacgc agccgccctc agtgtctggg      840
gccccagggc agagggtcac catctcctgc actgggagca gctccaacat cggggcaggt      900
tatgatgtac actggtacca gcaacttcca ggaacagccc ccaaactcct catctatgag      960
aacaccaatc ggccctcagg ggtccctgac cgattctctg gctccaagtc tggcacctca     1020
gcctccctgg ccatcactgg gctccaggct gaggatgagg ctgattatta ctgccagtcc     1080
tatgacagca gcctgagtgg ttggagggtg ttcggcggag ggaccaagct gaccgtccta     1140
ggtggtggtg gtggtagcgg cggcggcggc tctggtggtg gtggatccat ggccgaagtg     1200
cagctggtgc agtctggggc agaggtgaaa aagcccgggg agtctctgaa gatctcctgt     1260
aaggggtctg gatacagctt taccaactcc tggatcggat gggtgcgcca gatgcccggg     1320
aaaggcctgg agtggatggg aactcatttac cctgatgact ctgataccag atacagccca     1380
tccttccaag gccaggtcac catctcagcc gacagcgcca tcaacaccgc ctacctgcag     1440
tggagcagcc tgaaggcctc ggacaccgcc atgtattact gtgcgcgcca gtctacctac     1500
atctacggtg gttactacga tacctggggt caaggtactc tggtgaccgt ctcctcattc     1560
gtgcccgtgt tcctgcccgc caaacctact actcccctg cacctaggcc tcccacccca     1620
gccccaacaa tcgccagcca gcctctgtct ctgcggcccg aagcctgtag acctgctgcc     1680
ggcggagccg tgcacaccag aggcctggac ttcgcctgcg acatctacat ctgggcccct     1740
ctggccggca cctgtggcgt gctgctgctg agcctggtga tcaccctgta ctgcaaccac     1800
cggaacaaac ggggcagaaa gaaactcctg tatatattca acaaccatt tatgagacca     1860 gtacaaacta ctcaagagga agatggctgt agctgccgat ttccagaaga agaagaagga     1920
ggatgtgaac tgagagtgaa gttcagcaga tccgccgacg cccctgccta ccagcaggga     1980
cagaaccagc tgtacaacga gctgaacctg ggcagacggg aagagtacga cgtgctggac     2040
aagcggagag ccgggacccc cgagatgggc ggaaagccca cacggaagaa ccccccaggaa     2100 ggcctgtata cgaactgca gaaagacaag atggccgagg cctacagcga gatcggcatg     2160
aagggcgagc ggaggcgcgg caagggccac gatggcctgt accagggcct gagcaccgcc     2220
accaaggaca cctacgacgc cctgcacatg caggccctgc cccccaga               2268
```

```
<210> SEQ ID NO 50
<211> LENGTH: 756
<212> TYPE: PRT
<213> ORGANISM: Artificial Sequence
<220> FEATURE:
<223> OTHER INFORMATION: 6# CAR protein sequence

<400> SEQUENCE: 50

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
```

-continued

```
                20                   25                   30
Val Lys Pro Ser Gly Thr Leu Ser Leu Thr Cys Ala Val Ser Gly Gly
            35                   40                   45

Ser Ile Ser Ser Ser Asn Trp Trp Ser Trp Val Arg Gln Pro Pro Gly
        50                   55                   60

Lys Gly Leu Glu Trp Ile Gly Glu Ile Tyr His Ser Gly Ser Thr Asn
65                   70                   75                   80

Tyr Asn Pro Ser Leu Lys Ser Arg Val Thr Ile Ser Val Asp Lys Ser
                85                   90                   95

Lys Asn Gln Phe Ser Leu Lys Leu Ser Ser Val Thr Ala Ala Asp Thr
                100                  105                  110

Ala Val Tyr Tyr Cys Ala Arg Leu Pro Gly Tyr Glu Ser Ala Phe Asp
            115                  120                  125

Ile Trp Gly Gln Gly Thr Met Val Thr Val Ser Ser Gly Gly Gly Gly
        130                  135                  140

Ser Gly Gly Gly Gly Ser Gly Gly Gly Gly Ser Glu Ile Val Leu Thr
145                  150                  155                  160

Gln Ser Pro Gly Thr Leu Ser Leu Ser Pro Gly Glu Arg Ala Thr Leu
                165                  170                  175

Ser Cys Arg Ala Ser Gln Ser Val Ser Ser Ser Tyr Leu Ala Trp Tyr
            180                  185                  190

Gln Gln Lys Pro Gly Gln Ala Pro Arg Leu Leu Ile Tyr Gly Ala Ser
            195                  200                  205

Ser Arg Ala Thr Gly Ile Pro Asp Arg Phe Ser Gly Ser Gly Ser Gly
        210                  215                  220

Thr Asp Phe Thr Leu Thr Ile Ser Arg Leu Glu Pro Glu Asp Phe Ala
225                  230                  235                  240

Val Tyr Tyr Cys Gln Gln Ala Gly Leu Phe Pro Tyr Thr Phe Gly Gly
            245                  250                  255

Gly Thr Lys Val Glu Ile Lys Gly Gly Gly Gly Ser Gln Ser Val Val
            260                  265                  270

Thr Gln Pro Pro Ser Val Ser Gly Ala Pro Gly Gln Arg Val Thr Ile
            275                  280                  285

Ser Cys Thr Gly Ser Ser Ser Asn Ile Gly Ala Gly Tyr Asp Val His
        290                  295                  300

Trp Tyr Gln Gln Leu Pro Gly Thr Ala Pro Lys Leu Leu Ile Tyr Glu
305                  310                  315                  320

Asn Thr Asn Arg Pro Ser Gly Val Pro Asp Arg Phe Ser Gly Ser Lys
            325                  330                  335

Ser Gly Thr Ser Ala Ser Leu Ala Ile Thr Gly Leu Gln Ala Glu Asp
            340                  345                  350

Glu Ala Asp Tyr Tyr Cys Gln Ser Tyr Asp Ser Ser Leu Ser Gly Trp
            355                  360                  365

Arg Val Phe Gly Gly Gly Thr Lys Leu Thr Val Leu Gly Gly Gly Gly
        370                  375                  380

Gly Ser Gly Gly Gly Gly Ser Gly Gly Gly Gly Ser Met Ala Glu Val
385                  390                  395                  400

Gln Leu Val Gln Ser Gly Ala Glu Val Lys Lys Pro Gly Glu Ser Leu
                405                  410                  415

Lys Ile Ser Cys Lys Gly Ser Gly Tyr Ser Phe Thr Asn Ser Trp Ile
            420                  425                  430

Gly Trp Val Arg Gln Met Pro Gly Lys Gly Leu Glu Trp Met Gly Leu
            435                  440                  445
```

```
Ile Tyr Pro Asp Asp Ser Asp Thr Arg Tyr Ser Pro Ser Phe Gln Gly
    450                 455                 460

Gln Val Thr Ile Ser Ala Asp Ser Ala Ile Asn Thr Ala Tyr Leu Gln
465                 470                 475                 480

Trp Ser Ser Leu Lys Ala Ser Asp Thr Ala Met Tyr Tyr Cys Ala Arg
                485                 490                 495

Gln Ser Thr Tyr Ile Tyr Gly Gly Tyr Tyr Asp Thr Trp Gly Gln Gly
                500                 505                 510

Thr Leu Val Thr Val Ser Ser Phe Val Pro Val Phe Leu Pro Ala Lys
            515                 520                 525

Pro Thr Thr Thr Pro Ala Pro Arg Pro Pro Thr Pro Ala Pro Thr Ile
        530                 535                 540

Ala Ser Gln Pro Leu Ser Leu Arg Pro Glu Ala Cys Arg Pro Ala Ala
545                 550                 555                 560

Gly Gly Ala Val His Thr Arg Gly Leu Asp Phe Ala Cys Asp Ile Tyr
                565                 570                 575

Ile Trp Ala Pro Leu Ala Gly Thr Cys Gly Val Leu Leu Leu Ser Leu
                580                 585                 590

Val Ile Thr Leu Tyr Cys Asn His Arg Asn Lys Arg Gly Arg Lys Lys
            595                 600                 605

Leu Leu Tyr Ile Phe Lys Gln Pro Phe Met Arg Pro Val Gln Thr Thr
        610                 615                 620

Gln Glu Glu Asp Gly Cys Ser Cys Arg Phe Pro Glu Glu Glu Glu Gly
625                 630                 635                 640

Gly Cys Glu Leu Arg Val Lys Phe Ser Arg Ser Ala Asp Ala Pro Ala
                645                 650                 655

Tyr Gln Gln Gly Gln Asn Gln Leu Tyr Asn Glu Leu Asn Leu Gly Arg
                660                 665                 670

Arg Glu Glu Tyr Asp Val Leu Asp Lys Arg Arg Gly Arg Asp Pro Glu
            675                 680                 685

Met Gly Gly Lys Pro Arg Arg Lys Asn Pro Gln Glu Gly Leu Tyr Asn
        690                 695                 700

Glu Leu Gln Lys Asp Lys Met Ala Glu Ala Tyr Ser Glu Ile Gly Met
705                 710                 715                 720

Lys Gly Glu Arg Arg Arg Gly Lys Gly His Asp Gly Leu Tyr Gln Gly
                725                 730                 735

Leu Ser Thr Ala Thr Lys Asp Thr Tyr Asp Ala Leu His Met Gln Ala
                740                 745                 750

Leu Pro Pro Arg
        755
```

```
<210> SEQ ID NO 51
<211> LENGTH: 2259
<212> TYPE: DNA
<213> ORGANISM: Artificial Sequence
<220> FEATURE:
<223> OTHER INFORMATION: 7# CAR nucleic acid sequence

<400> SEQUENCE: 51
atggccctgc ctgtgacagc tctgctcctc cctctggccc tgctgctcca tgccgccaga      60
ccccagtctg tcgtgacgca gccgccctca gtgtctgggg ccccagggca gagggtcacc     120
atctcctgca ctgggagcag ctccaacatc ggggcaggtt atgatgtaca ctggtaccag     180
caacttccag gaacagcccc caaactcctc atctatgaga acaccaatcg gccctcaggg     240
```

```
gtccctgacc gattctctgg ctccaagtct ggcacctcag cctccctggc catcactggg      300
ctccaggctg aggatgaggc tgattattac tgccagtcct atgacagcag cctgagtggt      360
tggagggtgt tcggcggagg gaccaagctg accgtcctag gtggtggtgg tggtagcggc      420
ggcggcggct ctggtggtgg tggatccatg gccgaagtgc agctggtgca gtctggggca      480
gaggtgaaaa agcccgggga gtctctgaag atctcctgta aggggtctgg atacagcttt      540
accaactcct ggatcggatg ggtgcgccag atgcccggga aaggcctgga gtggatggga      600
ctcatttacc ctgatgactc tgataccaga tacagcccat ccttccaagg ccaggtcacc      660
atctcagccg acagcgccat caacaccgcc tacctgcagt ggagcagcct gaaggcctcg      720
gacaccgcca tgtattactg tgcgcgccag tctacctaca tctacggtgg ttactacgat      780
acctggggtc aaggtactct ggtgaccgtc tcctcaggcg gaggtgggtc ccaggtgcag      840
ctgcaggagt cgggcccagg actggtgaag ccttcggaga ccctgtccct cacctgcact      900
gtctctggtg gctccatcag tagttactac tggagctgga tccggcagcc cgccgggaag      960
ggactggagt ggattgggcg tatctatacc agtgggagca ccaactacaa cccctccctc      1020
aagagtcgag tcaccatgtc agtagacacg tccaagaacc agttctccct gaagctgagc      1080
tctgtgaccg ccgcggacac ggcggtgtac tactgcgcca gagacttgta cagagatgga      1140
atggacgtat ggggccaggg aacaactgtc accgtcagct caggtggcgg gggcagcggc      1200
ggaggcggat ccgaggcggg agggagtgac atccagatga cccagtctcc ttccaccctg      1260
tctgcatctg taggagacag agtcaccatc acttgccggg ccagtcagag tattagtagc      1320
tggttggcct ggtatcagca gaaaccaggg aaagccccta agctcctgat ctccgatgcc      1380
tccagtttgg aaagtggggt cccatcaagg ttcagcggca gtggatctgg gacagaattc      1440
actctcacca tcagcagcct gcagcctgat gattttgcaa cttattactg ccagcaggcc      1500
aatacctact ctcctacttt tggcggaggg accaaggttg agatcaaatt cgtgcccgtg      1560
ttcctgcccg ccaaacctac tactacccct gcacctaggc ctcccacccc agccccaaca      1620
atcgccagcc agcctctgtc tctgcggccc gaagctgta gacctgctgc cggcggagcc      1680
gtgcacacca gaggcctgga cttcgcctgc gacatctaca tctgggcccc tctggccggc      1740
acctgtggcg tgctgctgct gagcctggtg atcaccctgt actgcaacca ccggaacaaa      1800
cggggcagaa agaaactcct gtatatattc aaacaaccat ttatgagacc agtacaaact      1860
actcaagagg aagatggctg tagctgccga tttccagaag aagaagaagg aggatgtgaa      1920
ctgagagtga agttcagcag atccgccgac gcccctgcct accagcaggg acagaaccag      1980
ctgtacaacg agctgaacct gggcagacgg gaagagtacg acgtgctgga caagcggaga      2040
ggccgggacc ccgagatggg cggaaagccc agcggaagga ccccccagga aggcctgtat      2100
aacgaactgc agaaagacaa gatggccgag gcctacagcg agatcggcat gaagggcgag      2160
cggaggcgcg gcaagggcca cgatggcctg taccagggcc tgagcaccgc caccaaggac      2220
acctacgacg ccctgcacat gcaggccctg ccccccaga      2259
```

<210> SEQ ID NO 52
<211> LENGTH: 753
<212> TYPE: PRT
<213> ORGANISM: Artificial Sequence
<220> FEATURE:
<223> OTHER INFORMATION: 7# CAR protein sequence

<400> SEQUENCE: 52

Met Ala Leu Pro Val Thr Ala Leu Leu Leu Pro Leu Ala Leu Leu Leu

```
1               5                   10                  15

His Ala Ala Arg Pro Gln Ser Val Val Thr Gln Pro Pro Ser Val Ser
            20              25                  30

Gly Ala Pro Gly Gln Arg Val Thr Ile Ser Cys Thr Gly Ser Ser Ser
            35              40                  45

Asn Ile Gly Ala Gly Tyr Asp Val His Trp Tyr Gln Gln Leu Pro Gly
    50              55                  60

Thr Ala Pro Lys Leu Leu Ile Tyr Glu Asn Thr Asn Arg Pro Ser Gly
65              70                  75                  80

Val Pro Asp Arg Phe Ser Gly Ser Lys Ser Gly Thr Ser Ala Ser Leu
            85              90                  95

Ala Ile Thr Gly Leu Gln Ala Glu Asp Glu Ala Asp Tyr Tyr Cys Gln
            100             105                 110

Ser Tyr Asp Ser Ser Leu Ser Gly Trp Arg Val Phe Gly Gly Gly Thr
            115             120                 125

Lys Leu Thr Val Leu Gly Gly Gly Gly Ser Gly Gly Gly Gly Ser
    130             135                 140

Gly Gly Gly Gly Ser Met Ala Glu Val Gln Leu Val Gln Ser Gly Ala
145             150                 155                 160

Glu Val Lys Lys Pro Gly Glu Ser Leu Lys Ile Ser Cys Lys Gly Ser
            165             170                 175

Gly Tyr Ser Phe Thr Asn Ser Trp Ile Gly Trp Val Arg Gln Met Pro
            180             185                 190

Gly Lys Gly Leu Glu Trp Met Gly Leu Ile Tyr Pro Asp Asp Ser Asp
            195             200                 205

Thr Arg Tyr Ser Pro Ser Phe Gln Gly Gln Val Thr Ile Ser Ala Asp
    210             215                 220

Ser Ala Ile Asn Thr Ala Tyr Leu Gln Trp Ser Ser Leu Lys Ala Ser
225             230                 235                 240

Asp Thr Ala Met Tyr Tyr Cys Ala Arg Gln Ser Thr Tyr Ile Tyr Gly
            245             250                 255

Gly Tyr Tyr Asp Thr Trp Gly Gln Gly Thr Leu Val Thr Val Ser Ser
            260             265                 270

Gly Gly Gly Gly Ser Gln Val Gln Leu Gln Glu Ser Gly Pro Gly Leu
            275             280                 285

Val Lys Pro Ser Glu Thr Leu Ser Leu Thr Cys Thr Val Ser Gly Gly
    290             295                 300

Ser Ile Ser Ser Tyr Tyr Trp Ser Trp Ile Arg Gln Pro Ala Gly Lys
305             310                 315                 320

Gly Leu Glu Trp Ile Gly Arg Ile Tyr Thr Ser Gly Ser Thr Asn Tyr
            325             330                 335

Asn Pro Ser Leu Lys Ser Arg Val Thr Met Ser Val Asp Thr Ser Lys
            340             345                 350

Asn Gln Phe Ser Leu Lys Leu Ser Ser Val Thr Ala Ala Asp Thr Ala
            355             360                 365

Val Tyr Tyr Cys Ala Arg Asp Leu Tyr Arg Asp Gly Met Asp Val Trp
    370             375                 380

Gly Gln Gly Thr Thr Val Thr Val Ser Ser Gly Gly Gly Gly Ser Gly
385             390                 395                 400

Gly Gly Gly Ser Gly Gly Gly Gly Ser Asp Ile Gln Met Thr Gln Ser
            405             410                 415

Pro Ser Thr Leu Ser Ala Ser Val Gly Asp Arg Val Thr Ile Thr Cys
            420             425                 430
```

```
Arg Ala Ser Gln Ser Ile Ser Ser Trp Leu Ala Trp Tyr Gln Gln Lys
        435                 440                 445

Pro Gly Lys Ala Pro Lys Leu Leu Ile Ser Asp Ala Ser Ser Leu Glu
        450                 455                 460

Ser Gly Val Pro Ser Arg Phe Ser Gly Ser Gly Ser Gly Thr Glu Phe
465                 470                 475                 480

Thr Leu Thr Ile Ser Ser Leu Gln Pro Asp Asp Phe Ala Thr Tyr Tyr
                485                 490                 495

Cys Gln Gln Ala Asn Thr Tyr Ser Pro Thr Phe Gly Gly Gly Thr Lys
                500                 505                 510

Val Glu Ile Lys Phe Val Pro Val Phe Leu Pro Ala Lys Pro Thr Thr
        515                 520                 525

Thr Pro Ala Pro Arg Pro Pro Thr Pro Ala Pro Thr Ile Ala Ser Gln
        530                 535                 540

Pro Leu Ser Leu Arg Pro Glu Ala Cys Arg Pro Ala Ala Gly Gly Ala
545                 550                 555                 560

Val His Thr Arg Gly Leu Asp Phe Ala Cys Asp Ile Tyr Ile Trp Ala
                565                 570                 575

Pro Leu Ala Gly Thr Cys Gly Val Leu Leu Leu Ser Leu Val Ile Thr
                580                 585                 590

Leu Tyr Cys Asn His Arg Asn Lys Arg Gly Arg Lys Lys Leu Leu Tyr
        595                 600                 605

Ile Phe Lys Gln Pro Phe Met Arg Pro Val Gln Thr Thr Gln Glu Glu
        610                 615                 620

Asp Gly Cys Ser Cys Arg Phe Pro Glu Glu Glu Glu Gly Gly Cys Glu
625                 630                 635                 640

Leu Arg Val Lys Phe Ser Arg Ser Ala Asp Ala Pro Ala Tyr Gln Gln
                645                 650                 655

Gly Gln Asn Gln Leu Tyr Asn Glu Leu Asn Leu Gly Arg Arg Glu Glu
                660                 665                 670

Tyr Asp Val Leu Asp Lys Arg Arg Gly Arg Asp Pro Glu Met Gly Gly
        675                 680                 685

Lys Pro Arg Arg Lys Asn Pro Gln Glu Gly Leu Tyr Asn Glu Leu Gln
        690                 695                 700

Lys Asp Lys Met Ala Glu Ala Tyr Ser Glu Ile Gly Met Lys Gly Glu
705                 710                 715                 720

Arg Arg Arg Gly Lys Gly His Asp Gly Leu Tyr Gln Gly Leu Ser Thr
                725                 730                 735

Ala Thr Lys Asp Thr Tyr Asp Ala Leu His Met Gln Ala Leu Pro Pro
                740                 745                 750

Arg
```

<210> SEQ ID NO 53
<211> LENGTH: 2259
<212> TYPE: DNA
<213> ORGANISM: Artificial Sequence
<220> FEATURE:
<223> OTHER INFORMATION: 8# CAR nucleic acid sequence

<400> SEQUENCE: 53

```
atggccctgc ctgtgacagc tctgctcctc cctctggccc tgctgctcca tgccgccaga      60
ccccaggtgc agctgcagga gtcgggccca ggactggtga agccttcgga gaccctgtcc     120
ctcacctgca ctgtctctgg tggctccatc agtagttact actggagctg gatccggcag     180
```

```
cccgccggga aggggactgga gtggattggg cgtatctata ccagtgggag caccaactac      240
aacccctccc tcaagagtcg agtcaccatg tcagtagaca cgtccaagaa ccagttctcc      300
ctgaagctga gctctgtgac cgccgcggac acggcggtgt actactgcgc cagagacttg      360
tacagagatg gaatggacgt atggggccag ggaacaactg tcaccgtcag ctcaggtggc      420
gggggcagcg gcggaggcgg atccggaggc ggagggagtg acatccagat gacccagtct      480
ccttccaccc tgtctgcatc tgtaggagac agagtcacca tcacttgccg ggccagtcag      540
agtattagta gctggttggc ctggtatcag cagaaaccag ggaaagcccc taagctcctg      600
atctccgatg cctccagttt ggaaagtggg gtcccatcaa ggttcagcgg cagtggatct      660
gggacagaat tcactctcac catcagcagc ctgcagcctg atgattttgc aacttattac      720
tgccagcagg ccaatacctt ctctcctact tttggcggag ggaccaaggt tgagatcaaa      780
ggcggaggtg ggtcccagtc tgtcgtgacg cagccgccct cagtgtctgg ggccccaggg      840
cagagggtca ccatctcctg cactgggagc agctccaaca tcggggcagg ttatgatgta      900
cactggtacc agcaacttcc aggaacagcc cccaaactcc tcatctatga gaacaccaat      960
cggccctcag gggtccctga ccgattctct ggctccaagt ctggcacctc agcctccctg     1020
gccatcactg ggctccaggc tgaggatgag gctgattatt actgccagtc ctatgacagc     1080
agcctgagtg gttggagggt gttcggcgga gggaccaagc tgaccgtcct aggtggtggt     1140
ggtggtagcg gcggcggcgg ctctggtggt ggtggatcca tggccgaagt gcagctggtg     1200
cagtctgggg cagaggtgaa aaagcccggg gagtctctga gatctcctg  taaggggtct     1260 ggatacagct ttaccaactc ctggatcgga tgggtgcgcc agatgcccgg gaaaggcctg     1320
gagtggatgg gactcatttta ccctgatgac tctgatacca gatacagccc atccttccaa     1380
ggccaggtca ccatctcagc cgacagcgcc atcaacaccg cctacctgca gtggagcagc     1440
ctgaaggcct cggacaccgc catgtattac tgtgcgcgcc agtctaccta catctacggt     1500
ggttactacg atacctgggg tcaaggtact ctggtgaccg tctcctcatt cgtgcccgtg     1560
ttcctgcccg ccaaacctac tactacccct gcacctaggc ctcccacccc agccccaaca     1620
atcgccagcc agcctctgtc tctgcggccc gaagcctgta gacctgctgc cggcggagcc     1680
gtgcacacca gaggcctgga cttcgcctgc gacatctaca tctgggcccc tctggccggc     1740
acctgtggcg tgctgctgct gagcctggtg atcaccctgt actgcaacca ccggaacaaa     1800
cggggcagaa agaaactcct gtatatattc aaacaaccat ttatgagacc agtacaaact     1860
actcaagagg aagatggctg tagctgccga tttccagaag aagaagaagg aggatgtgaa     1920
ctgagagtga agttcagcag atccgccgac gcccctgcct accagcaggg acagaaccag     1980
ctgtacaacg agctgaacct gggcagacgg gaagagtacg acgtgctgga caagcggaga     2040
ggccgggacc ccgagatggg cggaaagccc agacggaaga accccccagga aggcctgtat     2100 aacgaactgc agaaagacaa gatggccgag gcctacagcg agatcggcat gaagggcgag     2160
cggaggcgcg gcaagggcca cgatggcctg taccagggcc tgagcaccgc caccaaggac     2220
acctacgacg ccctgcacat gcaggccctg cccccccaga                           2259
```

<210> SEQ ID NO 54
<211> LENGTH: 753
<212> TYPE: PRT
<213> ORGANISM: Artificial Sequence
<220> FEATURE:
<223> OTHER INFORMATION: 8# CAR protein sequence
<400> SEQUENCE: 54

-continued

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Ser Tyr Tyr Trp Ser Trp Ile Arg Gln Pro Ala Gly Lys
    50                  55                  60

Gly Leu Glu Trp Ile Gly Arg Ile Tyr Thr Ser Gly Ser Thr Asn Tyr
65                  70                  75                  80

Asn Pro Ser Leu Lys Ser Arg Val Thr Met Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Asp Leu Tyr Arg Asp Gly Met Asp Val Trp
        115                 120                 125

Gly Gln Gly Thr Thr Val Thr Val Ser Ser Gly Gly Gly Gly Ser Gly
    130                 135                 140

Gly Gly Gly Ser Gly Gly Gly Gly Ser Asp Ile Gln Met Thr Gln Ser
145                 150                 155                 160

Pro Ser Thr Leu Ser Ala Ser Val Gly Asp Arg Val Thr Ile Thr Cys
            165                 170                 175

Arg Ala Ser Gln Ser Ile Ser Ser Trp Leu Ala Trp Tyr Gln Gln Lys
            180                 185                 190

Pro Gly Lys Ala Pro Lys Leu Leu Ile Ser Asp Ala Ser Ser Leu Glu
            195                 200                 205

Ser Gly Val Pro Ser Arg Phe Ser Gly Ser Gly Ser Gly Thr Glu Phe
    210                 215                 220

Thr Leu Thr Ile Ser Ser Leu Gln Pro Asp Asp Phe Ala Thr Tyr Tyr
225                 230                 235                 240

Cys Gln Gln Ala Asn Thr Tyr Ser Pro Thr Phe Gly Gly Gly Thr Lys
            245                 250                 255

Val Glu Ile Lys Gly Gly Gly Gly Ser Gln Ser Val Val Thr Gln Pro
            260                 265                 270

Pro Ser Val Ser Gly Ala Pro Gly Gln Arg Val Thr Ile Ser Cys Thr
        275                 280                 285

Gly Ser Ser Ser Asn Ile Gly Ala Gly Tyr Asp Val His Trp Tyr Gln
    290                 295                 300

Gln Leu Pro Gly Thr Ala Pro Lys Leu Leu Ile Tyr Glu Asn Thr Asn
305                 310                 315                 320

Arg Pro Ser Gly Val Pro Asp Arg Phe Ser Gly Ser Lys Ser Gly Thr
            325                 330                 335

Ser Ala Ser Leu Ala Ile Thr Gly Leu Gln Ala Glu Asp Glu Ala Asp
            340                 345                 350

Tyr Tyr Cys Gln Ser Tyr Asp Ser Ser Leu Ser Gly Trp Arg Val Phe
        355                 360                 365

Gly Gly Gly Thr Lys Leu Thr Val Leu Gly Gly Gly Gly Ser Gly
    370                 375                 380

Gly Gly Gly Ser Gly Gly Gly Gly Ser Met Ala Glu Val Gln Leu Val
385                 390                 395                 400

Gln Ser Gly Ala Glu Val Lys Lys Pro Gly Glu Ser Leu Lys Ile Ser
            405                 410                 415
```

-continued

```
Cys Lys Gly Ser Gly Tyr Ser Phe Thr Asn Ser Trp Ile Gly Trp Val
            420                 425                 430

Arg Gln Met Pro Gly Lys Gly Leu Glu Trp Met Gly Leu Ile Tyr Pro
            435                 440                 445

Asp Asp Ser Asp Thr Arg Tyr Ser Pro Ser Phe Gln Gly Gln Val Thr
            450                 455                 460

Ile Ser Ala Asp Ser Ala Ile Asn Thr Ala Tyr Leu Gln Trp Ser Ser
465                 470                 475                 480

Leu Lys Ala Ser Asp Thr Ala Met Tyr Tyr Cys Ala Arg Gln Ser Thr
            485                 490                 495

Tyr Ile Tyr Gly Gly Tyr Tyr Asp Thr Trp Gly Gln Gly Thr Leu Val
            500                 505                 510

Thr Val Ser Ser Phe Val Pro Val Phe Leu Pro Ala Lys Pro Thr Thr
            515                 520                 525

Thr Pro Ala Pro Arg Pro Pro Thr Pro Ala Pro Thr Ile Ala Ser Gln
            530                 535                 540

Pro Leu Ser Leu Arg Pro Glu Ala Cys Arg Pro Ala Ala Gly Gly Ala
545                 550                 555                 560

Val His Thr Arg Gly Leu Asp Phe Ala Cys Asp Ile Tyr Ile Trp Ala
            565                 570                 575

Pro Leu Ala Gly Thr Cys Gly Val Leu Leu Leu Ser Leu Val Ile Thr
            580                 585                 590

Leu Tyr Cys Asn His Arg Asn Lys Arg Gly Arg Lys Lys Leu Leu Tyr
            595                 600                 605

Ile Phe Lys Gln Pro Phe Met Arg Pro Val Gln Thr Thr Gln Glu Glu
            610                 615                 620

Asp Gly Cys Ser Cys Arg Phe Pro Glu Glu Glu Glu Gly Gly Cys Glu
625                 630                 635                 640

Leu Arg Val Lys Phe Ser Arg Ser Ala Asp Ala Pro Ala Tyr Gln Gln
            645                 650                 655

Gly Gln Asn Gln Leu Tyr Asn Glu Leu Asn Leu Gly Arg Arg Glu Glu
            660                 665                 670

Tyr Asp Val Leu Asp Lys Arg Arg Gly Arg Asp Pro Glu Met Gly Gly
            675                 680                 685

Lys Pro Arg Arg Lys Asn Pro Gln Glu Gly Leu Tyr Asn Glu Leu Gln
            690                 695                 700

Lys Asp Lys Met Ala Glu Ala Tyr Ser Glu Ile Gly Met Lys Gly Glu
705                 710                 715                 720

Arg Arg Arg Gly Lys Gly His Asp Gly Leu Tyr Gln Gly Leu Ser Thr
            725                 730                 735

Ala Thr Lys Asp Thr Tyr Asp Ala Leu His Met Gln Ala Leu Pro Pro
            740                 745                 750

Arg
```

<210> SEQ ID NO 55
<211> LENGTH: 2247
<212> TYPE: DNA
<213> ORGANISM: Artificial Sequence
<220> FEATURE:
<223> OTHER INFORMATION: 9# CAR nucleic acid sequence

<400> SEQUENCE: 55

```
atggccctgc ctgtgacagc tctgctcctc cctctggccc tgctgctcca tgccgccaga       60
ccccagtctg tcgtgacgca gccgccctca gtgtctgggg ccccagggca gagggtcacc      120
```

-continued

```
atctcctgca ctgggagcag ctccaacatc ggggcaggtt atgatgtaca ctggtaccag     180
caacttccag gaacagcccc caaactcctc atctatgaga acaccaatcg gccctcaggg     240
gtccctgacc gattctctgg ctccaagtct ggcacctcag cctccctggc catcactggg     300
ctccaggctg aggatgaggc tgattattac tgccagtcct atgacagcag cctgagtggt     360
tggagggtgt tcggcggagg gaccaagctg accgtcctag gtggtggtgg tggtagccag     420
gtgcagctgc aggagtcggg cccaggactg gtgaagcctt cggggaccct gtccctcacc     480
tgcgctgtct ctggtggctc catcagcagt agtaactggt ggagttgggt ccgccagccc     540
ccagggaagg ggctggagtg gattggggaa atctatcata gtgggagcac caactacaac     600
ccgtccctca gagtcgagt caccatatca gtagacaagt ccaagaacca gttctccctg     660
aagctgagct ctgtgaccgc cgcggacacg gcggtgtact actgcgccag acttcctgga     720
tacgagtcag ctttcgacat atggggtcag ggtacaatgg tcaccgtcag ctcaggcagc     780
accagcggct ccggcaagcc tggctctggc gagggcagca caaagggaga aattgtgttg     840
acgcagtctc caggcaccct gtctttgtct ccaggggaaa gagccaccct ctcctgcagg     900
gccagtcaga gtgttagcag cagctactta gcctggtacc agcagaaacc tggccaggct     960
cccaggctcc tcatctatgg tgcatccagc agggccactg gcatcccaga caggttcagt    1020
ggcagtgggt ctgggacaga cttcactctc accatcagca gactggagcc tgaagatttt    1080
gcagtgtatt actgtcagca ggccggactc ttcccttaca cttttggcgg agggaccaag    1140
gttgagatca aggtggcgg gggcagcatg gccgaagtgc agctggtgca gtctggggca    1200
gaggtgaaaa agcccgggga gtctctgaag atctcctgta aggggtctgg atacagcttt    1260
accaactcct ggatcggatg ggtgcgccag atgcccggga aaggcctgga gtggatggga    1320
ctcatttacc ctgatgactc tgataccaga tacagcccat ccttccaagg ccaggtcacc    1380
atctcagccg acagcgccat caacaccgcc tacctgcagt ggagcagcct gaaggcctcg    1440
gacaccgcca tgtattactg tgcgcgccag tctacctaca tctacggtgg ttactacgat    1500
acctggggtc aaggtactct ggtgaccgtc tcctcattcg tgcccgtgtt cctgcccgcc    1560
aaacctacta ctacccctgc acctaggcct cccaccccag ccccaacaat cgccagccag    1620
cctctgtctc tgcggcccga agcctgtaga cctgctgccg gcggagccgt gcacaccaga    1680
ggcctggact cgcctgcgca catctacatc tgggcccctc tggccggcac ctgtggcgtg    1740
ctgctgctga gcctggtgat caccctgtac tgcaaccacc ggaacaaacg gggcagaaag    1800
aaactcctgt atatattcaa acaaccattt atgagaccag tacaaactac tcaagaggaa    1860
gatggctgta gctgccgatt ccagaagaa gaagaaggag gatgtgaact gagagtgaag    1920
ttcagcagat ccgccgacgc ccctgcctac cagcaggggac agaaccagct gtacaacgag    1980
ctgaacctgg gcagacggga gagtacgac gtgctggaca gcggagagg ccgggacccc    2040 gagatgggcg gaaagcccag acggaagaac ccccaggaag gcctgtataa cgaactgcag    2100
aaagacaaga tggccgaggc ctacagcgag atcggcatga aggggcgagcg gaggcgcggc    2160 aagggccacg atggcctgta ccagggcctg agcaccgcca ccaaggacac ctacgacgcc    2220
ctgcacatgc aggccctgcc ccccaga                                        2247
```

```
<210> SEQ ID NO 56
<211> LENGTH: 749
<212> TYPE: PRT
<213> ORGANISM: Artificial Sequence
<220> FEATURE:
<223> OTHER INFORMATION: 9# CAR protein sequence
```

<400> SEQUENCE: 56

```
Met Ala Leu Pro Val Thr Ala Leu Leu Leu Pro Leu Ala Leu Leu Leu
1               5                   10                  15

His Ala Ala Arg Pro Gln Ser Val Val Thr Gln Pro Pro Ser Val Ser
            20                  25                  30

Gly Ala Pro Gly Gln Arg Val Thr Ile Ser Cys Thr Gly Ser Ser Ser
        35                  40                  45

Asn Ile Gly Ala Gly Tyr Asp Val His Trp Tyr Gln Gln Leu Pro Gly
    50                  55                  60

Thr Ala Pro Lys Leu Leu Ile Tyr Glu Asn Thr Asn Arg Pro Ser Gly
65                  70                  75                  80

Val Pro Asp Arg Phe Ser Gly Ser Lys Ser Gly Thr Ser Ala Ser Leu
                85                  90                  95

Ala Ile Thr Gly Leu Gln Ala Glu Asp Glu Ala Asp Tyr Tyr Cys Gln
            100                 105                 110

Ser Tyr Asp Ser Ser Leu Ser Gly Trp Arg Val Phe Gly Gly Gly Thr
            115                 120                 125

Lys Leu Thr Val Leu Gly Gly Gly Gly Ser Gln Val Gln Leu Gln
    130                 135                 140

Glu Ser Gly Pro Gly Leu Val Lys Pro Ser Gly Thr Leu Ser Leu Thr
145                 150                 155                 160

Cys Ala Val Ser Gly Gly Ser Ile Ser Ser Asn Trp Trp Ser Trp
                165                 170                 175

Val Arg Gln Pro Pro Gly Lys Gly Leu Glu Trp Ile Gly Glu Ile Tyr
            180                 185                 190

His Ser Gly Ser Thr Asn Tyr Asn Pro Ser Leu Lys Ser Arg Val Thr
            195                 200                 205

Ile Ser Val Asp Lys Ser Lys Asn Gln Phe Ser Leu Lys Leu Ser Ser
    210                 215                 220

Val Thr Ala Ala Asp Thr Ala Val Tyr Tyr Cys Ala Arg Leu Pro Gly
225                 230                 235                 240

Tyr Glu Ser Ala Phe Asp Ile Trp Gly Gln Gly Thr Met Val Thr Val
                245                 250                 255

Ser Ser Gly Ser Thr Ser Gly Ser Gly Lys Pro Gly Ser Gly Glu Gly
            260                 265                 270

Ser Thr Lys Gly Glu Ile Val Leu Thr Gln Ser Pro Gly Thr Leu Ser
            275                 280                 285

Leu Ser Pro Gly Glu Arg Ala Thr Leu Ser Cys Arg Ala Ser Gln Ser
    290                 295                 300

Val Ser Ser Tyr Leu Ala Trp Tyr Gln Gln Lys Pro Gly Gln Ala
305                 310                 315                 320

Pro Arg Leu Leu Ile Tyr Gly Ala Ser Ser Arg Ala Thr Gly Ile Pro
                325                 330                 335

Asp Arg Phe Ser Gly Ser Gly Ser Gly Thr Asp Phe Thr Leu Thr Ile
            340                 345                 350

Ser Arg Leu Glu Pro Glu Asp Phe Ala Val Tyr Tyr Cys Gln Gln Ala
            355                 360                 365

Gly Leu Phe Pro Tyr Thr Phe Gly Gly Gly Thr Lys Val Glu Ile Lys
    370                 375                 380

Gly Gly Gly Gly Ser Met Ala Glu Val Gln Leu Val Gln Ser Gly Ala
385                 390                 395                 400

Glu Val Lys Lys Pro Gly Glu Ser Leu Lys Ile Ser Cys Lys Gly Ser
```

-continued

```
                 405              410              415
Gly Tyr Ser Phe Thr Asn Ser Trp Ile Gly Trp Val Arg Gln Met Pro
            420              425              430

Gly Lys Gly Leu Glu Trp Met Gly Leu Ile Tyr Pro Asp Asp Ser Asp
            435              440              445

Thr Arg Tyr Ser Pro Ser Phe Gln Gly Gln Val Thr Ile Ser Ala Asp
    450              455              460

Ser Ala Ile Asn Thr Ala Tyr Leu Gln Trp Ser Ser Leu Lys Ala Ser
465              470              475              480

Asp Thr Ala Met Tyr Tyr Cys Ala Arg Gln Ser Thr Tyr Ile Tyr Gly
            485              490              495

Gly Tyr Tyr Asp Thr Trp Gly Gln Gly Thr Leu Val Thr Val Ser Ser
            500              505              510

Phe Val Pro Val Phe Leu Pro Ala Lys Pro Thr Thr Thr Pro Ala Pro
            515              520              525

Arg Pro Pro Thr Pro Ala Pro Thr Ile Ala Ser Gln Pro Leu Ser Leu
    530              535              540

Arg Pro Glu Ala Cys Arg Pro Ala Ala Gly Gly Ala Val His Thr Arg
545              550              555              560

Gly Leu Asp Phe Ala Cys Asp Ile Tyr Ile Trp Ala Pro Leu Ala Gly
            565              570              575

Thr Cys Gly Val Leu Leu Leu Ser Leu Val Ile Thr Leu Tyr Cys Asn
            580              585              590

His Arg Asn Lys Arg Gly Arg Lys Lys Leu Leu Tyr Ile Phe Lys Gln
            595              600              605

Pro Phe Met Arg Pro Val Gln Thr Thr Gln Glu Glu Asp Gly Cys Ser
    610              615              620

Cys Arg Phe Pro Glu Glu Glu Glu Gly Gly Cys Glu Leu Arg Val Lys
625              630              635              640

Phe Ser Arg Ser Ala Asp Ala Pro Ala Tyr Gln Gln Gly Gln Asn Gln
            645              650              655

Leu Tyr Asn Glu Leu Asn Leu Gly Arg Arg Glu Glu Tyr Asp Val Leu
            660              665              670

Asp Lys Arg Arg Gly Arg Asp Pro Glu Met Gly Gly Lys Pro Arg Arg
            675              680              685

Lys Asn Pro Gln Glu Gly Leu Tyr Asn Glu Leu Gln Lys Asp Lys Met
    690              695              700

Ala Glu Ala Tyr Ser Glu Ile Gly Met Lys Gly Glu Arg Arg Arg Gly
705              710              715              720

Lys Gly His Asp Gly Leu Tyr Gln Gly Leu Ser Thr Ala Thr Lys Asp
            725              730              735

Thr Tyr Asp Ala Leu His Met Gln Ala Leu Pro Pro Arg
            740              745
```

```
<210> SEQ ID NO 57
<211> LENGTH: 2238
<212> TYPE: DNA
<213> ORGANISM: Artificial Sequence
<220> FEATURE:
<223> OTHER INFORMATION: 10# CAR nucleic acid sequence

<400> SEQUENCE: 57
atggccctgc ctgtgacagc tctgctcctc cctctggccc tgctgctcca tgccgccaga     60
ccccagtctg tcgtgacgca gccgccctca gtgtctgggg ccccagggca gagggtcacc     120
```

```
atctcctgca ctgggagcag ctccaacatc ggggcaggtt atgatgtaca ctggtaccag      180
caacttccag gaacagcccc caaactcctc atctatgaga acaccaatcg gccctcaggg      240
gtccctgacc gattctctgg ctccaagtct ggcacctcag cctccctggc catcactggg      300
ctccaggctg aggatgaggc tgattattac tgccagtcct atgacagcag cctgagtggt      360
tggagggtgt tcggcggagg gaccaagctg accgtcctag gtggtggtgg tggtagccag      420
gtgcagctgc aggagtcggg cccaggactg gtgaagcctt cggagaccct gtccctcacc      480
tgcactgtct ctggtggctc catcagtagt tactactgga gctggatccg gcagcccgcc      540
gggaagggac tggagtggat tgggcgtatc tataccagtg ggagcaccaa ctacaacccc      600
tccctcaaga gtcgagtcac catgtcagta gacacgtcca agaaccagtt ctccctgaag      660
ctgagctctg tgaccgccgc ggacacggcg gtgtactact cgccagagag cttgtacaga      720
gatggaatgg acgtatgggg ccagggaaca actgtcaccg tcagctcagg cagcaccagc      780
ggctccggca agcctggctc tggcgagggc agcacaaagg agacatcca gatgacccag      840 tctccttcca ccctgtctgc atctgtagga gacagagtca ccatcacttg ccgggccagt      900
cagagtatta gtagctggtt ggcctggtat cagcagaaac cagggaaagc ccctaagctc      960
ctgatctccg atgcctccag tttggaaagt ggggtcccat caaggttcag cggcagtgga     1020
tctgggacag aattcactct caccatcagc agcctgcagc ctgatgattt tgcaacttat     1080
tactgccagc aggccaatac ctactctcct acttttggcg gagggaccaa ggttgagatc     1140
aaaggtggcg ggggcagcat ggccgaagtg cagctggtgc agtctggggc agaggtgaaa     1200
aagcccgggg agtctctgaa gatctcctgt aaggggtctg gatacagctt taccaactcc     1260
tggatcggat gggtgcgcca gatgcccggg aaaggcctgg agtggatggg actcatttac     1320
cctgatgact ctgataccag atacagccca tccttccaag gccaggtcac catctcagcc     1380
gacagcgcca tcaacaccgc ctacctgcag tggagcagcc tgaaggcctc ggacaccgcc     1440
atgtattact gtgcgcgcca gtctacctac atctacggtg gttactacga tacctggggt     1500
caaggtactc tggtgaccgt ctcctcattc gtgcccgtgt cctgcccgc caaacctact     1560 actacccctg cacctaggcc tcccacccca gccccaacaa tcgccagcca gcctctgtct     1620
ctgcggcccg aagcctgtag acctgctgcc ggcggagccg tgcacaccag aggcctggac     1680
ttcgcctgcg acatctacat ctgggcccct ctggccggca cctgtggcgt gctgctgctg     1740
agcctggtga tcaccctgta ctgcaaccac cggaacaaac ggggcagaaa gaaactcctg     1800
tatatattca aacaaccatt tatgagacca gtacaaacta ctcaagagga agatggctgt     1860
agctgccgat ttccagaaga agaagaagga ggatgtgaac tgagagtgaa gttcagcaga     1920
tccgccgacg cccctgccta ccagcaggga cagaaccagc tgtacaacga gctgaacctg     1980
ggcagacggg aagagtacga cgtgctggac aagcggagag ccgggaccc cgagatgggc     2040 ggaaagccca gacggaagaa cccccaggaa ggcctgtata cgaactgca gaaagacaag     2100 atggccgagg cctacagcga gatcggcatg aagggcgagc ggaggcgcgg caaggccac      2160 gatggcctgt accagggcct gagcaccgcc accaaggaca cctacgacgc cctgcacatg     2220
caggccctgc cccccaga                                                    2238
```

<210> SEQ ID NO 58
<211> LENGTH: 746
<212> TYPE: PRT
<213> ORGANISM: Artificial Sequence
<220> FEATURE:
<223> OTHER INFORMATION: 10# CAR protein sequence -continued

<400> SEQUENCE: 58

Met Ala Leu Pro Val Thr Ala Leu Leu Leu Pro Leu Ala Leu Leu Leu
1               5                   10                  15

His Ala Ala Arg Pro Gln Ser Val Val Thr Gln Pro Pro Ser Val Ser
                20                  25                  30

Gly Ala Pro Gly Gln Arg Val Thr Ile Ser Cys Thr Gly Ser Ser Ser
            35                  40                  45

Asn Ile Gly Ala Gly Tyr Asp Val His Trp Tyr Gln Gln Leu Pro Gly
        50                  55                  60

Thr Ala Pro Lys Leu Leu Ile Tyr Glu Asn Thr Asn Arg Pro Ser Gly
65                  70                  75                  80

Val Pro Asp Arg Phe Ser Gly Ser Lys Ser Gly Thr Ser Ala Ser Leu
                85                  90                  95

Ala Ile Thr Gly Leu Gln Ala Glu Asp Glu Ala Asp Tyr Tyr Cys Gln
            100                 105                 110

Ser Tyr Asp Ser Ser Leu Ser Gly Trp Arg Val Phe Gly Gly Gly Thr
        115                 120                 125

Lys Leu Thr Val Leu Gly Gly Gly Gly Ser Gln Val Gln Leu Gln
    130                 135                 140

Glu Ser Gly Pro Gly Leu Val Lys Pro Ser Glu Thr Leu Ser Leu Thr
145                 150                 155                 160

Cys Thr Val Ser Gly Gly Ser Ile Ser Ser Tyr Tyr Trp Ser Trp Ile
                165                 170                 175

Arg Gln Pro Ala Gly Lys Gly Leu Glu Trp Ile Gly Arg Ile Tyr Thr
            180                 185                 190

Ser Gly Ser Thr Asn Tyr Asn Pro Ser Leu Lys Ser Arg Val Thr Met
        195                 200                 205

Ser Val Asp Thr Ser Lys Asn Gln Phe Ser Leu Lys Leu Ser Ser Val
    210                 215                 220

Thr Ala Ala Asp Thr Ala Val Tyr Tyr Cys Ala Arg Asp Leu Tyr Arg
225                 230                 235                 240

Asp Gly Met Asp Val Trp Gly Gln Gly Thr Thr Val Thr Val Ser Ser
                245                 250                 255

Gly Ser Thr Ser Gly Ser Gly Lys Pro Gly Ser Gly Glu Gly Ser Thr
            260                 265                 270

Lys Gly Asp Ile Gln Met Thr Gln Ser Pro Ser Thr Leu Ser Ala Ser
        275                 280                 285

Val Gly Asp Arg Val Thr Ile Thr Cys Arg Ala Ser Gln Ser Ile Ser
    290                 295                 300

Ser Trp Leu Ala Trp Tyr Gln Gln Lys Pro Gly Lys Ala Pro Lys Leu
305                 310                 315                 320

Leu Ile Ser Asp Ala Ser Ser Leu Glu Ser Gly Val Pro Ser Arg Phe
                325                 330                 335

Ser Gly Ser Gly Ser Gly Thr Glu Phe Thr Leu Thr Ile Ser Ser Leu
            340                 345                 350

Gln Pro Asp Asp Phe Ala Thr Tyr Tyr Cys Gln Gln Ala Asn Thr Tyr
        355                 360                 365

Ser Pro Thr Phe Gly Gly Gly Thr Lys Val Glu Ile Lys Gly Gly Gly
    370                 375                 380

Gly Ser Met Ala Glu Val Gln Leu Val Gln Ser Gly Ala Glu Val Lys
385                 390                 395                 400

Lys Pro Gly Glu Ser Leu Lys Ile Ser Cys Lys Gly Ser Gly Tyr Ser

-continued

```
              405              410              415
Phe Thr Asn Ser Trp Ile Gly Trp Val Arg Gln Met Pro Gly Lys Gly
          420              425              430

Leu Glu Trp Met Gly Leu Ile Tyr Pro Asp Asp Ser Asp Thr Arg Tyr
          435              440              445

Ser Pro Ser Phe Gln Gly Gln Val Thr Ile Ser Ala Asp Ser Ala Ile
      450              455              460

Asn Thr Ala Tyr Leu Gln Trp Ser Ser Leu Lys Ala Ser Asp Thr Ala
465              470              475              480

Met Tyr Tyr Cys Ala Arg Gln Ser Thr Tyr Ile Tyr Gly Gly Tyr Tyr
              485              490              495

Asp Thr Trp Gly Gln Gly Thr Leu Val Thr Val Ser Ser Phe Val Pro
          500              505              510

Val Phe Leu Pro Ala Lys Pro Thr Thr Thr Pro Ala Pro Arg Pro Pro
          515              520              525

Thr Pro Ala Pro Thr Ile Ala Ser Gln Pro Leu Ser Leu Arg Pro Glu
      530              535              540

Ala Cys Arg Pro Ala Ala Gly Gly Ala Val His Thr Arg Gly Leu Asp
545              550              555              560

Phe Ala Cys Asp Ile Tyr Ile Trp Ala Pro Leu Ala Gly Thr Cys Gly
              565              570              575

Val Leu Leu Leu Ser Leu Val Ile Thr Leu Tyr Cys Asn His Arg Asn
          580              585              590

Lys Arg Gly Arg Lys Lys Leu Leu Tyr Ile Phe Lys Gln Pro Phe Met
          595              600              605

Arg Pro Val Gln Thr Thr Gln Glu Glu Asp Gly Cys Ser Cys Arg Phe
      610              615              620

Pro Glu Glu Glu Glu Gly Gly Cys Glu Leu Arg Val Lys Phe Ser Arg
625              630              635              640

Ser Ala Asp Ala Pro Ala Tyr Gln Gln Gly Gln Asn Gln Leu Tyr Asn
              645              650              655

Glu Leu Asn Leu Gly Arg Arg Glu Glu Tyr Asp Val Leu Asp Lys Arg
          660              665              670

Arg Gly Arg Asp Pro Glu Met Gly Gly Lys Pro Arg Arg Lys Asn Pro
          675              680              685

Gln Glu Gly Leu Tyr Asn Glu Leu Gln Lys Asp Lys Met Ala Glu Ala
      690              695              700

Tyr Ser Glu Ile Gly Met Lys Gly Glu Arg Arg Arg Gly Lys Gly His
705              710              715              720

Asp Gly Leu Tyr Gln Gly Leu Ser Thr Ala Thr Lys Asp Thr Tyr Asp
          725              730              735

Ala Leu His Met Gln Ala Leu Pro Pro Arg
          740              745
```

```
<210> SEQ ID NO 59
<211> LENGTH: 2247
<212> TYPE: DNA
<213> ORGANISM: Artificial Sequence
<220> FEATURE:
<223> OTHER INFORMATION: 11# CAR nucleic acid sequence

<400> SEQUENCE: 59
atggccctgc ctgtgacagc tctgctcctc cctctggccc tgctgctcca tgccgccaga      60
cccgaaattg tgttgacgca gtctccaggc accctgtctt tgtctccagg ggaaagagcc     120
```

```
accctctcct gcagggccag tcagagtgtt agcagcagct acttagcctg gtaccagcag      180
aaacctggcc aggctcccag gctcctcatc tatggtgcat ccagcagggc cactggcatc      240
ccagacaggt tcagtggcag tgggtctggg acagacttca ctctcaccat cagcagactg      300
gagcctgaag attttgcagt gtattactgt cagcaggccg gactcttccc ttacactttt      360
ggcggaggga ccaaggttga gatcaaaggt ggcgggggca gcatggccga agtgcagctg      420
gtgcagtctg gggcagaggt gaaaaagccc ggggagtctc tgaagatctc ctgtaagggg      480
tctggataca gctttaccaa ctcctggatc ggatgggtgc gccagatgcc cgggaaaggc      540
ctggagtgga tgggactcat ttaccctgat gactctgata ccagatacag cccatccttc      600
caaggccagg tcaccatctc agccgacagc gccatcaaca ccgcctacct gcagtggagc      660
agcctgaagg cctcggacac cgccatgtat tactgtgcgc gccagtctac ctacatctac      720
ggtggttact acgatacctg gggtcaaggt actctggtga ccgtctcctc aggcagcacc      780
agcggctccg gcaagcctgg ctctggcgag ggcagcacaa agggacagtc tgtcgtgacg      840
cagccgccct cagtgtctgg ggccccaggg cagagggtca ccatctcctg cactgggagc      900
agctccaaca tcggggcagg ttatgatgta cactggtacc agcaacttcc aggaacagcc      960
cccaaactcc tcatctatga gaacaccaat cggccctcag gggtccctga ccgattctct     1020
ggctccaagt ctggcacctc agcctccctg gccatcactg gctccaggc tgaggatgag      1080 gctgattatt actgccagtc ctatgacagc agcctgagtg gttggagggt gttcggcgga     1140
gggaccaagc tgaccgtcct aggtggtggt ggtggtagcc aggtgcagct gcaggagtcg     1200
ggcccaggac tggtgaagcc ttcggggacc ctgtccctca cctgcgctgt ctctggtggc     1260
tccatcagca gtagtaactg gtggagttgg gtccgccagc ccccagggaa ggggctggag     1320
tggattgggg aaatctatca tagtgggagc accaactaca acccgtccct caagagtcga     1380
gtcaccatat cagtagacaa gtccaagaac cagttctccc tgaagctgag ctctgtgacc     1440
gccgcggaca cggcggtgta ctactgcgcc agacttcctg gatacgagtc agctttcgac     1500
atatggggtc agggtacaat ggtcaccgtc agctcattcg tgcccgtgtt cctgcccgcc     1560
aaacctacta ctacccctgc acctaggcct cccaccccag ccccaacaat cgccagccag     1620
cctctgtctc tgcggcccga agcctgtaga cctgctgccg gcggagccgt gcacaccaga     1680
ggcctggact cgcctgcgca catctacatc tgggcccctc tggccggcac ctgtggcgtg     1740
ctgctgctga gcctggtgat caccctgtac tgcaaccacc ggaacaaacg gggcagaaag     1800
aaactcctgt atatattcaa acaaccattt atgagaccag tacaaactac tcaagaggaa      1860
gatggctgta gctgccgatt ccagaagaa  gaagaaggag gatgtgaact gagagtgaag      1920
ttcagcagat ccgccgacgc ccctgcctac cagcagggac agaaccagct gtacaacgag      1980
ctgaacctgg gcagacggga gagtacgac  gtgctggaca gcggagagg ccgggacccc      2040 gagatgggcg gaaagcccag acggaagaac ccccaggaag ccctgtataa cgaactgcag      2100
aaagacaaga tggccgaggc ctacagcgag atcggcatga agggcgagcg gaggcgcggc     2160
aagggccacg atggcctgta ccagggcctg agcaccgcca ccaaggacac ctacgacgcc     2220
ctgcacatgc aggccctgcc ccccaga                                         2247
```

<210> SEQ ID NO 60
<211> LENGTH: 749
<212> TYPE: PRT
<213> ORGANISM: Artificial Sequence
<220> FEATURE:
<223> OTHER INFORMATION: 11# CAR protein sequence -continued

<400> SEQUENCE: 60

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Thr Leu
                20                  25                  30

Ser Leu Ser Pro Gly Glu Arg Ala Thr Leu Ser Cys Arg Ala Ser Gln
            35                  40                  45

Ser Val Ser Ser Ser Tyr Leu Ala Trp Tyr Gln Gln Lys Pro Gly Gln
        50                  55                  60

Ala Pro Arg Leu Leu Ile Tyr Gly Ala Ser Ser Arg Ala Thr Gly Ile
65                  70                  75                  80

Pro Asp Arg Phe Ser Gly Ser Gly Ser Gly Thr Asp Phe Thr Leu Thr
                85                  90                  95

Ile Ser Arg Leu Glu Pro Glu Asp Phe Ala Val Tyr Tyr Cys Gln Gln
            100                 105                 110

Ala Gly Leu Phe Pro Tyr Thr Phe Gly Gly Gly Thr Lys Val Glu Ile
            115                 120                 125

Lys Gly Gly Gly Gly Ser Met Ala Glu Val Gln Leu Val Gln Ser Gly
        130                 135                 140

Ala Glu Val Lys Lys Pro Gly Glu Ser Leu Lys Ile Ser Cys Lys Gly
145                 150                 155                 160

Ser Gly Tyr Ser Phe Thr Asn Ser Trp Ile Gly Trp Val Arg Gln Met
                165                 170                 175

Pro Gly Lys Gly Leu Glu Trp Met Gly Leu Ile Tyr Pro Asp Asp Ser
            180                 185                 190

Asp Thr Arg Tyr Ser Pro Ser Phe Gln Gly Gln Val Thr Ile Ser Ala
            195                 200                 205

Asp Ser Ala Ile Asn Thr Ala Tyr Leu Gln Trp Ser Ser Leu Lys Ala
        210                 215                 220

Ser Asp Thr Ala Met Tyr Tyr Cys Ala Arg Gln Ser Thr Tyr Ile Tyr
225                 230                 235                 240

Gly Gly Tyr Tyr Asp Thr Trp Gly Gln Gly Thr Leu Val Thr Val Ser
                245                 250                 255

Ser Gly Ser Thr Ser Gly Ser Gly Lys Pro Gly Ser Gly Glu Gly Ser
            260                 265                 270

Thr Lys Gly Gln Ser Val Val Thr Gln Pro Pro Ser Val Ser Gly Ala
        275                 280                 285

Pro Gly Gln Arg Val Thr Ile Ser Cys Thr Gly Ser Ser Ser Asn Ile
        290                 295                 300

Gly Ala Gly Tyr Asp Val His Trp Tyr Gln Gln Leu Pro Gly Thr Ala
305                 310                 315                 320

Pro Lys Leu Leu Ile Tyr Glu Asn Thr Asn Arg Pro Ser Gly Val Pro
                325                 330                 335

Asp Arg Phe Ser Gly Ser Lys Ser Gly Thr Ser Ala Ser Leu Ala Ile
            340                 345                 350

Thr Gly Leu Gln Ala Glu Asp Glu Ala Asp Tyr Tyr Cys Gln Ser Tyr
            355                 360                 365

Asp Ser Ser Leu Ser Gly Trp Arg Val Phe Gly Gly Gly Thr Lys Leu
        370                 375                 380

Thr Val Leu Gly Gly Gly Gly Gly Ser Gln Val Gln Leu Gln Glu Ser
385                 390                 395                 400

Gly Pro Gly Leu Val Lys Pro Ser Gly Thr Leu Ser Leu Thr Cys Ala
```

-continued

```
                    405                 410                 415

Val Ser Gly Gly Ser Ile Ser Ser Ser Asn Trp Trp Ser Trp Val Arg
        420                 425                 430

Gln Pro Pro Gly Lys Gly Leu Glu Trp Ile Gly Glu Ile Tyr His Ser
        435                 440                 445

Gly Ser Thr Asn Tyr Asn Pro Ser Leu Lys Ser Arg Val Thr Ile Ser
        450                 455                 460

Val Asp Lys Ser Lys Asn Gln Phe Ser Leu Lys Leu Ser Ser Val Thr
465                 470                 475                 480

Ala Ala Asp Thr Ala Val Tyr Tyr Cys Ala Arg Leu Pro Gly Tyr Glu
                485                 490                 495

Ser Ala Phe Asp Ile Trp Gly Gln Gly Thr Met Val Thr Val Ser Ser
                500                 505                 510

Phe Val Pro Val Phe Leu Pro Ala Lys Pro Thr Thr Thr Pro Ala Pro
        515                 520                 525

Arg Pro Pro Thr Pro Ala Pro Thr Ile Ala Ser Gln Pro Leu Ser Leu
        530                 535                 540

Arg Pro Glu Ala Cys Arg Pro Ala Ala Gly Gly Ala Val His Thr Arg
545                 550                 555                 560

Gly Leu Asp Phe Ala Cys Asp Ile Tyr Ile Trp Ala Pro Leu Ala Gly
                565                 570                 575

Thr Cys Gly Val Leu Leu Leu Ser Leu Val Ile Thr Leu Tyr Cys Asn
                580                 585                 590

His Arg Asn Lys Arg Gly Arg Lys Lys Leu Leu Tyr Ile Phe Lys Gln
        595                 600                 605

Pro Phe Met Arg Pro Val Gln Thr Thr Gln Glu Glu Asp Gly Cys Ser
        610                 615                 620

Cys Arg Phe Pro Glu Glu Glu Glu Gly Gly Cys Glu Leu Arg Val Lys
625                 630                 635                 640

Phe Ser Arg Ser Ala Asp Ala Pro Ala Tyr Gln Gln Gly Gln Asn Gln
                645                 650                 655

Leu Tyr Asn Glu Leu Asn Leu Gly Arg Arg Glu Glu Tyr Asp Val Leu
                660                 665                 670

Asp Lys Arg Arg Gly Arg Asp Pro Glu Met Gly Gly Lys Pro Arg Arg
        675                 680                 685

Lys Asn Pro Gln Glu Gly Leu Tyr Asn Glu Leu Gln Lys Asp Lys Met
        690                 695                 700

Ala Glu Ala Tyr Ser Glu Ile Gly Met Lys Gly Glu Arg Arg Arg Gly
705                 710                 715                 720

Lys Gly His Asp Gly Leu Tyr Gln Gly Leu Ser Thr Ala Thr Lys Asp
                725                 730                 735

Thr Tyr Asp Ala Leu His Met Gln Ala Leu Pro Pro Arg
        740                 745
```

<210> SEQ ID NO 61
<211> LENGTH: 2238
<212> TYPE: DNA
<213> ORGANISM: Artificial Sequence
<220> FEATURE:
<223> OTHER INFORMATION: 12# CAR nucleic acid sequence

<400> SEQUENCE: 61
atggccctgc ctgtgacagc tctgctcctc cctctggccc tgctgctcca tgccgccaga      60
cccgacatcc agatgaccca gtctcctcc accctgtctg catctgtagg agacagagtc     120

```
accatcactt gccgggccag tcagagtatt agtagctggt tggcctggta tcagcagaaa        180
ccagggaaag cccctaagct cctgatctcc gatgcctcca gtttggaaag tggggtccca        240
tcaaggttca gcggcagtgg atctgggaca gaattcactc tcaccatcag cagcctgcag        300
cctgatgatt ttgcaactta ttactgccag caggccaata cctactctcc tactttTggc        360
ggagggacca aggttgagat caaaggtggc ggggggcagca tggccgaagt gcagctggtg        420
cagtctgggg cagaggtgaa aaagcccggg gagtctctga agatctcctg taagggGtct        480
ggatacagct ttaccaactc ctggatcgga tgggtgcgcc agatgcccgg gaaaggcctg        540
gagtggatgg gactcattTa ccctgatgac tctgatacca gatacagccc atccttccaa        600
ggccaggtca ccatctcagc cgacagcgcc atcaacaccg cctacctgca gtggagcagc        660
ctgaaggcct cggacaccgc catgtattac tgtgcgcgcc agtctaccta catctacggt        720
ggttactacg atacctgggg tcaaggtact ctggtgaccg tctcctcagg cagcaccagc        780
ggctccggca gcctggctc tggcgagggc agcacaaagg acagtctgt cgtgacgcag        840 ccgccctcag tgtctggggc cccagggcag agggtcacca tctcctgcac tgggagcagc        900
tccaacatcg gggcaggtta tgatgtacac tggtaccagc aacttccagg aacagccccc        960
aaactcctca tctatgagaa caccaatcgg ccctcagggg tccctgaccg attctctggc       1020
tccaagtctg gcacctcagc ctccctggcc atcactgggc tccaggctga ggatgaggct       1080
gattattact gccagtccta tgacagcagc ctgagtggtt ggagggtgtt cggcggaggg       1140
accaagctga ccgtcctagg tggtggtggt ggtagccagg tgcagctgca ggagtcgggc       1200
ccaggactgg tgaagccttc ggagaccctg tccctcacct gcactgtctc tggtggctcc       1260
atcagtagtt actactggag ctggatccgg cagcccgccg ggaagggact ggagtggatt       1320
gggcgtatct ataccagtgg gagcaccaac tacaacccct ccctcaagag tcgagtcacc       1380
atgtcagtag acacgtccaa gaaccagttc tccctgaagc tgagctctgt gaccgccgcg       1440
gacacggcgg tgtactactg cgccagagac ttgtacagag atggaatgga cgtatggggc       1500
cagggaacaa ctgtcaccgt cagctcattc gtgcccgtgt tcctgcccgc caaacctact       1560 actaccctg cacctaggcc tcccacccca gccccaacaa tcgccagcca gcctctgtct       1620
ctgcggcccg aagcctgtag acctgctgcc ggcggagccg tgcacaccag aggcctggac       1680
ttcgcctgcg acatctacat ctgggcccct ctggccggca cctgtggcgt gctgctgctg       1740
agcctggtga tcaccctgta ctgcaaccac cggaacaaac ggggcagaaa gaaactcctg       1800
tatatattca acaaccatt tatgagacca gtacaaacta ctcaagagga agatggctgt       1860
agctgccgat ttccagaaga agaagaagga ggatgtgaac tgagagtgaa gttcagcaga       1920
tccgccgacg cccctgccta ccagcaggga cagaaccagc tgtacaacga gctgaacctg       1980
ggcagacggg aagagtacga cgtgctggac aagcggagag ccgggaccc cgagatgggc       2040 ggaaagccca cggaagaa cccccaggaa ggcctgtata cgaactgca gaaagacaag        2100 atggccgagg cctacagcga gatcggcatg aagggcgagc ggaggcgcgg caaggggccac       2160 gatggcctgt accagggcct gagcaccgcc accaaggaca cctacgacgc cctgcacatg       2220
caggccctgc cccccaga                                                      2238
```

<210> SEQ ID NO 62
<211> LENGTH: 746
<212> TYPE: PRT
<213> ORGANISM: Artificial Sequence
<220> FEATURE:
<223> OTHER INFORMATION: 12# CAR protein sequence -continued

```
<400> SEQUENCE: 62

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Thr Leu
            20                  25                  30

Ser Ala Ser Val Gly Asp Arg Val Thr Ile Thr Cys Arg Ala Ser Gln
        35                  40                  45

Ser Ile Ser Ser Trp Leu Ala Trp Tyr Gln Gln Lys Pro Gly Lys Ala
    50                  55                  60

Pro Lys Leu Leu Ile Ser Asp Ala Ser Ser Leu Glu Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Gln Gln Ala
            100                 105                 110

Asn Thr Tyr Ser Pro Thr Phe Gly Gly Gly Thr Lys Val Glu Ile Lys
        115                 120                 125

Gly Gly Gly Gly Ser Met Ala Glu Val Gln Leu Val Gln Ser Gly Ala
    130                 135                 140

Glu Val Lys Lys Pro Gly Glu Ser Leu Lys Ile Ser Cys Lys Gly Ser
145                 150                 155                 160

Gly Tyr Ser Phe Thr Asn Ser Trp Ile Gly Trp Val Arg Gln Met Pro
                165                 170                 175

Gly Lys Gly Leu Glu Trp Met Gly Leu Ile Tyr Pro Asp Asp Ser Asp
            180                 185                 190

Thr Arg Tyr Ser Pro Ser Phe Gln Gly Gln Val Thr Ile Ser Ala Asp
        195                 200                 205

Ser Ala Ile Asn Thr Ala Tyr Leu Gln Trp Ser Ser Leu Lys Ala Ser
    210                 215                 220

Asp Thr Ala Met Tyr Tyr Cys Ala Arg Gln Ser Thr Tyr Ile Tyr Gly
225                 230                 235                 240

Gly Tyr Tyr Asp Thr Trp Gly Gln Gly Thr Leu Val Thr Val Ser Ser
                245                 250                 255

Gly Ser Thr Ser Gly Ser Gly Lys Pro Gly Ser Gly Glu Gly Ser Thr
            260                 265                 270

Lys Gly Gln Ser Val Val Thr Gln Pro Pro Ser Val Ser Gly Ala Pro
        275                 280                 285

Gly Gln Arg Val Thr Ile Ser Cys Thr Gly Ser Ser Ser Asn Ile Gly
    290                 295                 300

Ala Gly Tyr Asp Val His Trp Tyr Gln Gln Leu Pro Gly Thr Ala Pro
305                 310                 315                 320

Lys Leu Leu Ile Tyr Glu Asn Thr Asn Arg Pro Ser Gly Val Pro Asp
                325                 330                 335

Arg Phe Ser Gly Ser Lys Ser Gly Thr Ser Ala Ser Leu Ala Ile Thr
            340                 345                 350

Gly Leu Gln Ala Glu Asp Glu Ala Asp Tyr Tyr Cys Gln Ser Tyr Asp
        355                 360                 365

Ser Ser Leu Ser Gly Trp Arg Val Phe Gly Gly Gly Thr Lys Leu Thr
    370                 375                 380

Val Leu Gly Gly Gly Gly Ser Gln Val Gln Leu Gln Glu Ser Gly
385                 390                 395                 400

Pro Gly Leu Val Lys Pro Ser Glu Thr Leu Ser Leu Thr Cys Thr Val
```

```
                    405                  410                  415

Ser Gly Gly Ser Ile Ser Ser Tyr Tyr Trp Ser Trp Ile Arg Gln Pro
            420                  425                  430

Ala Gly Lys Gly Leu Glu Trp Ile Gly Arg Ile Tyr Thr Ser Gly Ser
        435                  440                  445

Thr Asn Tyr Asn Pro Ser Leu Lys Ser Arg Val Thr Met Ser Val Asp
    450                  455                  460

Thr Ser Lys Asn Gln Phe Ser Leu Lys Leu Ser Ser Val Thr Ala Ala
465                  470                  475                  480

Asp Thr Ala Val Tyr Tyr Cys Ala Arg Asp Leu Tyr Arg Asp Gly Met
            485                  490                  495

Asp Val Trp Gly Gln Gly Thr Thr Val Thr Val Ser Ser Phe Val Pro
            500                  505                  510

Val Phe Leu Pro Ala Lys Pro Thr Thr Thr Pro Ala Pro Arg Pro Pro
        515                  520                  525

Thr Pro Ala Pro Thr Ile Ala Ser Gln Pro Leu Ser Leu Arg Pro Glu
        530                  535                  540

Ala Cys Arg Pro Ala Ala Gly Gly Ala Val His Thr Arg Gly Leu Asp
545                  550                  555                  560

Phe Ala Cys Asp Ile Tyr Ile Trp Ala Pro Leu Ala Gly Thr Cys Gly
            565                  570                  575

Val Leu Leu Leu Ser Leu Val Ile Thr Leu Tyr Cys Asn His Arg Asn
            580                  585                  590

Lys Arg Gly Arg Lys Lys Leu Leu Tyr Ile Phe Lys Gln Pro Phe Met
        595                  600                  605

Arg Pro Val Gln Thr Thr Gln Glu Glu Asp Gly Cys Ser Cys Arg Phe
        610                  615                  620

Pro Glu Glu Glu Glu Gly Gly Cys Glu Leu Arg Val Lys Phe Ser Arg
625                  630                  635                  640

Ser Ala Asp Ala Pro Ala Tyr Gln Gln Gly Gln Asn Gln Leu Tyr Asn
            645                  650                  655

Glu Leu Asn Leu Gly Arg Arg Glu Glu Tyr Asp Val Leu Asp Lys Arg
        660                  665                  670

Arg Gly Arg Asp Pro Glu Met Gly Gly Lys Pro Arg Arg Lys Asn Pro
        675                  680                  685

Gln Glu Gly Leu Tyr Asn Glu Leu Gln Lys Asp Lys Met Ala Glu Ala
    690                  695                  700

Tyr Ser Glu Ile Gly Met Lys Gly Glu Arg Arg Arg Gly Lys Gly His
705                  710                  715                  720

Asp Gly Leu Tyr Gln Gly Leu Ser Thr Ala Thr Lys Asp Thr Tyr Asp
            725                  730                  735

Ala Leu His Met Gln Ala Leu Pro Pro Arg
            740                  745

<210> SEQ ID NO 63
<211> LENGTH: 2235
<212> TYPE: DNA
<213> ORGANISM: Artificial Sequence
<220> FEATURE:
<223> OTHER INFORMATION: PXL1419 CAR nucleic acid sequence

<400> SEQUENCE: 63
atggccctgc ctgtgacagc tctgctcctc cctctggccc tgctgctcca tgccgccaga        60
ccccaggctg tgctgactca gccaccctcg gtgtctgaag cccccaggca gagggtcacc        120
```

```
atctcctgtt ctggaagcag ctccaacatc ggaaataatg ctgtaagctg gtaccagcag        180
ctcccaggaa aggctcccaa actcctcatc tattatgatg atctgctccc ctcagggatc        240
tctgaccgat tctctggctc caagtctggc acctcagcct ccctggccat cagtgggctc        300
cagtctgagg atgaggctga ttattactgt gcagcatggg atgacagcct gaatggttgg        360
gtgttcggcg gagggaccaa ggtcaccgtc ctaggtggtg gtggtggtag ccaggtgcag        420
ctgcaggagt cgggcccagg actggtgaag ccttcgggga ccctgtccct cacctgcgct        480
gtctctggtg gctccatcag cagtagtaac tggtggagtt gggtccgcca gcccccaggg        540
aaggggctgg agtggattgg ggaaatctat catagtggga gcaccaacta caacccgtcc        600
ctcaagagtc gagtcaccat atcagtagac aagtccaaga accagttctc cctgaagctg        660
agctctgtga ccgccgcgga cacggcggtg tactactgcg ccagacttcc tggatacgag        720
tcagctttcg acatatgggg tcagggtaca atggtcaccg tcagctcagg cagcaccagc        780
ggctccggca agcctggctc tggcgagggc agcacaaagg agaaattgt gttgacgcag         840 tctccaggca ccctgtcttt gtctccaggg gaaagagcca ccctctcctg cagggccagt        900
cagagtgtta gcagcagcta cttagcctgg taccagcaga aacctggcca ggctcccagg        960
ctcctcatct atggtgcatc cagcagggcc actggcatcc cagacaggtt cagtggcagt       1020
gggtctggga cagacttcac tctcaccatc agcagactgg agcctgaaga ttttgcagtg       1080
tattactgtc agcaggccgg actcttccct tacactttttg cgggagggac caaggttgag       1140
atcaaaggag gcggagggag tgaggtgcag ctggtgcagt ctggagcaga ggtgaaaaag       1200 cccgggggagt ctctgaagat ctcctgtaag ggttctggat acagctttac cagctactgg       1260
atcggctggg tgcgccagat gcccgggaaa ggcctggagt ggatggggat catctatcct       1320
ggtgactctg ataccagata cagcccgtcc ttccaaggcc aggtcaccat ctcagccgac       1380
aagtccatca gcaccgccta cctgcagtgg agcagcctga aggcctcgga caccgccatg       1440
tattactgtg cgcgcctgtc ttactcttgg tcttcttggt actgggattt ctggggtcaa       1500
ggtactctgg tgaccgtctc ctcattcgtg cccgtgttcc tgcccgccaa acctactact       1560 accccctgcac ctaggcctcc cacccccagcc ccaacaatcg ccagccagcc tctgtctctg      1620
cggcccgaag cctgtagacc tgctgccggc ggagccgtgc acaccagagg cctggacttc       1680
gcctgcgaca tctacatctg ggcccctctg ccggcacct gtggcgtgct gctgctgagc        1740
ctggtgatca ccctgtactg caaccaccgg aacaaacggg gcagaaagaa actcctgtat       1800
atattcaaac aaccatttat gagaccagta caaactactc aagaggaaga tggctgtagc       1860
tgccgatttc cagaagaaga agaaggagga tgtgaactga gagtgaagtt cagcagatcc       1920
gccgacgccc ctgcctacca gcagggacag aaccagctgt acaacgagct gaacctgggc       1980
agacgggaag agtacgacgt gctggacaag cggagaggcc gggaccccga gatgggcgga       2040
aagcccagac ggaagaaccc ccaggaaggc ctgtataacg aactgcagaa agacaagatg       2100
gccgaggcct acagcgagat cggcatgaag ggcgagcgga ggcgcggcaa gggccacgat       2160
ggcctgtacc agggcctgag caccgccacc aaggacacct acgacgccct gcacatgcag       2220 gcccctgcccc ccaga                                                         2235
```

<210> SEQ ID NO 64
<211> LENGTH: 745
<212> TYPE: PRT
<213> ORGANISM: Artificial Sequence
<220> FEATURE:
<223> OTHER INFORMATION: PXL1419 CAR protein sequence

<400> SEQUENCE: 64

Met Ala Leu Pro Val Thr Ala Leu Leu Leu Pro Leu Ala Leu Leu Leu
1                 5                   10                  15

His Ala Ala Arg Pro Gln Ala Val Leu Thr Gln Pro Pro Ser Val Ser
            20                  25                  30

Glu Ala Pro Arg Gln Arg Val Thr Ile Ser Cys Ser Gly Ser Ser Ser
        35                  40                  45

Asn Ile Gly Asn Asn Ala Val Ser Trp Tyr Gln Gln Leu Pro Gly Lys
    50                  55                  60

Ala Pro Lys Leu Leu Ile Tyr Tyr Asp Asp Leu Leu Pro Ser Gly Val
65                  70                  75                  80

Ser Asp Arg Phe Ser Gly Ser Lys Ser Gly Thr Ser Ala Ser Leu Ala
                85                  90                  95

Ile Ser Gly Leu Gln Ser Glu Asp Glu Ala Asp Tyr Tyr Cys Ala Ala
            100                 105                 110

Trp Asp Asp Ser Leu Asn Gly Trp Val Phe Gly Gly Gly Thr Lys Val
            115                 120                 125

Thr Val Leu Gly Gly Gly Gly Gly Ser Gln Val Gln Leu Gln Glu Ser
    130                 135                 140

Gly Pro Gly Leu Val Lys Pro Ser Gly Thr Leu Ser Leu Thr Cys Ala
145                 150                 155                 160

Val Ser Gly Gly Ser Ile Ser Ser Asn Trp Trp Ser Trp Val Arg
                165                 170                 175

Gln Pro Pro Gly Lys Gly Leu Glu Trp Ile Gly Glu Ile Tyr His Ser
            180                 185                 190

Gly Ser Thr Asn Tyr Asn Pro Ser Leu Lys Ser Arg Val Thr Ile Ser
            195                 200                 205

Val Asp Lys Ser Lys Asn Gln Phe Ser Leu Lys Leu Ser Ser Val Thr
    210                 215                 220

Ala Ala Asp Thr Ala Val Tyr Tyr Cys Ala Arg Leu Pro Gly Tyr Glu
225                 230                 235                 240

Ser Ala Phe Asp Ile Trp Gly Gln Gly Thr Met Val Thr Val Ser Ser
            245                 250                 255

Gly Ser Thr Ser Gly Ser Gly Lys Pro Gly Ser Gly Glu Gly Ser Thr
            260                 265                 270

Lys Gly Glu Ile Val Leu Thr Gln Ser Pro Gly Thr Leu Ser Leu Ser
            275                 280                 285

Pro Gly Glu Arg Ala Thr Leu Ser Cys Arg Ala Ser Gln Ser Val Ser
    290                 295                 300

Ser Ser Tyr Leu Ala Trp Tyr Gln Gln Lys Pro Gly Gln Ala Pro Arg
305                 310                 315                 320

Leu Leu Ile Tyr Gly Ala Ser Ser Arg Ala Thr Gly Ile Pro Asp Arg
                325                 330                 335

Phe Ser Gly Ser Gly Ser Gly Thr Asp Phe Thr Leu Thr Ile Ser Arg
            340                 345                 350

Leu Glu Pro Glu Asp Phe Ala Val Tyr Tyr Cys Gln Gln Ala Gly Leu
            355                 360                 365

Phe Pro Tyr Thr Phe Gly Gly Gly Thr Lys Val Glu Ile Lys Gly Gly
    370                 375                 380

Gly Gly Ser Glu Val Gln Leu Val Gln Ser Gly Ala Glu Val Lys Lys
385                 390                 395                 400

Pro Gly Glu Ser Leu Lys Ile Ser Cys Lys Gly Ser Gly Tyr Ser Phe

```
                  405              410              415
Thr Ser Tyr Trp Ile Gly Trp Val Arg Gln Met Pro Gly Lys Gly Leu
            420              425              430

Glu Trp Met Gly Ile Ile Tyr Pro Gly Asp Ser Asp Thr Arg Tyr Ser
            435              440              445

Pro Ser Phe Gln Gly Gln Val Thr Ile Ser Ala Asp Lys Ser Ile Ser
        450              455              460

Thr Ala Tyr Leu Gln Trp Ser Ser Leu Lys Ala Ser Asp Thr Ala Met
465              470              475              480

Tyr Tyr Cys Ala Arg Leu Ser Tyr Ser Trp Ser Ser Trp Tyr Trp Asp
                485              490              495

Phe Trp Gly Gln Gly Thr Leu Val Thr Val Ser Ser Phe Val Pro Val
            500              505              510

Phe Leu Pro Ala Lys Pro Thr Thr Thr Pro Ala Pro Arg Pro Pro Thr
            515              520              525

Pro Ala Pro Thr Ile Ala Ser Gln Pro Leu Ser Leu Arg Pro Glu Ala
        530              535              540

Cys Arg Pro Ala Ala Gly Gly Ala Val His Thr Arg Gly Leu Asp Phe
545              550              555              560

Ala Cys Asp Ile Tyr Ile Trp Ala Pro Leu Ala Gly Thr Cys Gly Val
                565              570              575

Leu Leu Leu Ser Leu Val Ile Thr Leu Tyr Cys Asn His Arg Asn Lys
            580              585              590

Arg Gly Arg Lys Lys Leu Leu Tyr Ile Phe Lys Gln Pro Phe Met Arg
            595              600              605

Pro Val Gln Thr Thr Gln Glu Glu Asp Gly Cys Ser Cys Arg Phe Pro
        610              615              620

Glu Glu Glu Glu Gly Gly Cys Glu Leu Arg Val Lys Phe Ser Arg Ser
625              630              635              640

Ala Asp Ala Pro Ala Tyr Gln Gln Gly Gln Asn Gln Leu Tyr Asn Glu
                645              650              655

Leu Asn Leu Gly Arg Arg Glu Glu Tyr Asp Val Leu Asp Lys Arg Arg
            660              665              670

Gly Arg Asp Pro Glu Met Gly Gly Lys Pro Arg Arg Lys Asn Pro Gln
            675              680              685

Glu Gly Leu Tyr Asn Glu Leu Gln Lys Asp Lys Met Ala Glu Ala Tyr
        690              695              700

Ser Glu Ile Gly Met Lys Gly Glu Arg Arg Gly Lys Gly His Asp
705              710              715              720

Gly Leu Tyr Gln Gly Leu Ser Thr Ala Thr Lys Asp Thr Tyr Asp Ala
            725              730              735

Leu His Met Gln Ala Leu Pro Pro Arg
            740              745
```

<210> SEQ ID NO 65
<211> LENGTH: 2235
<212> TYPE: DNA
<213> ORGANISM: Artificial Sequence
<220> FEATURE:
<223> OTHER INFORMATION: PXL1435 CAR nucleic acid sequence

<400> SEQUENCE: 65
atggcacttc ctgtgacagc cttgctcttg cccttagcac tgctgcttca tgcggcgaga        60
cctgaggtcc aacttgtgca atcaggagca gaagtgaaga agccaggcga atcacttaag       120

-continued

```
atttcctgca aaggatcagg atactcattt acatcatact ggatcggatg ggtccggcag    180
atgcccggca aaggattgga gtggatgggc atcatctacc ctggagattc agatacaaga    240
tactcacctt ccttccaagg ccaggtcacc atatcggctg acaaatcaat ctcaacagca    300
taccttcaat ggtcatcact aaagcatca gatacagcaa tgtactactg cgcaaggctt    360
agctattcat ggtcatcatg gtactgggat ttctgggggc aaggcacgct ggttacagtc    420
tcatccggag ggggagggag cgagatcgtc ctcactcagt ctccaggcac cctgtctttg    480
tcacctggag aacgggcaac actttcatgc agagcatcac aaagcgttag tagtagctat    540
cttgcctggt atcagcaaaa accgggccag gcacctagac tgctcattta tggagcttcc    600
tcaagagcaa caggaatccc tgaccggttc agcgggtccg gctctggtac tgatttcacc    660
ttaacaatct caagacttga acctgaagat ttcgcagtgt attattgtca gcaggcagga    720
ctcttcccgt atacattcgg cggaggcaca aaagtggaaa ttaaaggtag tacctccgga    780
tcaggaaagc cgggctctgg agaaggatct acaaagggcc aggttcaact tcaagaatcc    840
ggcccaggtt tggtaaagcc ttcaggtacc ttatcgctga cttgtgcagt gtcaggagga    900
tcaatctcca gtagtaattg gtggtcatgg gtccgacagc ctccagggaa aggactagag    960
tggattggcg agatttacca ctctggggagt accaactaca acccttcact aaatcacga    1020 gtcacaatta gtgttgataa atcaaagaat caattcagcc tcaagctatc atcagtgaca    1080
gcagcagata cagcggtcta ttattgtgct agacttccag gctacgaatc agcatttgat    1140
atctggggga caaggaaccat ggtaactgtt agtagcggag gaggtggctc ccaagcagta    1200
ctgacgcagc cgccctcagt gtcagaggcg ccaaggcaaa gagtaaccat aagttgttct    1260
ggatcttcca gcaatattgg taacaacgca gtgagctggt atcagcagct accgggaaag    1320
gctcccaagc tattgatata ttatgacgat cttcttcctt caggagtgtc agacaggttc    1380
tcgggttcta aatcaggcac atcagcatca cttgccatca gcggcctgca gagcgaagat    1440
gaagcagatt attattgtgc cgcgtgggat gattcactta acggatgggt gttcggcgga    1500
ggcacgaagg tgacagtact tggttttgta cctgtgtttc ttcctgcaaa gccgaccaca    1560
actcccgcac ctagacctcc aactccggca ccaaccattg catcacaacc tctaagtctg    1620
aggcccgagg catgcagacc tgcagcagga ggagcagtgc acacaagagg acttgatttc    1680
gcgtgtgata tctacatctg ggcacccctg gccggaacat gtggagtgct tcttcttttca    1740 cttgtgatca cactttactg caaccacaga aacaagcgcg gtagaaagaa gctactgtac    1800
atctttaaac aacctttcat gcgtcctgtg caaacaacac aagaagaaga tggatgctca    1860
tgcagatttc ctgaagaaga agaaggagga tgcgaactta gagtgaaatt cagccgatca    1920
gcagatgcac ctgcatacca acaaggacag aatcagctct ataatgagct gaatttggga    1980
agaagagaag aatacgatgt gcttgataag cgcagaggtc gagacccaga aatgggagga    2040
aagccgagga ggaagaatcc gcaagaagga ctatataatg agctccagaa ggataagatg    2100
gctgaagcat actcagaaat cggaatgaaa ggagaaagaa gaagaggaaa gggccatgat    2160
ggactttacc aaggactttc aacagcaaca aaggacactt acgatgcact tcacatgcaa    2220
gcacttcctc ctaga    2235
```

<210> SEQ ID NO 66
<211> LENGTH: 745
<212> TYPE: PRT
<213> ORGANISM: Artificial Sequence
<220> FEATURE:
<223> OTHER INFORMATION: PXL1435 CAR protein sequence -continued

```
<400> SEQUENCE: 66

Met Ala Leu Pro Val Thr Ala Leu Leu Leu Pro Leu Ala Leu Leu Leu
1               5                   10                  15

His Ala Ala Arg Pro Glu Val Gln Leu Val Gln Ser Gly Ala Glu Val
                20                  25                  30

Lys Lys Pro Gly Glu Ser Leu Lys Ile Ser Cys Lys Gly Ser Gly Tyr
            35                  40                  45

Ser Phe Thr Ser Tyr Trp Ile Gly Trp Val Arg Gln Met Pro Gly Lys
        50                  55                  60

Gly Leu Glu Trp Met Gly Ile Ile Tyr Pro Gly Asp Ser Asp Thr Arg
65                  70                  75                  80

Tyr Ser Pro Ser Phe Gln Gly Gln Val Thr Ile Ser Ala Asp Lys Ser
                85                  90                  95

Ile Ser Thr Ala Tyr Leu Gln Trp Ser Ser Leu Lys Ala Ser Asp Thr
            100                 105                 110

Ala Met Tyr Tyr Cys Ala Arg Leu Ser Tyr Ser Trp Ser Ser Trp Tyr
            115                 120                 125

Trp Asp Phe Trp Gly Gln Gly Thr Leu Val Thr Val Ser Ser Gly Gly
        130                 135                 140

Gly Gly Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Ser Tyr Leu Ala Trp Tyr Gln Gln Lys Pro Gly Gln Ala Pro
            180                 185                 190

Arg Leu Leu Ile Tyr Gly Ala Ser Ser Arg Ala Thr Gly Ile Pro Asp
            195                 200                 205

Arg Phe Ser Gly Ser Gly Ser Gly Thr Asp Phe Thr Leu Thr Ile Ser
        210                 215                 220

Arg Leu Glu Pro Glu Asp Phe Ala Val Tyr Tyr Cys Gln Gln Ala Gly
225                 230                 235                 240

Leu Phe Pro Tyr Thr Phe Gly Gly Gly Thr Lys Val Glu Ile Lys Gly
            245                 250                 255

Ser Thr Ser Gly Ser Gly Lys Pro Gly Ser Gly Glu Gly Ser Thr Lys
            260                 265                 270

Gly Gln Val Gln Leu Gln Glu Ser Gly Pro Gly Leu Val Lys Pro Ser
        275                 280                 285

Gly Thr Leu Ser Leu Thr Cys Ala Val Ser Gly Gly Ser Ile Ser Ser
        290                 295                 300

Ser Asn Trp Trp Ser Trp Val Arg Gln Pro Pro Gly Lys Gly Leu Glu
305                 310                 315                 320

Trp Ile Gly Glu Ile Tyr His Ser Gly Ser Thr Asn Tyr Asn Pro Ser
            325                 330                 335

Leu Lys Ser Arg Val Thr Ile Ser Val Asp Lys Ser Lys Asn Gln Phe
            340                 345                 350

Ser Leu Lys Leu Ser Ser Val Thr Ala Ala Asp Thr Ala Val Tyr Tyr
            355                 360                 365

Cys Ala Arg Leu Pro Gly Tyr Glu Ser Ala Phe Asp Ile Trp Gly Gln
        370                 375                 380

Gly Thr Met Val Thr Val Ser Ser Gly Gly Gly Ser Gln Ala Val
385                 390                 395                 400

Leu Thr Gln Pro Pro Ser Val Ser Glu Ala Pro Arg Gln Arg Val Thr
```

```
                       405             410             415

Ile Ser Cys Ser Gly Ser Ser Ser Asn Ile Gly Asn Asn Ala Val Ser
            420             425             430

Trp Tyr Gln Gln Leu Pro Gly Lys Ala Pro Lys Leu Leu Ile Tyr Tyr
            435             440             445

Asp Asp Leu Leu Pro Ser Gly Val Ser Asp Arg Phe Ser Gly Ser Lys
    450             455             460

Ser Gly Thr Ser Ala Ser Leu Ala Ile Ser Gly Leu Gln Ser Glu Asp
465             470             475             480

Glu Ala Asp Tyr Tyr Cys Ala Ala Trp Asp Asp Ser Leu Asn Gly Trp
            485             490             495

Val Phe Gly Gly Gly Thr Lys Val Thr Val Leu Gly Phe Val Pro Val
            500             505             510

Phe Leu Pro Ala Lys Pro Thr Thr Thr Pro Ala Pro Arg Pro Pro Thr
            515             520             525

Pro Ala Pro Thr Ile Ala Ser Gln Pro Leu Ser Leu Arg Pro Glu Ala
    530             535             540

Cys Arg Pro Ala Ala Gly Gly Ala Val His Thr Arg Gly Leu Asp Phe
545             550             555             560

Ala Cys Asp Ile Tyr Ile Trp Ala Pro Leu Ala Gly Thr Cys Gly Val
            565             570             575

Leu Leu Leu Ser Leu Val Ile Thr Leu Tyr Cys Asn His Arg Asn Lys
            580             585             590

Arg Gly Arg Lys Lys Leu Leu Tyr Ile Phe Lys Gln Pro Phe Met Arg
            595             600             605

Pro Val Gln Thr Thr Gln Glu Glu Asp Gly Cys Ser Cys Arg Phe Pro
    610             615             620

Glu Glu Glu Glu Gly Gly Cys Glu Leu Arg Val Lys Phe Ser Arg Ser
625             630             635             640

Ala Asp Ala Pro Ala Tyr Gln Gln Gly Gln Asn Gln Leu Tyr Asn Glu
            645             650             655

Leu Asn Leu Gly Arg Arg Glu Glu Tyr Asp Val Leu Asp Lys Arg Arg
            660             665             670

Gly Arg Asp Pro Glu Met Gly Gly Lys Pro Arg Arg Lys Asn Pro Gln
            675             680             685

Glu Gly Leu Tyr Asn Glu Leu Gln Lys Asp Lys Met Ala Glu Ala Tyr
    690             695             700

Ser Glu Ile Gly Met Lys Gly Glu Arg Arg Gly Lys Gly His Asp
705             710             715             720

Gly Leu Tyr Gln Gly Leu Ser Thr Ala Thr Lys Asp Thr Tyr Asp Ala
            725             730             735

Leu His Met Gln Ala Leu Pro Pro Arg
            740             745
```

<210> SEQ ID NO 67
<211> LENGTH: 2235
<212> TYPE: DNA
<213> ORGANISM: Artificial Sequence
<220> FEATURE:
<223> OTHER INFORMATION: PXL1436 CAR nucleic acid sequence

<400> SEQUENCE: 67
atggcacttc ctgtgacagc cttgctcttg cccttagcac tgctgcttca tgcggcgaga      60
cctgagatcg tcctcactca gtctccaggc accctgtctt tgtcacctgg agaacgggca     120

```
acactttcat gcagagcatc acaaagcgtt agtagtagct atcttgcctg gtatcagcaa        180
aaaccgggcc aggcacctag actgctcatt tatggagctt cctcaagagc aacaggaatc        240
cctgaccggt tcagcgggtc cggctctggt actgatttca ccttaacaat ctcaagactt        300
gaacctgaag atttcgcagt gtattattgt cagcaggcag gactcttccc gtatacattc        360
ggcggaggca caaaagtgga aattaaagga ggggggaggga gcgaggtcca acttgtgcaa        420
tcaggagcag aagtgaagaa gccaggcgaa tcacttaaga tttcctgcaa aggatcagga        480
tactcattta catcatactg gatcggatgg gtccggcaga tgcccggcaa aggattggag        540
tggatgggca tcatctaccc tggagattca gatacaagat actcaccttc cttccaaggc        600
caggtcacca tatcggctga caaatcaatc tcaacagcat accttcaatg gtcatcactt        660
aaagcatcag atacagcaat gtactactgc gcaaggctta gctattcatg gtcatcatgg        720
tactgggatt tctgggggca aggcacgctg gttacagtct catccggtag tacctccgga        780
tcaggaaagc cgggctctgg agaaggatct acaaagggcc aagcagtact gacgcagccg        840
ccctcagtgt cagaggcgcc aaggcaaaga gtaaccataa gttgttctgg atcttccagc        900
aatattggta acaacgcagt gagctggtat cagcagctac cgggaaaggc tcccaagcta        960
ttgatatatt atgacgatct tcttccttca ggagtgtcag acaggttctc gggttctaaa       1020
tcaggcacat cagcatcact tgccatcagc ggcctgcaga gcgaagatga agcagattat       1080
tattgtgccg cgtgggatga ttcacttaac ggatgggtgt tcggcggagg cacgaaggtg       1140
acagtacttg gtggaggagg tggctcccag gttcaacttc aagaatccgg cccaggtttg       1200
gtaaagcctt caggtacctt atcgctgact tgtgcagtgt caggaggatc aatctccagt       1260
agtaattggt ggtcatgggt ccgacagcct ccagggaaag gactagagtg gattggcgag       1320
atttaccact ctgggagtac caactacaac ccttcactta aatcacgagt cacaattagt       1380
gttgataaat caaagaatca attcagcctc aagctatcat cagtgacagc agcagataca       1440
gcggtctatt attgtgctag acttccaggc tacgaatcag catttgatat ctggggacaa       1500
ggaaccatgg taactgttag tagctttgta cctgtgtttc ttcctgcaaa gccgaccaca       1560
actcccgcac ctagacctcc aactccggca ccaaccattg catcacaacc tctaagtctg       1620
aggcccgagg catgcagacc tgcagcagga ggagcagtgc acacaagagg acttgatttc       1680
gcgtgtgata tctacatctg ggcacccctg gccggaacat gtggagtgct tcttctttca       1740
cttgtgatca cactttactg caaccacaga aacaagcgcg gtagaaagaa gctactgtac       1800
atctttaaac aacctttcat gcgtcctgtg caaacaacac aagaagaaga tggatgctca       1860
tgcagatttc ctgaagaaga agaaggagga tgcgaactta gagtgaaatt cagccgatca       1920
gcagatgcac ctgcatacca acaaggacag aatcagctct ataatgagct gaatttggga       1980
agaagagaag aatacgatgt gcttgataag cgcagaggtc gagacccaga aatgggagga       2040
aagccgagga ggaagaatcc gcaagaagga ctatataatg agctccagaa ggataagatg       2100
gctgaagcat actcagaaat cggaatgaaa ggagaaagaa gaagaggaaa gggccatgat       2160
ggactttacc aaggactttc aacagcaaca aaggacactt acgatgcact tcacatgcaa       2220
gcacttcctc ctaga                                                          2235
```

<210> SEQ ID NO 68
<211> LENGTH: 745
<212> TYPE: PRT
<213> ORGANISM: Artificial Sequence
<220> FEATURE:
<223> OTHER INFORMATION: PXL1436 CAR protein sequence -continued

<400> SEQUENCE: 68

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Thr Leu
                20                  25                  30

Ser Leu Ser Pro Gly Glu Arg Ala Thr Leu Ser Cys Arg Ala Ser Gln
            35                  40                  45

Ser Val Ser Ser Ser Tyr Leu Ala Trp Tyr Gln Gln Lys Pro Gly Gln
        50                  55                  60

Ala Pro Arg Leu Leu Ile Tyr Gly Ala Ser Ser Arg Ala Thr Gly Ile
65                  70                  75                  80

Pro Asp Arg Phe Ser Gly Ser Gly Ser Gly Thr Asp Phe Thr Leu Thr
                85                  90                  95

Ile Ser Arg Leu Glu Pro Glu Asp Phe Ala Val Tyr Tyr Cys Gln Gln
            100                 105                 110

Ala Gly Leu Phe Pro Tyr Thr Phe Gly Gly Gly Thr Lys Val Glu Ile
        115                 120                 125

Lys Gly Gly Gly Gly Ser Glu Val Gln Leu Val Gln Ser Gly Ala Glu
        130                 135                 140

Val Lys Lys Pro Gly Glu Ser Leu Lys Ile Ser Cys Lys Gly Ser Gly
145                 150                 155                 160

Tyr Ser Phe Thr Ser Tyr Trp Ile Gly Trp Val Arg Gln Met Pro Gly
                165                 170                 175

Lys Gly Leu Glu Trp Met Gly Ile Ile Tyr Pro Gly Asp Ser Asp Thr
            180                 185                 190

Arg Tyr Ser Pro Ser Phe Gln Gly Gln Val Thr Ile Ser Ala Asp Lys
        195                 200                 205

Ser Ile Ser Thr Ala Tyr Leu Gln Trp Ser Ser Leu Lys Ala Ser Asp
        210                 215                 220

Thr Ala Met Tyr Tyr Cys Ala Arg Leu Ser Tyr Ser Trp Ser Ser Trp
225                 230                 235                 240

Tyr Trp Asp Phe Trp Gly Gln Gly Thr Leu Val Thr Val Ser Ser Gly
                245                 250                 255

Ser Thr Ser Gly Ser Gly Lys Pro Gly Ser Gly Glu Gly Ser Thr Lys
            260                 265                 270

Gly Gln Ala Val Leu Thr Gln Pro Pro Ser Val Ser Glu Ala Pro Arg
        275                 280                 285

Gln Arg Val Thr Ile Ser Cys Ser Gly Ser Ser Ser Asn Ile Gly Asn
        290                 295                 300

Asn Ala Val Ser Trp Tyr Gln Gln Leu Pro Gly Lys Ala Pro Lys Leu
305                 310                 315                 320

Leu Ile Tyr Tyr Asp Asp Leu Leu Pro Ser Gly Val Ser Asp Arg Phe
                325                 330                 335

Ser Gly Ser Lys Ser Gly Thr Ser Ala Ser Leu Ala Ile Ser Gly Leu
            340                 345                 350

Gln Ser Glu Asp Glu Ala Asp Tyr Tyr Cys Ala Ala Trp Asp Asp Ser
        355                 360                 365

Leu Asn Gly Trp Val Phe Gly Gly Gly Thr Lys Val Thr Val Leu Gly
        370                 375                 380

Gly Gly Gly Gly Ser Gln Val Gln Leu Gln Glu Ser Gly Pro Gly Leu
385                 390                 395                 400

Val Lys Pro Ser Gly Thr Leu Ser Leu Thr Cys Ala Val Ser Gly Gly
```

```
                   405                410                415

Ser Ile Ser Ser Ser Asn Trp Trp Ser Trp Val Arg Gln Pro Pro Gly
           420                425                430

Lys Gly Leu Glu Trp Ile Gly Glu Ile Tyr His Ser Gly Ser Thr Asn
           435                440                445

Tyr Asn Pro Ser Leu Lys Ser Arg Val Thr Ile Ser Val Asp Lys Ser
   450                455                460

Lys Asn Gln Phe Ser Leu Lys Leu Ser Ser Val Thr Ala Ala Asp Thr
465                470                475                480

Ala Val Tyr Tyr Cys Ala Arg Leu Pro Gly Tyr Glu Ser Ala Phe Asp
               485                490                495

Ile Trp Gly Gln Gly Thr Met Val Thr Val Ser Ser Phe Val Pro Val
               500                505                510

Phe Leu Pro Ala Lys Pro Thr Thr Thr Pro Ala Pro Arg Pro Pro Thr
           515                520                525

Pro Ala Pro Thr Ile Ala Ser Gln Pro Leu Ser Leu Arg Pro Glu Ala
   530                535                540

Cys Arg Pro Ala Ala Gly Gly Ala Val His Thr Arg Gly Leu Asp Phe
545                550                555                560

Ala Cys Asp Ile Tyr Ile Trp Ala Pro Leu Ala Gly Thr Cys Gly Val
               565                570                575

Leu Leu Leu Ser Leu Val Ile Thr Leu Tyr Cys Asn His Arg Asn Lys
           580                585                590

Arg Gly Arg Lys Lys Leu Leu Tyr Ile Phe Lys Gln Pro Phe Met Arg
           595                600                605

Pro Val Gln Thr Thr Gln Glu Glu Asp Gly Cys Ser Cys Arg Phe Pro
   610                615                620

Glu Glu Glu Glu Gly Gly Cys Glu Leu Arg Val Lys Phe Ser Arg Ser
625                630                635                640

Ala Asp Ala Pro Ala Tyr Gln Gln Gly Gln Asn Gln Leu Tyr Asn Glu
               645                650                655

Leu Asn Leu Gly Arg Arg Glu Glu Tyr Asp Val Leu Asp Lys Arg Arg
           660                665                670

Gly Arg Asp Pro Glu Met Gly Gly Lys Pro Arg Arg Lys Asn Pro Gln
           675                680                685

Glu Gly Leu Tyr Asn Glu Leu Gln Lys Asp Lys Met Ala Glu Ala Tyr
   690                695                700

Ser Glu Ile Gly Met Lys Gly Glu Arg Arg Gly Lys Gly His Asp
705                710                715                720

Gly Leu Tyr Gln Gly Leu Ser Thr Ala Thr Lys Asp Thr Tyr Asp Ala
               725                730                735

Leu His Met Gln Ala Leu Pro Pro Arg
               740                745

<210> SEQ ID NO 69
<211> LENGTH: 2235
<212> TYPE: DNA
<213> ORGANISM: Artificial Sequence
<220> FEATURE:
<223> OTHER INFORMATION: PXL1437 CAR nucleic acid sequence

<400> SEQUENCE: 69
atggcacttc ctgtgacagc cttgctcttg cccttagcac tgctgcttca tgcggcgaga        60
cctcaggttc aacttcaaga atccggccca ggtttggtaa agccttcagg taccttatcg       120
```

-continued

```
ctgacttgtg cagtgtcagg aggatcaatc tccagtagta attggtggtc atgggtccga      180
cagcctccag ggaaaggact agagtggatt ggcgagattt accactctgg gagtaccaac      240 tacaacccctt cacttaaatc acgagtcaca attagtgttg ataaatcaaa gaatcaattc      300
agcctcaagc tatcatcagt gacagcagca gatacagcgg tctattattg tgctagactt      360
ccaggctacg aatcagcatt tgatatctgg ggacaaggaa ccatggtaac tgttagtagc      420
ggagggggag ggagccaagc agtactgacg cagccgccct cagtgtcaga ggcgccaagg      480
caaagagtaa ccataagttg ttctggatct tccagcaata ttggtaacaa cgcagtgagc      540
tggtatcagc agctaccggg aaaggctccc aagctattga tatattatga cgatcttctt      600
ccttcaggag tgtcagacag gttctcgggt tctaaatcag gcacatcagc atcacttgcc      660
atcagcggcc tgcagagcga agatgaagca gattattatt gtgccgcgtg ggatgattca      720
cttaacggat gggtgttcgg cggaggcacg aaggtgacag tacttggtgg tagtacctcc      780
ggatcaggaa agccgggctc tggagaagga tctacaaagg gcgaggtcca acttgtgcaa      840
tcaggagcag aagtgaagaa gccaggcgaa tcacttaaga tttcctgcaa aggatcagga      900
tactcattta catcatactg gatcggatgg gtccggcaga tgcccggcaa aggattggag      960
tggatgggca tcatctaccc tggagattca gatacaagat actcaccttc cttccaaggc     1020
caggtcacca tatcggctga caaatcaatc tcaacagcat accttcaatg gtcatcactt     1080
aaagcatcag atacagcaat gtactactgc gcaaggctta ctattcatg gtcatcatgg      1140 tactgggatt tctggggggca aggcacgctg gttacagtct catccggagg aggtggctcc     1200
gagatcgtcc tcactcagtc tccaggcacc ctgtctttgt cacctggaga acgggcaaca     1260
ctttcatgca gagcatcaca aagcgttagt agtagctatc ttgcctggta tcagcaaaaa     1320
ccgggccagg cacctagact gctcatttat ggagcttcct caagagcaac aggaatccct     1380
gaccggttca gcgggtccgg ctctggtact gatttcacct taacaatctc aagacttgaa     1440
cctgaagatt tcgcagtgta ttattgtcag caggcaggac tcttcccgta tacattcggc     1500
ggaggcacaa aagtggaaat aaatttgta cctgtgtttc ttcctgcaaa gccgaccaca      1560
actcccgcac ctagacctcc aactccggca ccaaccattg catcacaacc tctaagtctg     1620
aggcccgagg catgcagacc tgcagcagga ggagcagtgc acacaagagg acttgatttc     1680
gcgtgtgata tctacatctg ggcaccccctg gccggaacat gtggagtgct tcttctttca     1740
cttgtgatca cactttactg caaccacaga aacaagcgcg gtagaaagaa gctactgtac     1800
atctttaaac aacctttcat gcgtcctgtg caaacaacac aagaagaaga tggatgctca     1860
tgcagatttc ctgaagaaga gaaggagga tgcgaactta gagtgaaatt cagccgatca      1920
gcagatgcac ctgcatacca acaaggacag aatcagctct ataatgagct gaatttggga     1980
agaagagaag aatacgatgt gcttgataag cgcagaggtc gagacccaga atgggagga      2040 aagccgagga ggaagaatcc gcaagaagga ctatataatg agctccagaa ggataagatg     2100
gctgaagcat actcagaaat cggaatgaaa ggagaaagaa gaagaggaaa gggccatgat     2160
ggactttacc aaggactttc aacagcaaca aaggacactt acgatgcact tcacatgcaa     2220
gcacttcctc ctaga                                                    2235
```

<210> SEQ ID NO 70
<211> LENGTH: 745
<212> TYPE: PRT
<213> ORGANISM: Artificial Sequence
<220> FEATURE:
<223> OTHER INFORMATION: PXL1437 CAR protein sequence

<400> SEQUENCE: 70

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Gly Thr Leu Ser Leu Thr Cys Ala Val Ser Gly Gly
            35                  40                  45

Ser Ile Ser Ser Ser Asn Trp Trp Ser Trp Val Arg Gln Pro Pro Gly
        50                  55                  60

Lys Gly Leu Glu Trp Ile Gly Glu Ile Tyr His Ser Gly Ser Thr Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Leu Pro Gly Tyr Glu Ser Ala Phe Asp
            115                 120                 125

Ile Trp Gly Gln Gly Thr Met Val Thr Val Ser Ser Gly Gly Gly Gly
        130                 135                 140

Ser Gln Ala Val Leu Thr Gln Pro Pro Ser Val Ser Glu Ala Pro Arg
145                 150                 155                 160

Gln Arg Val Thr Ile Ser Cys Ser Gly Ser Ser Ser Asn Ile Gly Asn
                165                 170                 175

Asn Ala Val Ser Trp Tyr Gln Gln Leu Pro Gly Lys Ala Pro Lys Leu
            180                 185                 190

Leu Ile Tyr Tyr Asp Asp Leu Leu Pro Ser Gly Val Ser Asp Arg Phe
        195                 200                 205

Ser Gly Ser Lys Ser Gly Thr Ser Ala Ser Leu Ala Ile Ser Gly Leu
    210                 215                 220

Gln Ser Glu Asp Glu Ala Asp Tyr Tyr Cys Ala Ala Trp Asp Asp Ser
225                 230                 235                 240

Leu Asn Gly Trp Val Phe Gly Gly Gly Thr Lys Val Thr Val Leu Gly
            245                 250                 255

Gly Ser Thr Ser Gly Ser Gly Lys Pro Gly Ser Gly Glu Gly Ser Thr
            260                 265                 270

Lys Gly Glu Val Gln Leu Val Gln Ser Gly Ala Glu Val Lys Lys Pro
            275                 280                 285

Gly Glu Ser Leu Lys Ile Ser Cys Lys Gly Ser Gly Tyr Ser Phe Thr
    290                 295                 300

Ser Tyr Trp Ile Gly Trp Val Arg Gln Met Pro Gly Lys Gly Leu Glu
305                 310                 315                 320

Trp Met Gly Ile Ile Tyr Pro Gly Asp Ser Asp Thr Arg Tyr Ser Pro
                325                 330                 335

Ser Phe Gln Gly Gln Val Thr Ile Ser Ala Asp Lys Ser Ile Ser Thr
            340                 345                 350

Ala Tyr Leu Gln Trp Ser Ser Leu Lys Ala Ser Asp Thr Ala Met Tyr
            355                 360                 365

Tyr Cys Ala Arg Leu Ser Tyr Ser Trp Ser Ser Trp Tyr Trp Asp Phe
            370                 375                 380

Trp Gly Gln Gly Thr Leu Val Thr Val Ser Ser Gly Gly Gly Gly Ser
385                 390                 395                 400

Glu Ile Val Leu Thr Gln Ser Pro Gly Thr Leu Ser Leu Ser Pro Gly

-continued

```
                  405               410               415
Glu Arg Ala Thr Leu Ser Cys Arg Ala Ser Gln Ser Val Ser Ser Ser
            420               425               430

Tyr Leu Ala Trp Tyr Gln Gln Lys Pro Gly Gln Ala Pro Arg Leu Leu
        435               440               445

Ile Tyr Gly Ala Ser Ser Arg Ala Thr Gly Ile Pro Asp Arg Phe Ser
    450               455               460

Gly Ser Gly Ser Gly Thr Asp Phe Thr Leu Thr Ile Ser Arg Leu Glu
465               470               475               480

Pro Glu Asp Phe Ala Val Tyr Tyr Cys Gln Gln Ala Gly Leu Phe Pro
            485               490               495

Tyr Thr Phe Gly Gly Gly Thr Lys Val Glu Ile Lys Phe Val Pro Val
        500               505               510

Phe Leu Pro Ala Lys Pro Thr Thr Thr Pro Ala Pro Arg Pro Pro Thr
        515               520               525

Pro Ala Pro Thr Ile Ala Ser Gln Pro Leu Ser Leu Arg Pro Glu Ala
        530               535               540

Cys Arg Pro Ala Ala Gly Gly Ala Val His Thr Arg Gly Leu Asp Phe
545               550               555               560

Ala Cys Asp Ile Tyr Ile Trp Ala Pro Leu Ala Gly Thr Cys Gly Val
            565               570               575

Leu Leu Leu Ser Leu Val Ile Thr Leu Tyr Cys Asn His Arg Asn Lys
        580               585               590

Arg Gly Arg Lys Lys Leu Leu Tyr Ile Phe Lys Gln Pro Phe Met Arg
        595               600               605

Pro Val Gln Thr Thr Gln Glu Glu Asp Gly Cys Ser Cys Arg Phe Pro
    610               615               620

Glu Glu Glu Glu Gly Gly Cys Glu Leu Arg Val Lys Phe Ser Arg Ser
625               630               635               640

Ala Asp Ala Pro Ala Tyr Gln Gln Gly Gln Asn Gln Leu Tyr Asn Glu
            645               650               655

Leu Asn Leu Gly Arg Arg Glu Glu Tyr Asp Val Leu Asp Lys Arg Arg
        660               665               670

Gly Arg Asp Pro Glu Met Gly Gly Lys Pro Arg Arg Lys Asn Pro Gln
        675               680               685

Glu Gly Leu Tyr Asn Glu Leu Gln Lys Asp Lys Met Ala Glu Ala Tyr
        690               695               700

Ser Glu Ile Gly Met Lys Gly Glu Arg Arg Arg Gly Lys Gly His Asp
705               710               715               720

Gly Leu Tyr Gln Gly Leu Ser Thr Ala Thr Lys Asp Thr Tyr Asp Ala
            725               730               735

Leu His Met Gln Ala Leu Pro Pro Arg
        740               745
```